(12) United States Patent
Bedian

(10) Patent No.: US 12,252,550 B2
(45) Date of Patent: Mar. 18, 2025

(54) ANTIBODIES THAT BIND TO C1S AND USES THEREOF

(71) Applicant: DIANTHUS THERAPEUTICS OpCo, INC., New York, NY (US)

(72) Inventor: Vahe Bedian, Waltham, MA (US)

(73) Assignee: DIANTHUS THERAPEUTICS OPCO, INC., New York, NY (US)

(*) Notice: Subject to any disclaimer, the term of this patent is extended or adjusted under 35 U.S.C. 154(b) by 0 days.

(21) Appl. No.: 17/749,362

(22) Filed: May 20, 2022

(65) Prior Publication Data

US 2022/0380483 A1    Dec. 1, 2022

Related U.S. Application Data

(60) Provisional application No. 63/201,952, filed on May 20, 2021.

(51) Int. Cl.
| C07K 16/40 | (2006.01) |
| A61K 39/00 | (2006.01) |
| A61P 7/00  | (2006.01) |
| C07K 16/18 | (2006.01) |

(52) U.S. Cl.
CPC .............. C07K 16/40 (2013.01); A61P 7/00 (2018.01); A61K 2039/505 (2013.01); C07K 16/18 (2013.01); C07K 2317/24 (2013.01); C07K 2317/76 (2013.01)

(58) Field of Classification Search
CPC .......................... C07K 16/40; C07K 2317/24; C07K 2317/76; C07K 16/18; A61K 2039/505; A61P 7/00
See application file for complete search history.

(56) References Cited

U.S. PATENT DOCUMENTS

| 4,439,196 | A  | 3/1984  | Higuchi |
| 4,447,224 | A  | 5/1984  | DeCant, Jr. et al. |
| 4,447,233 | A  | 5/1984  | Mayfield |
| 4,487,603 | A  | 12/1984 | Harris |
| 4,596,556 | A  | 6/1986  | Morrow et al. |
| 4,790,824 | A  | 12/1988 | Morrow et al. |
| 4,816,567 | A  | 3/1989  | Cabilly et al. |
| 4,941,880 | A  | 7/1990  | Burns |
| 4,946,778 | A  | 8/1990  | Ladner et al. |
| 5,064,413 | A  | 11/1991 | McKinnon et al. |
| 5,260,203 | A  | 11/1993 | Adner et al. |
| 5,312,335 | A  | 5/1994  | McKinnon et al. |
| 5,383,851 | A  | 1/1995  | McKinnon, Jr. et al. |
| 5,399,163 | A  | 3/1995  | Peterson et al. |
| 6,005,079 | A  | 12/1999 | Casterman et al. |
| 6,096,002 | A  | 8/2000  | Landau |
| 6,620,135 | B1 | 9/2003  | Weston et al. |
| 7,670,600 | B2 | 3/2010  | Dall'Acqua et al. |
| 8,394,925 | B2 | 3/2013  | Chamberlain et al. |
| 2015/0133317 | A1* | 5/2015 | Robinson ........... C07K 16/1271 |
|  |  |  | 435/69.6 |
| 2016/0053002 | A1 | 2/2016 | Van Vlasselaer et al. |
| 2016/0090425 | A1 | 3/2016 | Rosenthal et al. |
| 2016/0215065 | A1* | 7/2016 | Lin ...................... A61P 43/00 |
| 2019/0010233 | A1 | 1/2019 | Liu et al. |
| 2020/0048332 | A1 | 2/2020 | Panicker et al. |
| 2021/0115116 | A1 | 4/2021 | Van Vlasselaer et al. |

FOREIGN PATENT DOCUMENTS

| EP | 0404097 A2      | 12/1990 |
| WO | 1988001649 A1   | 3/1988  |
| WO | 1993011161 A1   | 6/1993  |
| WO | 1994004678 A1   | 3/1994  |
| WO | 1994025591 A1   | 11/1994 |
| WO | 2012148497 A2   | 11/2012 |
| WO | 2015054670 A1   | 4/2015  |
| WO | 2018071676 A1   | 4/2018  |
| WO | 2018091661 A1   | 5/2018  |
| WO | 2022046888 A1   | 3/2022  |

OTHER PUBLICATIONS

Fernandez-Quintero, M.-L., et al., Germline-Dependent Antibody Paratope States and Pairing Specific VH-VL Interface Dynamics, Aug. 2021, Frontiers, 12, 675655 (Year: 2021).*
Rabia, L., et al Understanding and overcoming trade-offs between antibody affinity, specificity, stability, and solubility, 2018, Elsevier, 15(137); 365-374 (Year: 2018).*
Alegre et al., "Effect of a Single Amino Acid Mutation on the Activating and Immunosuppressive Properties of a "Humanized" OKT3 Monoclonal Antibody," J Immunol, 148(1):3461-3468 (1992).
Baert et al., "Influence of Immunogenicity on the Long-Term Efficacy of Infliximab in Crohn's Disease," (2003) New Engl. J. Med. 348:601-608.
Beniaminovitz et al., "Prevention of Rejection in Cardiac Transplantation by Blockade of the Interleukin-2 Receptor with a Monoclonal Antibody," (2000) New Engl. J. Med. 342(9):613-619.
Brown et al., "The Classical Pathway is the Dominant Complement Pathway Required for Innate Immunity to *Streptococcus pneumoniae* Infection in Mice," Proc Natl Acad Sci USA 99(26):16969-16974, 2002.
Budayova-Spano et al., "The Crystal Structure of the Zymogen Catalytic Domain of Complement Protease C1r Reveals that a Disruptive Mechanical Stress is Required to Trigger Activation of the C1 Complex," EMBO J. (2002) 21(3): 231-239.
Chothia et al., "Canonical Structures for the Hypervariable Regions of Immunoglobulins," (1987) J. Mol. Biol. 196:901-917.
Chothia et al., "Conformations of Immunoglobulin Hypervariable Regions," (1989) Nature 342: 877-883.
Clackson et al., "Making Antibody Fragments Using Phage Display Libraries," (1991) Nature 352:624-628. (Abstract Only).

(Continued)

*Primary Examiner* — Randall L Beane
*Assistant Examiner* — Lea S O'Brien
(74) *Attorney, Agent, or Firm* — Goodwin Procter LLP

(57) ABSTRACT

Embodiments that are provided for herein relate to antibodies and compositions that bind to C1s. Also provided are methods of producing the antibodies of the present disclosure, as well as uses of the provided antibodies and compositions for the treatment of C1s mediated diseases and disorders.

21 Claims, 4 Drawing Sheets

Specification includes a Sequence Listing.

(56) References Cited

OTHER PUBLICATIONS

Dall'Acqua et al., "Increasing the Affinity of a Human IgG1 for the Neonatal Fc Receptor: Biological Consequences," J Immunol, 169(9): 5171-5180 (2002).
David et al., "Protein Iodination with Solid State Lactoperoxidase," (1974) Biochemistry 13(5): 1014-1021. (Abstract Only).
Dombrowski et al., "Direct Submission," Marine Science Institute (Feb. 9, 2016) pp. 1-2.
Ghosh et al., "Natalizumab for Active Crohn's Disease," (2003) New Engl. J. Med. 348:24-32.
Herold et al., "Anti-CD3 Monoclonal Antibody in New-Onset Type 1 Diabetes Mellitus," (2002) New Engl. J. Med. 346(22): 1692-1698.
Holliger et al., "Diabodies: Small Bivalent and Bispecific Antibody Fragments," (1993) Proc. Natl. Acad. Sci. USA 90: 6444-6448.
Holliger et al., "Engineered Antibody Fragments and the Rise of Single Domains," (2005) Nat. Biotechnol. 23(9): 1126-1136.
International Search Report and Written Opinion for International PCT Application No. PCT/US2022/030189 dated Nov. 10, 2022.
Kabat et al., "Unusual Distributions of Amino Acids in Complementarity-Determining (Hypervariable) Segments of Heavy and Light Chains of Immunoglobulins and Their Possible Roles in Specificity of Antibody-Combining Sites," (1977) J. Biol. Chem. 252(19):6609-6616.
Kabat, "The Structural Basis for Antibody Complementary," Adv. Prot. Chem. (1978) 32:1-75. (Abstract Only).
Lathe, "Synthetic Oligonucleotide Probes Deduced from Amino Acid Sequence Data," J. Molec. Biol. (1985) 183:1-12.
Lee et al., "Prolonged Circulating Lives of Single Chain Fv Proteins Conjugated with Polyethylene Glycol: A Comparison of Conjugation Chemistries and Compounds," (1999) Bioconj. Chem. 10(6): 973-981. (Abstract Only).
Lipsky et al., "Infliximab and Methotrexate in the Treatment of Rheumatoid Arthritis," (2000) New Engl. J. Med. 343(22):1594-1602.
Liu et al., "Chimeric Mouse-Human IgG1 Antibody that can Mediate Lysis of Cancer Cells," Proc Natl. Acad. Sci., USA (1987) 84:3439-3443.
Liu et al., "Production of a Mouse-Human Chimeric Monoclonal Antibody to CD20 with Potent Fc-Dependent Biologic Activity," J. Immunology (1987) 139(10):3521-3526.
Liu et al., "Randomised, Double Blind, Placebo Controlled Study of Interferon Beta-1a in Relapsing-Remitting Multiple Sclerosis Analysed by Area under Disability/Time Curves," J. Neurol. Neurosurg. Psych. (1999) 67:451-456.
Marks et al., "By-Passing Immunization," J. Mol. Biol. (1991) 222: 581-597.
Milgrom et al., "Treatment of Allergic Asthma with Monoclonal Anti-IgE Antibody," New Engl. J. Med. (1999) 341:1966-1973.
Morrison et al., "Chimeric Human Antibody Molecules: Mouse Antigen-Binding Domains with Human Constant Region Domains," Proc. Natl. Acad. Sci. USA (1984) 81:6851-6855.
Muller, "[43] Determination of Affinity and Specificity of Anti-Hapten Antibodies by Competitive Radioimmunoassay," Meth. Enzymol. (1983) 92:589-601. (Abstract Only).
Muyldermans et al., "Recognition of Antigens by Single-Domain Antibody Fragments: the Superfluous Luxury of Paired Domains," (2001) Trends Biochem. Sci. 26(4):230-235.
Pain et al., "Preparation of Protein A-Peroxidase Monoconjugate Using a Heterobifunctional Reagent, and its Use in Enzyme Immunoassays," (1981) J. Immunol. Meth. 40(2): 219-230. (Abstract Only).
Pluckthun, "Antibodies from *Escherichia coli*," Nature (Oct. 4, 1990) vol. 347, No. 6292, pp. 497-498.
Portielji et al., "IL-12: A Promising Adjuvant for Cancer Vaccination," Cancer Immunol. Immunother. (2003) 52:133-144.
Presta, "Selection, Design, and Engineering of Therapeutic Antibodies," J. Allergy Clin. Immunol. (2005) 116(4):731-736.
Reichmann et al., "Reshaping Human Antibodies for Therapy," (1988) Nature 332(6162): 323-327.
Rowley et al., "A Protein Epitope Targeted by the Antibody Response to Kawasaki Disease," Pediatrics, Northwestern (Jan. 10, 2019) pp. 1-2.
Silva et al., "The S228P Mutation Prevents in Vivo and in Vitro IgG4 Fab-arm Exchange as Demonstrated using a Combination of Novel Quantitative Immunoassays and Physiological Matrix Preparation," J Biol Chem, 290(9):5462-5469 (2015).
Slamon et al., "Use of Chemotherapy Plus a Monoclonal Antibody against HER2 for Metastatic Breast Cancer that Overexpresses HER2," (2001) New Engl. J. Med. 344(11):783-792.
Tsurushita et al., "Humanization of a Chicken Anti-IL-12 Monoclonal Antibody," J. Immuno. Methods (2004) vol. 295, pp. 9-19.
Wen et al., "Poly(ethylene glycol)-Conjugated Anti-EGF Receptor Antibody C225 with Radiometal Chelator Attached to the Termini of Polymer Chains," (2001) Bioconj. Chem. 12(4): 545-553. (Abstract Only).
Xie, "A Highly Resolved Spatial and Functional Map of the Ruminant Gastrointestinal Microbiome," Unpublished (Nov. 20, 2020) pp. 1-4.
Yang et al., "A Randomized Trial of Bevacizumab, an Anti-Vascular Endothelial Growth Factor Antibody, for Metastatic Renal Cancer," (2003) New Engl. J. Med. 349(5):427-434.
Morrison, et al. Chimeric Human Antibody Molecules: Mouse Antigen-Binding Domains with Human Constant Region Domains, Pro. Natl. Aca. Sci. USA, vol. 81, pp. 6851-6855, Nov. 1984, Immunology.
Yang, et al, A Randomized Trial of Bevacizumab, an Anti-Vascular Endothelial Growth Factor Antibody, for Metastatic Renal Cancer, New England Journal of Medicine, Jul. 31, 2003; 349(5); 427-434.
Bayly-Jones, et al. The mystery behind membrane insertion: a review of the complement membrane attacl complex, Phil. Trans. R. Soc.; vol. 372, Feb. 21, 2016.
Grohar-Murray, et al. Self-care to manage fatigue among myasthenia gravis patients, Journal of Neuroscience Nusring, vol. 30 Issue 3, Jun. 1998.
Silva, et al. The S228P Mutation Prevents in Vivo and in Vitro IgG4 Fab-arm Exchange as Demonstrated using a Combination of Novel Quantitative Immunoassays and Physiological Matrix Preparation, The The Journal of Biological Chemistry, vol. 290, No. 9, pp. 5462-5469, Feb. 27, 2015.
Cella, et al., Brief measures of health-related quality of life for clinical research in neurology, Qual. Life Clin. Res. Neurol. 2012; 78:1860-1867.
Kusumoto, et al., Human genes for complement components C1r and C1s in a close tail-to-tail arrangement, Proc. Natl. Acad. Sci. USA 85(19), 7307-7311 (1988).
Krupp, et al., The Fatigue Severity Scale Application to Patients With Multiple Scelrosis and Systemic Lupus Erythematosus, Arch Neurol, vol. 46, Oct. 1989.
Fisk J.D. et al, Measuring the functional impact of fatigue: initial validation of the fatigue impact scale. Clin Infect Dis. 1994; 1: S79-S83.
Chalder T. et al., Development of a Fatigue Scale, Journal of Psychosom Resarch 1993; vol. 37, No. 2. pp 147-153.
Tsurushita, N., et al., Humanization of a chicken anti-IL-12 monoclonal antibody, Journal of Immunological Methods, 295 (2004) pp. 9-19.
Kohler, G., et al., Continuous cultures of fused cells secreting antibody of predefined specificity, Nature, vol. 256, Aug. 1975, pp. 495-497.
Penner, I., et al., The Fatigue Scale for Motor and Cognitive Functions (FSMC): validation of a new instrument to assess multiple sclerosis-related fatigue, Multiple Sclerosis, 2009; 15 (12), pp. 1509-1517.
Pain, et al., (1981) J. Immunol. Meth. 40:219.
U.S. Appl. No. 17/749,362 Non-Final Office Action dated Mar. 14, 2024.
Fernandez-Quintero, et al., Germline-Dependent Antibody Paratope States and Pairing Specific VH-VL Interface Dynamics, Frontiers in Immunology, vol. 12, 2021.
Rabia, L., et al. (2018) Understanding and overcoming trade-offs between antibody affinity, specificity, stability, and solubility, Biochem Eng. J. 15(137(; 365-374.

(56) References Cited

OTHER PUBLICATIONS

International Search Report and Written Opinion for International Application PCT/US23/80658 dated Apr. 3, 2024.
GenBank AAA51852 1 Complement Component C1s [*Homo sapiens*]—Protein—NCBI.

* cited by examiner

ANTIBODIES THAT BIND TO C1S AND USES THEREOF

CROSS-REFERENCE TO RELATED APPLICATION

The present application claims priority to U.S. Provisional Application No. 63/201,952, filed May 20, 2021, which is hereby incorporated by reference in its entirety.

FIELD OF THE INVENTION

The field of the invention is immunology, in particular therapeutic antibodies, and treatment of disease with those antibodies.

BACKGROUND

The complement system is a well-known effector mechanism of the innate immune response, providing not only protection against pathogens and other harmful agents but also recovery from injury. Complement activation due to autoantibodies and alloantibodies can lead to damage to normal cells or rejection of transplanted tissue. The complement pathway comprises a number of proteins that typically exist in the body in inactive form. The classical complement pathway is triggered by activation of the first component of complement, referred to as the C1 complex, which consists of C1q, C1r, and C1s proteins. Upon binding of C1 to an immune complex or other activator, the C1s component, a diisopropyl fluorophosphate (DFP)-sensitive serine protease, cleaves complement components C4 and C2 to initiate activation of the classical complement pathway. The classical complement pathway appears to play a role in many diseases and disorders. For example, sutimlimab, an antibody that inhibits C1s, is currently being investigated for treatment of hemolysis in adults with cold agglutinin disease, however, the dosing and lack of specificity for C1s, the active form, as opposed to the zymogen proC1s, and its physical properties, such as its lack of specificity, which requires a very high dose to be administerested, may limits its use. Therefore, there is a need in the art for compounds that treat a complement classical pathway-mediated disease or disorder. The embodiments provided for here in satisfies these needs as well as others.

SUMMARY

In some embodiments, antibodies, such as recombinant antibodies, or an antigen binding fragments thereof that binds to a C1s are provided. In some embodiments, the antibody or antigen binding fragment thereof comprises an amino acid sequence, or a variant thereof, as provided for herein.

In some embodiments, isolated nucleic acid molecules encoding an antibody, or an antigen binding fragment thereof, a heavy chain variable region, a light chain variable region, heavy chain, or light chain as provided herein are provided.

In some embodiments, expression vectors comprising a nucleic acid molecule as provided for herein are provided.

In some embodiments, host cells comprising a nucleic acid molecule as provided for herein are provided.

In some embodiments, antibodies, or antigen-binding fragments produced by the host cells are provided.

In some embodiments, methods of producing a polypeptide comprising a heavy chain variable region or light chain variable region as provided herein are provided. In some embodiments, the methods comprise growing a host cell under conditions so that the host cell expresses a polypeptide comprising the heavy chain variable region or the light chain variable region; and purifying the polypeptide comprising the heavy chain variable region and/or the light chain variable region.

In some embodiments, methods of treating a subject with a C1s mediated disorder are provided. In some embodiments, the methods comprise administering to the subject an antibody, or antigen binding fragment thereof, as provided herein or a pharmaceutical composition comprising the same. In some embodiments, the C1s mediated disorder is selected from hemolysis, Cold Agglutinin Disease, Immune Thrombocytopenia (ITP), Myastenia Gravis, Glomerulopaties, Atypical Hemolytic uremic syndrome, antiphospholipid antibody syndrome, or transplant rejection.

In some embodiments, antibodies, or antigen binding fragments thereof, as provided herein, or a pharmaceutical composition comprising the same, for use as a medicament are provided.

In some embodiments, use of the antibodies, or antigen binding fragments thereof, as provided for herein, or a pharmaceutical composition comprising the same are provided for the treatment of a C1s mediated disorder, such as, but not limited to hemolysis, Cold Agglutinin Disease, Immune Thrombocytopenia (ITP), Myastenia Gravis, Glomerulopaties, Atypical Hemolytic uremic syndrome, antiphospholipid antibody syndrome, or transplant rejection. or as provided for herein.

In some embodiments, an antibody, or an antigen binding fragment thereof, is provided, wherein the antibody or antibody fragment comprises:
  (a) a heavy chain variable region comprising heavy chain HCDR1, HCDR2, and HCDR3 sequences, wherein the heavy chain HCDR1 sequence has the amino acid sequence of SEQ ID NO: 9; the heavy chain HCDR2 has the amino acid sequence of SEQ ID NO: 10 and the heavy chain HCDR3 sequence has the amino acid sequence of SEQ ID NO: 11 or variants of any of the foregoing; and (ii) a light chain variable region comprising light chain LCDR1, LCDR2, and LCDR3 sequences, wherein the light chain LCDR1 sequence has the amino acid sequence SEQ ID NO: 12; the light chain LCDR2 sequence has the amino acid sequence of SEQ ID NO: 13; and the light chain LCDR3 sequence has the amino acid sequence of SEQ ID NO: 14; or variants of any of the foregoing;
  (b) a heavy chain variable region comprising heavy chain HCDR1, HCDR2, and HCDR3 sequences, wherein the heavy chain HCDR1 sequence has the amino acid sequence of SEQ ID NO: 15; the heavy chain HCDR2 has the amino acid sequence of SEQ ID NO: 16 and the heavy chain HCDR3 sequence has the amino acid sequence of SEQ ID NO: 17 or variants of any of the foregoing; and (ii) a light chain variable region comprising light chain LCDR1, LCDR2, and LCDR3 sequences, wherein the light chain LCDR1 sequence has the amino acid sequence SEQ ID NO: 18; the light chain LCDR2 sequence has the amino acid sequence of SEQ ID NO: 19; and the light chain LCDR3 sequence has the amino acid sequence of SEQ ID NO: 20; or variants of any of the foregoing; or
  (c) a heavy chain variable region comprising heavy chain HCDR1, HCDR2, and HCDR3 sequences, wherein the heavy chain HCDR1 sequence has the amino acid sequence of SEQ ID NO: 21; the heavy chain HCDR2 has the amino acid sequence of SEQ ID NO: 22 and the heavy chain HCDR3 sequence has the amino acid sequence of SEQ ID NO: 23 or variants of any of the foregoing; and (ii) a light chain variable region comprising light chain LCDR1, LCDR2, and LCDR3 sequences, wherein the light chain LCDR1 sequence has the amino acid sequence SEQ ID NO: 24; the light chain LCDR2 sequence has the amino acid sequence of SEQ ID NO: 25; and the light chain LCDR3 sequence has the amino acid sequence of SEQ ID NO: 26; or variants of any of the foregoing.

In some embodiments, an antibody, or an antigen binding fragment thereof, is provided, wherein the antibody or antibody fragment comprises:

(a) a heavy chain variable region comprising heavy chain HCDR1, HCDR2, and HCDR3 sequences, wherein the heavy chain HCDR1 sequence has the amino acid sequence of SEQ ID NO: 27; the heavy chain HCDR2 has the amino acid sequence of SEQ ID NO: 28 and the heavy chain HCDR3 sequence has the amino acid sequence of SEQ ID NO: 11 or variants of any of the foregoing; and (ii) a light chain variable region comprising light chain LCDR1, LCDR2, and LCDR3 sequences, wherein the light chain LCDR1 sequence has the amino acid sequence SEQ ID NO: 29; the light chain LCDR2 sequence has the amino acid sequence of SEQ ID NO: 30; and the light chain LCDR3 sequence has the amino acid sequence of SEQ ID NO: 31; or variants of any of the foregoing;

(b) a heavy chain variable region comprising heavy chain HCDR1, HCDR2, and HCDR3 sequences, wherein the heavy chain HCDR1 sequence has the amino acid sequence of SEQ ID NO: 32; the heavy chain HCDR2 has the amino acid sequence of SEQ ID NO: 33 and the heavy chain HCDR3 sequence has the amino acid sequence of SEQ ID NO: 17 or variants of any of the foregoing; and (ii) a light chain variable region comprising light chain LCDR1, LCDR2, and LCDR3 sequences, wherein the light chain LCDR1 sequence has the amino acid sequence SEQ ID NO: 34; the light chain LCDR2 sequence has the amino acid sequence of SEQ ID NO: 35; and the light chain LCDR3 sequence has the amino acid sequence of SEQ ID NO: 36; or variants of any of the foregoing; or (c) a heavy chain variable region comprising heavy chain HCDR1, HCDR2, and HCDR3 sequences, wherein the heavy chain HCDR1 sequence has the amino acid sequence of SEQ ID NO: 37; the heavy chain HCDR2 has the amino acid sequence of SEQ ID NO: 38 and the heavy chain HCDR3 sequence has the amino acid sequence of SEQ ID NO: 23 or variants of any of the foregoing; and (ii) a light chain variable region comprising light chain LCDR1, LCDR2, and LCDR3 sequences, wherein the light chain LCDR1 sequence has the amino acid sequence SEQ ID NO: 39; the light chain LCDR2 sequence has the amino acid sequence of SEQ ID NO: 40; and the light chain LCDR3 sequence has the amino acid sequence of SEQ ID NO: 41; or variants of any of the foregoing.

In some embodiments, an antibody, or an antigen binding fragment thereof, is provided, wherein the antibody or antibody fragment comprises:

(a) a heavy chain variable region comprising heavy chain HCDR1, HCDR2, and HCDR3 sequences, wherein the heavy chain HCDR1 sequence has the amino acid sequence of SEQ ID NO: 42; the heavy chain HCDR2 has the amino acid sequence of SEQ ID NO: 43 and the heavy chain HCDR3 sequence has the amino acid sequence of SEQ ID NO: 44 or variants of any of the foregoing; and (ii) a light chain variable region comprising light chain LCDR1, LCDR2, and LCDR3 sequences, wherein the light chain LCDR1 sequence has the amino acid sequence SEQ ID NO: 45; the light chain LCDR2 sequence has the amino acid sequence of SEQ ID NO: 30; and the light chain LCDR3 sequence has the amino acid sequence of SEQ ID NO: 14; or variants of any of the foregoing;

(b) a heavy chain variable region comprising heavy chain HCDR1, HCDR2, and HCDR3 sequences, wherein the heavy chain HCDR1 sequence has the amino acid sequence of SEQ ID NO: 46; the heavy chain HCDR2 has the amino acid sequence of SEQ ID NO: 47 and the heavy chain HCDR3 sequence has the amino acid sequence of SEQ ID NO: 48 or variants of any of the foregoing; and (ii) a light chain variable region comprising light chain LCDR1, LCDR2, and LCDR3 sequences, wherein the light chain LCDR1 sequence has the amino acid sequence SEQ ID NO: 49; the light chain LCDR2 sequence has the amino acid sequence of SEQ ID NO: 35; and the light chain LCDR3 sequence has the amino acid sequence of SEQ ID NO: 20; or variants of any of the foregoing; or (c) a heavy chain variable region comprising heavy chain HCDR1, HCDR2, and HCDR3 sequences, wherein the heavy chain HCDR1 sequence has the amino acid sequence of SEQ ID NO: 50; the heavy chain HCDR2 has the amino acid sequence of SEQ ID NO: 51 and the heavy chain HCDR3 sequence has the amino acid sequence of SEQ ID NO: 52 or variants of any of the foregoing; and (ii) a light chain variable region comprising light chain LCDR1, LCDR2, and LCDR3 sequences, wherein the light chain LCDR1 sequence has the amino acid sequence SEQ ID NO: 53; the light chain LCDR2 sequence has the amino acid sequence of SEQ ID NO: 40; and the light chain LCDR3 sequence has the amino acid sequence of SEQ ID NO: 26; or variants of any of the foregoing.

In some embodiments, an antibody, or an antigen binding fragment thereof, is provided, wherein the antibody or antibody fragment comprises:

a. the HCDR1, HCDR2 and HCDR3 are selected from SEQ ID NO: 9, SEQ ID NO: 10, SEQ ID NO: 11, respectively, from SEQ ID NO: 27, SEQ ID NO: 28, SEQ ID NO: 11, respectively, and from SEQ ID NO: 42, SEQ ID NO: 43, SEQ ID NO: 44, respectively, and the LCDR1, LCDR2 and LCDR3 are selected from from SEQ ID NO: 12, SEQ ID NO: 13, SEQ ID NO: 14, respectively, from SEQ ID NO: 29, SEQ ID NO: 30, SEQ ID NO: 31, respectively, and from SEQ ID NO: 45, SEQ ID NO: 30, SEQ ID NO: 14, respectively; or b. the HCDR1, HCDR2 and HCDR3 are selected from SEQ ID NO: 15, SEQ ID NO: 16, SEQ ID NO: 17, respectively, from SEQ ID NO: 32, SEQ ID NO: 33, SEQ ID NO: 17, respectively, and from SEQ ID NO: 46, SEQ ID NO: 47, SEQ ID NO: 48, respectively, and the LCDR1, LCDR2 and LCDR3 are selected from from SEQ ID NO: 18, SEQ ID NO: 19, SEQ ID NO: 20, respectively, from SEQ ID NO: 34, SEQ ID NO: 35, SEQ ID NO: 36, respectively, and from SEQ ID NO: 49, SEQ ID NO: 35, SEQ ID NO: 20, respectively; or c. the HCDR1, HCDR2 and HCDR3 are selected from SEQ ID NO: 21, SEQ ID NO: 22, SEQ ID NO: 23, respectively, SEQ ID NO: 37, SEQ ID NO: 38, SEQ ID NO: 23, respectively, and SEQ ID NO: 50, SEQ ID NO: 51, SEQ ID NO: 52, respectively, and the LCDR1, LCDR2 and LCDR3 are selected from SEQ ID NO: 24, SEQ ID NO: 25, SEQ ID NO: 26, respectively, SEQ ID NO: 39, SEQ ID NO: 40, SEQ ID NO: 41, respectively, and SEQ ID NO: 53, SEQ ID NO: 40, SEQ ID NO: 26, respectively.

In some embodiments, a variant of an antibody or antigen binding fragment thereof is provided, wherein the variant has 1-10 substitutions, deletions, or insertions.

In some embodiments, a variant of an antibody or antigen binding fragment thereof is provided, wherein the variant has 1-10 conservative substitutions.

In some embodiments, a recombinant antibody or antigen binding fragment thereof is provided, wherein the recombinant antibody or antigen binding fragment thereof binds to a C1s. In some embodiments, the recombinant antibody or antigen binding fragment thereof is an antibody or antigen binding fragment thereof as provided for herein.

In some embodiments, an isolated nucleic acid molecule is provided. In some embodiments, the isolated nucleic acid molecule encodes an antibody or antigen binding fragment thereof, a heavy chain variable region, a light chain variable region, a heavy chain, a light chain, or a combination thereof. In some embodiments, the antibody or antigen binding fragment thereof, a heavy chain variable region, a light chain variable region, a heavy chain, or light chain are as provided for herein.

In some embodiments, an expression vector is provided. In some embodiments, the expression vector comprises a nucleic acid molecule as provided for herein.

In some embodiments a host cell is provided. In some embodiments, the host cell comprises a nucleic acid molecule or expression vector as provided for herein. In some embodiments, the host cell comprises a nucleic acid molecule as provided for herein. In some embodiments, the host cell comprises an expression vector as provided for herein.

In some embodiments, an antibody or antigen binding fragment thereof is provided, wherein the antibody or antigen binding fragment thereof is produced by the host cell.

In some embodiments, a pharmaceutical composition is provided. In some embodiments, the pharmaceutical composition comprises an antibody or antigen binding fragment thereof as provided for herein.

In some embodiments, a method of producing a polypeptide comprising a heavy chain variable region or a light chain variable region is provided. In some embodiments, the method comprises (a) growing a host cell as provided for herein under conditions so that the host cell expresses the polypeptide comprising the heavy chain variable region or the light chain variable region; and (b) purifying the polypeptide comprising the heavy chain or the light chain variable regions. In some embodiments, the heavy chain variable region is as provided for herein. In some embodiments, the light chain variable region is as provided for herein.

In some embodiments, a method of producing an antibody or an antigen binding fragment of the antibody is provided. In some embodiments, the antibody or antigen binding fragment bind to human C1s. In some embodiments, the method comprises (a) growing a host cell as provided for herein under conditions so that the host cell expresses the polypeptide or polypeptides comprising the immunoglobulin heavy chain variable region and/or the immunoglobulin light chain variable region, thereby producing the antibody or the antigen binding fragment of the antibody; and (b) purifying the antibody or the antigen-binding fragment of the antibody.

In some embodiments, a method of treating a subject with a C1s mediated disorder is provided. In some embodiments, the method comprises administering to the subject an antibody or antigen binding fragment thereof as provided for herein, or a pharmaceutical composition as provided for herein.

In some embodiments, an antibody or antigen binding fragment thereof or a pharmaceutical composition is provided, wherein the antibody or antigen binding fragment thereof or the pharmaceutical composition are for the use in the treatment of a C1s mediated disorder. In some embodiments, the antibody or antigen binding fragment thereof is as provided for herein. In some embodiments, the pharmaceutical composition is as provided for herein. In some embodiments, the C1s mediated disorder is as provided for herein. In some embodiments, the C1s mediated disorder is hemolysis or Cold Agglutinin Disease.

In some embodiments, an antibody or antigen binding fragment thereof or a pharmaceutical composition is provided, wherein the antibody or antigen binding fragment thereof or the pharmaceutical composition are for the use as a medicament. In some embodiments, the antibody or antigen binding fragment thereof is as provided for herein. In some embodiments, the pharmaceutical composition is as provided for herein.

In some embodiments, a use of an antibody or antigen binding fragment thereof or a pharmaceutical composition is provided, wherein the use is for the treatment of a C1s mediated disorder. In some embodiments, the antibody or antigen binding fragment thereof is as provided for herein. In some embodiments, the pharmaceutical composition is as provided for herein. In some embodiments, the C1s mediated disorder is as provided for herein.

DETAILED DESCRIPTION

Figure 1:
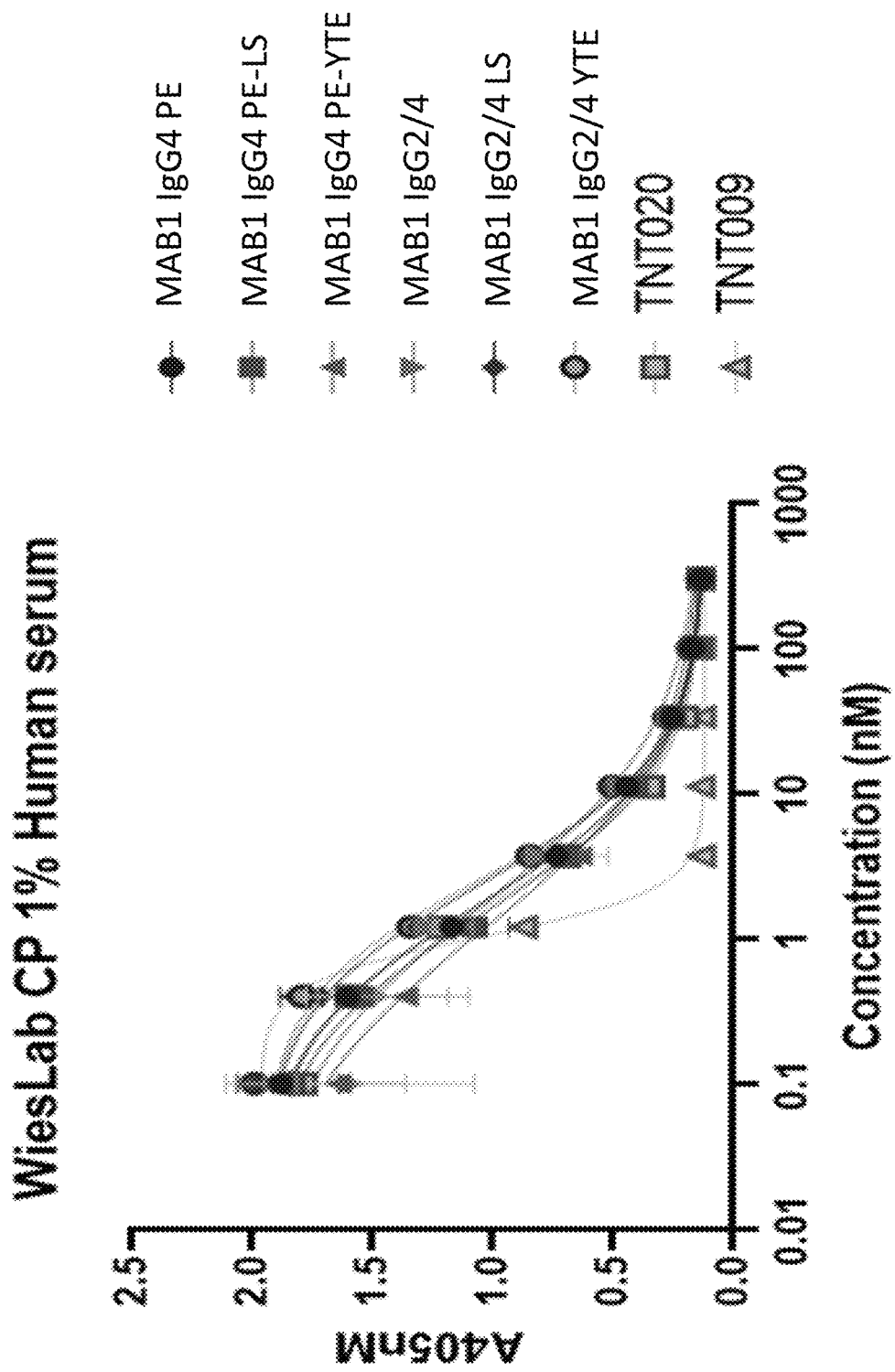
FIG. 1 shows the dose response of six 4O11g antibodies that differ in their Fc regions, along with TNT009 and TNT020, in the Wieslab classical pathway kit used according to manufacturer's instruction.

Provided herein are binding proteins, e.g., antibodies, or fragments, thereof, that selectively bind to C1s and have low binding to the zymogen proC1s. In some embodiments, the antibodies inhibit activation of the classical complement pathway and can be used in methods to treat complement mediated disorders, such as, but not limited to those provided for herein. In some embodiments, the selectivity for C1s over proC1s can be used to reduce or prevent target mediated clearance of the therapeutic antibody, thus requiring lower doses and frequency of administration of the antibody.

Before the present compositions and methods are described, it is to be understood that the scope of the invention is not limited to the particular processes, compositions, or methodologies described herein, as these may vary. It is also to be understood that the terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. Although any methods and materials similar or equivalent to those described herein can be used in the practice or testing of embodiments of the methods and systems disclosed herein, the preferred methods, devices, and materials are now described.

The following explanations of terms and methods are provided to better describe the present disclosure and to guide those of ordinary skill in the art in the practice of the present disclosure.

As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements, unless the context clearly indicates otherwise. For example, the phrase "A or B" refers to A alone or B alone. The phrase "A, B, or a combination thereof" refers to A alone, B alone, or a combination of A and B. Similarly, "one or more of A and B" refers to A, B, or a combination of both A and B. The phrase "A and B" refers to a combination of A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless otherwise defined, all technical and scientific terms used herein have the same meaning as commonly understood to one of ordinary skill in the art. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies (single domain antibody) and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the CHI domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_H$ domains of an antibody, wherein these domains are present in a single polypeptide chain. Generally, the Fv polypeptide further comprises a polypeptide linker between the Vu and $V_H$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "single-domain antibody" is an immunologically functional immunoglobulin fragment containing only the variable region of a heavy chain or the variable region of a light chain. In some instances, two or more Vu regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90:6444-6448. For a review of engineered antibody variants generally see Holliger and Hudson (2005) *Nat. Biotechnol.* 23:1126-1136.

Typically, a variant antibody or antigen binding fragment of the antibodies provided herein retain at least 10% of its C1s binding activity (when compared to a parental antibody that is modified) when that activity is expressed on a molar basis. In some embodiments, a variant antibody (or antigen fragment thereof), or antigen binding fragment of an antibody provided herein, retains at least 20%, 50%, 70%, 80%, 90%, 95% or 100% or more of the C1s binding affinity as the parental antibody. As described herein, it is also intended that an antibody or antigen binding fragment of the invention can include conservative or non-conservative amino acid substitutions, which can also be referred to as "conservative variants" or "function conserved variants" of the antibody, that do not substantially alter its biologic activity.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations and/or post-translational modifications that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example. See also Presta (2005) *J. Allergy Clin. Immunol.* 116:731.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) *Proc. Natl. Acad. Sci. USA* 81:6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In some embodiments, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. However, in bifunctional or bispecific antibodies, the two binding sites are, in general, not the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56

(CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) J. Mol. Biol. 196:901-917). The CDRs can also be referenced according to the IMGT system for the identification of CDRs, which is described in Lefranc MP. Unique database numbering system for immunogenetic analysis. Immunol Today (1997) 18:509. As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

As used herein, "specific binding" or "immunospecific binding" or "binds immunospecifically" refer to antibody binding to a predetermined antigen at a much higher affinity than for another antigen(s) (e.g. selectively binds the active form of complement component C1s as compared to inactive C1s, which can also be referred to as proC1s zymogen). In some embodiments, the antibody binds the predetermined antigen with a dissociation constant ($K_D$)) of $10^{-7}$ M or less, and such $K_D$ is at least two-fold less than its $K_D$ for binding to a non-specific antigen (e.g., BSA, casein, or another non-specific polypeptide).

The phrases "an antibody recognizing C1s" and "an antibody specific for C1s" are used interchangeably herein with the term "an antibody which binds immunospecifically to C1s." In some embodiments, the antibody binds specifically or preferentially to C1s, such as the active form of C1s over other proteins, such as, but not limited to, the inactive form of C1s (proC1s). The degree of specificity necessary for an anti-C1s antibody may depend on the intended use of the antibody, and at any rate is defined by its suitability for use for an intended purpose. In some embodiments, the antibody, or binding compound derived from the antigen-binding site of an antibody, of the contemplated method binds to its antigen (active form of C1s), with an affinity that is at least two fold greater, at least ten times greater, at least 20-times greater, or at least 100-times greater than the affinity with any other antigen, including, but not limited to inactive C1s.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The term "homolog" means protein sequences having between 40% and 100% sequence identity to a reference sequence. Percent identity between two peptide chains can be determined by pair wise alignment using the default settings of the AlignX module of Vector NTI v.9.0.0 (Invitrogen™ Corp., Carlsbad, Calif.) or other suitable alignment software, such as BLAST. In some embodiments, the antibody, or antigen binding fragment thereof has, at least 50, 60, 70, 80, 90, 91, 92, 93, 94, 95, 96, 97, 98, or 99% homology or identity to a sequence described herein. In some embodiments, the antibody has conservative substitutions as compared to a sequence described herein. Exemplary conservative substitutions are illustrated in Table 1 and are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE 1

Table: Exemplary Conservative Substitutions:

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. As described herein, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

The term "in combination with" as used herein means that the described agents can be administered to an animal or subject together in a mixture, concurrently as single agents or sequentially as single agents in any order.

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics "Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

In some embodiments, the antibody is a monoclonal antibody which binds to C1s. The sequence of active C1s is as follows (SEQ ID NO: 56): Residues 1-15 (SEQ ID NO: 75) constitute the signal peptide which is cleaved during translation, and residues 16-688 (SEQ ID NO: 76) constitute the mature protein.

```
                                              (SEQ ID NO: 56)
MWCIVLFSLLAWVYAEPTMYGEILSPNYPQAYPSEVEKSWDIEVPEGYGIH

LYFTHLDIELSENCAYDSVQIISGDTEEGRLCGQRSSNNPHSPIVEEFQVP

YNKLQVIFKSDFSNEERFTGFAAYYVATDINECTDFVDVPCSHFCNNFIGG

YFCSCPPEYFLHDDMKNCGVNCSGDVFTALIGEIASPNYPKPYPENSRCEY

QIRLEKGFQVVVTLRREDFDVEAADSAGNCLDSLVFVAGDRQFGPYCGHGF

PGPLNIETKSNALDIIFQTDLTGQKKGWKLRYHGDPMPCPKEDTPNSVWEP

AKAKYVFRDVVQITCLDGFEVVEGRVGATSFYSTCQSNGKWSNSKLKCQPV

DCGIPESIENGKVEDPESTLFGSVIRYTCEEPYYYMENGGGGEYHCAGNGS

WVNEVLGPELPKCVPVCGVPREPFEEKQRIIGGSDADIKNFPWQVFFDNPW

AGGALINEYWVLTAAHVVEGNREPTMYVGSTSVQTSRLAKSKMLTPEHVFI

HPGWKLLEVPEGRTNFDNDIALVRLKDPVKMGPTVSPICLPGTSSDYNLMD

GDLGLISGWGRTEKRDRAVRLKAARLPVAPLRKCKEVKVEKPTADAEAYVF

TPNMICAGGEKGMDSCKGDSGGAFAVQDPNDKTKFYAAGLVSWGPQCGTYG

LYTRVKNYVDWIMKTMQENSTPRED (SEQ ID NO: 75)
MWCIVLFSLLAWVYA (SEQ ID NO: 76)
EPTMYGEILSPNYPQAYPSEVEKSWDIEVPEGYGIHLYFTHLDIELSENCA

YDSVQIISGDTEEGRLCGQRSSNNPHSPIVEEFQVPYNKLQVIFKSDFSNE

ERFTGFAAYYVATDINECTDFVDVPCSHFCNNFIGGYFCSCPPEYFLHDDM

KNCGVNCSGDVFTALIGEIASPNYPKPYPENSRCEYQIRLEKGFQVVVTLR

REDFDVEAADSAGNCLDSLVFVAGDRQFGPYCGHGFPGPLNIETKSNALDI

IFQTDLTGQKKGWKLRYHGDPMPCPKEDTPNSVWEPAKAKYVFRDVVQITC

LDGFEVVEGRVGATSFYSTCQSNGKWSNSKLKCQPVDCGIPESIENGKVED

PESTLFGSVIRYTCEEPYYYMENGGGGEYHCAGNGSWVNEVLGPELPKCVP

VCGVPREPFEEKQRIIGGSDADIKNFPWQVFFDNPWAGGALINEYWVLTAA

HVVEGNREPTMYVGSTSVQTSRLAKSKMLTPEHVFIHPGWKLLEVPEGRTN

FDNDIALVRLKDPVKMGPTVSPICLPGTSSDYNLMDGDLGLISGWGRTEKR

DRAVRLKAARLPVAPLRKCKEVKVEKPTADAEAYVFTPNMICAGGEKGMDS

CKGDSGGAFAVQDPNDKTKFYAAGLVSWGPQCGTYGLYTRVKNYVDWIMKT

MQENSTPRED
```

The difference between inactive C1s and active C1s is that inactive proC1s is cleaved at the peptide bond between R437 and I438 and undergoes a conformational change. The two fragments generated by this cleavage remain associated by a disulfide bond. Without wishing to be bound by a particular theory, proC1s is a single chain 86,000 Da protein that is the native form of C1s proteins (e.g. serine protease). C1s is a subunit of the C1 complex which is the first complement component in the cascade referred to as the classical pathway of complement. ProC1s is an inactive zymogen until C1 is activated. C1 complex binds to and is activated by antigen-antibody complexes (immune complexes) yielding C1r enzyme. C1r enzyme in the C1 complex activates proC1s generating C1s enzyme. C1 complex is a non-covalent calcium-dependent complex of one C1q, two C1r and two C1s molecules. C1q binds through two or more of its six arms to the Fc domains of IgG or IgM. The binding of multiple arms to immune complexes causes the two C1r proteins in the complex (protease zymogens) to activate producing two proteases that cleave and activate the two proC1s in the complex (Morikis, D. and Lambris, J. D. (2005)). This activation of proC1s is caused by cleavage into the two chain C1s enzyme with 58,000 and 28,000 dalton fragments.

In some embodiments, the antibody comprises a Fc domain. The Fc domain can be linked to the heavy or light chain of the antibody. In some embodiments, the Fc domain comprises a mutation to extend the half-life of the antibody. In some embodiments, the Fc domain comprises a mutation such as those described in U.S. Pat. No. 7,670,600, which is hereby incorporated by reference in its entirety. In some embodiment, the constant region comprises a mutation at position at amino acid residue 428 relative to a wild-type human IgG constant domain, numbered according to the EU numbering index of Kabat. Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

Other mutations can be used in the Fc domain, such as those provided for in U.S. Pat. No. 8,394,925, which is hereby incorporated by reference in its entirety. In some embodiments, the Fc region is a variant Fc region comprising amino acid substitutions at positions 428 and 434, wherein the amino acid substitutions are a leucine that is not the wild-type amino acid at position 428 and a serine that is not the wild-type amino acid at position 434, wherein the polypeptide is an antibody and wherein numbering is according to the EU Index in Kabat et al. In some embodiments, the Fc region comprises a S228P, L235E, M428L, or N434S substitution. In some embodiments, the Fc region comprises a M428L substitution. In some embodiments, the Fc region comprises a N434S substitution. In some embodiments, the Fc region comprises a M428L and a N434S substitution. In some embodiments, the Fc region comprises a M252Y, S254T, and/or T256E substitution.

In some embodiments, the antibody comprises a constant region as set forth below with or without the mutations provided for the list below.

>IgG4 S228P L235E LS
(SEQ ID NO: 7)
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPPCPAPEFEGGPSVFLFPPKPKDTLMISRTPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCS

VLHEALHSHYTQKSLSLSLGK

>IgG4 S228P L235E YTE
(SEQ ID NO: 8)
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPPCPAPEFEGGPSVFLFPPKPKDTLYITREPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCS

VMHEALHNHYTQKSLSLSLGK

In some embodiments, the antibody comprises a constant region as provided herein, wherein the C-terminal lysine (K) amino acid has been deleted. In some embodiments, the antibody comprises a constant region as set follows:

>IgG4 S228P L235E LS-trunc
(SEQ ID NO: 57)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVLHEALHSHYTQKSLSLSLG

>IgG4 S228P L235E YTE-trunc
(SEQ ID NO: 58)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLYITREPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLG

In some embodiments, the antibody, such as the light chain, comprises a kappa constant region, such as the human constant domain, which can comprise a sequence of:

>Human kappa constant domain
(SEQ ID NO: 65)
RTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSF

NRGEC

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen. In some embodiments, the antibodies are used to detect the active form of C1s. In some embodiments, the antibodies are used to detect the active form preferentially (specifically) over the inactive form of C1s.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

Antibody Conjugates

The antibodies provided for herein may also be conjugated to a chemical moiety. The chemical moiety may be, inter alia, a polymer, a radionuclide or a cytotoxic factor. In some embodiments, this can be referred to as an antibody drug conjugate. In some embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)). Examples of chemical moieties include, but are not limited to, anti-mitotics, such as calicheamicins (e.g. ozogamicin), monomethyl auristatin E, mertansine, and the like. Other examples include, but are not limited to, biologically active anti-microtubule agents, alkylating agents and DNA minor groove binding agents. Other examples of are provided herein and below. The chemical moiety can be linked to the antibody through a linking group (maleimide), a cleavable linker, such as a cathepsin cleavable linkers (valine-citrulline), and in some embodiments, one or more spacers (e.g. para-aminobenzylcarbamate).

The antibodies and antibody fragments of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, 152Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

In some embodiments, antibodies (e.g. an anti-C1s antibody) are provided herein. In some embodiments, the antibody is a recombinant antibody that binds to C1s. In some embodiments, the antibody binds to the active form of C1s. In some embodiments, the antibody binds to active form preferentially over the inactive form of C1s. In some embodiments, the antibody binds to the active form with an affinity that is at least 10, 20, 30, 40, 50, 60, 70, 80, 90, 100, or 200% higher as compared to its affinity for the inactive form of C1s. In some embodiments, the C1s protein is a human C1s protein, such as the active form of C1s. In some embodiments, the antibody does not specifically bind to the inactive form of the C1s protein. As used herein, the term "recombinant antibody" refers to an antibody that is not naturally occurring. In some embodiments, the term "recombinant antibody" refers to an antibody that is not isolated from a human subject. In some embodiments, the antibody binds with at least 100× more affinity to the active form of C1s as compared to proC1s.

In some embodiments, an antibody, or antigen binding fragment thereof is provided, wherein the antibody or antibody fragment comprises a peptide selected from the following table, which illustrate the CDRs based on Kabat numbering.

TABLE 2

Kabat CDRs

| Ab ID No | HCDR1 | HCDR2 | HCDR3 | LCDR1 | LCDR2 | LCDR3 |
|---|---|---|---|---|---|---|
| MAb1 | ELSMH (SEQ ID NO: 9) | TFDPEEGET IYAQKFQG (SEQ ID NO: 10) | EGLAGRPFDS (SEQ ID NO: 11) | RASQSISSW LA (SEQ ID NO: 12) | KASSLES (SEQ ID NO: 13) | QQYNSYSWT (SEQ ID NO: 14) |
| MAb2 | DYYMS (SEQ ID NO: 15) | YISRSGSTKY YADSVKG (SEQ ID NO: 16) | DETDYALDY (SEQ ID NO: 17) | QASQDISNY LN (SEQ ID NO: 18) | DASNLET (SEQ ID NO: 19) | QQYEDLPLT (SEQ ID NO: 20) |
| MAb3 | DYGMS (SEQ ID NO: 21) | GINWEGGST GYADSVKG (SEQ ID NO: 22) | DEQLGGNYY YYYYMDV (SEQ ID NO: 23) | RASQGIRN DLG (SEQ ID NO: 24) | TASNLQS (SEQ ID NO: 25) | LQYNSYPLT (SEQ ID NO: 26) |

The CDRs in the above-identified table can also be referred to according to Chothia CDRs or IMGT CDRs. These are illustrated in the following tables for the different antibodies.

TABLE 3

CHOTHIA CDRS

| Ab ID No | HCDR1 | HCDR2 | HCDR3 | LCDR1 | LCDR2 | LCDR3 |
|---|---|---|---|---|---|---|
| MAb1 | GDTLTEL (SEQ ID NO: 27) | DPEEGE (SEQ ID NO: 28) | EGLAGRPFDS (SEQ ID NO: 11) | SQSISSW (SEQ ID NO: 29) | KAS (SEQ ID NO: 30) | YNSYSW (SEQ ID NO: 31) |
| MAb2 | GFTFSDY (SEQ ID NO: 32) | SRSGST (SEQ ID NO: 33) | DETDYALDY (SEQ ID NO: 17) | SQDISNY (SEQ ID NO: 34) | DAS (SEQ ID NO: 35) | YEDLPL (SEQ ID NO: 36) |
| MAb3 | GFTFDDY (SEQ ID NO: 37) | NWEGGS (SEQ ID NO: 38) | DEQLGGNYY YYYYMDV (SEQ ID NO: 23) | SQGIRND (SEQ ID NO: 39) | TAS (SEQ ID NO: 40) | YNSYPL (SEQ ID NO: 41) |

TABLE 4

IMGT CDRS

| Ab ID No | HCDR1 | HCDR2 | HCDR3 | LCDR1 | LCDR2 | LCDR3 |
|---|---|---|---|---|---|---|
| MAb1 | GDTLTEL S (SEQ ID NO: 42) | FDPEEGET (SEQ ID NO: 43) | VTEGLAGRPF DS (SEQ ID NO: 44) | QSISSW (SEQ ID NO: 45) | KAS (SEQ ID NO: 30) | QQYNSYSWT (SEQ ID NO: 14) |
| MAb2 | GFTFSDY Y (SEQ ID NO: 46) | ISRSGSTK (SEQ ID NO: 47) | ARDETDYAL DY (SEQ ID NO: 48) | QDISNY (SEQ ID NO: 49) | DAS (SEQ ID NO: 35) | QQYEDLPLT (SEQ ID NO: 20) |
| MAb3 | GFTFDDY G (SEQ ID NO: 50) | INWEGGST (SEQ ID NO: 51) | ARDEQLGGN YYYYYYMDV (SEQ ID NO: 52) | QGIRND (SEQ ID NO: 53) | TAS (SEQ ID NO: 40) | LQYNSYPLT (SEQ ID NO: 26) |

In some embodiments, an antibody, or antibody binding fragment thereof, comprises a heavy or light chain CDR as provided in the tables above. In some embodiments, an antibody, or antibody binding fragment thereof, comprises a light chain LCDR having a sequence of SEQ ID NO: 12, 13, 14, 18, 19, 20, 24, 25, 26, 29, 30, 31, 34, 35, 36, 39, 40, 41, 45, 49, 53, or a combination thereof. In some embodiments, the light chain LCDR comprises a sequence of SEQ ID NO: 12. In some embodiments, the light chain LCDR comprises a sequence of SEQ ID NO: 13. In some embodiments, the light chain LCDR comprises a sequence of SEQ ID NO: 14. In some embodiments, the light chain LCDR comprises a sequence of SEQ ID NO: 18. In some embodiments, the light chain LCDR comprises a sequence of SEQ ID NO: 19. In some embodiments, the light chain LCDR comprises a sequence of SEQ ID NO: 20. In some embodiments, the light chain LCDR comprises a sequence of SEQ ID NO: 24. In some embodiments, the light chain LCDR comprises a sequence of SEQ ID NO: 25. In some embodiments, the light chain LCDR comprises a sequence of SEQ ID NO: 26. In some embodiments, the light chain LCDR comprises a sequence of SEQ ID NO: 29. In some embodiments, the light chain LCDR comprises a sequence of SEQ ID NO: 30. In some embodiments, the light chain LCDR comprises a sequence of SEQ ID NO: 31. In some embodiments, the light chain LCDR comprises a sequence of SEQ ID NO: 34. In some embodiments, the light chain LCDR comprises a sequence of SEQ ID NO: 35. In some embodiments, the light chain LCDR comprises a sequence of SEQ ID NO: 36. In some embodiments, the light chain LCDR comprises a sequence of SEQ ID NO: 39. In some embodiments, the light chain LCDR comprises a sequence of SEQ ID NO: 40. In some embodiments, the light chain LCDR comprises a sequence of SEQ ID NO: 41. In some embodiments, the light chain LCDR comprises a sequence of SEQ ID NO: 45. In some embodiments, the light chain LCDR comprises a sequence of SEQ ID NO: 49. In some embodiments, the light chain LCDR comprises a sequence of SEQ ID NO: 53. In some embodiments, the light chain LCDR comprises a sequence that is a combination of one or more of SED ID NO: 12, 13, 14, 18, 19, 20, 24, 25, 26, 29, 30, 31, 34, 35, 36, 39, 40, 41, 45, 49, and 53. In some embodiments, an antibody, or antibody binding fragment thereof, comprises a heavy chain HCDR having a sequence of SEQ ID NO: 9, 10, 11, 15, 16, 17, 21, 22, 23, 27, 28, 32, 33, 37, 38, 42, 43, 44, 46, 47, 48, 50, 51, or 52. In some embodiments, the heavy chain HCDR comprises a sequence of SEQ ID NO: 9. In some embodiments, the heavy chain HCDR comprises a sequence of SEQ ID NO: 10. In some embodiments, the heavy chain HCDR comprises a sequence of SEQ ID NO: 11. In some embodiments, the heavy chain HCDR comprises a sequence of SEQ ID NO: 15. In some embodiments, the heavy chain HCDR comprises a sequence of SEQ ID NO: 16. In some embodiments, the heavy chain HCDR comprises a sequence of SEQ ID NO: 17. In some embodiments, the heavy chain HCDR comprises a sequence of SEQ ID NO: 21. In some embodiments, the heavy chain HCDR comprises a sequence of SEQ ID NO: 22. In some embodiments, the heavy chain HCDR comprises a sequence of SEQ ID NO: 23. In some embodiments, the heavy chain HCDR comprises a sequence of SEQ ID NO: 27. In some embodiments, the heavy chain HCDR comprises a sequence of SEQ ID NO: 28. In some embodiments, the heavy chain HCDR comprises a sequence of SEQ ID NO: 32. In some embodiments, the heavy chain HCDR comprises a sequence of SEQ ID NO: 33. In some embodiments, the heavy chain HCDR comprises a sequence of SEQ ID NO: 37. In some embodiments, the heavy chain HCDR comprises a sequence of SEQ ID NO: 38. In some embodiments, the heavy chain HCDR comprises a sequence of SEQ ID NO: 42. In some embodiments, the heavy chain HCDR comprises a sequence of SEQ ID NO: 43. In some embodiments, the heavy chain HCDR comprises a sequence of SEQ ID NO: 44. In some embodiments, the heavy chain HCDR comprises a sequence of SEQ ID NO: 46. In some embodiments, the heavy chain HCDR comprises a sequence of SEQ ID NO: 47. In some embodiments, the heavy chain HCDR comprises a sequence of SEQ ID NO: 48. In some embodiments, the heavy chain HCDR comprises a sequence of SEQ ID NO: 50. In some embodiments, the heavy chain HCDR comprises a sequence of SEQ ID NO: 51. In some embodiments, the heavy chain HCDR comprises a sequence of SEQ ID NO: 52. In some embodiments, the heavy chain HCDR comprises a sequence that is a combination of one or more of SEQ ID NO: 9, 10, 11, 15, 16, 17, 21, 22, 23, 27, 28, 32, 33, 37, 38, 42, 43, 44, 46, 47, 48, 50, 51, and 52. It is to be understood that the CDRs referenced in the embodiments throughout the present specification can be interchanged with the CDRs that are characterized by different formats, such as Chothia and IMGT, which are illustrated in the tables above.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 13, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 13, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 13, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 19, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 19, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 19, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 25, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 25, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 12, the LCDR2 has a sequence of SEQ ID NO: 25, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 13, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 13, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 13, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 19, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 19, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 19, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 25, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 25, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 18, the LCDR2 has a sequence of SEQ ID NO: 25, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 13, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 13, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 13, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 19, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 19, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 19, and the LCDR3 has a sequence of SEQ ID NO: 26.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 25, and the LCDR3 has a sequence of SEQ ID NO: 14.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 25, and the LCDR3 has a sequence of SEQ ID NO: 20.

In some embodiments, an antibody, or antibody binding fragment thereof, comprises a light chain variable region having a LCDR1, a LCDR2, and a LCDR3, wherein the LCDR1 has a sequence of SEQ ID NO: 24, the LCDR2 has a sequence of SEQ ID NO: 25, and the LCDR3 has a sequence of SEQ ID NO: 26.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 10, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 10, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 10, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 16, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 16, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 16, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 22, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 22, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 9, the HCDR2 has a sequence of SEQ ID NO: 22, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 10, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 10, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 10, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 16, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 16, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 16, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 22, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 22, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 15, the HCDR2 has a sequence of SEQ ID NO: 22, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 10, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 10, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 10, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 16, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 16, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 16, and the HCDR3 has a sequence of SEQ ID NO: 23.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 22, and the HCDR3 has a sequence of SEQ ID NO: 11.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 22, and the HCDR3 has a sequence of SEQ ID NO: 17.

In some embodiments, an antibody, or antibody binding fragment thereof, comprises a heavy chain variable region having a HCDR1, a HCDR2, and a HCDR3, wherein the HCDR1 has a sequence of SEQ ID NO: 21, the HCDR2 has a sequence of SEQ ID NO: 22, and the HCDR3 has a sequence of SEQ ID NO: 23.

For clarity, the following tables are provided depicting non-limiting exemplary combinations of light chain (Table 5) and heavy chain (Table 6) CDRs.

TABLE 5

|  | LCDR1 | LCDR2 | LCDR3 |
|---|---|---|---|
| $V_LA$ | SEQ ID NO: 12 | SEQ ID NO: 13 | SEQ ID NO: 14 |
| $V_LB$ | SEQ ID NO: 12 | SEQ ID NO: 13 | SEQ ID NO: 20 |
| $V_LC$ | SEQ ID NO: 12 | SEQ ID NO: 13 | SEQ ID NO: 26 |
| $V_LD$ | SEQ ID NO: 12 | SEQ ID NO: 19 | SEQ ID NO: 14 |
| $V_LE$ | SEQ ID NO: 12 | SEQ ID NO: 19 | SEQ ID NO: 20 |
| $V_LF$ | SEQ ID NO: 12 | SEQ ID NO: 19 | SEQ ID NO: 26 |
| $V_LG$ | SEQ ID NO: 12 | SEQ ID NO: 25 | SEQ ID NO: 14 |
| $V_LH$ | SEQ ID NO: 12 | SEQ ID NO: 25 | SEQ ID NO: 20 |
| $V_LI$ | SEQ ID NO: 12 | SEQ ID NO: 25 | SEQ ID NO: 26 |
| $V_LJ$ | SEQ ID NO: 18 | SEQ ID NO: 13 | SEQ ID NO: 14 |

TABLE 5-continued

|  | LCDR1 | LCDR2 | LCDR3 |
|---|---|---|---|
| $V_LK$ | SEQ ID NO: 18 | SEQ ID NO: 13 | SEQ ID NO: 20 |
| $V_LL$ | SEQ ID NO: 18 | SEQ ID NO: 13 | SEQ ID NO: 26 |
| $V_LM$ | SEQ ID NO: 18 | SEQ ID NO: 19 | SEQ ID NO: 14 |
| $V_LN$ | SEQ ID NO: 18 | SEQ ID NO: 19 | SEQ ID NO: 20 |
| $V_LO$ | SEQ ID NO: 18 | SEQ ID NO: 19 | SEQ ID NO: 26 |
| $V_LP$ | SEQ ID NO: 18 | SEQ ID NO: 25 | SEQ ID NO: 14 |
| $V_LQ$ | SEQ ID NO: 18 | SEQ ID NO: 25 | SEQ ID NO: 20 |
| $V_LR$ | SEQ ID NO: 18 | SEQ ID NO: 25 | SEQ ID NO: 26 |
| $V_LS$ | SEQ ID NO: 24 | SEQ ID NO: 13 | SEQ ID NO: 14 |
| $V_LT$ | SEQ ID NO: 24 | SEQ ID NO: 13 | SEQ ID NO: 20 |
| $V_LU$ | SEQ ID NO: 24 | SEQ ID NO: 13 | SEQ ID NO: 26 |
| $V_LV$ | SEQ ID NO: 24 | SEQ ID NO: 19 | SEQ ID NO: 14 |
| $V_LW$ | SEQ ID NO: 24 | SEQ ID NO: 19 | SEQ ID NO: 20 |
| $V_LX$ | SEQ ID NO: 24 | SEQ ID NO: 19 | SEQ ID NO: 26 |
| $V_LY$ | SEQ ID NO: 24 | SEQ ID NO: 25 | SEQ ID NO: 14 |
| $V_LZ$ | SEQ ID NO: 24 | SEQ ID NO: 25 | SEQ ID NO: 20 |
| $V_LAB$ | SEQ ID NO: 24 | SEQ ID NO: 25 | SEQ ID NO: 26 |

TABLE 6

|  | HCDR1 | HCDR2 | HCDR3 |
|---|---|---|---|
| $V_HA$ | SEQ ID NO: 9 | SEQ ID NO: 10 | SEQ ID NO: 11 |
| $V_HB$ | SEQ ID NO: 9 | SEQ ID NO: 10 | SEQ ID NO: 17 |
| $V_HC$ | SEQ ID NO: 9 | SEQ ID NO: 10 | SEQ ID NO: 23 |
| $V_HD$ | SEQ ID NO: 9 | SEQ ID NO: 16 | SEQ ID NO: 11 |
| $V_HE$ | SEQ ID NO: 9 | SEQ ID NO: 16 | SEQ ID NO: 17 |
| $V_HF$ | SEQ ID NO: 9 | SEQ ID NO: 16 | SEQ ID NO: 23 |
| $V_HG$ | SEQ ID NO: 9 | SEQ ID NO: 22 | SEQ ID NO: 11 |
| $V_HH$ | SEQ ID NO: 9 | SEQ ID NO: 22 | SEQ ID NO: 17 |
| $V_HI$ | SEQ ID NO: 9 | SEQ ID NO: 22 | SEQ ID NO: 23 |
| $V_HJ$ | SEQ ID NO: 15 | SEQ ID NO: 10 | SEQ ID NO: 11 |
| $V_HK$ | SEQ ID NO: 15 | SEQ ID NO: 10 | SEQ ID NO: 17 |
| $V_HL$ | SEQ ID NO: 15 | SEQ ID NO: 10 | SEQ ID NO: 23 |
| $V_HM$ | SEQ ID NO: 15 | SEQ ID NO: 16 | SEQ ID NO: 11 |
| $V_HN$ | SEQ ID NO: 15 | SEQ ID NO: 16 | SEQ ID NO: 17 |
| $V_HO$ | SEQ ID NO: 15 | SEQ ID NO: 16 | SEQ ID NO: 23 |
| $V_HP$ | SEQ ID NO: 15 | SEQ ID NO: 22 | SEQ ID NO: 11 |
| $V_HQ$ | SEQ ID NO: 15 | SEQ ID NO: 22 | SEQ ID NO: 17 |
| $V_HR$ | SEQ ID NO: 15 | SEQ ID NO: 22 | SEQ ID NO: 23 |
| $V_HS$ | SEQ ID NO: 21 | SEQ ID NO: 10 | SEQ ID NO: 11 |
| $V_HT$ | SEQ ID NO: 21 | SEQ ID NO: 10 | SEQ ID NO: 17 |
| $V_HU$ | SEQ ID NO: 21 | SEQ ID NO: 10 | SEQ ID NO: 23 |
| $V_HV$ | SEQ ID NO: 21 | SEQ ID NO: 16 | SEQ ID NO: 11 |
| $V_HW$ | SEQ ID NO: 21 | SEQ ID NO: 16 | SEQ ID NO: 17 |
| $V_HX$ | SEQ ID NO: 21 | SEQ ID NO: 16 | SEQ ID NO: 23 |
| $V_HY$ | SEQ ID NO: 21 | SEQ ID NO: 22 | SEQ ID NO: 11 |
| $V_HZ$ | SEQ ID NO: 21 | SEQ ID NO: 22 | SEQ ID NO: 17 |
| $V_HAB$ | SEQ ID NO: 21 | SEQ ID NO: 22 | SEQ ID NO: 23 |

In some embodiments, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences. The following combinations are provided with reference to Table 5 and 6 above. Thus, for example, an antibody or antibody binding fragment thereof comprising $V_LA$ and $V_HA$ is understood to comprise a light chain having a LCDR1 of SEQ ID NO: 12, a LCDR2 of SEQ ID NO: 13, a LCDR3 of SEQ ID NO: 14, a HCDR1 of SEQ ID NO: 9, a HCDR2 of SEQ ID NO: 10, and a HCDR3 of SEQ ID NO: 11.

Accordingly, in some embodiments, an antibody or antibody binding fragment thereof comprises $V_LA$ and $V_HA$. In some embodiments, an antibody or antibody binding fragment thereof comprises $V_LB$ and $V_HA$. In some embodiments, an antibody or antibody binding fragment thereof comprises $V_LC$ and $V_HA$. In some embodiments, an antibody or antibody binding fragment thereof comprises $V_LD$ and $V_HA$. In some embodiments, an antibody or antibody binding fragment thereof comprises $V_L$E and $V_H$A. In some embodiments, an antibody or antibody binding fragment thereof comprises $V_L$F and $V_H$A. In some embodiments, an antibody or antibody binding fragment thereof comprises $V_L$G and $V_H$A. In some embodiments, an antibody or antibody binding fragment thereof comprises $V_L$H and $V_H$A. In some embodiments, an antibody or antibody binding fragment thereof comprises $V_L$I and $V_H$A. In some embodiments, an antibody or antibody binding fragment thereof comprises $V_L$J and $V_H$A. In some embodiments, an antibody or antibody binding fragment thereof comprises $V_L$K and $V_H$A. In some embodiments, an antibody or antibody binding fragment thereof comprises $V_L$L and $V_H$A. In some embodiments, an antibody or antibody binding fragment thereof comprises $V_L$M and $V_H$A. In some embodiments, an antibody or antibody binding fragment thereof comprises $V_L$N and $V_H$A. In some embodiments, an antibody or antibody binding fragment thereof comprises $V_L$O and $V_H$A. In some embodiments, an antibody or antibody binding fragment thereof comprises $V_L$P and $V_H$A. In some embodiments, an antibody or antibody binding fragment thereof comprises $V_L$Q and $V_H$A. In some embodiments, an antibody or antibody binding fragment thereof comprises $V_L$R and $V_H$A. In some embodiments, an antibody or antibody binding fragment thereof comprises $V_L$S and $V_H$A. In some embodiments, an antibody or antibody binding fragment thereof comprises $V_L$T and $V_H$A. In some embodiments, an antibody or antibody binding fragment thereof comprises $V_L$U and $V_H$A. In some embodiments, an antibody or antibody binding fragment thereof comprises $V_L$V and $V_H$A. In some embodiments, an antibody or antibody binding fragment thereof comprises $V_L$W and $V_H$A. In some embodiments, an antibody or antibody binding fragment thereof comprises $V_L$X and $V_H$A. In some embodiments, an antibody or antibody binding fragment thereof comprises $V_L$Y and $V_H$A. In some embodiments, an antibody or antibody binding fragment thereof comprises $V_L$Z and $V_H$A. In some embodiments, an antibody or antibody binding fragment thereof comprises $V_L$AB and $V_H$A.

In some embodiments, an antibody or antibody binding fragment thereof comprises $V_L$A and $V_H$B. In some embodiments, an antibody or antibody binding fragment thereof comprises $V_L$B and $V_H$B. In some embodiments, an antibody or antibody binding fragment thereof comprises $V_L$C and $V_H$B. In some embodiments, an antibody or antibody binding fragment thereof comprises $V_L$D and $V_H$B. In some embodiments, an antibody or antibody binding fragment thereof comprises $V_L$E and $V_H$B. In some embodiments, an antibody or antibody binding fragment thereof comprises $V_L$F and $V_H$B. In some embodiments, an antibody or antibody binding fragment thereof comprises $V_L$G and $V_H$B. In some embodiments, an antibody or antibody binding fragment thereof comprises $V_L$H and $V_H$B. In some embodiments, an antibody or antibody binding fragment thereof comprises $V_L$I and $V_H$B. In some embodiments, an antibody or antibody binding fragment thereof comprises $V_L$J and $V_H$B. In some embodiments, an antibody or antibody binding fragment thereof comprises $V_L$K and $V_H$B. In some embodiments, an antibody or antibody binding fragment thereof comprises $V_L$L and $V_H$B. In some embodiments, an antibody or antibody binding fragment thereof comprises $V_L$M and $V_H$B. In some embodiments, an antibody or antibody binding fragment thereof comprises $V_L$N and $V_H$B. In some embodiments, an antibody or antibody binding fragment thereof comprises $V_L$O and $V_H$B. In some embodiments, an antibody or antibody binding fragment thereof comprises $V_L$P and $V_H$B. In some embodiments, an antibody or antibody binding fragment thereof comprises $V_L$Q and $V_H$B. In some embodiments, an antibody or antibody binding fragment thereof comprises $V_L$R and $V_H$B. In some embodiments, an antibody or antibody binding fragment thereof comprises $V_L$S and $V_H$B. In some embodiments, an antibody or antibody binding fragment thereof comprises $V_L$T and $V_H$B. In some embodiments, an antibody or antibody binding fragment thereof comprises $V_L$U and $V_H$B. In some embodiments, an antibody or antibody binding fragment thereof comprises $V_L$V and $V_H$B. In some embodiments, an antibody or antibody binding fragment thereof comprises $V_L$W and $V_H$B. In some embodiments, an antibody or antibody binding fragment thereof comprises $V_L$X and $V_H$B. In some embodiments, an antibody or antibody binding fragment thereof comprises $V_L$Y and $V_H$B. In some embodiments, an antibody or antibody binding fragment thereof comprises $V_L$Z and $V_H$B. In some embodiments, an antibody or antibody binding fragment thereof comprises $V_L$AB and $V_H$B.

In some embodiments, an antibody or antibody binding fragment thereof comprises $V_L$A and $V_H$C. In some embodiments, an antibody or antibody binding fragment thereof comprises $V_L$B and $V_H$C. In some embodiments, an antibody or antibody binding fragment thereof comprises $V_L$C and $V_H$C. In some embodiments, an antibody or antibody binding fragment thereof comprises $V_L$D and $V_H$C. In some embodiments, an antibody or antibody binding fragment thereof comprises $V_L$E and $V_H$C. In some embodiments, an antibody or antibody binding fragment thereof comprises $V_L$F and $V_H$C. In some embodiments, an antibody or antibody binding fragment thereof comprises $V_L$G and $V_H$C. In some embodiments, an antibody or antibody binding fragment thereof comprises $V_L$H and $V_H$C. In some embodiments, an antibody or antibody binding fragment thereof comprises $V_L$I and $V_H$C. In some embodiments, an antibody or antibody binding fragment thereof comprises $V_L$J and $V_H$C. In some embodiments, an antibody or antibody binding fragment thereof comprises $V_L$K and $V_H$C. In some embodiments, an antibody or antibody binding fragment thereof comprises $V_L$L and $V_H$C. In some embodiments, an antibody or antibody binding fragment thereof comprises $V_L$M and $V_H$C. In some embodiments, an antibody or antibody binding fragment thereof comprises $V_L$N and $V_H$C. In some embodiments, an antibody or antibody binding fragment thereof comprises $V_L$O and $V_H$C. In some embodiments, an antibody or antibody binding fragment thereof comprises $V_L$P and $V_H$C. In some embodiments, an antibody or antibody binding fragment thereof comprises $V_L$Q and $V_H$C. In some embodiments, an antibody or antibody binding fragment thereof comprises $V_L$R and $V_H$C. In some embodiments, an antibody or antibody binding fragment thereof comprises $V_L$S and $V_H$C. In some embodiments, an antibody or antibody binding fragment thereof comprises $V_L$T and $V_H$C. In some embodiments, an antibody or antibody binding fragment thereof comprises $V_L$U and $V_H$C. In some embodiments, an antibody or antibody binding fragment thereof comprises $V_L$V and $V_H$C. In some embodiments, an antibody or antibody binding fragment thereof comprises $V_L$W and $V_H$C. In some embodiments, an antibody or antibody binding fragment thereof comprises $V_L$X and $V_H$C. In some embodiments, an antibody or antibody binding fragment thereof comprises $V_L$Y and $V_H$C. In some embodiments, an antibody or antibody binding fragment thereof comprises $V_L$Z and $V_H$C. In some embodiments, an antibody or antibody binding fragment thereof comprises $V_L$AB and $V_H$C.

In some embodiments, an antibody or antibody binding fragment thereof comprises $V_L A$ and $V_H D$. In some embodiments, an antibody or antibody binding fragment thereof comprises $V_L B$ and $V_H D$. In some embodiments, an antibody or antibody binding fragment thereof comprises $V_L C$ and $V_H D$. In some embodiments, an antibody or antibody binding fragment thereof comprises $V_L D$ and $V_H D$. In some embodiments, an antibody or antibody binding fragment thereof comprises $V_L E$ and $V_H D$. In some embodiments, an antibody or antibody binding fragment thereof comprises $V_L F$ and $V_H D$. In some embodiments, an antibody or antibody binding fragment thereof comprises $V_L G$ and $V_H D$. In some embodiments, an antibody or antibody binding fragment thereof comprises $V_L H$ and $V_H D$. In some embodiments, an antibody or antibody binding fragment thereof comprises $V_L I$ and $V_H D$. In some embodiments, an antibody or antibody binding fragment thereof comprises $V_L J$ and $V_H D$. In some embodiments, an antibody or antibody binding fragment thereof comprises $V_L K$ and $V_H D$. In some embodiments, an antibody or antibody binding fragment thereof comprises $V_L L$ and $V_H D$. In some embodiments, an antibody or antibody binding fragment thereof comprises $V_L M$ and $V_H D$. In some embodiments, an antibody or antibody binding fragment thereof comprises $V_L N$ and $V_H D$. In some embodiments, an antibody or antibody binding fragment thereof comprises $V_L O$ and $V_H D$. In some embodiments, an antibody or antibody binding fragment thereof comprises $V_L P$ and $V_H D$. In some embodiments, an antibody or antibody binding fragment thereof comprises $V_L Q$ and $V_H D$. In some embodiments, an antibody or antibody binding fragment thereof comprises $V_L R$ and $V_H D$. In some embodiments, an antibody or antibody binding fragment thereof comprises $V_L S$ and $V_H D$. In some embodiments, an antibody or antibody binding fragment thereof comprises $V_L T$ and $V_H D$. In some embodiments, an antibody or antibody binding fragment thereof comprises $V_L U$ and $V_H D$. In some embodiments, an antibody or antibody binding fragment thereof comprises $V_L V$ and $V_H D$. In some embodiments, an antibody or antibody binding fragment thereof comprises $V_L W$ and $V_H D$. In some embodiments, an antibody or antibody binding fragment thereof comprises $V_L X$ and $V_H D$. In some embodiments, an antibody or antibody binding fragment thereof comprises $V_L Y$ and $V_H D$. In some embodiments, an antibody or antibody binding fragment thereof comprises $V_L Z$ and $V_H D$. In some embodiments, an antibody or antibody binding fragment thereof comprises $V_L AB$ and $V_H D$.

In some embodiments, an antibody or antibody binding fragment thereof comprises $V_L A$ and $V_H E$. In some embodiments, an antibody or antibody binding fragment thereof comprises $V_L B$ and $V_H E$. In some embodiments, an antibody or antibody binding fragment thereof comprises $V_L C$ and $V_H E$. In some embodiments, an antibody or antibody binding fragment thereof comprises $V_L D$ and $V_H E$. In some embodiments, an antibody or antibody binding fragment thereof comprises $V_L E$ and $V_H E$. In some embodiments, an antibody or antibody binding fragment thereof comprises $V_L F$ and $V_H E$. In some embodiments, an antibody or antibody binding fragment thereof comprises $V_L G$ and $V_H E$. In some embodiments, an antibody or antibody binding fragment thereof comprises $V_L H$ and $V_H E$. In some embodiments, an antibody or antibody binding fragment thereof comprises $V_L I$ and $V_H E$. In some embodiments, an antibody or antibody binding fragment thereof comprises $V_L J$ and $V_H E$. In some embodiments, an antibody or antibody binding fragment thereof comprises $V_L K$ and $V_H E$. In some embodiments, an antibody or antibody binding fragment thereof comprises $V_L L$ and $V_H E$. In some embodiments, an antibody or antibody binding fragment thereof comprises $V_L M$ and $V_H E$. In some embodiments, an antibody or antibody binding fragment thereof comprises $V_L N$ and $V_H E$. In some embodiments, an antibody or antibody binding fragment thereof comprises $V_L O$ and $V_H E$. In some embodiments, an antibody or antibody binding fragment thereof comprises $V_L P$ and $V_H E$. In some embodiments, an antibody or antibody binding fragment thereof comprises $V_L Q$ and $V_H E$. In some embodiments, an antibody or antibody binding fragment thereof comprises $V_L R$ and $V_H E$. In some embodiments, an antibody or antibody binding fragment thereof comprises $V_L S$ and $V_H E$. In some embodiments, an antibody or antibody binding fragment thereof comprises $V_L T$ and $V_H E$. In some embodiments, an antibody or antibody binding fragment thereof comprises $V_L U$ and $V_H E$. In some embodiments, an antibody or antibody binding fragment thereof comprises $V_L V$ and $V_H E$. In some embodiments, an antibody or antibody binding fragment thereof comprises $V_L W$ and $V_H E$. In some embodiments, an antibody or antibody binding fragment thereof comprises $V_L X$ and $V_H E$. In some embodiments, an antibody or antibody binding fragment thereof comprises $V_L Y$ and $V_H E$. In some embodiments, an antibody or antibody binding fragment thereof comprises $V_L Z$ and $V_H E$. In some embodiments, an antibody or antibody binding fragment thereof comprises $V_L AB$ and $V_H E$.

In some embodiments, an antibody or antibody binding fragment thereof comprises $V_L A$ and $V_H F$. In some embodiments, an antibody or antibody binding fragment thereof comprises $V_L B$ and $V_H F$. In some embodiments, an antibody or antibody binding fragment thereof comprises $V_L C$ and $V_H F$. In some embodiments, an antibody or antibody binding fragment thereof comprises $V_L D$ and $V_H F$. In some embodiments, an antibody or antibody binding fragment thereof comprises $V_L E$ and $V_H F$. In some embodiments, an antibody or antibody binding fragment thereof comprises $V_L F$ and $V_H F$. In some embodiments, an antibody or antibody binding fragment thereof comprises $V_L G$ and $V_H F$. In some embodiments, an antibody or antibody binding fragment thereof comprises $V_L H$ and $V_H F$. In some embodiments, an antibody or antibody binding fragment thereof comprises $V_L I$ and $V_H F$. In some embodiments, an antibody or antibody binding fragment thereof comprises $V_L J$ and $V_H F$. In some embodiments, an antibody or antibody binding fragment thereof comprises $V_L K$ and $V_H F$. In some embodiments, an antibody or antibody binding fragment thereof comprises $V_L L$ and $V_H F$. In some embodiments, an antibody or antibody binding fragment thereof comprises $V_L M$ and $V_H F$. In some embodiments, an antibody or antibody binding fragment thereof comprises $V_L N$ and $V_H F$. In some embodiments, an antibody or antibody binding fragment thereof comprises $V_L O$ and $V_H F$. In some embodiments, an antibody or antibody binding fragment thereof comprises $V_L P$ and $V_H F$. In some embodiments, an antibody or antibody binding fragment thereof comprises $V_L Q$ and $V_H F$. In some embodiments, an antibody or antibody binding fragment thereof comprises $V_L R$ and $V_H F$. In some embodiments, an antibody or antibody binding fragment thereof comprises $V_L S$ and $V_H F$. In some embodiments, an antibody or antibody binding fragment thereof comprises $V_L T$ and $V_H F$. In some embodiments, an antibody or antibody binding fragment thereof comprises $V_L U$ and $V_H F$. In some embodiments, an antibody or antibody binding fragment thereof comprises $V_L V$ and $V_H F$. In some embodiments, an antibody or antibody binding fragment thereof comprises $V_L W$ and $V_H F$. In some embodiments, an antibody or antibody binding fragment thereof comprises $V_LX$ and $V_HF$. In some embodiments, an antibody or antibody binding fragment thereof comprises $V_LY$ and $V_HF$. In some embodiments, an antibody or antibody binding fragment thereof comprises $V_LZ$ and $V_HF$. In some embodiments, an antibody or antibody binding fragment thereof comprises $V_LAB$ and $V_HF$.

In some embodiments, an antibody or antibody binding fragment thereof comprises $V_LA$ and $V_HG$. In some embodiments, an antibody or antibody binding fragment thereof comprises $V_LB$ and $V_HG$. In some embodiments, an antibody or antibody binding fragment thereof comprises $V_LC$ and $V_HG$. In some embodiments, an antibody or antibody binding fragment thereof comprises $V_LD$ and $V_HG$. In some embodiments, an antibody or antibody binding fragment thereof comprises $V_LE$ and $V_HG$. In some embodiments, an antibody or antibody binding fragment thereof comprises $V_LF$ and $V_HG$. In some embodiments, an antibody or antibody binding fragment thereof comprises $V_LG$ and $V_HG$. In some embodiments, an antibody or antibody binding fragment thereof comprises $V_LH$ and $V_HG$. In some embodiments, an antibody or antibody binding fragment thereof comprises $V_LI$ and $V_HG$. In some embodiments, an antibody or antibody binding fragment thereof comprises $V_LJ$ and $V_HG$. In some embodiments, an antibody or antibody binding fragment thereof comprises $V_LK$ and $V_HG$. In some embodiments, an antibody or antibody binding fragment thereof comprises $V_LL$ and $V_HG$. In some embodiments, an antibody or antibody binding fragment thereof comprises $V_LM$ and $V_HG$. In some embodiments, an antibody or antibody binding fragment thereof comprises $V_LN$ and $V_HG$. In some embodiments, an antibody or antibody binding fragment thereof comprises $V_LO$ and $V_HG$. In some embodiments, an antibody or antibody binding fragment thereof comprises $V_LP$ and $V_HG$. In some embodiments, an antibody or antibody binding fragment thereof comprises $V_LQ$ and $V_HG$. In some embodiments, an antibody or antibody binding fragment thereof comprises $V_LR$ and $V_HG$. In some embodiments, an antibody or antibody binding fragment thereof comprises $V_LS$ and $V_HG$. In some embodiments, an antibody or antibody binding fragment thereof comprises $V_LT$ and $V_HG$. In some embodiments, an antibody or antibody binding fragment thereof comprises $V_LU$ and $V_HG$. In some embodiments, an antibody or antibody binding fragment thereof comprises $V_LV$ and $V_HG$. In some embodiments, an antibody or antibody binding fragment thereof comprises $V_LW$ and $V_HG$. In some embodiments, an antibody or antibody binding fragment thereof comprises $V_LX$ and $V_HG$. In some embodiments, an antibody or antibody binding fragment thereof comprises $V_LY$ and $V_HG$. In some embodiments, an antibody or antibody binding fragment thereof comprises $V_LZ$ and $V_HG$. In some embodiments, an antibody or antibody binding fragment thereof comprises $V_LAB$ and $V_HG$.

In some embodiments, an antibody or antibody binding fragment thereof comprises $V_LA$ and $V_HH$. In some embodiments, an antibody or antibody binding fragment thereof comprises $V_LB$ and $V_HH$. In some embodiments, an antibody or antibody binding fragment thereof comprises $V_LC$ and $V_HH$. In some embodiments, an antibody or antibody binding fragment thereof comprises $V_LD$ and $V_HH$. In some embodiments, an antibody or antibody binding fragment thereof comprises $V_LE$ and $V_HH$. In some embodiments, an antibody or antibody binding fragment thereof comprises $V_LF$ and $V_HH$. In some embodiments, an antibody or antibody binding fragment thereof comprises $V_LG$ and $V_HH$. In some embodiments, an antibody or antibody binding fragment thereof comprises $V_LH$ and $V_HH$. In some embodiments, an antibody or antibody binding fragment thereof comprises $V_LI$ and $V_HH$. In some embodiments, an antibody or antibody binding fragment thereof comprises $V_LJ$ and $V_HH$. In some embodiments, an antibody or antibody binding fragment thereof comprises $V_LK$ and $V_HH$. In some embodiments, an antibody or antibody binding fragment thereof comprises $V_LL$ and $V_HH$. In some embodiments, an antibody or antibody binding fragment thereof comprises $V_LM$ and $V_HH$. In some embodiments, an antibody or antibody binding fragment thereof comprises $V_LN$ and $V_HH$. In some embodiments, an antibody or antibody binding fragment thereof comprises $V_LO$ and $V_HH$. In some embodiments, an antibody or antibody binding fragment thereof comprises $V_LP$ and $V_HH$. In some embodiments, an antibody or antibody binding fragment thereof comprises $V_LQ$ and $V_HH$. In some embodiments, an antibody or antibody binding fragment thereof comprises $V_LR$ and $V_HH$. In some embodiments, an antibody or antibody binding fragment thereof comprises $V_LS$ and $V_HH$. In some embodiments, an antibody or antibody binding fragment thereof comprises $V_LT$ and $V_HH$. In some embodiments, an antibody or antibody binding fragment thereof comprises $V_LU$ and $V_HH$. In some embodiments, an antibody or antibody binding fragment thereof comprises $V_LV$ and $V_HH$. In some embodiments, an antibody or antibody binding fragment thereof comprises $V_LW$ and $V_HH$. In some embodiments, an antibody or antibody binding fragment thereof comprises $V_LX$ and $V_HH$. In some embodiments, an antibody or antibody binding fragment thereof comprises $V_LY$ and $V_HH$. In some embodiments, an antibody or antibody binding fragment thereof comprises $V_LZ$ and $V_HH$. In some embodiments, an antibody or antibody binding fragment thereof comprises $V_LAB$ and $V_HH$.

In some embodiments, an antibody or antibody binding fragment thereof comprises $V_LA$ and $V_HI$. In some embodiments, an antibody or antibody binding fragment thereof comprises $V_LB$ and $V_HI$. In some embodiments, an antibody or antibody binding fragment thereof comprises $V_LC$ and $V_HI$. In some embodiments, an antibody or antibody binding fragment thereof comprises $V_LD$ and $V_HI$. In some embodiments, an antibody or antibody binding fragment thereof comprises $V_LE$ and $V_HI$. In some embodiments, an antibody or antibody binding fragment thereof comprises $V_LF$ and $V_HI$. In some embodiments, an antibody or antibody binding fragment thereof comprises $V_LG$ and $V_HI$. In some embodiments, an antibody or antibody binding fragment thereof comprises $V_LH$ and $V_HI$. In some embodiments, an antibody or antibody binding fragment thereof comprises $V_LI$ and $V_HI$. In some embodiments, an antibody or antibody binding fragment thereof comprises $V_LJ$ and $V_HI$. In some embodiments, an antibody or antibody binding fragment thereof comprises $V_LK$ and $V_HI$. In some embodiments, an antibody or antibody binding fragment thereof comprises $V_LL$ and $V_HI$. In some embodiments, an antibody or antibody binding fragment thereof comprises $V_LM$ and $V_HI$. In some embodiments, an antibody or antibody binding fragment thereof comprises $V_LN$ and $V_HI$. In some embodiments, an antibody or antibody binding fragment thereof comprises $V_LO$ and $V_HI$. In some embodiments, an antibody or antibody binding fragment thereof comprises $V_LP$ and $V_HI$. In some embodiments, an antibody or antibody binding fragment thereof comprises $V_LQ$ and $V_HI$. In some embodiments, an antibody or antibody binding fragment thereof comprises $V_LR$ and $V_HI$. In some embodiments, an antibody or antibody binding fragment thereof comprises $V_LS$ and $V_HI$. In some embodiments, an antibody or antibody binding fragment thereof comprises $V_L T$ and $V_H I$. In some embodiments, an antibody or antibody binding fragment thereof comprises $V_L U$ and $V_H I$. In some embodiments, an antibody or antibody binding fragment thereof comprises $V_L V$ and $V_H I$. In some embodiments, an antibody or antibody binding fragment thereof comprises $V_L W$ and $V_H I$. In some embodiments, an antibody or antibody binding fragment thereof comprises $V_L X$ and $V_H I$. In some embodiments, an antibody or antibody binding fragment thereof comprises $V_L Y$ and $V_H I$. In some embodiments, an antibody or antibody binding fragment thereof comprises $V_L Z$ and $V_H I$. In some embodiments, an antibody or antibody binding fragment thereof comprises $V_L AB$ and $V_H I$.

In some embodiments, an antibody or antibody binding fragment thereof comprises $V_L A$ and $V_H J$. In some embodiments, an antibody or antibody binding fragment thereof comprises $V_L B$ and $V_H J$. In some embodiments, an antibody or antibody binding fragment thereof comprises $V_L C$ and $V_H J$. In some embodiments, an antibody or antibody binding fragment thereof comprises $V_L D$ and $V_H J$. In some embodiments, an antibody or antibody binding fragment thereof comprises $V_L E$ and $V_H J$. In some embodiments, an antibody or antibody binding fragment thereof comprises $V_L F$ and $V_H J$. In some embodiments, an antibody or antibody binding fragment thereof comprises $V_L G$ and $V_H J$. In some embodiments, an antibody or antibody binding fragment thereof comprises $V_L H$ and $V_H J$. In some embodiments, an antibody or antibody binding fragment thereof comprises $V_L I$ and $V_H J$. In some embodiments, an antibody or antibody binding fragment thereof comprises $V_L J$ and $V_H J$. In some embodiments, an antibody or antibody binding fragment thereof comprises $V_L K$ and $V_H J$. In some embodiments, an antibody or antibody binding fragment thereof comprises $V_L L$ and $V_H J$. In some embodiments, an antibody or antibody binding fragment thereof comprises $V_L M$ and $V_H J$. In some embodiments, an antibody or antibody binding fragment thereof comprises $V_L N$ and $V_H J$. In some embodiments, an antibody or antibody binding fragment thereof comprises $V_L O$ and $V_H J$. In some embodiments, an antibody or antibody binding fragment thereof comprises $V_L P$ and $V_H J$. In some embodiments, an antibody or antibody binding fragment thereof comprises $V_L Q$ and $V_H J$. In some embodiments, an antibody or antibody binding fragment thereof comprises $V_L R$ and $V_H J$. In some embodiments, an antibody or antibody binding fragment thereof comprises $V_L S$ and $V_H J$. In some embodiments, an antibody or antibody binding fragment thereof comprises $V_L T$ and $V_H J$. In some embodiments, an antibody or antibody binding fragment thereof comprises $V_L U$ and $V_H J$. In some embodiments, an antibody or antibody binding fragment thereof comprises $V_L V$ and $V_H J$. In some embodiments, an antibody or antibody binding fragment thereof comprises $V_L W$ and $V_H J$. In some embodiments, an antibody or antibody binding fragment thereof comprises $V_L X$ and $V_H J$. In some embodiments, an antibody or antibody binding fragment thereof comprises $V_L Y$ and $V_H J$. In some embodiments, an antibody or antibody binding fragment thereof comprises $V_L Z$ and $V_H J$. In some embodiments, an antibody or antibody binding fragment thereof comprises $V_L AB$ and $V_H J$.

In some embodiments, an antibody or antibody binding fragment thereof comprises $V_L A$ and $V_H K$. In some embodiments, an antibody or antibody binding fragment thereof comprises $V_L B$ and $V_H K$. In some embodiments, an antibody or antibody binding fragment thereof comprises $V_L C$ and $V_H K$. In some embodiments, an antibody or antibody binding fragment thereof comprises $V_L D$ and $V_H K$. In some embodiments, an antibody or antibody binding fragment thereof comprises $V_L E$ and $V_H K$. In some embodiments, an antibody or antibody binding fragment thereof comprises $V_L F$ and $V_H K$. In some embodiments, an antibody or antibody binding fragment thereof comprises $V_L G$ and $V_H K$. In some embodiments, an antibody or antibody binding fragment thereof comprises $V_L H$ and $V_H K$. In some embodiments, an antibody or antibody binding fragment thereof comprises $V_L I$ and $V_H K$. In some embodiments, an antibody or antibody binding fragment thereof comprises $V_L J$ and $V_H K$. In some embodiments, an antibody or antibody binding fragment thereof comprises $V_L K$ and $V_H K$. In some embodiments, an antibody or antibody binding fragment thereof comprises $V_L L$ and $V_H K$. In some embodiments, an antibody or antibody binding fragment thereof comprises $V_L M$ and $V_H K$. In some embodiments, an antibody or antibody binding fragment thereof comprises $V_L N$ and $V_H K$. In some embodiments, an antibody or antibody binding fragment thereof comprises $V_L O$ and $V_H K$. In some embodiments, an antibody or antibody binding fragment thereof comprises $V_L P$ and $V_H K$. In some embodiments, an antibody or antibody binding fragment thereof comprises $V_L Q$ and $V_H K$. In some embodiments, an antibody or antibody binding fragment thereof comprises $V_L R$ and $V_H K$. In some embodiments, an antibody or antibody binding fragment thereof comprises $V_L S$ and $V_H K$. In some embodiments, an antibody or antibody binding fragment thereof comprises $V_L T$ and $V_H K$. In some embodiments, an antibody or antibody binding fragment thereof comprises $V_L U$ and $V_H K$. In some embodiments, an antibody or antibody binding fragment thereof comprises $V_L V$ and $V_H K$. In some embodiments, an antibody or antibody binding fragment thereof comprises $V_L W$ and $V_H K$. In some embodiments, an antibody or antibody binding fragment thereof comprises $V_L X$ and $V_H K$. In some embodiments, an antibody or antibody binding fragment thereof comprises $V_L Y$ and $V_H K$. In some embodiments, an antibody or antibody binding fragment thereof comprises $V_L Z$ and $V_H K$. In some embodiments, an antibody or antibody binding fragment thereof comprises $V_L AB$ and $V_H K$.

In some embodiments, an antibody or antibody binding fragment thereof comprises $V_L A$ and $V_H L$. In some embodiments, an antibody or antibody binding fragment thereof comprises $V_L B$ and $V_H L$. In some embodiments, an antibody or antibody binding fragment thereof comprises $V_L C$ and $V_H L$. In some embodiments, an antibody or antibody binding fragment thereof comprises $V_L D$ and $V_H L$. In some embodiments, an antibody or antibody binding fragment thereof comprises $V_L E$ and $V_H L$. In some embodiments, an antibody or antibody binding fragment thereof comprises $V_L F$ and $V_H L$. In some embodiments, an antibody or antibody binding fragment thereof comprises $V_L G$ and $V_H L$. In some embodiments, an antibody or antibody binding fragment thereof comprises $V_L H$ and $V_H L$. In some embodiments, an antibody or antibody binding fragment thereof comprises $V_L I$ and $V_H L$. In some embodiments, an antibody or antibody binding fragment thereof comprises $V_L J$ and $V_H L$. In some embodiments, an antibody or antibody binding fragment thereof comprises $V_L K$ and $V_H L$. In some embodiments, an antibody or antibody binding fragment thereof comprises $V_L L$ and $V_H L$. In some embodiments, an antibody or antibody binding fragment thereof comprises $V_L M$ and $V_H L$. In some embodiments, an antibody or antibody binding fragment thereof comprises $V_L N$ and $V_H L$. In some embodiments, an antibody or antibody binding fragment thereof comprises $V_L O$ and $V_H L$. In some embodiments, an antibody or antibody binding fragment thereof comprises $V_L P$ and $V_H L$. In some embodiments, an antibody or antibody binding fragment thereof comprises $V_LQ$ and $V_HL$. In some embodiments, an antibody or antibody binding fragment thereof comprises $V_LR$ and $V_HL$. In some embodiments, an antibody or antibody binding fragment thereof comprises $V_LS$ and $V_HL$. In some embodiments, an antibody or antibody binding fragment thereof comprises $V_LT$ and $V_HL$. In some embodiments, an antibody or antibody binding fragment thereof comprises $V_LU$ and $V_HL$. In some embodiments, an antibody or antibody binding fragment thereof comprises $V_LV$ and $V_HL$. In some embodiments, an antibody or antibody binding fragment thereof comprises $V_LW$ and $V_HL$. In some embodiments, an antibody or antibody binding fragment thereof comprises $V_LX$ and $V_HL$. In some embodiments, an antibody or antibody binding fragment thereof comprises $V_LY$ and $V_HL$. In some embodiments, an antibody or antibody binding fragment thereof comprises $V_LZ$ and $V_HL$. In some embodiments, an antibody or antibody binding fragment thereof comprises $V_LAB$ and $V_HL$.

In some embodiments, an antibody or antibody binding fragment thereof comprises $V_LA$ and $V_HM$. In some embodiments, an antibody or antibody binding fragment thereof comprises $V_LB$ and $V_HM$. In some embodiments, an antibody or antibody binding fragment thereof comprises $V_LC$ and $V_HM$. In some embodiments, an antibody or antibody binding fragment thereof comprises $V_LD$ and $V_HM$. In some embodiments, an antibody or antibody binding fragment thereof comprises $V_LE$ and $V_HM$. In some embodiments, an antibody or antibody binding fragment thereof comprises $V_LF$ and $V_HM$. In some embodiments, an antibody or antibody binding fragment thereof comprises $V_LG$ and $V_HM$. In some embodiments, an antibody or antibody binding fragment thereof comprises $V_LH$ and $V_HM$. In some embodiments, an antibody or antibody binding fragment thereof comprises $V_LI$ and $V_HM$. In some embodiments, an antibody or antibody binding fragment thereof comprises $V_LJ$ and $V_HM$. In some embodiments, an antibody or antibody binding fragment thereof comprises $V_LK$ and $V_HM$. In some embodiments, an antibody or antibody binding fragment thereof comprises $V_LL$ and $V_HM$. In some embodiments, an antibody or antibody binding fragment thereof comprises $V_LM$ and $V_HM$. In some embodiments, an antibody or antibody binding fragment thereof comprises $V_LN$ and $V_HM$. In some embodiments, an antibody or antibody binding fragment thereof comprises $V_LO$ and $V_HM$. In some embodiments, an antibody or antibody binding fragment thereof comprises $V_LP$ and $V_HIM$. In some embodiments, an antibody or antibody binding fragment thereof comprises $V_LQ$ and $V_HM$. In some embodiments, an antibody or antibody binding fragment thereof comprises $V_LR$ and $V_HIM$. In some embodiments, an antibody or antibody binding fragment thereof comprises $V_LS$ and $V_HIM$. In some embodiments, an antibody or antibody binding fragment thereof comprises $V_LT$ and $V_HM$. In some embodiments, an antibody or antibody binding fragment thereof comprises $V_LU$ and $V_HIM$. In some embodiments, an antibody or antibody binding fragment thereof comprises $V_LV$ and $V_HM$. In some embodiments, an antibody or antibody binding fragment thereof comprises $V_LW$ and $V_HM$. In some embodiments, an antibody or antibody binding fragment thereof comprises $V_LX$ and $V_HM$. In some embodiments, an antibody or antibody binding fragment thereof comprises $V_LY$ and $V_HM$. In some embodiments, an antibody or antibody binding fragment thereof comprises $V_LZ$ and $V_HM$. In some embodiments, an antibody or antibody binding fragment thereof comprises $V_LAB$ and $V_HM$.

In some embodiments, an antibody or antibody binding fragment thereof comprises $V_LA$ and $V_HN$. In some embodiments, an antibody or antibody binding fragment thereof comprises $V_LB$ and $V_HN$. In some embodiments, an antibody or antibody binding fragment thereof comprises $V_LC$ and $V_HN$. In some embodiments, an antibody or antibody binding fragment thereof comprises $V_LD$ and $V_HN$. In some embodiments, an antibody or antibody binding fragment thereof comprises $V_LE$ and $V_HN$. In some embodiments, an antibody or antibody binding fragment thereof comprises $V_LF$ and $V_HN$. In some embodiments, an antibody or antibody binding fragment thereof comprises $V_LG$ and $V_HN$. In some embodiments, an antibody or antibody binding fragment thereof comprises $V_LH$ and $V_HN$. In some embodiments, an antibody or antibody binding fragment thereof comprises $V_LI$ and $V_HN$. In some embodiments, an antibody or antibody binding fragment thereof comprises $V_LJ$ and $V_HN$. In some embodiments, an antibody or antibody binding fragment thereof comprises $V_LK$ and $V_HN$. In some embodiments, an antibody or antibody binding fragment thereof comprises $V_LL$ and $V_HN$. In some embodiments, an antibody or antibody binding fragment thereof comprises $V_LM$ and $V_HN$. In some embodiments, an antibody or antibody binding fragment thereof comprises $V_LN$ and $V_HN$. In some embodiments, an antibody or antibody binding fragment thereof comprises $V_LO$ and $V_HN$. In some embodiments, an antibody or antibody binding fragment thereof comprises $V_LP$ and $V_HN$. In some embodiments, an antibody or antibody binding fragment thereof comprises $V_LQ$ and $V_HN$. In some embodiments, an antibody or antibody binding fragment thereof comprises $V_LR$ and $V_HN$. In some embodiments, an antibody or antibody binding fragment thereof comprises $V_LS$ and $V_HN$. In some embodiments, an antibody or antibody binding fragment thereof comprises $V_LT$ and $V_HN$. In some embodiments, an antibody or antibody binding fragment thereof comprises $V_LU$ and $V_HN$. In some embodiments, an antibody or antibody binding fragment thereof comprises $V_LV$ and $V_HN$. In some embodiments, an antibody or antibody binding fragment thereof comprises $V_LW$ and $V_HN$. In some embodiments, an antibody or antibody binding fragment thereof comprises $V_LX$ and $V_HN$. In some embodiments, an antibody or antibody binding fragment thereof comprises $V_LY$ and $V_HN$. In some embodiments, an antibody or antibody binding fragment thereof comprises $V_LZ$ and $V_HN$. In some embodiments, an antibody or antibody binding fragment thereof comprises $V_LAB$ and $V_HIN$.

In some embodiments, an antibody or antibody binding fragment thereof comprises $V_LA$ and $V_HO$. In some embodiments, an antibody or antibody binding fragment thereof comprises $V_LB$ and $V_HO$. In some embodiments, an antibody or antibody binding fragment thereof comprises $V_LC$ and $V_HO$. In some embodiments, an antibody or antibody binding fragment thereof comprises $V_LD$ and $V_HO$. In some embodiments, an antibody or antibody binding fragment thereof comprises $V_LE$ and $V_HO$. In some embodiments, an antibody or antibody binding fragment thereof comprises $V_LF$ and $V_HO$. In some embodiments, an antibody or antibody binding fragment thereof comprises $V_LG$ and $V_HO$. In some embodiments, an antibody or antibody binding fragment thereof comprises $V_LH$ and $V_HO$. In some embodiments, an antibody or antibody binding fragment thereof comprises $V_LI$ and $V_HO$. In some embodiments, an antibody or antibody binding fragment thereof comprises $V_LJ$ and $V_HO$. In some embodiments, an antibody or antibody binding fragment thereof comprises $V_LK$ and $V_HO$. In some embodiments, an antibody or antibody binding fragment thereof comprises $V_L$L and $V_H$O. In some embodiments, an antibody or antibody binding fragment thereof comprises $V_L$M and $V_H$O. In some embodiments, an antibody or antibody binding fragment thereof comprises $V_L$N and $V_H$O. In some embodiments, an antibody or antibody binding fragment thereof comprises $V_L$O and $V_H$O. In some embodiments, an antibody or antibody binding fragment thereof comprises $V_L$P and $V_H$O. In some embodiments, an antibody or antibody binding fragment thereof comprises $V_L$Q and $V_H$O. In some embodiments, an antibody or antibody binding fragment thereof comprises $V_L$R and $V_H$O. In some embodiments, an antibody or antibody binding fragment thereof comprises $V_L$S and $V_H$O. In some embodiments, an antibody or antibody binding fragment thereof comprises $V_L$T and $V_H$O. In some embodiments, an antibody or antibody binding fragment thereof comprises $V_L$U and $V_H$O. In some embodiments, an antibody or antibody binding fragment thereof comprises $V_L$V and $V_H$O. In some embodiments, an antibody or antibody binding fragment thereof comprises $V_L$W and $V_H$O. In some embodiments, an antibody or antibody binding fragment thereof comprises $V_L$X and $V_H$O. In some embodiments, an antibody or antibody binding fragment thereof comprises $V_L$Y and $V_H$O. In some embodiments, an antibody or antibody binding fragment thereof comprises $V_L$Z and $V_H$O. In some embodiments, an antibody or antibody binding fragment thereof comprises $V_L$AB and $V_H$O.

In some embodiments, an antibody or antibody binding fragment thereof comprises $V_L$A and $V_H$P. In some embodiments, an antibody or antibody binding fragment thereof comprises $V_L$B and $V_H$P. In some embodiments, an antibody or antibody binding fragment thereof comprises $V_L$C and $V_H$P. In some embodiments, an antibody or antibody binding fragment thereof comprises $V_L$D and $V_H$P. In some embodiments, an antibody or antibody binding fragment thereof comprises $V_L$E and $V_H$P. In some embodiments, an antibody or antibody binding fragment thereof comprises $V_L$F and $V_H$P. In some embodiments, an antibody or antibody binding fragment thereof comprises $V_L$G and $V_H$P. In some embodiments, an antibody or antibody binding fragment thereof comprises $V_L$H and $V_H$P. In some embodiments, an antibody or antibody binding fragment thereof comprises $V_L$I and $V_H$P. In some embodiments, an antibody or antibody binding fragment thereof comprises $V_L$J and $V_H$P. In some embodiments, an antibody or antibody binding fragment thereof comprises $V_L$K and $V_H$P. In some embodiments, an antibody or antibody binding fragment thereof comprises $V_L$L and $V_H$P. In some embodiments, an antibody or antibody binding fragment thereof comprises $V_L$M and $V_H$P. In some embodiments, an antibody or antibody binding fragment thereof comprises $V_L$N and $V_H$P. In some embodiments, an antibody or antibody binding fragment thereof comprises $V_L$O and $V_H$P. In some embodiments, an antibody or antibody binding fragment thereof comprises $V_L$P and $V_H$P. In some embodiments, an antibody or antibody binding fragment thereof comprises $V_L$Q and $V_H$P. In some embodiments, an antibody or antibody binding fragment thereof comprises $V_L$R and $V_H$P. In some embodiments, an antibody or antibody binding fragment thereof comprises $V_L$S and $V_H$P. In some embodiments, an antibody or antibody binding fragment thereof comprises $V_L$T and $V_H$P. In some embodiments, an antibody or antibody binding fragment thereof comprises $V_L$U and $V_H$P. In some embodiments, an antibody or antibody binding fragment thereof comprises $V_L$V and $V_H$P. In some embodiments, an antibody or antibody binding fragment thereof comprises $V_L$W and $V_H$P. In some embodiments, an antibody or antibody binding fragment thereof comprises $V_L$X and $V_H$P. In some embodiments, an antibody or antibody binding fragment thereof comprises $V_L$Y and $V_H$P. In some embodiments, an antibody or antibody binding fragment thereof comprises $V_L$Z and $V_H$P. In some embodiments, an antibody or antibody binding fragment thereof comprises $V_L$AB and $V_H$P.

In some embodiments, an antibody or antibody binding fragment thereof comprises $V_L$A and $V_H$Q. In some embodiments, an antibody or antibody binding fragment thereof comprises $V_L$B and $V_H$Q. In some embodiments, an antibody or antibody binding fragment thereof comprises $V_L$C and $V_H$Q. In some embodiments, an antibody or antibody binding fragment thereof comprises $V_L$D and $V_H$Q. In some embodiments, an antibody or antibody binding fragment thereof comprises $V_L$E and $V_H$Q. In some embodiments, an antibody or antibody binding fragment thereof comprises $V_L$F and $V_H$Q. In some embodiments, an antibody or antibody binding fragment thereof comprises $V_L$G and $V_H$Q. In some embodiments, an antibody or antibody binding fragment thereof comprises $V_L$H and $V_H$Q. In some embodiments, an antibody or antibody binding fragment thereof comprises $V_L$I and $V_H$Q. In some embodiments, an antibody or antibody binding fragment thereof comprises $V_L$J and $V_H$Q. In some embodiments, an antibody or antibody binding fragment thereof comprises $V_L$K and $V_H$Q. In some embodiments, an antibody or antibody binding fragment thereof comprises $V_L$L and $V_H$Q. In some embodiments, an antibody or antibody binding fragment thereof comprises $V_L$M and $V_H$Q. In some embodiments, an antibody or antibody binding fragment thereof comprises $V_L$N and $V_H$Q. In some embodiments, an antibody or antibody binding fragment thereof comprises $V_L$O and $V_H$Q. In some embodiments, an antibody or antibody binding fragment thereof comprises $V_L$P and $V_H$Q. In some embodiments, an antibody or antibody binding fragment thereof comprises $V_L$Q and $V_H$Q. In some embodiments, an antibody or antibody binding fragment thereof comprises $V_L$R and $V_H$Q. In some embodiments, an antibody or antibody binding fragment thereof comprises $V_L$S and $V_H$Q. In some embodiments, an antibody or antibody binding fragment thereof comprises $V_L$T and $V_H$Q. In some embodiments, an antibody or antibody binding fragment thereof comprises $V_L$U and $V_H$Q. In some embodiments, an antibody or antibody binding fragment thereof comprises $V_L$V and $V_H$Q. In some embodiments, an antibody or antibody binding fragment thereof comprises $V_L$W and $V_H$Q. In some embodiments, an antibody or antibody binding fragment thereof comprises $V_L$X and $V_H$Q. In some embodiments, an antibody or antibody binding fragment thereof comprises $V_L$Y and $V_H$Q. In some embodiments, an antibody or antibody binding fragment thereof comprises $V_L$Z and $V_H$Q. In some embodiments, an antibody or antibody binding fragment thereof comprises $V_L$AB and $V_H$Q.

In some embodiments, an antibody or antibody binding fragment thereof comprises $V_L$A and $V_H$R. In some embodiments, an antibody or antibody binding fragment thereof comprises $V_L$B and $V_H$R. In some embodiments, an antibody or antibody binding fragment thereof comprises $V_L$C and $V_H$R. In some embodiments, an antibody or antibody binding fragment thereof comprises $V_L$D and $V_H$R. In some embodiments, an antibody or antibody binding fragment thereof comprises $V_L$E and $V_H$R. In some embodiments, an antibody or antibody binding fragment thereof comprises $V_L$F and $V_H$R. In some embodiments, an antibody or antibody binding fragment thereof comprises $V_L$G and $V_H$R. In some embodiments, an antibody or antibody binding fragment thereof comprises $V_L$H and $V_H$R. In some embodiments, an antibody or antibody binding fragment thereof comprises $V_L I$ and $V_H R$. In some embodiments, an antibody or antibody binding fragment thereof comprises $V_L J$ and $V_H R$. In some embodiments, an antibody or antibody binding fragment thereof comprises $V_H K$ and $V_H R$. In some embodiments, an antibody or antibody binding fragment thereof comprises $V_L L$ and $V_H R$. In some embodiments, an antibody or antibody binding fragment thereof comprises $V_L M$ and $V_H R$. In some embodiments, an antibody or antibody binding fragment thereof comprises $V_L N$ and $V_H R$. In some embodiments, an antibody or antibody binding fragment thereof comprises $V_L O$ and $V_H R$. In some embodiments, an antibody or antibody binding fragment thereof comprises $V_L P$ and $V_H R$. In some embodiments, an antibody or antibody binding fragment thereof comprises $V_L Q$ and $V_H R$. In some embodiments, an antibody or antibody binding fragment thereof comprises $V_L R$ and $V_H R$. In some embodiments, an antibody or antibody binding fragment thereof comprises $V_L S$ and $V_H R$. In some embodiments, an antibody or antibody binding fragment thereof comprises $V_L T$ and $V_H R$. In some embodiments, an antibody or antibody binding fragment thereof comprises $V_L U$ and $V_H R$. In some embodiments, an antibody or antibody binding fragment thereof comprises $V_L V$ and $V_H R$. In some embodiments, an antibody or antibody binding fragment thereof comprises $V_L W$ and $V_H R$. In some embodiments, an antibody or antibody binding fragment thereof comprises $V_L X$ and $V_H R$. In some embodiments, an antibody or antibody binding fragment thereof comprises $V_L Y$ and $V_H R$. In some embodiments, an antibody or antibody binding fragment thereof comprises $V_L Z$ and $V_H R$. In some embodiments, an antibody or antibody binding fragment thereof comprises $V_L AB$ and $V_H R$.

In some embodiments, an antibody or antibody binding fragment thereof comprises $V_L A$ and $V_H S$. In some embodiments, an antibody or antibody binding fragment thereof comprises $V_L B$ and $V_H S$. In some embodiments, an antibody or antibody binding fragment thereof comprises $V_L C$ and $V_H S$. In some embodiments, an antibody or antibody binding fragment thereof comprises $V_L D$ and $V_H S$. In some embodiments, an antibody or antibody binding fragment thereof comprises $V_L E$ and $V_H S$. In some embodiments, an antibody or antibody binding fragment thereof comprises $V_L F$ and $V_H IS$. In some embodiments, an antibody or antibody binding fragment thereof comprises $V_L G$ and $V_H S$. In some embodiments, an antibody or antibody binding fragment thereof comprises $V_L H$ and $V_H S$. In some embodiments, an antibody or antibody binding fragment thereof comprises $V_L I$ and $V_H IS$. In some embodiments, an antibody or antibody binding fragment thereof comprises $V_L J$ and $V_H S$. In some embodiments, an antibody or antibody binding fragment thereof comprises $V_L K$ and $V_H S$. In some embodiments, an antibody or antibody binding fragment thereof comprises $V_L L$ and $V_H S$. In some embodiments, an antibody or antibody binding fragment thereof comprises $V_L M$ and $V_H S$. In some embodiments, an antibody or antibody binding fragment thereof comprises $V_L N$ and $V_H S$. In some embodiments, an antibody or antibody binding fragment thereof comprises $V_L O$ and $V_H S$. In some embodiments, an antibody or antibody binding fragment thereof comprises $V_L P$ and $V_H S$. In some embodiments, an antibody or antibody binding fragment thereof comprises $V_L Q$ and $V_H S$. In some embodiments, an antibody or antibody binding fragment thereof comprises $V_L R$ and $V_H S$. In some embodiments, an antibody or antibody binding fragment thereof comprises $V_L S$ and $V_H S$. In some embodiments, an antibody or antibody binding fragment thereof comprises $V_L T$ and $V_H S$. In some embodiments, an antibody or antibody binding fragment thereof comprises $V_L U$ and $V_H S$. In some embodiments, an antibody or antibody binding fragment thereof comprises $V_L V$ and $V_H S$. In some embodiments, an antibody or antibody binding fragment thereof comprises $V_L W$ and $V_H S$. In some embodiments, an antibody or antibody binding fragment thereof comprises $V_L X$ and $V_H S$. In some embodiments, an antibody or antibody binding fragment thereof comprises $V_L Y$ and $V_H S$. In some embodiments, an antibody or antibody binding fragment thereof comprises $V_L Z$ and $V_H S$. In some embodiments, an antibody or antibody binding fragment thereof comprises $V_L AB$ and $V_H IS$.

In some embodiments, an antibody or antibody binding fragment thereof comprises $V_L A$ and $V_H T$. In some embodiments, an antibody or antibody binding fragment thereof comprises $V_L B$ and $V_H T$. In some embodiments, an antibody or antibody binding fragment thereof comprises $V_L C$ and $V_H T$. In some embodiments, an antibody or antibody binding fragment thereof comprises $V_L D$ and $V_H T$. In some embodiments, an antibody or antibody binding fragment thereof comprises $V_L E$ and $V_H T$. In some embodiments, an antibody or antibody binding fragment thereof comprises $V_L F$ and $V_H T$. In some embodiments, an antibody or antibody binding fragment thereof comprises $V_L G$ and $V_H T$. In some embodiments, an antibody or antibody binding fragment thereof comprises $V_L H$ and $V_H T$. In some embodiments, an antibody or antibody binding fragment thereof comprises $V_L I$ and $V_H T$. In some embodiments, an antibody or antibody binding fragment thereof comprises $V_L J$ and $V_H T$. In some embodiments, an antibody or antibody binding fragment thereof comprises $V_L K$ and $V_H T$. In some embodiments, an antibody or antibody binding fragment thereof comprises $V_L L$ and $V_H T$. In some embodiments, an antibody or antibody binding fragment thereof comprises $V_L M$ and $V_H T$. In some embodiments, an antibody or antibody binding fragment thereof comprises $V_L N$ and $V_H T$. In some embodiments, an antibody or antibody binding fragment thereof comprises $V_L O$ and $V_H T$. In some embodiments, an antibody or antibody binding fragment thereof comprises $V_L P$ and $V_H T$. In some embodiments, an antibody or antibody binding fragment thereof comprises $V_L Q$ and $V_H T$. In some embodiments, an antibody or antibody binding fragment thereof comprises $V_L R$ and $V_H T$. In some embodiments, an antibody or antibody binding fragment thereof comprises $V_L S$ and $V_H T$. In some embodiments, an antibody or antibody binding fragment thereof comprises $V_L T$ and $V_H T$. In some embodiments, an antibody or antibody binding fragment thereof comprises $V_L U$ and $V_H T$. In some embodiments, an antibody or antibody binding fragment thereof comprises $V_L V$ and $V_H T$. In some embodiments, an antibody or antibody binding fragment thereof comprises $V_L W$ and $V_H T$. In some embodiments, an antibody or antibody binding fragment thereof comprises $V_L X$ and $V_H T$. In some embodiments, an antibody or antibody binding fragment thereof comprises $V_L Y$ and $V_H T$. In some embodiments, an antibody or antibody binding fragment thereof comprises $V_L Z$ and $V_H T$. In some embodiments, an antibody or antibody binding fragment thereof comprises $V_L AB$ and $V_H IT$.

In some embodiments, an antibody or antibody binding fragment thereof comprises $V_L A$ and $V_H U$. In some embodiments, an antibody or antibody binding fragment thereof comprises $V_L B$ and $V_H U$. In some embodiments, an antibody or antibody binding fragment thereof comprises $V_L C$ and $V_H U$. In some embodiments, an antibody or antibody binding fragment thereof comprises $V_L D$ and $V_H U$. In some embodiments, an antibody or antibody binding fragment thereof comprises $V_LE$ and $V_HU$. In some embodiments, an antibody or antibody binding fragment thereof comprises $V_LF$ and $V_HU$. In some embodiments, an antibody or antibody binding fragment thereof comprises $V_LG$ and $V_HU$. In some embodiments, an antibody or antibody binding fragment thereof comprises $V_LH$ and $V_HU$. In some embodiments, an antibody or antibody binding fragment thereof comprises $V_LI$ and $V_HU$. In some embodiments, an antibody or antibody binding fragment thereof comprises $V_LJ$ and $V_HU$. In some embodiments, an antibody or antibody binding fragment thereof comprises $V_LK$ and $V_HU$. In some embodiments, an antibody or antibody binding fragment thereof comprises $V_LL$ and $V_HU$. In some embodiments, an antibody or antibody binding fragment thereof comprises $V_LM$ and $V_HU$. In some embodiments, an antibody or antibody binding fragment thereof comprises $V_LN$ and $V_HU$. In some embodiments, an antibody or antibody binding fragment thereof comprises $V_LO$ and $V_HU$. In some embodiments, an antibody or antibody binding fragment thereof comprises $V_LP$ and $V_HU$. In some embodiments, an antibody or antibody binding fragment thereof comprises $V_LQ$ and $V_HU$. In some embodiments, an antibody or antibody binding fragment thereof comprises $V_LR$ and $V_HU$. In some embodiments, an antibody or antibody binding fragment thereof comprises $V_LS$ and $V_HU$. In some embodiments, an antibody or antibody binding fragment thereof comprises $V_LT$ and $V_HU$. In some embodiments, an antibody or antibody binding fragment thereof comprises $V_LU$ and $V_HU$. In some embodiments, an antibody or antibody binding fragment thereof comprises $V_LV$ and $V_HU$. In some embodiments, an antibody or antibody binding fragment thereof comprises $V_LW$ and $V_HU$. In some embodiments, an antibody or antibody binding fragment thereof comprises $V_LX$ and $V_HU$. In some embodiments, an antibody or antibody binding fragment thereof comprises $V_LY$ and $V_HU$. In some embodiments, an antibody or antibody binding fragment thereof comprises $V_LZ$ and $V_HU$. In some embodiments, an antibody or antibody binding fragment thereof comprises $V_LAB$ and $V_HU$.

In some embodiments, an antibody or antibody binding fragment thereof comprises $V_LA$ and $V_HV$. In some embodiments, an antibody or antibody binding fragment thereof comprises $V_LB$ and $V_HV$. In some embodiments, an antibody or antibody binding fragment thereof comprises $V_LC$ and $V_HV$. In some embodiments, an antibody or antibody binding fragment thereof comprises $V_LD$ and $V_HV$. In some embodiments, an antibody or antibody binding fragment thereof comprises $V_LE$ and $V_HV$. In some embodiments, an antibody or antibody binding fragment thereof comprises $V_LF$ and $V_HV$. In some embodiments, an antibody or antibody binding fragment thereof comprises $V_LG$ and $V_HV$. In some embodiments, an antibody or antibody binding fragment thereof comprises $V_LH$ and $V_HV$. In some embodiments, an antibody or antibody binding fragment thereof comprises $V_LI$ and $V_HV$. In some embodiments, an antibody or antibody binding fragment thereof comprises $V_LJ$ and $V_HV$. In some embodiments, an antibody or antibody binding fragment thereof comprises $V_LK$ and $V_HV$. In some embodiments, an antibody or antibody binding fragment thereof comprises $V_LL$ and $V_HV$. In some embodiments, an antibody or antibody binding fragment thereof comprises $V_LM$ and $V_HV$. In some embodiments, an antibody or antibody binding fragment thereof comprises $V_LN$ and $V_HV$. In some embodiments, an antibody or antibody binding fragment thereof comprises $V_LO$ and $V_HV$. In some embodiments, an antibody or antibody binding fragment thereof comprises $V_LP$ and $V_HIV$. In some embodiments, an antibody or antibody binding fragment thereof comprises $V_LQ$ and $V_HV$. In some embodiments, an antibody or antibody binding fragment thereof comprises $V_LR$ and $V_HIV$. In some embodiments, an antibody or antibody binding fragment thereof comprises $V_LS$ and $V_HIV$. In some embodiments, an antibody or antibody binding fragment thereof comprises $V_LT$ and $V_HV$. In some embodiments, an antibody or antibody binding fragment thereof comprises $V_LU$ and $V_HV$. In some embodiments, an antibody or antibody binding fragment thereof comprises $V_LV$ and $V_HIV$. In some embodiments, an antibody or antibody binding fragment thereof comprises $V_LW$ and $V_HV$. In some embodiments, an antibody or antibody binding fragment thereof comprises $V_LX$ and $V_HV$. In some embodiments, an antibody or antibody binding fragment thereof comprises $V_LY$ and $V_HV$. In some embodiments, an antibody or antibody binding fragment thereof comprises $V_LZ$ and $V_HV$. In some embodiments, an antibody or antibody binding fragment thereof comprises $V_LAB$ and $V_HIV$.

In some embodiments, an antibody or antibody binding fragment thereof comprises $V_LA$ and $V_HW$. In some embodiments, an antibody or antibody binding fragment thereof comprises $V_LB$ and $V_HW$. In some embodiments, an antibody or antibody binding fragment thereof comprises $V_LC$ and $V_HW$. In some embodiments, an antibody or antibody binding fragment thereof comprises $V_LD$ and $V_HW$. In some embodiments, an antibody or antibody binding fragment thereof comprises $V_LE$ and $V_HW$. In some embodiments, an antibody or antibody binding fragment thereof comprises $V_LF$ and $V_HW$. In some embodiments, an antibody or antibody binding fragment thereof comprises $V_LG$ and $V_HW$. In some embodiments, an antibody or antibody binding fragment thereof comprises $V_LH$ and $V_HW$. In some embodiments, an antibody or antibody binding fragment thereof comprises $V_LI$ and $V_HW$. In some embodiments, an antibody or antibody binding fragment thereof comprises $V_LJ$ and $V_HW$. In some embodiments, an antibody or antibody binding fragment thereof comprises $V_LK$ and $V_HW$. In some embodiments, an antibody or antibody binding fragment thereof comprises $V_LL$ and $V_HW$. In some embodiments, an antibody or antibody binding fragment thereof comprises $V_LM$ and $V_HW$. In some embodiments, an antibody or antibody binding fragment thereof comprises $V_LN$ and $V_HW$. In some embodiments, an antibody or antibody binding fragment thereof comprises $V_LO$ and $V_HW$. In some embodiments, an antibody or antibody binding fragment thereof comprises $V_LP$ and $V_HW$. In some embodiments, an antibody or antibody binding fragment thereof comprises $V_LQ$ and $V_HW$. In some embodiments, an antibody or antibody binding fragment thereof comprises $V_LR$ and $V_HW$. In some embodiments, an antibody or antibody binding fragment thereof comprises $V_LS$ and $V_HW$. In some embodiments, an antibody or antibody binding fragment thereof comprises $V_LT$ and $V_HW$. In some embodiments, an antibody or antibody binding fragment thereof comprises $V_LU$ and $V_HW$. In some embodiments, an antibody or antibody binding fragment thereof comprises $V_LV$ and $V_HW$. In some embodiments, an antibody or antibody binding fragment thereof comprises $V_LW$ and $V_HW$. In some embodiments, an antibody or antibody binding fragment thereof comprises $V_LX$ and $V_HW$. In some embodiments, an antibody or antibody binding fragment thereof comprises $V_LY$ and $V_HW$. In some embodiments, an antibody or antibody binding fragment thereof comprises $V_LZ$ and $V_HW$. In some embodiments, an antibody or antibody binding fragment thereof comprises $V_LAB$ and $V_HW$.

In some embodiments, an antibody or antibody binding fragment thereof comprises $V_LA$ and $V_HX$. In some embodiments, an antibody or antibody binding fragment thereof comprises $V_LB$ and $V_HX$. In some embodiments, an antibody or antibody binding fragment thereof comprises $V_LC$ and $V_HX$. In some embodiments, an antibody or antibody binding fragment thereof comprises $V_LD$ and $V_HX$. In some embodiments, an antibody or antibody binding fragment thereof comprises $V_LE$ and $V_HX$. In some embodiments, an antibody or antibody binding fragment thereof comprises $V_LF$ and $V_HX$. In some embodiments, an antibody or antibody binding fragment thereof comprises $V_LG$ and $V_HX$. In some embodiments, an antibody or antibody binding fragment thereof comprises $V_LH$ and $V_HX$. In some embodiments, an antibody or antibody binding fragment thereof comprises $V_LI$ and $V_HX$. In some embodiments, an antibody or antibody binding fragment thereof comprises $V_LJ$ and $V_HX$. In some embodiments, an antibody or antibody binding fragment thereof comprises $V_LK$ and $V_HX$. In some embodiments, an antibody or antibody binding fragment thereof comprises $V_LL$ and $V_HX$. In some embodiments, an antibody or antibody binding fragment thereof comprises $V_LM$ and $V_HX$. In some embodiments, an antibody or antibody binding fragment thereof comprises $V_LN$ and $V_HX$. In some embodiments, an antibody or antibody binding fragment thereof comprises $V_LO$ and $V_HX$. In some embodiments, an antibody or antibody binding fragment thereof comprises $V_LP$ and $V_HX$. In some embodiments, an antibody or antibody binding fragment thereof comprises $V_LQ$ and $V_HX$. In some embodiments, an antibody or antibody binding fragment thereof comprises $V_LR$ and $V_HX$. In some embodiments, an antibody or antibody binding fragment thereof comprises $V_LS$ and $V_HX$. In some embodiments, an antibody or antibody binding fragment thereof comprises $V_LT$ and $V_HX$. In some embodiments, an antibody or antibody binding fragment thereof comprises $V_LU$ and $V_HX$. In some embodiments, an antibody or antibody binding fragment thereof comprises $V_LV$ and $V_HX$. In some embodiments, an antibody or antibody binding fragment thereof comprises $V_LW$ and $V_HX$. In some embodiments, an antibody or antibody binding fragment thereof comprises $V_LX$ and $V_HX$. In some embodiments, an antibody or antibody binding fragment thereof comprises $V_LY$ and $V_HX$. In some embodiments, an antibody or antibody binding fragment thereof comprises $V_LZ$ and $V_HX$. In some embodiments, an antibody or antibody binding fragment thereof comprises $V_LAB$ and $V_HX$.

In some embodiments, an antibody or antibody binding fragment thereof comprises $V_LA$ and $V_HY$. In some embodiments, an antibody or antibody binding fragment thereof comprises $V_LB$ and $V_HY$. In some embodiments, an antibody or antibody binding fragment thereof comprises $V_LC$ and $V_HY$. In some embodiments, an antibody or antibody binding fragment thereof comprises $V_LD$ and $V_HY$. In some embodiments, an antibody or antibody binding fragment thereof comprises $V_LE$ and $V_HY$. In some embodiments, an antibody or antibody binding fragment thereof comprises $V_LF$ and $V_HY$. In some embodiments, an antibody or antibody binding fragment thereof comprises $V_LG$ and $V_HY$. In some embodiments, an antibody or antibody binding fragment thereof comprises $V_LH$ and $V_HY$. In some embodiments, an antibody or antibody binding fragment thereof comprises $V_LI$ and $V_HY$. In some embodiments, an antibody or antibody binding fragment thereof comprises $V_LJ$ and $V_HY$. In some embodiments, an antibody or antibody binding fragment thereof comprises $V_LK$ and $V_HY$. In some embodiments, an antibody or antibody binding fragment thereof comprises $V_LL$ and $V_HY$. In some embodiments, an antibody or antibody binding fragment thereof comprises $V_LM$ and $V_HY$. In some embodiments, an antibody or antibody binding fragment thereof comprises $V_LN$ and $V_HY$. In some embodiments, an antibody or antibody binding fragment thereof comprises $V_LO$ and $V_HY$. In some embodiments, an antibody or antibody binding fragment thereof comprises $V_LP$ and $V_HY$. In some embodiments, an antibody or antibody binding fragment thereof comprises $V_LQ$ and $V_HY$. In some embodiments, an antibody or antibody binding fragment thereof comprises $V_LR$ and $V_HY$. In some embodiments, an antibody or antibody binding fragment thereof comprises $V_LS$ and $V_HY$. In some embodiments, an antibody or antibody binding fragment thereof comprises $V_LT$ and $V_HY$. In some embodiments, an antibody or antibody binding fragment thereof comprises $V_LU$ and $V_HY$. In some embodiments, an antibody or antibody binding fragment thereof comprises $V_LV$ and $V_HY$. In some embodiments, an antibody or antibody binding fragment thereof comprises $V_LW$ and $V_HY$. In some embodiments, an antibody or antibody binding fragment thereof comprises $V_LX$ and $V_HY$. In some embodiments, an antibody or antibody binding fragment thereof comprises $V_LY$ and $V_HY$. In some embodiments, an antibody or antibody binding fragment thereof comprises $V_LZ$ and $V_HY$. In some embodiments, an antibody or antibody binding fragment thereof comprises $V_LAB$ and $V_HY$.

In some embodiments, an antibody or antibody binding fragment thereof comprises $V_LA$ and $V_HZ$. In some embodiments, an antibody or antibody binding fragment thereof comprises $V_LB$ and $V_HZ$. In some embodiments, an antibody or antibody binding fragment thereof comprises $V_LC$ and $V_HZ$. In some embodiments, an antibody or antibody binding fragment thereof comprises $V_LD$ and $V_HZ$. In some embodiments, an antibody or antibody binding fragment thereof comprises $V_LE$ and $V_HZ$. In some embodiments, an antibody or antibody binding fragment thereof comprises $V_LF$ and $V_HZ$. In some embodiments, an antibody or antibody binding fragment thereof comprises $V_LG$ and $V_HZ$. In some embodiments, an antibody or antibody binding fragment thereof comprises $V_LH$ and $V_HZ$. In some embodiments, an antibody or antibody binding fragment thereof comprises $V_LI$ and $V_HZ$. In some embodiments, an antibody or antibody binding fragment thereof comprises $V_LJ$ and $V_HZ$. In some embodiments, an antibody or antibody binding fragment thereof comprises $V_LK$ and $V_HZ$. In some embodiments, an antibody or antibody binding fragment thereof comprises $V_LL$ and $V_HZ$. In some embodiments, an antibody or antibody binding fragment thereof comprises $V_LM$ and $V_HZ$. In some embodiments, an antibody or antibody binding fragment thereof comprises $V_LN$ and $V_HZ$. In some embodiments, an antibody or antibody binding fragment thereof comprises $V_LO$ and $V_HZ$. In some embodiments, an antibody or antibody binding fragment thereof comprises $V_LP$ and $V_HZ$. In some embodiments, an antibody or antibody binding fragment thereof comprises $V_LQ$ and $V_HZ$. In some embodiments, an antibody or antibody binding fragment thereof comprises $V_LR$ and $V_HZ$. In some embodiments, an antibody or antibody binding fragment thereof comprises $V_LS$ and $V_HZ$. In some embodiments, an antibody or antibody binding fragment thereof comprises $V_LT$ and $V_HZ$. In some embodiments, an antibody or antibody binding fragment thereof comprises $V_LU$ and $V_HZ$. In some embodiments, an antibody or antibody binding fragment thereof comprises $V_LV$ and $V_HZ$. In some embodiments, an antibody or antibody binding fragment thereof comprises $V_LW$ and $V_HZ$. In some embodiments, an antibody or antibody binding fragment thereof comprises $V_LX$ and $V_HZ$. In some embodiments, an antibody or antibody binding fragment thereof comprises $V_LY$ and $V_HZ$. In some embodiments, an antibody or antibody binding fragment thereof comprises $V_LZ$ and $V_HZ$. In some embodiments, an antibody or antibody binding fragment thereof comprises $V_LAB$ and $V_HZ$.

In some embodiments, an antibody or antibody binding fragment thereof comprises $V_LA$ and $V_HAB$. In some embodiments, an antibody or antibody binding fragment thereof comprises $V_LB$ and $V_HAB$. In some embodiments, an antibody or antibody binding fragment thereof comprises $V_LC$ and $V_HAB$. In some embodiments, an antibody or antibody binding fragment thereof comprises $V_LD$ and $V_HAB$. In some embodiments, an antibody or antibody binding fragment thereof comprises $V_LE$ and $V_HAB$. In some embodiments, an antibody or antibody binding fragment thereof comprises $V_LF$ and $V_HAB$. In some embodiments, an antibody or antibody binding fragment thereof comprises $V_LG$ and $V_HAB$. In some embodiments, an antibody or antibody binding fragment thereof comprises $V_LH$ and $V_HAB$. In some embodiments, an antibody or antibody binding fragment thereof comprises $V_LI$ and $V_HAB$. In some embodiments, an antibody or antibody binding fragment thereof comprises $V_LJ$ and $V_HAB$. In some embodiments, an antibody or antibody binding fragment thereof comprises $V_LK$ and $V_HAB$. In some embodiments, an antibody or antibody binding fragment thereof comprises $V_LL$ and $V_HAB$. In some embodiments, an antibody or antibody binding fragment thereof comprises $V_LM$ and $V_HAB$. In some embodiments, an antibody or antibody binding fragment thereof comprises $V_LN$ and $V_HAB$. In some embodiments, an antibody or antibody binding fragment thereof comprises $V_LO$ and $V_HAB$. In some embodiments, an antibody or antibody binding fragment thereof comprises $V_LP$ and $V_HAB$. In some embodiments, an antibody or antibody binding fragment thereof comprises $V_LQ$ and $V_HAB$. In some embodiments, an antibody or antibody binding fragment thereof comprises $V_LR$ and $V_HAB$. In some embodiments, an antibody or antibody binding fragment thereof comprises $V_LS$ and $V_HAB$. In some embodiments, an antibody or antibody binding fragment thereof comprises $V_LT$ and $V_HAB$. In some embodiments, an antibody or antibody binding fragment thereof comprises $V_LU$ and $V_HAB$. In some embodiments, an antibody or antibody binding fragment thereof comprises $V_LV$ and $V_HAB$. In some embodiments, an antibody or antibody binding fragment thereof comprises $V_LW$ and $V_HAB$. In some embodiments, an antibody or antibody binding fragment thereof comprises $V_LX$ and $V_HAB$. In some embodiments, an antibody or antibody binding fragment thereof comprises $V_LY$ and $V_HAB$. In some embodiments, an antibody or antibody binding fragment thereof comprises $V_LZ$ and $V_HAB$. In some embodiments, an antibody or antibody binding fragment thereof comprises $V_LAB$ and $V_HAB$. The different CDR motifs can be combined in any combination including those not depicted in the table above. For example, the following embodiments are provided as non-limiting examples of such combinations.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence of SEQ ID NO: 12; the light chain LCDR2 has the amino acid sequence of SEQ ID NO: 13; and the light chain LCDR3 sequence has the amino acid sequence of SEQ ID NO: 14 and (ii) a heavy chain variable region comprising heavy chain HCDR1, HCDR2, and HCDR3 sequences, wherein the heavy chain HCDR1 sequence has the amino acid sequence of SEQ ID NO: 9; the heavy chain HCDR2 sequence has the amino acid sequence of SEQ ID NO: 10; and the heavy chain HCDR3 sequence has the amino acid sequence of SEQ ID NO: 11; or variants of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence of SEQ ID NO: 18; the light chain LCDR2 has the amino acid sequence of SEQ ID NO: 19; and the light chain LCDR3 sequence has the amino acid sequence of SEQ ID NO: 20 and (ii) a heavy chain variable region comprising heavy chain HCDR1, HCDR2, and HCDR3 sequences, wherein the heavy chain HCDR1 sequence has the amino acid sequence of SEQ ID NO: 15; the heavy chain HCDR2 sequence has the amino acid sequence of SEQ ID NO: 16; and the heavy chain HCDR3 sequence has the amino acid sequence of SEQ ID NO: 17; or variants of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence of SEQ ID NO: 24; the light chain LCDR2 has the amino acid sequence of SEQ ID NO: 25; and the light chain LCDR3 sequence has the amino acid sequence of SEQ ID NO: 26 and (ii) a heavy chain variable region comprising heavy chain HCDR1, HCDR2, and HCDR3 sequences, wherein the heavy chain HCDR1 sequence has the amino acid sequence of SEQ ID NO: 21; the heavy chain HCDR2 sequence has the amino acid sequence of SEQ ID NO: 22; and the heavy chain HCDR3 sequence has the amino acid sequence of SEQ ID NO: 23; or variants of any of the foregoing.

Although the preceding paragraphs may make reference to CDRs under the Kabat system the equivalent CDR sequences can be used from the IMGT and CHOTHIA designations.

For clarity, the following tables are provided depicting non-limiting exemplary combinations of light chain (Table 7) and heavy chain (Table 8) CDRs using IMGT designations:

TABLE 7

| Combination | LCDR1 | LCDR2 | LCDR3 |
| --- | --- | --- | --- |
| $V_L$Aa | SEQ ID NO: 45 | SEQ ID NO: 30 | SEQ ID NO: 14 |
| $V_L$Ba | SEQ ID NO: 45 | SEQ ID NO: 30 | SEQ ID NO: 20 |
| $V_L$Ca | SEQ ID NO: 45 | SEQ ID NO: 30 | SEQ ID NO: 26 |
| $V_L$Da | SEQ ID NO: 45 | SEQ ID NO: 35 | SEQ ID NO: 14 |
| $V_L$Ea | SEQ ID NO: 45 | SEQ ID NO: 35 | SEQ ID NO: 20 |
| $V_L$Fa | SEQ ID NO: 45 | SEQ ID NO: 35 | SEQ ID NO: 26 |
| $V_L$Ga | SEQ ID NO: 45 | SEQ ID NO: 40 | SEQ ID NO: 14 |
| $V_L$Ha | SEQ ID NO: 45 | SEQ ID NO: 40 | SEQ ID NO: 20 |
| $V_L$Ia | SEQ ID NO: 45 | SEQ ID NO: 40 | SEQ ID NO: 26 |
| $V_L$Ja | SEQ ID NO: 49 | SEQ ID NO: 30 | SEQ ID NO: 14 |
| $V_L$Ka | SEQ ID NO: 49 | SEQ ID NO: 30 | SEQ ID NO: 20 |
| $V_L$La | SEQ ID NO: 49 | SEQ ID NO: 30 | SEQ ID NO: 26 |
| $V_L$Ma | SEQ ID NO: 49 | SEQ ID NO: 35 | SEQ ID NO: 14 |
| $V_L$Na | SEQ ID NO: 49 | SEQ ID NO: 35 | SEQ ID NO: 20 |
| $V_L$Oa | SEQ ID NO: 49 | SEQ ID NO: 35 | SEQ ID NO: 26 |
| $V_L$Pa | SEQ ID NO: 49 | SEQ ID NO: 40 | SEQ ID NO: 14 |
| $V_L$Qa | SEQ ID NO: 49 | SEQ ID NO: 40 | SEQ ID NO: 20 |
| $V_L$Ra | SEQ ID NO: 49 | SEQ ID NO: 40 | SEQ ID NO: 26 |
| $V_L$Sa | SEQ ID NO: 53 | SEQ ID NO: 30 | SEQ ID NO: 14 |
| $V_L$Ta | SEQ ID NO: 53 | SEQ ID NO: 30 | SEQ ID NO: 20 |

TABLE 7-continued

| Combination | LCDR1 | LCDR2 | LCDR3 |
| --- | --- | --- | --- |
| $V_L$Ua | SEQ ID NO: 53 | SEQ ID NO: 30 | SEQ ID NO: 26 |
| $V_L$Va | SEQ ID NO: 53 | SEQ ID NO: 35 | SEQ ID NO: 14 |
| $V_L$Wa | SEQ ID NO: 53 | SEQ ID NO: 35 | SEQ ID NO: 20 |
| $V_L$Xa | SEQ ID NO: 53 | SEQ ID NO: 35 | SEQ ID NO: 26 |
| $V_L$Ya | SEQ ID NO: 53 | SEQ ID NO: 40 | SEQ ID NO: 14 |
| $V_L$Za | SEQ ID NO: 53 | SEQ ID NO: 40 | SEQ ID NO: 20 |
| $V_L$ABa | SEQ ID NO: 53 | SEQ ID NO: 40 | SEQ ID NO: 26 |

TABLE 8

| Combination | HCDR1 | HCDR2 | HCDR3 |
| --- | --- | --- | --- |
| $V_H$Aa | SEQ ID NO: 42 | SEQ ID NO: 43 | SEQ ID NO: 44 |
| $V_H$Ba | SEQ ID NO: 42 | SEQ ID NO: 43 | SEQ ID NO: 48 |
| $V_H$Ca | SEQ ID NO: 42 | SEQ ID NO: 43 | SEQ ID NO: 52 |
| $V_H$Da | SEQ ID NO: 42 | SEQ ID NO: 47 | SEQ ID NO: 44 |
| $V_H$Ea | SEQ ID NO: 42 | SEQ ID NO: 47 | SEQ ID NO: 48 |
| $V_H$Fa | SEQ ID NO: 42 | SEQ ID NO: 47 | SEQ ID NO: 52 |
| $V_H$Ga | SEQ ID NO: 42 | SEQ ID NO: 51 | SEQ ID NO: 44 |
| $V_H$Ha | SEQ ID NO: 42 | SEQ ID NO: 51 | SEQ ID NO: 48 |
| $V_H$Ia | SEQ ID NO: 42 | SEQ ID NO: 51 | SEQ ID NO: 52 |
| $V_H$Ja | SEQ ID NO: 46 | SEQ ID NO: 43 | SEQ ID NO: 44 |
| $V_H$Ka | SEQ ID NO: 46 | SEQ ID NO: 43 | SEQ ID NO: 48 |
| $V_H$La | SEQ ID NO: 46 | SEQ ID NO: 43 | SEQ ID NO: 52 |
| $V_H$Ma | SEQ ID NO: 46 | SEQ ID NO: 47 | SEQ ID NO: 44 |
| $V_H$Na | SEQ ID NO: 46 | SEQ ID NO: 47 | SEQ ID NO: 48 |
| $V_H$Oa | SEQ ID NO: 46 | SEQ ID NO: 47 | SEQ ID NO: 52 |
| $V_H$Pa | SEQ ID NO: 46 | SEQ ID NO: 51 | SEQ ID NO: 44 |
| $V_H$Qa | SEQ ID NO: 46 | SEQ ID NO: 51 | SEQ ID NO: 48 |
| $V_H$Ra | SEQ ID NO: 46 | SEQ ID NO: 51 | SEQ ID NO: 52 |
| $V_H$Sa | SEQ ID NO: 50 | SEQ ID NO: 43 | SEQ ID NO: 44 |
| $V_H$Ta | SEQ ID NO: 50 | SEQ ID NO: 43 | SEQ ID NO: 48 |
| $V_H$Ua | SEQ ID NO: 50 | SEQ ID NO: 43 | SEQ ID NO: 52 |
| $V_H$Va | SEQ ID NO: 50 | SEQ ID NO: 47 | SEQ ID NO: 44 |
| $V_H$Wa | SEQ ID NO: 50 | SEQ ID NO: 47 | SEQ ID NO: 48 |
| $V_H$Xa | SEQ ID NO: 50 | SEQ ID NO: 47 | SEQ ID NO: 52 |
| $V_H$Ya | SEQ ID NO: 50 | SEQ ID NO: 51 | SEQ ID NO: 44 |
| $V_H$Za | SEQ ID NO: 50 | SEQ ID NO: 51 | SEQ ID NO: 48 |
| $V_H$ABa | SEQ ID NO: 50 | SEQ ID NO: 51 | SEQ ID NO: 52 |

In some embodiments, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences. The following combinations are provided with reference to Table 7 and Table 8 above. Thus, for example, an antibody or antibody binding fragment thereof comprising $V_L$Aa and $V_H$Aa is understood to comprise a light chain having a LCDR1 of SEQ ID NO: 45, a LCDR2 of SEQ ID NO: 30, a LCDR3 of SEQ ID NO: 14, a HCDR1 of SEQ ID NO: 42, a HCDR2 of SEQ ID NO: 43, and a HCDR3 of SEQ ID NO: 44.

Accordingly, in some embodiments, an antibody or antibody binding fragment thereof comprises $V_L$Aa and $V_H$Aa. In some embodiments, an antibody or antibody binding fragment thereof comprises $V_L$Ba and $V_H$Aa. In some embodiments, an antibody or antibody binding fragment thereof comprises $V_L$Ca and $V_H$Aa. In some embodiments, an antibody or antibody binding fragment thereof comprises $V_L$Da and $V_H$Aa. In some embodiments, an antibody or antibody binding fragment thereof comprises $V_L$Ea and $V_H$Aa. In some embodiments, an antibody or antibody binding fragment thereof comprises $V_L$Fa and $V_H$Aa. In some embodiments, an antibody or antibody binding fragment thereof comprises $V_L$Ga and $V_H$Aa. In some embodiments, an antibody or antibody binding fragment thereof comprises $V_L$Ha and $V_H$Aa. In some embodiments, an antibody or antibody binding fragment thereof comprises $V_L$Ia and $V_H$Aa. In some embodiments, an antibody or antibody binding fragment thereof comprises $V_L$Ja and $V_H$Aa. In some embodiments, an antibody or antibody binding fragment thereof comprises $V_L$Ka and $V_H$Aa. In some embodiments, an antibody or antibody binding fragment thereof comprises $V_L$La and $V_H$Aa. In some embodiments, an antibody or antibody binding fragment thereof comprises $V_L$Ma and $V_H$Aa. In some embodiments, an antibody or antibody binding fragment thereof comprises $V_L$Na and $V_H$Aa. In some embodiments, an antibody or antibody binding fragment thereof comprises $V_L$Oa and $V_H$Aa. In some embodiments, an antibody or antibody binding fragment thereof comprises $V_L$Pa and $V_H$Aa. In some embodiments, an antibody or antibody binding fragment thereof comprises $V_L$Qa and $V_H$Aa. In some embodiments, an antibody or antibody binding fragment thereof comprises $V_L$Ra and $V_H$Aa. In some embodiments, an antibody or antibody binding fragment thereof comprises $V_L$Sa and $V_H$Aa. In some embodiments, an antibody or antibody binding fragment thereof comprises $V_L$Ta and $V_H$Aa. In some embodiments, an antibody or antibody binding fragment thereof comprises $V_L$Ua and $V_H$Aa. In some embodiments, an antibody or antibody binding fragment thereof comprises $V_L$Va and $V_H$Aa. In some embodiments, an antibody or antibody binding fragment thereof comprises $V_L$Wa and $V_H$Aa. In some embodiments, an antibody or antibody binding fragment thereof comprises $V_L$Xa and $V_H$Aa. In some embodiments, an antibody or antibody binding fragment thereof comprises $V_L$Ya and $V_H$Aa. In some embodiments, an antibody or antibody binding fragment thereof comprises $V_L$Za and $V_H$Aa. In some embodiments, an antibody or antibody binding fragment thereof comprises $V_L$ABa and $V_H$Aa.

In some embodiments, an antibody or antibody binding fragment thereof comprises $V_L$Aa and $V_H$Ba. In some embodiments, an antibody or antibody binding fragment thereof comprises $V_L$Ba and $V_H$Ba. In some embodiments, an antibody or antibody binding fragment thereof comprises $V_L$Ca and $V_H$Ba. In some embodiments, an antibody or antibody binding fragment thereof comprises $V_L$Da and $V_H$Ba. In some embodiments, an antibody or antibody binding fragment thereof comprises $V_L$Ea and $V_H$Ba. In some embodiments, an antibody or antibody binding fragment thereof comprises $V_L$Fa and $V_H$Ba. In some embodiments, an antibody or antibody binding fragment thereof comprises $V_L$Ga and $V_H$Ba. In some embodiments, an antibody or antibody binding fragment thereof comprises $V_L$Ha and $V_H$Ba. In some embodiments, an antibody or antibody binding fragment thereof comprises $V_L$Ia and $V_H$Ba. In some embodiments, an antibody or antibody binding fragment thereof comprises $V_L$Ja and $V_H$Ba. In some embodiments, an antibody or antibody binding fragment thereof comprises $V_L$Ka and $V_H$Ba. In some embodiments, an antibody or antibody binding fragment thereof comprises $V_L$La and $V_H$Ba. In some embodiments, an antibody or antibody binding fragment thereof comprises $V_L$Ma and $V_H$Ba. In some embodiments, an antibody or antibody binding fragment thereof comprises $V_L$Na and $V_H$Ba. In some embodiments, an antibody or antibody binding fragment thereof comprises $V_L$Oa and $V_H$Ba. In some embodiments, an antibody or antibody binding fragment thereof comprises $V_L$Pa and $V_H$Ba. In some embodiments, an antibody or antibody binding fragment thereof comprises $V_L$Qa and $V_H$Ba. In some embodiments, an antibody or antibody binding fragment thereof comprises $V_L$Ra and $V_H$Ba. In some embodiments, an antibody or antibody binding fragment thereof comprises $V_L$Sa and $V_H$Ba. In some embodiments, an antibody or antibody binding fragment thereof comprises $V_L$Ta and $V_H$Ba. In some embodiments, an antibody or antibody binding fragment thereof comprises $V_L$Ua and $V_H$Ba. In some embodiments, an antibody or antibody binding fragment thereof comprises $V_L$Va and $V_H$Ba. In some embodiments, an antibody or antibody binding fragment thereof comprises $V_L$Wa and $V_H$Ba. In some embodiments, an antibody or antibody binding fragment thereof comprises $V_L$Xa and $V_H$Ba. In some embodiments, an antibody or antibody binding fragment thereof comprises $V_L$Ya and $V_H$Ba. In some embodiments, an antibody or antibody binding fragment thereof comprises $V_L$Za and $V_H$Ba. In some embodiments, an antibody or antibody binding fragment thereof comprises $V_L$ABa and $V_H$Ba.

In some embodiments, an antibody or antibody binding fragment thereof comprises $V_L$Aa and $V_H$Ca. In some embodiments, an antibody or antibody binding fragment thereof comprises $V_L$Ba and $V_H$Ca. In some embodiments, an antibody or antibody binding fragment thereof comprises $V_L$Ca and $V_H$Ca. In some embodiments, an antibody or antibody binding fragment thereof comprises $V_L$Da and $V_H$Ca. In some embodiments, an antibody or antibody binding fragment thereof comprises $V_L$Ea and $V_H$Ca. In some embodiments, an antibody or antibody binding fragment thereof comprises $V_L$Fa and $V_H$Ca. In some embodiments, an antibody or antibody binding fragment thereof comprises $V_L$Ga and $V_H$Ca. In some embodiments, an antibody or antibody binding fragment thereof comprises $V_L$Ha and $V_H$Ca. In some embodiments, an antibody or antibody binding fragment thereof comprises $V_L$Ia and $V_H$Ca. In some embodiments, an antibody or antibody binding fragment thereof comprises $V_L$Ja and $V_H$Ca. In some embodiments, an antibody or antibody binding fragment thereof comprises $V_L$Ka and $V_H$Ca. In some embodiments, an antibody or antibody binding fragment thereof comprises $V_L$La and $V_H$Ca. In some embodiments, an antibody or antibody binding fragment thereof comprises $V_L$Ma and $V_H$Ca. In some embodiments, an antibody or antibody binding fragment thereof comprises $V_L$Na and $V_H$Ca. In some embodiments, an antibody or antibody binding fragment thereof comprises $V_L$Oa and $V_H$Ca. In some embodiments, an antibody or antibody binding fragment thereof comprises $V_L$Pa and $V_H$Ca. In some embodiments, an antibody or antibody binding fragment thereof comprises $V_L$Qa and $V_H$Ca. In some embodiments, an antibody or antibody binding fragment thereof comprises $V_L$Ra and $V_H$Ca. In some embodiments, an antibody or antibody binding fragment thereof comprises $V_L$Sa and $V_H$Ca. In some embodiments, an antibody or antibody binding fragment thereof comprises $V_L$Ta and $V_H$Ca. In some embodiments, an antibody or antibody binding fragment thereof comprises $V_L$Ua and $V_H$Ca. In some embodiments, an antibody or antibody binding fragment thereof comprises $V_L$Va and $V_H$Ca. In some embodiments, an antibody or antibody binding fragment thereof comprises $V_L$Wa and $V_H$Ca. In some embodiments, an antibody or antibody binding fragment thereof comprises $V_L$Xa and $V_H$Ca. In some embodiments, an antibody or antibody binding fragment thereof comprises $V_L$Ya and $V_H$Ca. In some embodiments, an antibody or antibody binding fragment thereof comprises $V_L$Za and $V_H$Ca. In some embodiments, an antibody or antibody binding fragment thereof comprises $V_L$ABa and $V_H$Ca.

In some embodiments, an antibody or antibody binding fragment thereof comprises $V_L$Aa and $V_H$Da. In some embodiments, an antibody or antibody binding fragment thereof comprises $V_L$Ba and $V_H$Da. In some embodiments, an antibody or antibody binding fragment thereof comprises $V_L$Ca and $V_H$Da. In some embodiments, an antibody or antibody binding fragment thereof comprises $V_L$Da and $V_H$Da. In some embodiments, an antibody or antibody binding fragment thereof comprises $V_L$Ea and $V_H$Da. In some embodiments, an antibody or antibody binding fragment thereof comprises $V_L$Fa and $V_H$Da. In some embodiments, an antibody or antibody binding fragment thereof comprises $V_L$Ga and $V_H$Da. In some embodiments, an antibody or antibody binding fragment thereof comprises $V_L$Ha and $V_H$Da. In some embodiments, an antibody or antibody binding fragment thereof comprises $V_L$Ia and $V_H$Da. In some embodiments, an antibody or antibody binding fragment thereof comprises $V_L$Ja and $V_H$Da. In some embodiments, an antibody or antibody binding fragment thereof comprises $V_L$Ka and $V_H$Da. In some embodiments, an antibody or antibody binding fragment thereof comprises $V_L$La and $V_H$Da. In some embodiments, an antibody or antibody binding fragment thereof comprises $V_L$Ma and $V_H$Da. In some embodiments, an antibody or antibody binding fragment thereof comprises $V_L$Na and $V_H$Da. In some embodiments, an antibody or antibody binding fragment thereof comprises $V_L$Oa and $V_H$Da. In some embodiments, an antibody or antibody binding fragment thereof comprises $V_L$Pa and $V_H$Da. In some embodiments, an antibody or antibody binding fragment thereof comprises $V_L$Qa and $V_H$Da. In some embodiments, an antibody or antibody binding fragment thereof comprises $V_L$Ra and $V_H$Da. In some embodiments, an antibody or antibody binding fragment thereof comprises $V_L$Sa and $V_H$Da. In some embodiments, an antibody or antibody binding fragment thereof comprises $V_L$Ta and $V_H$Da. In some embodiments, an antibody or antibody binding fragment thereof comprises $V_L$Ua and $V_H$Da. In some embodiments, an antibody or antibody binding fragment thereof comprises $V_L$Va and $V_H$Da. In some embodiments, an antibody or antibody binding fragment thereof comprises $V_L$Wa and $V_H$Da. In some embodiments, an antibody or antibody binding fragment thereof comprises $V_L$Xa and $V_H$Da. In some embodiments, an antibody or antibody binding fragment thereof comprises $V_L$Ya and $V_H$Da. In some embodiments, an antibody or antibody binding fragment thereof comprises $V_L$Za and $V_H$Da. In some embodiments, an antibody or antibody binding fragment thereof comprises $V_L$ABa and $V_H$Da.

In some embodiments, an antibody or antibody binding fragment thereof comprises $V_L$Aa and $V_H$Ea. In some embodiments, an antibody or antibody binding fragment thereof comprises $V_L$Ba and $V_H$Ea. In some embodiments, an antibody or antibody binding fragment thereof comprises $V_L$Ca and $V_H$Ea. In some embodiments, an antibody or antibody binding fragment thereof comprises $V_L$Da and $V_H$Ea. In some embodiments, an antibody or antibody binding fragment thereof comprises $V_L$Ea and $V_H$Ea. In some embodiments, an antibody or antibody binding fragment thereof comprises $V_L$ Fa and $V_H$Ea. In some embodiments, an antibody or antibody binding fragment thereof comprises $V_L$Ga and $V_H$Ea. In some embodiments, an antibody or antibody binding fragment thereof comprises $V_L$Ha and $V_H$Ea. In some embodiments, an antibody or antibody binding fragment thereof comprises $V_L$Ia and $V_H$Ea. In some embodiments, an antibody or antibody binding fragment thereof comprises $V_L$Ja and $V_H$Ea. In some embodiments, an antibody or antibody binding fragment thereof comprises $V_L$Ka and $V_H$Ea. In some embodiments, an antibody or antibody binding fragment thereof comprises $V_L$La and $V_H$Ea. In some embodiments, an antibody or antibody binding fragment thereof comprises $V_L$Ma and $V_H$Ea. In some embodiments, an antibody or antibody binding fragment thereof comprises $V_L$Na and $V_H$Ea. In some embodiments, an antibody or antibody binding fragment thereof comprises $V_L$Oa and $V_H$Ea. In some embodiments, an antibody or antibody binding fragment thereof comprises $V_L$Pa and $V_H$Ea. In some embodiments, an antibody or antibody binding fragment thereof comprises $V_L$Qa and $V_H$Ea. In some embodiments, an antibody or antibody binding fragment thereof comprises $V_L$Ra and $V_H$Ea. In some embodiments, an antibody or antibody binding fragment thereof comprises $V_L$Sa and $V_H$Ea. In some embodiments, an antibody or antibody binding fragment thereof comprises $V_L$Ta and $V_H$Ea. In some embodiments, an antibody or antibody binding fragment thereof comprises $V_L$Ua and $V_H$Ea. In some embodiments, an antibody or antibody binding fragment thereof comprises $V_L$Va and $V_H$Ea. In some embodiments, an antibody or antibody binding fragment thereof comprises $V_L$Wa and $V_H$Ea. In some embodiments, an antibody or antibody binding fragment thereof comprises $V_L$Xa and $V_H$Ea. In some embodiments, an antibody or antibody binding fragment thereof comprises $V_L$Ya and $V_H$Ea. In some embodiments, an antibody or antibody binding fragment thereof comprises $V_L$Za and $V_H$Ea. In some embodiments, an antibody or antibody binding fragment thereof comprises $V_L$ABa and $V_H$Ea. In some embodiments, an antibody or antibody binding fragment thereof comprises $V_L$Aa and $V_H$Fa. In some embodiments, an antibody or antibody binding fragment thereof comprises $V_L$Ba and $V_H$Fa. In some embodiments, an antibody or antibody binding fragment thereof comprises $V_L$Ca and $V_H$Fa. In some embodiments, an antibody or antibody binding fragment thereof comprises $V_L$Da and $V_H$Fa. In some embodiments, an antibody or antibody binding fragment thereof comprises $V_L$Ea and $V_H$Fa. In some embodiments, an antibody or antibody binding fragment thereof comprises $V_L$Fa and $V_H$Fa. In some embodiments, an antibody or antibody binding fragment thereof comprises $V_L$Ga and $V_H$Fa. In some embodiments, an antibody or antibody binding fragment thereof comprises $V_L$Ha and $V_H$Fa. In some embodiments, an antibody or antibody binding fragment thereof comprises $V_L$Ia and $V_H$Fa. In some embodiments, an antibody or antibody binding fragment thereof comprises $V_L$Ja and $V_H$Fa. In some embodiments, an antibody or antibody binding fragment thereof comprises $V_L$Ka and $V_H$Fa. In some embodiments, an antibody or antibody binding fragment thereof comprises $V_L$La and $V_H$Fa. In some embodiments, an antibody or antibody binding fragment thereof comprises $V_L$Ma and $V_H$Fa. In some embodiments, an antibody or antibody binding fragment thereof comprises $V_L$Na and $V_H$Fa. In some embodiments, an antibody or antibody binding fragment thereof comprises $V_L$Oa and $V_H$Fa. In some embodiments, an antibody or antibody binding fragment thereof comprises $V_L$Pa and $V_H$Fa. In some embodiments, an antibody or antibody binding fragment thereof comprises $V_L$Qa and $V_H$Fa. In some embodiments, an antibody or antibody binding fragment thereof comprises $V_L$Ra and $V_H$Fa. In some embodiments, an antibody or antibody binding fragment thereof comprises $V_L$Sa and $V_H$Fa. In some embodiments, an antibody or antibody binding fragment thereof comprises $V_L$Ta and $V_H$Fa. In some embodiments, an antibody or antibody binding fragment thereof comprises $V_L$Ua and $V_H$Fa. In some embodiments, an antibody or antibody binding fragment thereof comprises $V_L$Va and $V_H$Fa. In some embodiments, an antibody or antibody binding fragment thereof comprises $V_L$Wa and $V_H$Fa. In some embodiments, an antibody or antibody binding fragment thereof comprises $V_L$Xa and $V_H$Fa. In some embodiments, an antibody or antibody binding fragment thereof comprises $V_L$Ya and $V_H$Fa. In some embodiments, an antibody or antibody binding fragment thereof comprises $V_L$Za and $V_H$Fa. In some embodiments, an antibody or antibody binding fragment thereof comprises $V_L$ABa and $V_H$Fa.

In some embodiments, an antibody or antibody binding fragment thereof comprises $V_L$Aa and $V_H$Ga. In some embodiments, an antibody or antibody binding fragment thereof comprises $V_L$Ba and $V_H$Ga. In some embodiments, an antibody or antibody binding fragment thereof comprises $V_L$Ca and $V_H$Ga. In some embodiments, an antibody or antibody binding fragment thereof comprises $V_L$Da and $V_H$Ga. In some embodiments, an antibody or antibody binding fragment thereof comprises $V_L$Ea and $V_H$Ga. In some embodiments, an antibody or antibody binding fragment thereof comprises $V_L$Fa and $V_H$Ga. In some embodiments, an antibody or antibody binding fragment thereof comprises $V_L$Ga and $V_H$Ga. In some embodiments, an antibody or antibody binding fragment thereof comprises $V_L$Ha and $V_H$Ga. In some embodiments, an antibody or antibody binding fragment thereof comprises $V_L$Ia and $V_H$Ga. In some embodiments, an antibody or antibody binding fragment thereof comprises $V_L$Ja and $V_H$Ga. In some embodiments, an antibody or antibody binding fragment thereof comprises $V_L$Ka and $V_H$Ga. In some embodiments, an antibody or antibody binding fragment thereof comprises $V_L$La and $V_H$Ga. In some embodiments, an antibody or antibody binding fragment thereof comprises $V_L$Ma and $V_H$Ga. In some embodiments, an antibody or antibody binding fragment thereof comprises $V_L$Na and $V_H$Ga. In some embodiments, an antibody or antibody binding fragment thereof comprises $V_L$Oa and $V_H$Ga. In some embodiments, an antibody or antibody binding fragment thereof comprises $V_L$Pa and $V_H$Ga. In some embodiments, an antibody or antibody binding fragment thereof comprises $V_L$Qa and $V_H$Ga. In some embodiments, an antibody or antibody binding fragment thereof comprises $V_L$Ra and $V_H$Ga. In some embodiments, an antibody or antibody binding fragment thereof comprises $V_L$Sa and $V_H$Ga. In some embodiments, an antibody or antibody binding fragment thereof comprises $V_L$Ta and $V_H$Ga. In some embodiments, an antibody or antibody binding fragment thereof comprises $V_L$Ua and $V_H$Ga. In some embodiments, an antibody or antibody binding fragment thereof comprises $V_L$Va and $V_H$Ga. In some embodiments, an antibody or antibody binding fragment thereof comprises $V_L$Wa and $V_H$Ga. In some embodiments, an antibody or antibody binding fragment thereof comprises $V_L$Xa and $V_H$Ga. In some embodiments, an antibody or antibody binding fragment thereof comprises $V_L$Ya and $V_H$Ga. In some embodiments, an antibody or antibody binding fragment thereof comprises $V_L$Za and $V_H$Ga. In some embodiments, an antibody or antibody binding fragment thereof comprises $V_L$ABa and $V_H$Ga.

In some embodiments, an antibody or antibody binding fragment thereof comprises $V_L$Aa and $V_H$Ha. In some embodiments, an antibody or antibody binding fragment thereof comprises $V_L$Ba and $V_H$Ha. In some embodiments, an antibody or antibody binding fragment thereof comprises $V_L$Ca and $V_H$Ha. In some embodiments, an antibody or antibody binding fragment thereof comprises $V_L$Da and $V_H$Ha. In some embodiments, an antibody or antibody binding fragment thereof comprises $V_L$Ea and $V_H$Ha. In some embodiments, an antibody or antibody binding fragment thereof comprises $V_L$Fa and $V_H$Ha. In some embodiments, an antibody or antibody binding fragment thereof comprises $V_L$Ga and $V_H$Ha. In some embodiments, an antibody or antibody binding fragment thereof comprises $V_L$Ha and $V_H$Ha. In some embodiments, an antibody or antibody binding fragment thereof comprises $V_L$Ia and $V_H$Ha. In some embodiments, an antibody or antibody binding fragment thereof comprises $V_L$Ja and $V_H$Ha. In some embodiments, an antibody or antibody binding fragment thereof comprises $V_L$Ka and $V_H$Ha. In some embodiments, an antibody or antibody binding fragment thereof comprises $V_L$La and $V_H$Ha. In some embodiments, an antibody or antibody binding fragment thereof comprises $V_L$Ma and $V_H$Ha. In some embodiments, an antibody or antibody binding fragment thereof comprises $V_L$Na and $V_H$Ha. In some embodiments, an antibody or antibody binding fragment thereof comprises $V_L$Oa and $V_H$Ha. In some embodiments, an antibody or antibody binding fragment thereof comprises $V_L$Pa and $V_H$Ha. In some embodiments, an antibody or antibody binding fragment thereof comprises $V_L$Qa and $V_H$Ha. In some embodiments, an antibody or antibody binding fragment thereof comprises $V_L$Ra and $V_H$Ha. In some embodiments, an antibody or antibody binding fragment thereof comprises $V_L$Sa and $V_H$Ha. In some embodiments, an antibody or antibody binding fragment thereof comprises $V_L$Ta and $V_H$Ha. In some embodiments, an antibody or antibody binding fragment thereof comprises $V_L$Ua and $V_H$Ha. In some embodiments, an antibody or antibody binding fragment thereof comprises $V_L$Va and $V_H$Ha. In some embodiments, an antibody or antibody binding fragment thereof comprises $V_L$Wa and $V_H$Ha. In some embodiments, an antibody or antibody binding fragment thereof comprises $V_L$Xa and $V_H$Ha. In some embodiments, an antibody or antibody binding fragment thereof comprises $V_L$Ya and $V_H$Ha. In some embodiments, an antibody or antibody binding fragment thereof comprises $V_L$Za and $V_H$Ha. In some embodiments, an antibody or antibody binding fragment thereof comprises $V_L$ABa and $V_H$Ha.

In some embodiments, an antibody or antibody binding fragment thereof comprises $V_L$Aa and $V_H$Ia. In some embodiments, an antibody or antibody binding fragment thereof comprises $V_L$Ba and $V_H$Ia. In some embodiments, an antibody or antibody binding fragment thereof comprises $V_L$Ca and $V_H$Ia. In some embodiments, an antibody or antibody binding fragment thereof comprises $V_L$Da and $V_H$Ia. In some embodiments, an antibody or antibody binding fragment thereof comprises $V_L$Ea and $V_H$Ia. In some embodiments, an antibody or antibody binding fragment thereof comprises $V_L$Fa and $V_H$Ia. In some embodiments, an antibody or antibody binding fragment thereof comprises $V_L$Ga and $V_H$Ia. In some embodiments, an antibody or antibody binding fragment thereof comprises $V_L$Ha and $V_H$Ia. In some embodiments, an antibody or antibody binding fragment thereof comprises $V_L$Ia and $V_H$Ia. In some embodiments, an antibody or antibody binding fragment thereof comprises $V_L$Ja and $V_H$Ia. In some embodiments, an antibody or antibody binding fragment thereof comprises $V_L$Ka and $V_H$Ia. In some embodiments, an antibody or antibody binding fragment thereof comprises $V_L$La and $V_H$Ia. In some embodiments, an antibody or antibody binding fragment thereof comprises $V_L$Ma and $V_H$Ia. In some embodiments, an antibody or antibody binding fragment thereof comprises $V_L$Na and $V_H$Ia. In some embodiments, an antibody or antibody binding fragment thereof comprises $V_L$Oa and $V_H$Ia. In some embodiments, an antibody or antibody binding fragment thereof comprises $V_L$Pa and $V_H$Ia. In some embodiments, an antibody or antibody binding fragment thereof comprises $V_L$Qa and $V_H$Ia. In some embodiments, an antibody or antibody binding fragment thereof comprises $V_L$Ra and $V_H$Ia. In some embodiments, an antibody or antibody binding fragment thereof comprises $V_L$Sa and $V_H$Ia. In some embodiments, an antibody or antibody binding fragment thereof comprises $V_L$Ta and $V_H$Ia. In some embodiments, an antibody or antibody binding fragment thereof comprises $V_L$Ua and $V_H$Ia. In some embodiments, an antibody or antibody binding fragment thereof comprises $V_L$Va and $V_H$Ia. In some embodiments, an antibody or antibody binding fragment thereof comprises $V_L$Wa and $V_H$Ia. In some embodiments, an antibody or antibody binding fragment thereof comprises $V_L$Xa and $V_H$Ia. In some embodiments, an antibody or antibody binding fragment thereof comprises $V_L$Ya and $V_H$Ia. In some embodiments, an antibody or antibody binding fragment thereof comprises $V_L$Za and $V_H$Ia. In some embodiments, an antibody or antibody binding fragment thereof comprises $V_L$ABa and $V_H$Ia.

In some embodiments, an antibody or antibody binding fragment thereof comprises $V_L$Aa and $V_H$Ja. In some embodiments, an antibody or antibody binding fragment thereof comprises $V_L$Ba and $V_H$Ja. In some embodiments, an antibody or antibody binding fragment thereof comprises $V_L$Ca and $V_H$Ja. In some embodiments, an antibody or antibody binding fragment thereof comprises $V_L$Da and $V_H$Ja. In some embodiments, an antibody or antibody binding fragment thereof comprises $V_L$Ea and $V_H$Ja. In some embodiments, an antibody or antibody binding fragment thereof comprises $V_L$Fa and $V_H$Ja. In some embodiments, an antibody or antibody binding fragment thereof comprises $V_L$Ga and $V_H$Ja. In some embodiments, an antibody or antibody binding fragment thereof comprises $V_L$Ha and $V_H$Ja. In some embodiments, an antibody or antibody binding fragment thereof comprises $V_L$Ia and $V_H$Ja. In some embodiments, an antibody or antibody binding fragment thereof comprises $V_L$Ja and $V_H$Ja. In some embodiments, an antibody or antibody binding fragment thereof comprises $V_L$Ka and $V_H$Ja. In some embodiments, an antibody or antibody binding fragment thereof comprises $V_L$La and $V_H$Ja. In some embodiments, an antibody or antibody binding fragment thereof comprises $V_L$Ma and $V_H$Ja. In some embodiments, an antibody or antibody binding fragment thereof comprises $V_L$Na and $V_H$Ja. In some embodiments, an antibody or antibody binding fragment thereof comprises $V_L$Oa and $V_H$Ja. In some embodiments, an antibody or antibody binding fragment thereof comprises $V_L$Pa and $V_H$Ja. In some embodiments, an antibody or antibody binding fragment thereof comprises $V_L$Qa and $V_H$Ja. In some embodiments, an antibody or antibody binding fragment thereof comprises $V_L$Ra and $V_H$Ja. In some embodiments, an antibody or antibody binding fragment thereof comprises $V_L$Sa and $V_H$Ja. In some embodiments, an antibody or antibody binding fragment thereof comprises $V_L$Ta and $V_H$Ja. In some embodiments, an antibody or antibody binding fragment thereof comprises $V_L$Ua and $V_H$Ja. In some embodiments, an antibody or antibody binding fragment thereof comprises $V_L$Va and $V_H$Ja. In some embodiments, an antibody or antibody binding fragment thereof comprises $V_L$Wa and $V_H$Ja. In some embodiments, an antibody or antibody binding fragment thereof comprises $V_L$Xa and $V_H$Ja. In some embodiments, an antibody or antibody binding fragment thereof comprises $V_L$Ya and $V_H$Ja. In some embodiments, an antibody or antibody binding fragment thereof comprises $V_L$Za and $V_H$Ja. In some embodiments, an antibody or antibody binding fragment thereof comprises $V_L$ABa and $V_H$Ja.

In some embodiments, an antibody or antibody binding fragment thereof comprises $V_L$Aa and $V_H$Ka. In some embodiments, an antibody or antibody binding fragment thereof comprises $V_L$Ba and $V_H$Ka. In some embodiments, an antibody or antibody binding fragment thereof comprises $V_L$Ca and $V_H$Ka. In some embodiments, an antibody or antibody binding fragment thereof comprises $V_L$Da and $V_H$Ka. In some embodiments, an antibody or antibody binding fragment thereof comprises $V_L$Ea and $V_H$Ka. In some embodiments, an antibody or antibody binding fragment thereof comprises $V_L$Fa and $V_H$Ka. In some embodiments, an antibody or antibody binding fragment thereof comprises $V_L$Ga and $V_H$Ka. In some embodiments, an antibody or antibody binding fragment thereof comprises $V_L$Ha and $V_H$Ka. In some embodiments, an antibody or antibody binding fragment thereof comprises $V_L$Ia and $V_H$Ka. In some embodiments, an antibody or antibody binding fragment thereof comprises $V_L$Ja and $V_H$Ka. In some embodiments, an antibody or antibody binding fragment thereof comprises $V_L$Ka and $V_H$Ka. In some embodiments, an antibody or antibody binding fragment thereof comprises $V_L$La and $V_H$Ka. In some embodiments, an antibody or antibody binding fragment thereof comprises $V_L$Ma and $V_H$Ka. In some embodiments, an antibody or antibody binding fragment thereof comprises $V_L$Na and $V_H$Ka. In some embodiments, an antibody or antibody binding fragment thereof comprises $V_L$Oa and $V_H$Ka. In some embodiments, an antibody or antibody binding fragment thereof comprises $V_L$Pa and $V_H$Ka. In some embodiments, an antibody or antibody binding fragment thereof comprises $V_L$Qa and $V_H$Ka. In some embodiments, an antibody or antibody binding fragment thereof comprises $V_L$Ra and $V_H$Ka. In some embodiments, an antibody or antibody binding fragment thereof comprises $V_L$Sa and $V_H$Ka. In some embodiments, an antibody or antibody binding fragment thereof comprises $V_L$Ta and $V_H$Ka. In some embodiments, an antibody or antibody binding fragment thereof comprises $V_L$Ua and $V_H$Ka. In some embodiments, an antibody or antibody binding fragment thereof comprises $V_L$Va and $V_H$Ka. In some embodiments, an antibody or antibody binding fragment thereof comprises $V_L$Wa and $V_H$Ka. In some embodiments, an antibody or antibody binding fragment thereof comprises $V_L$Xa and $V_H$Ka. In some embodiments, an antibody or antibody binding fragment thereof comprises $V_L$Ya and $V_H$Ka. In some embodiments, an antibody or antibody binding fragment thereof comprises $V_L$Za and $V_H$Ka. In some embodiments, an antibody or antibody binding fragment thereof comprises $V_L$ABa and $V_H$Ka.

In some embodiments, an antibody or antibody binding fragment thereof comprises $V_L$Aa and $V_H$La. In some embodiments, an antibody or antibody binding fragment thereof comprises $V_L$Ba and $V_H$La. In some embodiments, an antibody or antibody binding fragment thereof comprises $V_L$Ca and $V_H$La. In some embodiments, an antibody or antibody binding fragment thereof comprises $V_L$Da and $V_H$La. In some embodiments, an antibody or antibody binding fragment thereof comprises $V_L$Ea and $V_H$La. In some embodiments, an antibody or antibody binding fragment thereof comprises $V_L$Fa and $V_H$La. In some embodiments, an antibody or antibody binding fragment thereof comprises $V_L$Ga and $V_H$La. In some embodiments, an antibody or antibody binding fragment thereof comprises $V_L$Ha and $V_H$La. In some embodiments, an antibody or antibody binding fragment thereof comprises $V_L$Ia and $V_H$La. In some embodiments, an antibody or antibody binding fragment thereof comprises $V_L$Ja and $V_H$La. In some embodiments, an antibody or antibody binding fragment thereof comprises $V_L$Ka and $V_H$La. In some embodiments, an antibody or antibody binding fragment thereof comprises $V_L$La and $V_H$La. In some embodiments, an antibody or antibody binding fragment thereof comprises $V_L$Ma and $V_H$La. In some embodiments, an antibody or antibody binding fragment thereof comprises $V_L$Na and $V_H$La. In some embodiments, an antibody or antibody binding fragment thereof comprises $V_L$Oa and $V_H$La. In some embodiments, an antibody or antibody binding fragment thereof comprises $V_L$Pa and $V_H$La. In some embodiments, an antibody or antibody binding fragment thereof comprises $V_L$Qa and $V_H$La. In some embodiments, an antibody or antibody binding fragment thereof comprises $V_L$Ra and $V_H$La. In some embodiments, an antibody or antibody binding fragment thereof comprises $V_L$Sa and $V_H$La. In some embodiments, an antibody or antibody binding fragment thereof comprises $V_L$Ta and $V_H$La. In some embodiments, an antibody or antibody binding fragment thereof comprises $V_L$Ua and $V_H$La. In some embodiments, an antibody or antibody binding fragment thereof comprises $V_L$Va and $V_H$La. In some embodiments, an antibody or antibody binding fragment thereof comprises $V_L$Wa and $V_H$La. In some embodiments, an antibody or antibody binding fragment thereof comprises $V_L$Xa and $V_H$La. In some embodiments, an antibody or antibody binding fragment thereof comprises $V_L$Ya and $V_H$La. In some embodiments, an antibody or antibody binding fragment thereof comprises $V_L$Za and $V_H$La. In some embodiments, an antibody or antibody binding fragment thereof comprises $V_L$ABa and $V_H$La.

In some embodiments, an antibody or antibody binding fragment thereof comprises $V_L$Aa and $V_H$Ma. In some embodiments, an antibody or antibody binding fragment thereof comprises $V_L$Ba and $V_H$Ma. In some embodiments, an antibody or antibody binding fragment thereof comprises $V_L$Ca and $V_H$Ma. In some embodiments, an antibody or antibody binding fragment thereof comprises $V_L$Da and $V_H$Ma. In some embodiments, an antibody or antibody binding fragment thereof comprises $V_L$Ea and $V_H$Ma. In some embodiments, an antibody or antibody binding fragment thereof comprises $V_L$Fa and $V_H$Ma. In some embodiments, an antibody or antibody binding fragment thereof comprises $V_L$Ga and $V_H$Ma. In some embodiments, an antibody or antibody binding fragment thereof comprises $V_L$Ha and $V_H$Ma. In some embodiments, an antibody or antibody binding fragment thereof comprises $V_L$Ia and $V_H$Ma. In some embodiments, an antibody or antibody binding fragment thereof comprises $V_L$Ja and $V_H$Ma. In some embodiments, an antibody or antibody binding fragment thereof comprises $V_L$Ka and $V_H$Ma. In some embodiments, an antibody or antibody binding fragment thereof comprises $V_L$La and $V_H$Ma. In some embodiments, an antibody or antibody binding fragment thereof comprises $V_L$Ma and $V_H$Ma. In some embodiments, an antibody or antibody binding fragment thereof comprises $V_L$Na and $V_H$Ma. In some embodiments, an antibody or antibody binding fragment thereof comprises $V_L$Oa and $V_H$Ma. In some embodiments, an antibody or antibody binding fragment thereof comprises $V_L$Pa and $V_H$Ma. In some embodiments, an antibody or antibody binding fragment thereof comprises $V_L$Qa and $V_H$Ma. In some embodiments, an antibody or antibody binding fragment thereof comprises $V_L$Ra and $V_H$Ma. In some embodiments, an antibody or antibody binding fragment thereof comprises $V_L$Sa and $V_H$Ma. In some embodiments, an antibody or antibody binding fragment thereof comprises $V_L$Ta and $V_H$Ma. In some embodiments, an antibody or antibody binding fragment thereof comprises $V_L$Ua and $V_H$Ma. In some embodiments, an antibody or antibody binding fragment thereof comprises $V_L$Va and $V_H$Ma. In some embodiments, an antibody or antibody binding fragment thereof comprises $V_L$Wa and $V_H$Ma. In some embodiments, an antibody or antibody binding fragment thereof comprises $V_L$Xa and $V_H$Ma. In some embodiments, an antibody or antibody binding fragment thereof comprises $V_L$Ya and $V_H$Ma. In some embodiments, an antibody or antibody binding fragment thereof comprises $V_L$Za and $V_H$Ma. In some embodiments, an antibody or antibody binding fragment thereof comprises $V_L$ABa and $V_H$Ma.

In some embodiments, an antibody or antibody binding fragment thereof comprises $V_L$Aa and $V_H$Na. In some embodiments, an antibody or antibody binding fragment thereof comprises $V_L$Ba and $V_H$Na. In some embodiments, an antibody or antibody binding fragment thereof comprises $V_L$Ca and $V_H$Na. In some embodiments, an antibody or antibody binding fragment thereof comprises $V_L$Da and $V_H$Na. In some embodiments, an antibody or antibody binding fragment thereof comprises $V_L$Ea and $V_H$Na. In some embodiments, an antibody or antibody binding fragment thereof comprises $V_L$Fa and $V_H$Na. In some embodiments, an antibody or antibody binding fragment thereof comprises $V_L$Ga and $V_H$Na. In some embodiments, an antibody or antibody binding fragment thereof comprises $V_L$Ha and $V_H$Na. In some embodiments, an antibody or antibody binding fragment thereof comprises $V_L$Ia and $V_H$Na. In some embodiments, an antibody or antibody binding fragment thereof comprises $V_L$Ja and $V_H$Na. In some embodiments, an antibody or antibody binding fragment thereof comprises $V_L$Ka and $V_H$Na. In some embodiments, an antibody or antibody binding fragment thereof comprises $V_L$La and $V_H$Na. In some embodiments, an antibody or antibody binding fragment thereof comprises $V_L$Ma and $V_H$Na. In some embodiments, an antibody or antibody binding fragment thereof comprises $V_L$Na and $V_H$Na. In some embodiments, an antibody or antibody binding fragment thereof comprises $V_L$Oa and $V_H$Na. In some embodiments, an antibody or antibody binding fragment thereof comprises $V_L$Pa and $V_H$Na. In some embodiments, an antibody or antibody binding fragment thereof comprises $V_L$Qa and $V_H$Na. In some embodiments, an antibody or antibody binding fragment thereof comprises $V_L$Ra and $V_H$Na. In some embodiments, an antibody or antibody binding fragment thereof comprises $V_L$Sa and $V_H$Na. In some embodiments, an antibody or antibody binding fragment thereof comprises $V_L$Ta and $V_H$Na. In some embodiments, an antibody or antibody binding fragment thereof comprises $V_L$Ua and $V_H$Na. In some embodiments, an antibody or antibody binding fragment thereof comprises $V_L$Va and $V_H$Na. In some embodiments, an antibody or antibody binding fragment thereof comprises $V_L$Wa and $V_H$Na. In some embodiments, an antibody or antibody binding fragment thereof comprises $V_L$Xa and $V_H$Na. In some embodiments, an antibody or antibody binding fragment thereof comprises $V_L$Ya and $V_H$Na. In some embodiments, an antibody or antibody binding fragment thereof comprises $V_L$Za and $V_H$Na. In some embodiments, an antibody or antibody binding fragment thereof comprises $V_L$ABa and $V_H$Na.

In some embodiments, an antibody or antibody binding fragment thereof comprises $V_L$Aa and $V_H$Oa. In some embodiments, an antibody or antibody binding fragment thereof comprises $V_L$Ba and $V_H$Oa. In some embodiments, an antibody or antibody binding fragment thereof comprises $V_L$Ca and $V_H$Oa. In some embodiments, an antibody or antibody binding fragment thereof comprises $V_L$Da and $V_H$Oa. In some embodiments, an antibody or antibody binding fragment thereof comprises $V_L$Ea and $V_H$Oa. In some embodiments, an antibody or antibody binding fragment thereof comprises $V_L$Fa and $V_H$Oa. In some embodiments, an antibody or antibody binding fragment thereof comprises $V_L$Ga and $V_H$Oa. In some embodiments, an antibody or antibody binding fragment thereof comprises $V_L$Ha and $V_H$Oa. In some embodiments, an antibody or antibody binding fragment thereof comprises $V_L$Ia and $V_H$Oa. In some embodiments, an antibody or antibody binding fragment thereof comprises $V_L$Ja and $V_H$Oa. In some embodiments, an antibody or antibody binding fragment thereof comprises $V_L$Ka and $V_H$Oa. In some embodiments, an antibody or antibody binding fragment thereof comprises $V_L$La and $V_H$Oa. In some embodiments, an antibody or antibody binding fragment thereof comprises $V_L$Ma and $V_H$Oa. In some embodiments, an antibody or antibody binding fragment thereof comprises $V_L$Na and $V_H$Oa. In some embodiments, an antibody or antibody binding fragment thereof comprises $V_L$Oa and $V_H$Oa. In some embodiments, an antibody or antibody binding fragment thereof comprises $V_L$Pa and $V_H$Oa. In some embodiments, an antibody or antibody binding fragment thereof comprises $V_L$Qa and $V_H$Oa. In some embodiments, an antibody or antibody binding fragment thereof comprises $V_L$Ra and $V_H$Oa. In some embodiments, an antibody or antibody binding fragment thereof comprises $V_L$Sa and $V_H$Oa. In some embodiments, an antibody or antibody binding fragment thereof comprises $V_L$Ta and $V_H$Oa. In some embodiments, an antibody or antibody binding fragment thereof comprises $V_L$Ua and $V_H$Oa. In some embodiments, an antibody or antibody binding fragment thereof comprises $V_L$Va and $V_H$Oa. In some embodiments, an antibody or antibody binding fragment thereof comprises $V_L$Wa and $V_H$Oa. In some embodiments, an antibody or antibody binding fragment thereof comprises $V_L$Xa and $V_H$Oa. In some embodiments, an antibody or antibody binding fragment thereof comprises $V_L$Ya and $V_H$Oa. In some embodiments, an antibody or antibody binding fragment thereof comprises $V_L$Za and $V_H$Oa. In some embodiments, an antibody or antibody binding fragment thereof comprises $V_L$ABa and $V_H$Oa.

In some embodiments, an antibody or antibody binding fragment thereof comprises $V_L$Aa and $V_H$Pa. In some embodiments, an antibody or antibody binding fragment thereof comprises $V_L$Ba and $V_H$Pa. In some embodiments, an antibody or antibody binding fragment thereof comprises $V_L$Ca and $V_H$Pa. In some embodiments, an antibody or antibody binding fragment thereof comprises $V_L$Da and $V_H$Pa. In some embodiments, an antibody or antibody binding fragment thereof comprises $V_L$Ea and $V_H$Pa. In some embodiments, an antibody or antibody binding fragment thereof comprises $V_L$ Fa and $V_H$Pa. In some embodiments, an antibody or antibody binding fragment thereof comprises $V_L$Ga and $V_H$Pa. In some embodiments, an antibody or antibody binding fragment thereof comprises $V_L$Ha and $V_H$Pa. In some embodiments, an antibody or antibody binding fragment thereof comprises $V_L$Ia and $V_H$Pa. In some embodiments, an antibody or antibody binding fragment thereof comprises $V_L$Ja and $V_H$Pa. In some embodiments, an antibody or antibody binding fragment thereof comprises $V_L$Ka and $V_H$Pa. In some embodiments, an antibody or antibody binding fragment thereof comprises $V_L$La and $V_H$Pa. In some embodiments, an antibody or antibody binding fragment thereof comprises $V_L$Ma and $V_H$Pa. In some embodiments, an antibody or antibody binding fragment thereof comprises $V_L$Na and $V_H$Pa. In some embodiments, an antibody or antibody binding fragment thereof comprises $V_L$Oa and $V_H$Pa. In some embodiments, an antibody or antibody binding fragment thereof comprises $V_L$Pa and $V_H$Pa. In some embodiments, an antibody or antibody binding fragment thereof comprises $V_L$Qa and $V_H$Pa. In some embodiments, an antibody or antibody binding fragment thereof comprises $V_L$Ra and $V_H$Pa. In some embodiments, an antibody or antibody binding fragment thereof comprises $V_L$Sa and $V_H$Pa. In some embodiments, an antibody or antibody binding fragment thereof comprises $V_L$Ta and $V_H$Pa. In some embodiments, an antibody or antibody binding fragment thereof comprises $V_L$Ua and $V_H$Pa. In some embodiments, an antibody or antibody binding fragment thereof comprises $V_L$Va and $V_H$Pa. In some embodiments, an antibody or antibody binding fragment thereof comprises $V_L$Wa and $V_H$Pa. In some embodiments, an antibody or antibody binding fragment thereof comprises $V_L$Xa and $V_H$Pa. In some embodiments, an antibody or antibody binding fragment thereof comprises $V_L$Ya and $V_H$Pa. In some embodiments, an antibody or antibody binding fragment thereof comprises $V_L$Za and $V_H$Pa. In some embodiments, an antibody or antibody binding fragment thereof comprises $V_L$ABa and $V_H$Pa.

In some embodiments, an antibody or antibody binding fragment thereof comprises $V_L$Aa and $V_H$Qa. In some embodiments, an antibody or antibody binding fragment thereof comprises $V_L$Ba and $V_H$Qa. In some embodiments, an antibody or antibody binding fragment thereof comprises $V_L$Ca and $V_H$Qa. In some embodiments, an antibody or antibody binding fragment thereof comprises $V_L$Da and $V_H$Qa. In some embodiments, an antibody or antibody binding fragment thereof comprises $V_L$Ea and $V_H$Qa. In some embodiments, an antibody or antibody binding fragment thereof comprises $V_L$Fa and $V_H$Qa. In some embodiments, an antibody or antibody binding fragment thereof comprises $V_L$Ga and $V_H$Qa. In some embodiments, an antibody or antibody binding fragment thereof comprises $V_L$Ha and $V_H$Qa. In some embodiments, an antibody or antibody binding fragment thereof comprises $V_L$Ia and $V_H$Qa. In some embodiments, an antibody or antibody binding fragment thereof comprises $V_L$Ja and $V_H$Qa. In some embodiments, an antibody or antibody binding fragment thereof comprises $V_L$Ka and $V_H$Qa. In some embodiments, an antibody or antibody binding fragment thereof comprises $V_L$La and $V_H$Qa. In some embodiments, an antibody or antibody binding fragment thereof comprises $V_L$Ma and $V_H$Qa. In some embodiments, an antibody or antibody binding fragment thereof comprises $V_L$Na and $V_H$Qa. In some embodiments, an antibody or antibody binding fragment thereof comprises $V_L$Oa and $V_H$Qa. In some embodiments, an antibody or antibody binding fragment thereof comprises $V_L$Pa and $V_H$Qa. In some embodiments, an antibody or antibody binding fragment thereof comprises $V_L$Qa and $V_H$Qa. In some embodiments, an antibody or antibody binding fragment thereof comprises $V_L$Ra and $V_H$Qa. In some embodiments, an antibody or antibody binding fragment thereof comprises $V_L$Sa and $V_H$Qa. In some embodiments, an antibody or antibody binding fragment thereof comprises $V_L$Ta and $V_H$Qa. In some embodiments, an antibody or antibody binding fragment thereof comprises $V_L$Ua and $V_H$Qa. In some embodiments, an antibody or antibody binding fragment thereof comprises $V_L$Va and $V_H$Qa. In some embodiments, an antibody or antibody binding fragment thereof comprises $V_L$Wa and $V_H$Qa. In some embodiments, an antibody or antibody binding fragment thereof comprises $V_L$Xa and $V_H$Qa. In some embodiments, an antibody or antibody binding fragment thereof comprises $V_L$Ya and $V_H$Qa. In some embodiments, an antibody or antibody binding fragment thereof comprises $V_L$Za and $V_H$Qa. In some embodiments, an antibody or antibody binding fragment thereof comprises $V_L$ABa and $V_H$Qa.

In some embodiments, an antibody or antibody binding fragment thereof comprises $V_L$Aa and $V_H$Ra. In some embodiments, an antibody or antibody binding fragment thereof comprises $V_L$Ba and $V_H$Ra. In some embodiments, an antibody or antibody binding fragment thereof comprises $V_L$Ca and $V_H$Ra. In some embodiments, an antibody or antibody binding fragment thereof comprises $V_L$Da and $V_H$Ra. In some embodiments, an antibody or antibody binding fragment thereof comprises $V_L$Ea and $V_H$Ra. In some embodiments, an antibody or antibody binding fragment thereof comprises $V_L$Fa and $V_H$Ra. In some embodiments, an antibody or antibody binding fragment thereof comprises $V_L$Ga and $V_H$Ra. In some embodiments, an antibody or antibody binding fragment thereof comprises $V_L$Ha and $V_H$Ra. In some embodiments, an antibody or antibody binding fragment thereof comprises $V_L$Ia and $V_H$Ra. In some embodiments, an antibody or antibody binding fragment thereof comprises $V_L$Ja and $V_H$Ra. In some embodiments, an antibody or antibody binding fragment thereof comprises $V_L$Ka and $V_H$Ra. In some embodiments, an antibody or antibody binding fragment thereof comprises $V_L$La and $V_H$Ra. In some embodiments, an antibody or antibody binding fragment thereof comprises $V_L$Ma and $V_H$Ra. In some embodiments, an antibody or antibody binding fragment thereof comprises $V_L$Na and $V_H$Ra. In some embodiments, an antibody or antibody binding fragment thereof comprises $V_L$Oa and $V_H$Ra. In some embodiments, an antibody or antibody binding fragment thereof comprises $V_L$Pa and $V_H$Ra. In some embodiments, an antibody or antibody binding fragment thereof comprises $V_L$Qa and $V_H$Ra. In some embodiments, an antibody or antibody binding fragment thereof comprises $V_L$Ra and $V_H$Ra. In some embodiments, an antibody or antibody binding fragment thereof comprises $V_L$Sa and $V_H$Ra. In some embodiments, an antibody or antibody binding fragment thereof comprises $V_L$Ta and $V_H$Ra. In some embodiments, an antibody or antibody binding fragment thereof comprises $V_L$Ua and $V_H$Ra. In some embodiments, an antibody or antibody binding fragment thereof comprises $V_L$Va and $V_H$Ra. In some embodiments, an antibody or antibody binding fragment thereof comprises $V_L$Wa and $V_H$Ra. In some embodiments, an antibody or antibody binding fragment thereof comprises $V_L$Xa and $V_H$Ra. In some embodiments, an antibody or antibody binding fragment thereof comprises $V_L$Ya and $V_H$Ra. In some embodiments, an antibody or antibody binding fragment thereof comprises $V_L$Za and $V_H$Ra. In some embodiments, an antibody or antibody binding fragment thereof comprises $V_L$ABa and $V_H$Ra.

In some embodiments, an antibody or antibody binding fragment thereof comprises $V_L$Aa and $V_H$Sa. In some embodiments, an antibody or antibody binding fragment thereof comprises $V_L$Ba and $V_H$Sa. In some embodiments, an antibody or antibody binding fragment thereof comprises $V_L$Ca and $V_H$Sa. In some embodiments, an antibody or antibody binding fragment thereof comprises $V_L$Da and $V_H$Sa. In some embodiments, an antibody or antibody binding fragment thereof comprises $V_L$Ea and $V_H$Sa. In some embodiments, an antibody or antibody binding fragment thereof comprises $V_L$Fa and $V_H$Sa. In some embodiments, an antibody or antibody binding fragment thereof comprises $V_L$Ga and $V_H$Sa. In some embodiments, an antibody or antibody binding fragment thereof comprises $V_L$Ha and $V_H$Sa. In some embodiments, an antibody or antibody binding fragment thereof comprises $V_L$Ia and $V_H$Sa. In some embodiments, an antibody or antibody binding fragment thereof comprises $V_L$Ja and $V_H$Sa. In some embodiments, an antibody or antibody binding fragment thereof comprises $V_L$Ka and $V_H$Sa. In some embodiments, an antibody or antibody binding fragment thereof comprises $V_L$La and $V_H$Sa. In some embodiments, an antibody or antibody binding fragment thereof comprises $V_L$Ma and $V_H$Sa. In some embodiments, an antibody or antibody binding fragment thereof comprises $V_L$Na and $V_H$Sa. In some embodiments, an antibody or antibody binding fragment thereof comprises $V_L$Oa and $V_H$Sa. In some embodiments, an antibody or antibody binding fragment thereof comprises $V_L$Pa and $V_H$Sa. In some embodiments, an antibody or antibody binding fragment thereof comprises $V_L$Qa and $V_H$Sa. In some embodiments, an antibody or antibody binding fragment thereof comprises $V_L$Ra and $V_H$Sa. In some embodiments, an antibody or antibody binding fragment thereof comprises $V_L$Sa and $V_H$Sa. In some embodiments, an antibody or antibody binding fragment thereof comprises $V_L$Ta and $V_H$Sa. In some embodiments, an antibody or antibody binding fragment thereof comprises $V_L$Ua and $V_H$Sa. In some embodiments, an antibody or antibody binding fragment thereof comprises $V_L$Va and $V_H$Sa. In some embodiments, an antibody or antibody binding fragment thereof comprises $V_L$Wa and $V_H$Sa. In some embodiments, an antibody or antibody binding fragment thereof comprises $V_L$Xa and $V_H$Sa. In some embodiments, an antibody or antibody binding fragment thereof comprises $V_L$Ya and $V_H$Sa. In some embodiments, an antibody or antibody binding fragment thereof comprises $V_L$Za and $V_H$Sa. In some embodiments, an antibody or antibody binding fragment thereof comprises $V_L$ABa and $V_H$Sa.

In some embodiments, an antibody or antibody binding fragment thereof comprises $V_L$Aa and $V_H$Ta. In some embodiments, an antibody or antibody binding fragment thereof comprises $V_L$Ba and $V_H$Ta. In some embodiments, an antibody or antibody binding fragment thereof comprises $V_L$Ca and $V_H$Ta. In some embodiments, an antibody or antibody binding fragment thereof comprises $V_L$Da and $V_H$Ta. In some embodiments, an antibody or antibody binding fragment thereof comprises $V_L$Ea and $V_H$Ta. In some embodiments, an antibody or antibody binding fragment thereof comprises $V_L$Fa and $V_H$Ta. In some embodiments, an antibody or antibody binding fragment thereof comprises $V_L$Ga and $V_H$Ta. In some embodiments, an antibody or antibody binding fragment thereof comprises $V_L$Ha and $V_H$Ta. In some embodiments, an antibody or antibody binding fragment thereof comprises $V_L$Ia and $V_H$Ta. In some embodiments, an antibody or antibody binding fragment thereof comprises $V_L$Ja and $V_H$Ta. In some embodiments, an antibody or antibody binding fragment thereof comprises $V_L$Ka and $V_H$Ta. In some embodiments, an antibody or antibody binding fragment thereof comprises $V_L$La and $V_H$Ta. In some embodiments, an antibody or antibody binding fragment thereof comprises $V_L$Ma and $V_H$Ta. In some embodiments, an antibody or antibody binding fragment thereof comprises $V_L$Na and $V_H$Ta. In some embodiments, an antibody or antibody binding fragment thereof comprises $V_L$Oa and $V_H$Ta. In some embodiments, an antibody or antibody binding fragment thereof comprises $V_L$Pa and $V_H$Ta. In some embodiments, an antibody or antibody binding fragment thereof comprises $V_L$Qa and $V_H$Ta. In some embodiments, an antibody or antibody binding fragment thereof comprises $V_L$Ra and $V_H$Ta. In some embodiments, an antibody or antibody binding fragment thereof comprises $V_L$Sa and $V_H$Ta. In some embodiments, an antibody or antibody binding fragment thereof comprises $V_L$Ta and $V_H$Ta. In some embodiments, an antibody or antibody binding fragment thereof comprises $V_L$Ua and $V_H$Ta. In some embodiments, an antibody or antibody binding fragment thereof comprises $V_L$Va and $V_H$Ta. In some embodiments, an antibody or antibody binding fragment thereof comprises $V_L$Wa and $V_H$Ta. In some embodiments, an antibody or antibody binding fragment thereof comprises $V_L$Xa and $V_H$Ta. In some embodiments, an antibody or antibody binding fragment thereof comprises $V_L$Ya and $V_H$Ta. In some embodiments, an antibody or antibody binding fragment thereof comprises $V_L$Za and $V_H$Ta. In some embodiments, an antibody or antibody binding fragment thereof comprises $V_L$ABa and $V_H$Ta.

In some embodiments, an antibody or antibody binding fragment thereof comprises $V_L$Aa and $V_H$Ua. In some embodiments, an antibody or antibody binding fragment thereof comprises $V_L$Ba and $V_H$Ua. In some embodiments, an antibody or antibody binding fragment thereof comprises $V_L$Ca and $V_H$Ua. In some embodiments, an antibody or antibody binding fragment thereof comprises $V_L$Da and $V_H$Ua. In some embodiments, an antibody or antibody binding fragment thereof comprises $V_L$Ea and $V_H$Ua. In some embodiments, an antibody or antibody binding fragment thereof comprises $V_L$Fa and $V_H$Ua. In some embodiments, an antibody or antibody binding fragment thereof comprises $V_L$Ga and $V_H$Ua. In some embodiments, an antibody or antibody binding fragment thereof comprises $V_L$Ha and $V_H$Ua. In some embodiments, an antibody or antibody binding fragment thereof comprises $V_L$Ia and $V_H$Ua. In some embodiments, an antibody or antibody binding fragment thereof comprises $V_L$Ja and $V_H$Ua. In some embodiments, an antibody or antibody binding fragment thereof comprises $V_L$Ka and $V_H$Ua. In some embodiments, an antibody or antibody binding fragment thereof comprises $V_L$La and $V_H$Ua. In some embodiments, an antibody or antibody binding fragment thereof comprises $V_L$Ma and $V_H$Ua. In some embodiments, an antibody or antibody binding fragment thereof comprises $V_L$Na and $V_H$Ua. In some embodiments, an antibody or antibody binding fragment thereof comprises $V_L$Oa and $V_H$Ua. In some embodiments, an antibody or antibody binding fragment thereof comprises $V_L$Pa and $V_H$Ua. In some embodiments, an antibody or antibody binding fragment thereof comprises $V_L$Qa and $V_H$Ua. In some embodiments, an antibody or antibody binding fragment thereof comprises $V_L$Ra and $V_H$Ua. In some embodiments, an antibody or antibody binding fragment thereof comprises $V_L$Sa and $V_H$Ua. In some embodiments, an antibody or antibody binding fragment thereof comprises $V_L$Ta and $V_H$Ua. In some embodiments, an antibody or antibody binding fragment thereof comprises $V_L$Ua and $V_H$Ua. In some embodiments, an antibody or antibody binding fragment thereof comprises $V_L$Va and $V_H$Ua. In some embodiments, an antibody or antibody binding fragment thereof comprises $V_L$Wa and $V_H$Ua. In some embodiments, an antibody or antibody binding fragment thereof comprises $V_L$Xa and $V_H$Ua. In some embodiments, an antibody or antibody binding fragment thereof comprises $V_L$Ya and $V_H$Ua. In some embodiments, an antibody or antibody binding fragment thereof comprises $V_L$Za and $V_H$Ua. In some embodiments, an antibody or antibody binding fragment thereof comprises $V_L$ABa and $V_H$Ua.

In some embodiments, an antibody or antibody binding fragment thereof comprises $V_L$Aa and $V_H$Va. In some embodiments, an antibody or antibody binding fragment thereof comprises $V_L$Ba and $V_H$Va. In some embodiments, an antibody or antibody binding fragment thereof comprises $V_L$Ca and $V_H$Va. In some embodiments, an antibody or antibody binding fragment thereof comprises $V_L$Da and $V_H$Va. In some embodiments, an antibody or antibody binding fragment thereof comprises $V_L$Ea and $V_H$Va. In some embodiments, an antibody or antibody binding fragment thereof comprises $V_L$Fa and $V_H$Va. In some embodiments, an antibody or antibody binding fragment thereof comprises $V_L$Ga and $V_H$Va. In some embodiments, an antibody or antibody binding fragment thereof comprises $V_L$Ha and $V_H$Va. In some embodiments, an antibody or antibody binding fragment thereof comprises $V_L$Ia and $V_H$Va. In some embodiments, an antibody or antibody binding fragment thereof comprises $V_L$Ja and $V_H$Va. In some embodiments, an antibody or antibody binding fragment thereof comprises $V_L$Ka and $V_H$Va. In some embodiments, an antibody or antibody binding fragment thereof comprises $V_L$La and $V_H$Va. In some embodiments, an antibody or antibody binding fragment thereof comprises $V_L$Ma and $V_H$Va. In some embodiments, an antibody or antibody binding fragment thereof comprises $V_L$Na and $V_H$Va. In some embodiments, an antibody or antibody binding fragment thereof comprises $V_L$Oa and $V_H$Va. In some embodiments, an antibody or antibody binding fragment thereof comprises $V_L$Pa and $V_H$Va. In some embodiments, an antibody or antibody binding fragment thereof comprises $V_L$Qa and $V_H$Va. In some embodiments, an antibody or antibody binding fragment thereof comprises $V_L$Ra and $V_H$Va. In some embodiments, an antibody or antibody binding fragment thereof comprises $V_L$Sa and $V_H$Va. In some embodiments, an antibody or antibody binding fragment thereof comprises $V_L$Ta and $V_H$Va. In some embodiments, an antibody or antibody binding fragment thereof comprises $V_L$Ua and $V_H$Va. In some embodiments, an antibody or antibody binding fragment thereof comprises $V_L$Va and $V_H$Va. In some embodiments, an antibody or antibody binding fragment thereof comprises $V_L$Wa and $V_H$Va. In some embodiments, an antibody or antibody binding fragment thereof comprises $V_L$Xa and $V_H$Va. In some embodiments, an antibody or antibody binding fragment thereof comprises $V_L$Ya and $V_H$Va. In some embodiments, an antibody or antibody binding fragment thereof comprises $V_L$Za and $V_H$Va. In some embodiments, an antibody or antibody binding fragment thereof comprises $V_L$ABa and $V_H$Va.

In some embodiments, an antibody or antibody binding fragment thereof comprises $V_L$Aa and $V_H$Wa. In some embodiments, an antibody or antibody binding fragment thereof comprises $V_L$Ba and $V_H$Wa. In some embodiments, an antibody or antibody binding fragment thereof comprises $V_L$Ca and $V_H$Wa. In some embodiments, an antibody or antibody binding fragment thereof comprises $V_L$Da and $V_H$Wa. In some embodiments, an antibody or antibody binding fragment thereof comprises $V_L$Ea and $V_H$Wa. In some embodiments, an antibody or antibody binding fragment thereof comprises $V_L$Fa and $V_H$Wa. In some embodiments, an antibody or antibody binding fragment thereof comprises $V_L$Ga and $V_H$Wa. In some embodiments, an antibody or antibody binding fragment thereof comprises $V_L$Ha and $V_H$Wa. In some embodiments, an antibody or antibody binding fragment thereof comprises $V_L$Ia and $V_H$Wa. In some embodiments, an antibody or antibody binding fragment thereof comprises $V_L$Ja and $V_H$Wa. In some embodiments, an antibody or antibody binding fragment thereof comprises $V_L$Ka and $V_H$Wa. In some embodiments, an antibody or antibody binding fragment thereof comprises $V_L$La and $V_H$Wa. In some embodiments, an antibody or antibody binding fragment thereof comprises $V_L$Ma and $V_H$Wa. In some embodiments, an antibody or antibody binding fragment thereof comprises $V_L$Na and $V_H$Wa. In some embodiments, an antibody or antibody binding fragment thereof comprises $V_L$Oa and $V_H$Wa. In some embodiments, an antibody or antibody binding fragment thereof comprises $V_L$Pa and $V_H$Wa. In some embodiments, an antibody or antibody binding fragment thereof comprises $V_L$Qa and $V_H$Wa. In some embodiments, an antibody or antibody binding fragment thereof comprises $V_L$Ra and $V_H$Wa. In some embodiments, an antibody or antibody binding fragment thereof comprises $V_L$Sa and $V_H$Wa. In some embodiments, an antibody or antibody binding fragment thereof comprises $V_L$Ta and $V_H$Wa. In some embodiments, an antibody or antibody binding fragment thereof comprises $V_L$Ua and $V_H$Wa. In some embodiments, an antibody or antibody binding fragment thereof comprises $V_L$Va and $V_H$Wa. In some embodiments, an antibody or antibody binding fragment thereof comprises $V_L$Wa and $V_H$Wa. In some embodiments, an antibody or antibody binding fragment thereof comprises $V_L$Xa and $V_H$Wa. In some embodiments, an antibody or antibody binding fragment thereof comprises $V_L$Ya and $V_H$Wa. In some embodiments, an antibody or antibody binding fragment thereof comprises $V_L$Za and $V_H$Wa. In some embodiments, an antibody or antibody binding fragment thereof comprises $V_L$ABa and $V_H$Wa.

In some embodiments, an antibody or antibody binding fragment thereof comprises $V_L$Aa and $V_H$Xa. In some embodiments, an antibody or antibody binding fragment thereof comprises $V_L$Ba and $V_H$Xa. In some embodiments, an antibody or antibody binding fragment thereof comprises $V_L$Ca and $V_H$Xa. In some embodiments, an antibody or antibody binding fragment thereof comprises $V_L$Da and $V_H$Xa. In some embodiments, an antibody or antibody binding fragment thereof comprises $V_L$Ea and $V_H$Xa. In some embodiments, an antibody or antibody binding fragment thereof comprises $V_L$Fa and $V_H$Xa. In some embodiments, an antibody or antibody binding fragment thereof comprises $V_L$Ga and $V_H$Xa. In some embodiments, an antibody or antibody binding fragment thereof comprises $V_L$Ha and $V_H$Xa. In some embodiments, an antibody or antibody binding fragment thereof comprises $V_L$Ia and $V_H$Xa. In some embodiments, an antibody or antibody binding fragment thereof comprises $V_L$Ja and $V_H$Xa. In some embodiments, an antibody or antibody binding fragment thereof comprises $V_L$Ka and $V_H$Xa. In some embodiments, an antibody or antibody binding fragment thereof comprises $V_L$La and $V_H$Xa. In some embodiments, an antibody or antibody binding fragment thereof comprises $V_L$Ma and $V_H$Xa. In some embodiments, an antibody or antibody binding fragment thereof comprises $V_L$Na and $V_H$Xa. In some embodiments, an antibody or antibody binding fragment thereof comprises $V_L$Oa and $V_H$Xa. In some embodiments, an antibody or antibody binding fragment thereof comprises $V_L$Pa and $V_H$Xa. In some embodiments, an antibody or antibody binding fragment thereof comprises $V_L$Qa and $V_H$Xa. In some embodiments, an antibody or antibody binding fragment thereof comprises $V_L$Ra and $V_H$Xa. In some embodiments, an antibody or antibody binding fragment thereof comprises $V_L$Sa and $V_H$Xa. In some embodiments, an antibody or antibody binding fragment thereof comprises $V_L$Ta and $V_H$Xa. In some embodiments, an antibody or antibody binding fragment thereof comprises $V_L$Ua and $V_H$Xa. In some embodiments, an antibody or antibody binding fragment thereof comprises $V_L$Va and $V_H$Xa. In some embodiments, an antibody or antibody binding fragment thereof comprises $V_L$Wa and $V_H$Xa. In some embodiments, an antibody or antibody binding fragment thereof comprises $V_L$Xa and $V_H$Xa. In some embodiments, an antibody or antibody binding fragment thereof comprises $V_L$Ya and $V_H$Xa. In some embodiments, an antibody or antibody binding fragment thereof comprises $V_L$Za and $V_H$Xa. In some embodiments, an antibody or antibody binding fragment thereof comprises $V_L$ABa and $V_H$Xa.

In some embodiments, an antibody or antibody binding fragment thereof comprises $V_L$Aa and $V_H$Ya. In some embodiments, an antibody or antibody binding fragment thereof comprises $V_L$Ba and $V_H$Ya. In some embodiments, an antibody or antibody binding fragment thereof comprises $V_L$Ca and $V_H$Ya. In some embodiments, an antibody or antibody binding fragment thereof comprises $V_L$Da and $V_H$Ya. In some embodiments, an antibody or antibody binding fragment thereof comprises $V_L$Ea and $V_H$Ya. In some embodiments, an antibody or antibody binding fragment thereof comprises $V_L$ Fa and $V_H$Ya. In some embodiments, an antibody or antibody binding fragment thereof comprises $V_L$Ga and $V_H$Ya. In some embodiments, an antibody or antibody binding fragment thereof comprises $V_L$Ha and $V_H$Ya. In some embodiments, an antibody or antibody binding fragment thereof comprises $V_L$Ia and $V_H$Ya. In some embodiments, an antibody or antibody binding fragment thereof comprises $V_L$Ja and $V_H$Ya. In some embodiments, an antibody or antibody binding fragment thereof comprises $V_L$Ka and $V_H$Ya. In some embodiments, an antibody or antibody binding fragment thereof comprises $V_L$La and $V_H$Ya. In some embodiments, an antibody or antibody binding fragment thereof comprises $V_L$Ma and $V_H$Ya. In some embodiments, an antibody or antibody binding fragment thereof comprises $V_L$Na and $V_H$Ya. In some embodiments, an antibody or antibody binding fragment thereof comprises $V_L$Oa and $V_H$Ya. In some embodiments, an antibody or antibody binding fragment thereof comprises $V_L$Pa and $V_H$Ya. In some embodiments, an antibody or antibody binding fragment thereof comprises $V_L$Qa and $V_H$Ya. In some embodiments, an antibody or antibody binding fragment thereof comprises $V_L$Ra and $V_H$Ya. In some embodiments, an antibody or antibody binding fragment thereof comprises $V_L$Sa and $V_H$Ya. In some embodiments, an antibody or antibody binding fragment thereof comprises $V_L$Ta and $V_H$Ya. In some embodiments, an antibody or antibody binding fragment thereof comprises $V_L$Ua and $V_H$Ya. In some embodiments, an antibody or antibody binding fragment thereof comprises $V_L$Va and $V_H$Ya. In some embodiments, an antibody or antibody binding fragment thereof comprises $V_L$Wa and $V_H$Ya. In some embodiments, an antibody or antibody binding fragment thereof comprises $V_L$Xa and $V_H$Ya. In some embodiments, an antibody or antibody binding fragment thereof comprises $V_L$Ya and $V_H$Ya. In some embodiments, an antibody or antibody binding fragment thereof comprises $V_L$Za and $V_H$Ya. In some embodiments, an antibody or antibody binding fragment thereof comprises $V_L$ABa and $V_H$Ya.

In some embodiments, an antibody or antibody binding fragment thereof comprises $V_L$Aa and $V_H$Za. In some embodiments, an antibody or antibody binding fragment thereof comprises $V_L$Ba and $V_H$Za. In some embodiments, an antibody or antibody binding fragment thereof comprises $V_L$Ca and $V_H$Za. In some embodiments, an antibody or antibody binding fragment thereof comprises $V_L$Da and $V_H$Za. In some embodiments, an antibody or antibody binding fragment thereof comprises $V_L$Ea and $V_H$Za. In some embodiments, an antibody or antibody binding fragment thereof comprises $V_L$ Fa and $V_H$Za. In some embodiments, an antibody or antibody binding fragment thereof comprises $V_L$Ga and $V_H$Za. In some embodiments, an antibody or antibody binding fragment thereof comprises $V_L$Ha and $V_H$Za. In some embodiments, an antibody or antibody binding fragment thereof comprises $V_L$Ia and $V_H$Za. In some embodiments, an antibody or antibody binding fragment thereof comprises $V_L$Ja and $V_H$Za. In some embodiments, an antibody or antibody binding fragment thereof comprises $V_L$Ka and $V_H$Za. In some embodiments, an antibody or antibody binding fragment thereof comprises $V_L$La and $V_H$Za. In some embodiments, an antibody or antibody binding fragment thereof comprises $V_L$Ma and $V_H$Za. In some embodiments, an antibody or antibody binding fragment thereof comprises $V_L$Na and $V_H$Za. In some embodiments, an antibody or antibody binding fragment thereof comprises $V_L$Oa and $V_H$Za. In some embodiments, an antibody or antibody binding fragment thereof comprises $V_L$Pa and $V_H$Za. In some embodiments, an antibody or antibody binding fragment thereof comprises $V_L$Qa and $V_H$Za. In some embodiments, an antibody or antibody binding fragment thereof comprises $V_L$Ra and $V_H$Za. In some embodiments, an antibody or antibody binding fragment thereof comprises $V_L$Sa and $V_H$Za. In some embodiments, an antibody or antibody binding fragment thereof comprises $V_L$Ta and $V_H$Za. In some embodiments, an antibody or antibody binding fragment thereof comprises $V_L$Ua and $V_H$Za. In some embodiments, an antibody or antibody binding fragment thereof comprises $V_L$Va and $V_H$Za. In some embodiments, an antibody or antibody binding fragment thereof comprises $V_L$Wa and $V_H$Za. In some embodiments, an antibody or antibody binding fragment thereof comprises $V_L$Xa and $V_H$Za. In some embodiments, an antibody or antibody binding fragment thereof comprises $V_L$Ya and $V_H$Za. In some embodiments, an antibody or antibody binding fragment thereof comprises $V_L$Za and $V_H$Za. In some embodiments, an antibody or antibody binding fragment thereof comprises $V_L$ABa and $V_H$Za.

In some embodiments, an antibody or antibody binding fragment thereof comprises $V_L$Aa and $V_H$ABa. In some embodiments, an antibody or antibody binding fragment thereof comprises $V_L$Ba and $V_H$ABa. In some embodiments, an antibody or antibody binding fragment thereof comprises $V_L$Ca and $V_H$ABa. In some embodiments, an antibody or antibody binding fragment thereof comprises $V_L$Da and $V_H$ABa. In some embodiments, an antibody or antibody binding fragment thereof comprises $V_L$Ea and $V_H$ABa. In some embodiments, an antibody or antibody binding fragment thereof comprises $V_L$Fa and $V_H$ABa. In some embodiments, an antibody or antibody binding fragment thereof comprises $V_L$Ga and $V_H$ABa. In some embodiments, an antibody or antibody binding fragment thereof comprises $V_L$Ha and $V_H$ABa. In some embodiments, an antibody or antibody binding fragment thereof comprises $V_L$Ia and $V_H$ABa. In some embodiments, an antibody or antibody binding fragment thereof comprises $V_L$Ja and $V_H$ABa. In some embodiments, an antibody or antibody binding fragment thereof comprises $V_L$Ka and $V_H$ABa. In some embodiments, an antibody or antibody binding fragment thereof comprises $V_L$La and $V_H$ABa. In some embodiments, an antibody or antibody binding fragment thereof comprises $V_L$Ma and $V_H$ABa. In some embodiments, an antibody or antibody binding fragment thereof comprises $V_L$Na and $V_H$ABa. In some embodiments, an antibody or antibody binding fragment thereof comprises $V_L$Oa and $V_H$ABa. In some embodiments, an antibody or antibody binding fragment thereof comprises $V_L$Pa and $V_H$ABa. In some embodiments, an antibody or antibody binding fragment thereof comprises $V_L$Qa and $V_H$ABa. In some embodiments, an antibody or antibody binding fragment thereof comprises $V_L$Ra and $V_H$ABa. In some embodiments, an antibody or antibody binding fragment thereof comprises $V_L$Sa and $V_H$ABa. In some embodiments, an antibody or antibody binding fragment thereof comprises $V_L$Ta and $V_H$ABa. In some embodiments, an antibody or antibody binding fragment thereof comprises $V_L$Ua and $V_H$ABa. In some embodiments, an antibody or antibody binding fragment thereof comprises $V_L$Va and $V_H$ABa. In some embodiments, an antibody or antibody binding fragment thereof comprises $V_L$Wa and $V_H$ABa. In some embodiments, an antibody or antibody binding fragment thereof comprises $V_L$Xa and $V_H$ABa. In some embodiments, an antibody or antibody binding fragment thereof comprises $V_L$Ya and $V_H$ABa. In some embodiments, an antibody or antibody binding fragment thereof comprises $V_L$Za and $V_H$ABa. In some embodiments, an antibody or antibody binding fragment thereof comprises $V_L$ABa and $V_H$ABa.

The equivalent CDRs may also be used from the CHOTHIA designation. For clarity, the following tables are provided depicting non-limiting exemplary combinations of light chain (Table 9) and heavy chain (Table 10) CDRs using IMGT designations:

TABLE 9

| Combination | LCDR1 | LCDR2 | LCDR3 |
|---|---|---|---|
| $V_L$Ab | SEQ ID NO: 29 | SEQ ID NO: 30 | SEQ ID NO: 31 |
| $V_L$Bb | SEQ ID NO: 29 | SEQ ID NO: 30 | SEQ ID NO: 36 |
| $V_L$Cb | SEQ ID NO: 29 | SEQ ID NO: 30 | SEQ ID NO: 41 |
| $V_L$Db | SEQ ID NO: 29 | SEQ ID NO: 35 | SEQ ID NO: 31 |
| $V_L$Eb | SEQ ID NO: 29 | SEQ ID NO: 35 | SEQ ID NO: 36 |
| $V_L$Fb | SEQ ID NO: 29 | SEQ ID NO: 35 | SEQ ID NO: 41 |
| $V_L$Gb | SEQ ID NO: 29 | SEQ ID NO: 40 | SEQ ID NO: 31 |
| $V_L$Hb | SEQ ID NO: 29 | SEQ ID NO: 40 | SEQ ID NO: 36 |
| $V_L$Ib | SEQ ID NO: 29 | SEQ ID NO: 40 | SEQ ID NO: 41 |
| $V_L$Jb | SEQ ID NO: 34 | SEQ ID NO: 30 | SEQ ID NO: 31 |
| $V_L$Kb | SEQ ID NO: 34 | SEQ ID NO: 30 | SEQ ID NO: 36 |
| $V_L$Lb | SEQ ID NO: 34 | SEQ ID NO: 30 | SEQ ID NO: 41 |
| $V_L$Mb | SEQ ID NO: 34 | SEQ ID NO: 35 | SEQ ID NO: 31 |
| $V_L$Nb | SEQ ID NO: 34 | SEQ ID NO: 35 | SEQ ID NO: 36 |
| $V_L$Ob | SEQ ID NO: 34 | SEQ ID NO: 35 | SEQ ID NO: 41 |
| $V_L$Pb | SEQ ID NO: 34 | SEQ ID NO: 40 | SEQ ID NO: 31 |
| $V_L$Qb | SEQ ID NO: 34 | SEQ ID NO: 40 | SEQ ID NO: 36 |
| $V_L$Rb | SEQ ID NO: 34 | SEQ ID NO: 40 | SEQ ID NO: 41 |
| $V_L$Sb | SEQ ID NO: 39 | SEQ ID NO: 30 | SEQ ID NO: 31 |
| $V_L$Tb | SEQ ID NO: 39 | SEQ ID NO: 30 | SEQ ID NO: 36 |
| $V_L$Ub | SEQ ID NO: 39 | SEQ ID NO: 30 | SEQ ID NO: 41 |
| $V_L$Vb | SEQ ID NO: 39 | SEQ ID NO: 35 | SEQ ID NO: 31 |
| $V_L$Wb | SEQ ID NO: 39 | SEQ ID NO: 35 | SEQ ID NO: 36 |
| $V_L$Xb | SEQ ID NO: 39 | SEQ ID NO: 35 | SEQ ID NO: 41 |
| $V_L$Yb | SEQ ID NO: 39 | SEQ ID NO: 40 | SEQ ID NO: 31 |
| $V_L$Zb | SEQ ID NO: 39 | SEQ ID NO: 40 | SEQ ID NO: 36 |
| $V_L$ABb | SEQ ID NO: 39 | SEQ ID NO: 40 | SEQ ID NO: 41 |

TABLE 10

| Combination | HCDR1 | HCDR2 | HCDR3 |
|---|---|---|---|
| $V_H$Ab | SEQ ID NO: 27 | SEQ ID NO: 28 | SEQ ID NO: 11 |
| $V_H$Bb | SEQ ID NO: 27 | SEQ ID NO: 28 | SEQ ID NO: 17 |
| $V_H$Cb | SEQ ID NO: 27 | SEQ ID NO: 28 | SEQ ID NO: 23 |
| $V_H$Db | SEQ ID NO: 27 | SEQ ID NO: 33 | SEQ ID NO: 11 |
| $V_H$Eb | SEQ ID NO: 27 | SEQ ID NO: 33 | SEQ ID NO: 17 |
| $V_H$Fb | SEQ ID NO: 27 | SEQ ID NO: 33 | SEQ ID NO: 23 |
| $V_H$Gb | SEQ ID NO: 27 | SEQ ID NO: 38 | SEQ ID NO: 11 |
| $V_H$Hb | SEQ ID NO: 27 | SEQ ID NO: 38 | SEQ ID NO: 17 |
| $V_H$Ib | SEQ ID NO: 27 | SEQ ID NO: 38 | SEQ ID NO: 23 |
| $V_H$Jb | SEQ ID NO: 32 | SEQ ID NO: 28 | SEQ ID NO: 11 |
| $V_H$Kb | SEQ ID NO: 32 | SEQ ID NO: 28 | SEQ ID NO: 17 |
| $V_H$Lb | SEQ ID NO: 32 | SEQ ID NO: 28 | SEQ ID NO: 23 |
| $V_H$Mb | SEQ ID NO: 32 | SEQ ID NO: 33 | SEQ ID NO: 11 |
| $V_H$Nb | SEQ ID NO: 32 | SEQ ID NO: 33 | SEQ ID NO: 17 |
| $V_H$Ob | SEQ ID NO: 32 | SEQ ID NO: 33 | SEQ ID NO: 23 |
| $V_H$Pb | SEQ ID NO: 32 | SEQ ID NO: 38 | SEQ ID NO: 11 |
| $V_H$Qb | SEQ ID NO: 32 | SEQ ID NO: 38 | SEQ ID NO: 17 |
| $V_H$Rb | SEQ ID NO: 32 | SEQ ID NO: 38 | SEQ ID NO: 23 |
| $V_H$Sb | SEQ ID NO: 37 | SEQ ID NO: 28 | SEQ ID NO: 11 |
| $V_H$Tb | SEQ ID NO: 37 | SEQ ID NO: 28 | SEQ ID NO: 17 |
| $V_H$Ub | SEQ ID NO: 37 | SEQ ID NO: 28 | SEQ ID NO: 23 |
| $V_H$Vb | SEQ ID NO: 37 | SEQ ID NO: 33 | SEQ ID NO: 11 |
| $V_H$Wb | SEQ ID NO: 37 | SEQ ID NO: 33 | SEQ ID NO: 17 |
| $V_H$Xb | SEQ ID NO: 37 | SEQ ID NO: 33 | SEQ ID NO: 23 |
| $V_H$Yb | SEQ ID NO: 37 | SEQ ID NO: 38 | SEQ ID NO: 11 |
| $V_H$Zb | SEQ ID NO: 37 | SEQ ID NO: 38 | SEQ ID NO: 17 |
| $V_H$ABb | SEQ ID NO: 37 | SEQ ID NO: 38 | SEQ ID NO: 23 |

In some embodiments, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences. The following combinations are provided with reference to Table 9 and Table 10 above. Thus, for example, an antibody or antibody binding fragment thereof comprising $V_L$Ab and $V_H$Ab is understood to comprise a light chain having a LCDR1 of SEQ ID NO: 29, a LCDR2 of SEQ ID NO: 30, a LCDR3 of SEQ ID NO: 31, a HCDR1 of SEQ ID NO: 27, a HCDR2 of SEQ ID NO: 28, and a HCDR3 of SEQ ID NO: 11.

Accordingly, in some embodiments, an antibody or antibody binding fragment thereof comprises $V_L$Ab and $V_H$Ab. In some embodiments, an antibody or antibody binding fragment thereof comprises $V_L$Bb and $V_H$Ab. In some embodiments, an antibody or antibody binding fragment thereof comprises $V_L$Cb and $V_H$Ab. In some embodiments, an antibody or antibody binding fragment thereof comprises $V_L$Db and $V_H$Ab. In some embodiments, an antibody or antibody binding fragment thereof comprises $V_L$Eb and $V_H$Ab. In some embodiments, an antibody or antibody binding fragment thereof comprises $V_L$Fb and $V_H$Ab. In some embodiments, an antibody or antibody binding fragment thereof comprises $V_L$Gb and $V_H$Ab. In some embodiments, an antibody or antibody binding fragment thereof comprises $V_L$Hb and $V_H$Ab. In some embodiments, an antibody or antibody binding fragment thereof comprises $V_L$Ib and $V_H$Ab. In some embodiments, an antibody or antibody binding fragment thereof comprises $V_L$Jb and $V_H$Ab. In some embodiments, an antibody or antibody binding fragment thereof comprises $V_L$Kb and $V_H$Ab. In some embodiments, an antibody or antibody binding fragment thereof comprises $V_L$Lb and $V_H$Ab. In some embodiments, an antibody or antibody binding fragment thereof comprises $V_L$Mb and $V_H$Ab. In some embodiments, an antibody or antibody binding fragment thereof comprises $V_L$Nb and $V_H$Ab. In some embodiments, an antibody or antibody binding fragment thereof comprises $V_L$Ob and $V_H$Ab. In some embodiments, an antibody or antibody binding fragment thereof comprises $V_L$Pb and $V_H$Ab. In some embodiments, an antibody or antibody binding fragment thereof comprises $V_L$Qb and $V_H$Ab. In some embodiments, an antibody or antibody binding fragment thereof comprises $V_L$Rb and $V_H$Ab. In some embodiments, an antibody or antibody binding fragment thereof comprises $V_L$Sb and $V_H$Ab. In some embodiments, an antibody or antibody binding fragment thereof comprises $V_L$Tb and $V_H$Ab. In some embodiments, an antibody or antibody binding fragment thereof comprises $V_L$Ub and $V_H$Ab. In some embodiments, an antibody or antibody binding fragment thereof comprises $V_L$Vb and $V_H$Ab. In some embodiments, an antibody or antibody binding fragment thereof comprises $V_L$Wb and $V_H$Ab. In some embodiments, an antibody or antibody binding fragment thereof comprises $V_L$Xb and $V_H$Ab. In some embodiments, an antibody or antibody binding fragment thereof comprises $V_L$Yb and $V_H$Ab. In some embodiments, an antibody or antibody binding fragment thereof comprises $V_L$Zb and $V_H$Ab. In some embodiments, an antibody or antibody binding fragment thereof comprises $V_L$ABb and $V_H$Ab.

In some embodiments, an antibody or antibody binding fragment thereof comprises $V_L$Ab and $V_H$Bb. In some embodiments, an antibody or antibody binding fragment thereof comprises $V_L$Bb and $V_H$Bb. In some embodiments, an antibody or antibody binding fragment thereof comprises $V_L$Cb and $V_H$Bb. In some embodiments, an antibody or antibody binding fragment thereof comprises $V_L$Db and $V_H$Bb. In some embodiments, an antibody or antibody binding fragment thereof comprises $V_L$Eb and $V_H$Bb. In some embodiments, an antibody or antibody binding fragment thereof comprises $V_L$Fb and $V_H$Bb. In some embodiments, an antibody or antibody binding fragment thereof comprises $V_L$Gb and $V_H$Bb. In some embodiments, an antibody or antibody binding fragment thereof comprises $V_L$Hb and $V_H$Bb. In some embodiments, an antibody or antibody binding fragment thereof comprises $V_L$Ib and $V_H$Bb. In some embodiments, an antibody or antibody binding fragment thereof comprises $V_L$Jb and $V_H$Bb. In some embodiments, an antibody or antibody binding fragment thereof comprises $V_L$Kb and $V_H$Bb. In some embodiments, an antibody or antibody binding fragment thereof comprises $V_L$Lb and $V_H$Bb. In some embodiments, an antibody or antibody binding fragment thereof comprises $V_L$Mb and $V_H$Bb. In some embodiments, an antibody or antibody binding fragment thereof comprises $V_L$Nb and $V_H$Bb. In some embodiments, an antibody or antibody binding fragment thereof comprises $V_L$Ob and $V_H$Bb. In some embodiments, an antibody or antibody binding fragment thereof comprises $V_L$Pb and $V_H$Bb. In some embodiments, an antibody or antibody binding fragment thereof comprises $V_L$Qb and $V_H$Bb. In some embodiments, an antibody or antibody binding fragment thereof comprises $V_L$Rb and $V_H$Bb. In some embodiments, an antibody or antibody binding fragment thereof comprises $V_L$Sb and $V_H$Bb. In some embodiments, an antibody or antibody binding fragment thereof comprises $V_L$Tb and $V_H$Bb. In some embodiments, an antibody or antibody binding fragment thereof comprises $V_L$Ub and $V_H$Bb. In some embodiments, an antibody or antibody binding fragment thereof comprises $V_L$Vb and $V_H$Bb. In some embodiments, an antibody or antibody binding fragment thereof comprises $V_L$Wb and $V_H$Bb. In some embodiments, an antibody or antibody binding fragment thereof comprises $V_L$Xb and $V_H$Bb. In some embodiments, an antibody or antibody binding fragment thereof comprises $V_L$Yb and $V_H$Bb. In some embodiments, an antibody or antibody binding fragment thereof comprises $V_L$Zb and $V_H$Bb. In some embodiments, an antibody or antibody binding fragment thereof comprises $V_L$ABb and $V_H$Bb.

In some embodiments, an antibody or antibody binding fragment thereof comprises $V_L$Ab and $V_H$Cb. In some embodiments, an antibody or antibody binding fragment thereof comprises $V_L$Bb and $V_H$Cb. In some embodiments, an antibody or antibody binding fragment thereof comprises $V_L$Cb and $V_H$Cb. In some embodiments, an antibody or antibody binding fragment thereof comprises $V_L$Db and $V_H$Cb. In some embodiments, an antibody or antibody binding fragment thereof comprises $V_L$Eb and $V_H$Cb. In some embodiments, an antibody or antibody binding fragment thereof comprises $V_L$Fb and $V_H$Cb. In some embodiments, an antibody or antibody binding fragment thereof comprises $V_L$Gb and $V_H$Cb. In some embodiments, an antibody or antibody binding fragment thereof comprises $V_L$Hb and $V_H$Cb. In some embodiments, an antibody or antibody binding fragment thereof comprises $V_L$Ib and $V_H$Cb. In some embodiments, an antibody or antibody binding fragment thereof comprises $V_L$Jb and $V_H$Cb. In some embodiments, an antibody or antibody binding fragment thereof comprises $V_L$Kb and $V_H$Cb. In some embodiments, an antibody or antibody binding fragment thereof comprises $V_L$Lb and $V_H$Cb. In some embodiments, an antibody or antibody binding fragment thereof comprises $V_L$Mb and $V_H$Cb. In some embodiments, an antibody or antibody binding fragment thereof comprises $V_L$Nb and $V_H$Cb. In some embodiments, an antibody or antibody binding fragment thereof comprises $V_L$Ob and $V_H$Cb. In some embodiments, an antibody or antibody binding fragment thereof comprises $V_L$Pb and $V_H$Cb. In some embodiments, an antibody or antibody binding fragment thereof comprises $V_L$Qb and $V_H$Cb. In some embodiments, an antibody or antibody binding fragment thereof comprises $V_L$Rb and $V_H$Cb. In some embodiments, an antibody or antibody binding fragment thereof comprises $V_L$Sb and $V_H$Cb. In some embodiments, an antibody or antibody binding fragment thereof comprises $V_L$Tb and $V_H$Cb. In some embodiments, an antibody or antibody binding fragment thereof comprises $V_L$Ub and $V_H$Cb. In some embodiments, an antibody or antibody binding fragment thereof comprises $V_L$Vb and $V_H$Cb. In some embodiments, an antibody or antibody binding fragment thereof comprises $V_L$Wb and $V_H$Cb. In some embodiments, an antibody or antibody binding fragment thereof comprises $V_L$Xb and $V_H$Cb. In some embodiments, an antibody or antibody binding fragment thereof comprises $V_L$Yb and $V_H$Cb. In some embodiments, an antibody or antibody binding fragment thereof comprises $V_L$Zb and $V_H$Cb. In some embodiments, an antibody or antibody binding fragment thereof comprises $V_L$ABb and $V_H$Cb.

In some embodiments, an antibody or antibody binding fragment thereof comprises $V_L$Ab and $V_H$Db. In some embodiments, an antibody or antibody binding fragment thereof comprises $V_L$Bb and $V_H$Db. In some embodiments, an antibody or antibody binding fragment thereof comprises $V_L$Cb and $V_H$Db. In some embodiments, an antibody or antibody binding fragment thereof comprises $V_L$Db and $V_H$Db. In some embodiments, an antibody or antibody binding fragment thereof comprises $V_L$Eb and $V_H$Db. In some embodiments, an antibody or antibody binding fragment thereof comprises $V_L$Fb and $V_H$Db. In some embodiments, an antibody or antibody binding fragment thereof comprises $V_L$Gb and $V_H$Db. In some embodiments, an antibody or antibody binding fragment thereof comprises $V_L$Hb and $V_H$Db. In some embodiments, an antibody or antibody binding fragment thereof comprises $V_L$Ib and $V_H$Db. In some embodiments, an antibody or antibody binding fragment thereof comprises $V_L$Jb and $V_H$Db. In some embodiments, an antibody or antibody binding fragment thereof comprises $V_L$Kb and $V_H$Db. In some embodiments, an antibody or antibody binding fragment thereof comprises $V_L$Lb and $V_H$Db. In some embodiments, an antibody or antibody binding fragment thereof comprises $V_L$Mb and $V_H$Db. In some embodiments, an antibody or antibody binding fragment thereof comprises $V_L$Nb and $V_H$Db. In some embodiments, an antibody or antibody binding fragment thereof comprises $V_L$Ob and $V_H$Db. In some embodiments, an antibody or antibody binding fragment thereof comprises $V_L$Pb and $V_H$Db. In some embodiments, an antibody or antibody binding fragment thereof comprises $V_L$Qb and $V_H$Db. In some embodiments, an antibody or antibody binding fragment thereof comprises $V_L$Rb and $V_H$Db. In some embodiments, an antibody or antibody binding fragment thereof comprises $V_L$Sb and $V_H$Db. In some embodiments, an antibody or antibody binding fragment thereof comprises $V_L$Tb and $V_H$Db. In some embodiments, an antibody or antibody binding fragment thereof comprises $V_L$Ub and $V_H$Db. In some embodiments, an antibody or antibody binding fragment thereof comprises $V_L$Vb and $V_H$Db. In some embodiments, an antibody or antibody binding fragment thereof comprises $V_L$Wb and $V_H$Db. In some embodiments, an antibody or antibody binding fragment thereof comprises $V_L$Xb and $V_H$Db. In some embodiments, an antibody or antibody binding fragment thereof comprises $V_L$Yb and $V_H$Db. In some embodiments, an antibody or antibody binding fragment thereof comprises $V_L$Zb and $V_H$Db. In some embodiments, an antibody or antibody binding fragment thereof comprises $V_L$ABb and $V_H$Db.

In some embodiments, an antibody or antibody binding fragment thereof comprises $V_L$Ab and $V_H$Eb. In some embodiments, an antibody or antibody binding fragment thereof comprises $V_L$Bb and $V_H$Eb. In some embodiments, an antibody or antibody binding fragment thereof comprises $V_L$Cb and $V_H$Eb. In some embodiments, an antibody or antibody binding fragment thereof comprises $V_L$Db and $V_H$Eb. In some embodiments, an antibody or antibody binding fragment thereof comprises $V_L$Eb and $V_H$Eb. In some embodiments, an antibody or antibody binding fragment thereof comprises $V_L$Fb and $V_H$Eb. In some embodiments, an antibody or antibody binding fragment thereof comprises $V_L$Gb and $V_H$Eb. In some embodiments, an antibody or antibody binding fragment thereof comprises $V_L$Hb and $V_H$Eb. In some embodiments, an antibody or antibody binding fragment thereof comprises $V_L$Ib and $V_H$Eb. In some embodiments, an antibody or antibody binding fragment thereof comprises $V_L$Jb and $V_H$Eb. In some embodiments, an antibody or antibody binding fragment thereof comprises $V_L$Kb and $V_H$Eb. In some embodiments, an antibody or antibody binding fragment thereof comprises $V_L$Lb and $V_H$Eb. In some embodiments, an antibody or antibody binding fragment thereof comprises $V_L$Mb and $V_H$Eb. In some embodiments, an antibody or antibody binding fragment thereof comprises $V_L$Nb and $V_H$Eb. In some embodiments, an antibody or antibody binding fragment thereof comprises $V_L$Ob and $V_H$Eb. In some embodiments, an antibody or antibody binding fragment thereof comprises $V_L$Pb and $V_H$Eb. In some embodiments, an antibody or antibody binding fragment thereof comprises $V_L$Qb and $V_H$Eb. In some embodiments, an antibody or antibody binding fragment thereof comprises $V_L$Rb and $V_H$Eb. In some embodiments, an antibody or antibody binding fragment thereof comprises $V_L$Sb and $V_H$Eb. In some embodiments, an antibody or antibody binding fragment thereof comprises $V_L$Tb and $V_H$Eb. In some embodiments, an antibody or antibody binding fragment thereof comprises $V_L$Ub and $V_H$Eb. In some embodiments, an antibody or antibody binding fragment thereof comprises $V_L$Vb and $V_H$Eb. In some embodiments, an antibody or antibody binding fragment thereof comprises $V_L$Wb and $V_H$Eb. In some embodiments, an antibody or antibody binding fragment thereof comprises $V_L$Xb and $V_H$Eb. In some embodiments, an antibody or antibody binding fragment thereof comprises $V_L$Yb and $V_H$Eb. In some embodiments, an antibody or antibody binding fragment thereof comprises $V_L$Zb and $V_H$Eb. In some embodiments, an antibody or antibody binding fragment thereof comprises $V_L$ABb and $V_H$Eb.

In some embodiments, an antibody or antibody binding fragment thereof comprises $V_L$Ab and $V_H$Fb. In some embodiments, an antibody or antibody binding fragment thereof comprises $V_L$Bb and $V_H$Fb. In some embodiments, an antibody or antibody binding fragment thereof comprises $V_L$Cb and $V_H$Fb. In some embodiments, an antibody or antibody binding fragment thereof comprises $V_L$Db and $V_H$Fb. In some embodiments, an antibody or antibody binding fragment thereof comprises $V_L$Eb and $V_H$Fb. In some embodiments, an antibody or antibody binding fragment thereof comprises $V_L$Fb and $V_H$Fb. In some embodiments, an antibody or antibody binding fragment thereof comprises $V_L$Gb and $V_H$Fb. In some embodiments, an antibody or antibody binding fragment thereof comprises $V_L$Hb and $V_H$Fb. In some embodiments, an antibody or antibody binding fragment thereof comprises $V_L$Ib and $V_H$Fb. In some embodiments, an antibody or antibody binding fragment thereof comprises $V_L$Jb and $V_H$Fb. In some embodiments, an antibody or antibody binding fragment thereof comprises $V_L$Kb and $V_H$Fb. In some embodiments, an antibody or antibody binding fragment thereof comprises $V_L$Lb and $V_H$Fb. In some embodiments, an antibody or antibody binding fragment thereof comprises $V_L$Mb and $V_H$Fb. In some embodiments, an antibody or antibody binding fragment thereof comprises $V_L$Nb and $V_H$Fb. In some embodiments, an antibody or antibody binding fragment thereof comprises $V_L$Ob and $V_H$Fb. In some embodiments, an antibody or antibody binding fragment thereof comprises $V_L$Pb and $V_H$Fb. In some embodiments, an antibody or antibody binding fragment thereof comprises $V_L$Qb and $V_H$Fb. In some embodiments, an antibody or antibody binding fragment thereof comprises $V_L$Rb and $V_H$Fb. In some embodiments, an antibody or antibody binding fragment thereof comprises $V_L$Sb and $V_H$Fb. In some embodiments, an antibody or antibody binding fragment thereof comprises $V_L$Tb and $V_H$Fb. In some embodiments, an antibody or antibody binding fragment thereof comprises $V_L$Ub and $V_H$Fb. In some embodiments, an antibody or antibody binding fragment thereof comprises $V_L$Vb and $V_H$Fb. In some embodiments, an antibody or antibody binding fragment thereof comprises $V_L$Wb and $V_H$Fb. In some embodiments, an antibody or antibody binding fragment thereof comprises $V_L$Xb and $V_H$Fb. In some embodiments, an antibody or antibody binding fragment thereof comprises $V_L$Yb and $V_H$Fb. In some embodiments, an antibody or antibody binding fragment thereof comprises $V_L$Zb and $V_H$Fb. In some embodiments, an antibody or antibody binding fragment thereof comprises $V_L$ABb and $V_H$Fb.

In some embodiments, an antibody or antibody binding fragment thereof comprises $V_L$Ab and $V_H$Gb. In some embodiments, an antibody or antibody binding fragment thereof comprises $V_L$Bb and $V_H$Gb. In some embodiments, an antibody or antibody binding fragment thereof comprises $V_L$Cb and $V_H$Gb. In some embodiments, an antibody or antibody binding fragment thereof comprises $V_L$Db and $V_HGb$. In some embodiments, an antibody or antibody binding fragment thereof comprises $V_LEb$ and $V_HGb$. In some embodiments, an antibody or antibody binding fragment thereof comprises $V_LFb$ and $V_HGb$. In some embodiments, an antibody or antibody binding fragment thereof comprises $V_LGb$ and $V_HGb$. In some embodiments, an antibody or antibody binding fragment thereof comprises $V_LHb$ and $V_HGb$. In some embodiments, an antibody or antibody binding fragment thereof comprises $V_LIb$ and $V_HGb$. In some embodiments, an antibody or antibody binding fragment thereof comprises $V_LJb$ and $V_HGb$. In some embodiments, an antibody or antibody binding fragment thereof comprises $V_LKb$ and $V_HGb$. In some embodiments, an antibody or antibody binding fragment thereof comprises $V_LLb$ and $V_HGb$. In some embodiments, an antibody or antibody binding fragment thereof comprises $V_LMb$ and $V_HGb$. In some embodiments, an antibody or antibody binding fragment thereof comprises $V_LNb$ and $V_HGb$. In some embodiments, an antibody or antibody binding fragment thereof comprises $V_LOb$ and $V_HGb$. In some embodiments, an antibody or antibody binding fragment thereof comprises $V_LPb$ and $V_HGb$. In some embodiments, an antibody or antibody binding fragment thereof comprises $V_LQb$ and $V_HGb$. In some embodiments, an antibody or antibody binding fragment thereof comprises $V_LRb$ and $V_HGb$. In some embodiments, an antibody or antibody binding fragment thereof comprises $V_LSb$ and $V_HGb$. In some embodiments, an antibody or antibody binding fragment thereof comprises $V_LTb$ and $V_HGb$. In some embodiments, an antibody or antibody binding fragment thereof comprises $V_LUb$ and $V_HGb$. In some embodiments, an antibody or antibody binding fragment thereof comprises $V_LVb$ and $V_HGb$. In some embodiments, an antibody or antibody binding fragment thereof comprises $V_LWb$ and $V_HGb$. In some embodiments, an antibody or antibody binding fragment thereof comprises $V_LXb$ and $V_HGb$. In some embodiments, an antibody or antibody binding fragment thereof comprises $V_LYb$ and $V_HGb$. In some embodiments, an antibody or antibody binding fragment thereof comprises $V_LZb$ and $V_HGb$. In some embodiments, an antibody or antibody binding fragment thereof comprises $V_LABb$ and $V_HGb$.

In some embodiments, an antibody or antibody binding fragment thereof comprises $V_LAb$ and $V_HHb$. In some embodiments, an antibody or antibody binding fragment thereof comprises $V_LBb$ and $V_HHb$. In some embodiments, an antibody or antibody binding fragment thereof comprises $V_LCb$ and $V_HHb$. In some embodiments, an antibody or antibody binding fragment thereof comprises $V_LDb$ and $V_HHb$. In some embodiments, an antibody or antibody binding fragment thereof comprises $V_LEb$ and $V_HHb$. In some embodiments, an antibody or antibody binding fragment thereof comprises $V_LFb$ and $V_Hb$. In some embodiments, an antibody or antibody binding fragment thereof comprises $V_LGb$ and $V_HHb$. In some embodiments, an antibody or antibody binding fragment thereof comprises $V_LHb$ and $V_HHb$. In some embodiments, an antibody or antibody binding fragment thereof comprises $V_LIb$ and $V_HHb$. In some embodiments, an antibody or antibody binding fragment thereof comprises $V_LJb$ and $V_HHb$. In some embodiments, an antibody or antibody binding fragment thereof comprises $V_LKb$ and $V_HHb$. In some embodiments, an antibody or antibody binding fragment thereof comprises $V_LLb$ and $V_HHb$. In some embodiments, an antibody or antibody binding fragment thereof comprises $V_LMb$ and $V_HHb$. In some embodiments, an antibody or antibody binding fragment thereof comprises $V_LNb$ and $V_HHb$. In some embodiments, an antibody or antibody binding fragment thereof comprises $V_LOb$ and $V_HHb$. In some embodiments, an antibody or antibody binding fragment thereof comprises $V_LPb$ and $V_HHb$. In some embodiments, an antibody or antibody binding fragment thereof comprises $V_LQb$ and $V_HHb$. In some embodiments, an antibody or antibody binding fragment thereof comprises $V_LRb$ and $V_HHb$. In some embodiments, an antibody or antibody binding fragment thereof comprises $V_LSb$ and $V_HHb$. In some embodiments, an antibody or antibody binding fragment thereof comprises $V_LTb$ and $V_HHb$. In some embodiments, an antibody or antibody binding fragment thereof comprises $V_LUb$ and $V_HHb$. In some embodiments, an antibody or antibody binding fragment thereof comprises $V_LVb$ and $V_HHb$. In some embodiments, an antibody or antibody binding fragment thereof comprises $V_LWb$ and $V_HHb$. In some embodiments, an antibody or antibody binding fragment thereof comprises $V_LXb$ and $V_HHb$. In some embodiments, an antibody or antibody binding fragment thereof comprises $V_LYb$ and $V_HHb$. In some embodiments, an antibody or antibody binding fragment thereof comprises $V_LZb$ and $V_HHb$. In some embodiments, an antibody or antibody binding fragment thereof comprises $V_LABb$ and $V_HHb$.

In some embodiments, an antibody or antibody binding fragment thereof comprises $V_LAb$ and $V_HIb$. In some embodiments, an antibody or antibody binding fragment thereof comprises $V_LBb$ and $V_HIb$. In some embodiments, an antibody or antibody binding fragment thereof comprises $V_LCb$ and $V_HIb$. In some embodiments, an antibody or antibody binding fragment thereof comprises $V_LDb$ and $V_HIb$. In some embodiments, an antibody or antibody binding fragment thereof comprises $V_LEb$ and $V_HIb$. In some embodiments, an antibody or antibody binding fragment thereof comprises $V_LFb$ and $V_HIb$. In some embodiments, an antibody or antibody binding fragment thereof comprises $V_LGb$ and $V_HIb$. In some embodiments, an antibody or antibody binding fragment thereof comprises $V_LHb$ and $V_HIb$. In some embodiments, an antibody or antibody binding fragment thereof comprises $V_LIb$ and $V_HIb$. In some embodiments, an antibody or antibody binding fragment thereof comprises $V_LJb$ and $V_HIb$. In some embodiments, an antibody or antibody binding fragment thereof comprises $V_LKb$ and $V_HIb$. In some embodiments, an antibody or antibody binding fragment thereof comprises $V_LLb$ and $V_HIb$. In some embodiments, an antibody or antibody binding fragment thereof comprises $V_LMb$ and $V_HIb$. In some embodiments, an antibody or antibody binding fragment thereof comprises $V_LNb$ and $V_HIb$. In some embodiments, an antibody or antibody binding fragment thereof comprises $V_LOb$ and $V_HIb$. In some embodiments, an antibody or antibody binding fragment thereof comprises $V_LPb$ and $V_HIb$. In some embodiments, an antibody or antibody binding fragment thereof comprises $V_LQb$ and $V_HIb$. In some embodiments, an antibody or antibody binding fragment thereof comprises $V_LRb$ and $V_HIb$. In some embodiments, an antibody or antibody binding fragment thereof comprises $V_LSb$ and $V_HIb$. In some embodiments, an antibody or antibody binding fragment thereof comprises $V_LTb$ and $V_HIb$. In some embodiments, an antibody or antibody binding fragment thereof comprises $V_LUb$ and $V_HIb$. In some embodiments, an antibody or antibody binding fragment thereof comprises $V_LVb$ and $V_HIb$. In some embodiments, an antibody or antibody binding fragment thereof comprises $V_LWb$ and $V_HIb$. In some embodiments, an antibody or antibody binding fragment thereof comprises $V_LXb$ and $V_HIb$. In some embodiments, an antibody or antibody binding fragment thereof comprises $V_L$Yb and $V_H$Ib. In some embodiments, an antibody or antibody binding fragment thereof comprises $V_L$Zb and $V_H$Ib. In some embodiments, an antibody or antibody binding fragment thereof comprises $V_L$ABb and $V_H$Ib.

In some embodiments, an antibody or antibody binding fragment thereof comprises $V_L$Ab and $V_H$Jb. In some embodiments, an antibody or antibody binding fragment thereof comprises $V_L$Bb and $V_H$Jb. In some embodiments, an antibody or antibody binding fragment thereof comprises $V_L$Cb and $V_H$Jb. In some embodiments, an antibody or antibody binding fragment thereof comprises $V_L$Db and $V_H$Jb. In some embodiments, an antibody or antibody binding fragment thereof comprises $V_L$Eb and $V_H$Jb. In some embodiments, an antibody or antibody binding fragment thereof comprises $V_L$Fb and $V_H$Jb. In some embodiments, an antibody or antibody binding fragment thereof comprises $V_L$Gb and $V_H$Jb. In some embodiments, an antibody or antibody binding fragment thereof comprises $V_L$Hb and $V_H$Jb. In some embodiments, an antibody or antibody binding fragment thereof comprises $V_L$Ib and $V_H$Jb. In some embodiments, an antibody or antibody binding fragment thereof comprises $V_L$Jb and $V_H$Jb. In some embodiments, an antibody or antibody binding fragment thereof comprises $V_L$Kb and $V_H$Jb. In some embodiments, an antibody or antibody binding fragment thereof comprises $V_L$Lb and $V_H$Jb. In some embodiments, an antibody or antibody binding fragment thereof comprises $V_L$Mb and $V_H$Jb. In some embodiments, an antibody or antibody binding fragment thereof comprises $V_L$Nb and $V_H$Jb. In some embodiments, an antibody or antibody binding fragment thereof comprises $V_L$Ob and $V_H$Jb. In some embodiments, an antibody or antibody binding fragment thereof comprises $V_L$Pb and $V_H$Jb. In some embodiments, an antibody or antibody binding fragment thereof comprises $V_L$Qb and $V_H$Jb. In some embodiments, an antibody or antibody binding fragment thereof comprises $V_L$Rb and $V_H$Jb. In some embodiments, an antibody or antibody binding fragment thereof comprises $V_L$Sb and $V_H$Jb. In some embodiments, an antibody or antibody binding fragment thereof comprises $V_L$Tb and $V_H$Jb. In some embodiments, an antibody or antibody binding fragment thereof comprises $V_L$Ub and $V_H$Jb. In some embodiments, an antibody or antibody binding fragment thereof comprises $V_L$Vb and $V_H$Jb. In some embodiments, an antibody or antibody binding fragment thereof comprises $V_L$Wb and $V_H$Jb. In some embodiments, an antibody or antibody binding fragment thereof comprises $V_L$Xb and $V_H$Jb. In some embodiments, an antibody or antibody binding fragment thereof comprises $V_L$Yb and $V_H$Jb. In some embodiments, an antibody or antibody binding fragment thereof comprises $V_L$Zb and $V_H$Jb. In some embodiments, an antibody or antibody binding fragment thereof comprises $V_L$ABb and $V_H$Jb.

In some embodiments, an antibody or antibody binding fragment thereof comprises $V_L$Ab and $V_H$Kb. In some embodiments, an antibody or antibody binding fragment thereof comprises $V_L$Bb and $V_H$Kb. In some embodiments, an antibody or antibody binding fragment thereof comprises $V_L$Cb and $V_H$Kb. In some embodiments, an antibody or antibody binding fragment thereof comprises $V_L$Db and $V_H$Kb. In some embodiments, an antibody or antibody binding fragment thereof comprises $V_L$Eb and $V_H$Kb. In some embodiments, an antibody or antibody binding fragment thereof comprises $V_L$Fb and $V_H$Kb. In some embodiments, an antibody or antibody binding fragment thereof comprises $V_L$Gb and $V_H$Kb. In some embodiments, an antibody or antibody binding fragment thereof comprises $V_L$Hb and $V_H$Kb. In some embodiments, an antibody or antibody binding fragment thereof comprises $V_L$Ib and $V_H$Kb. In some embodiments, an antibody or antibody binding fragment thereof comprises $V_L$Jb and $V_H$Kb. In some embodiments, an antibody or antibody binding fragment thereof comprises $V_L$Kb and $V_H$Kb. In some embodiments, an antibody or antibody binding fragment thereof comprises $V_L$Lb and $V_H$Kb. In some embodiments, an antibody or antibody binding fragment thereof comprises $V_L$Mb and $V_H$Kb. In some embodiments, an antibody or antibody binding fragment thereof comprises $V_L$Nb and $V_H$Kb. In some embodiments, an antibody or antibody binding fragment thereof comprises $V_L$Ob and $V_H$Kb. In some embodiments, an antibody or antibody binding fragment thereof comprises $V_L$Pb and $V_H$Kb. In some embodiments, an antibody or antibody binding fragment thereof comprises $V_L$Qb and $V_H$Kb. In some embodiments, an antibody or antibody binding fragment thereof comprises $V_L$Rb and $V_H$Kb. In some embodiments, an antibody or antibody binding fragment thereof comprises $V_L$Sb and $V_H$Kb. In some embodiments, an antibody or antibody binding fragment thereof comprises $V_L$Tb and $V_H$Kb. In some embodiments, an antibody or antibody binding fragment thereof comprises $V_L$Ub and $V_H$Kb. In some embodiments, an antibody or antibody binding fragment thereof comprises $V_L$Vb and $V_H$Kb. In some embodiments, an antibody or antibody binding fragment thereof comprises $V_L$Wb and $V_H$Kb. In some embodiments, an antibody or antibody binding fragment thereof comprises $V_L$Xb and $V_H$Kb. In some embodiments, an antibody or antibody binding fragment thereof comprises $V_L$Yb and $V_H$Kb. In some embodiments, an antibody or antibody binding fragment thereof comprises $V_L$Zb and $V_H$Kb. In some embodiments, an antibody or antibody binding fragment thereof comprises $V_L$ABb and $V_H$Kb.

In some embodiments, an antibody or antibody binding fragment thereof comprises $V_L$Ab and $V_H$Lb. In some embodiments, an antibody or antibody binding fragment thereof comprises $V_L$Bb and $V_H$Lb. In some embodiments, an antibody or antibody binding fragment thereof comprises $V_L$Cb and $V_H$Lb. In some embodiments, an antibody or antibody binding fragment thereof comprises $V_L$Db and $V_H$Lb. In some embodiments, an antibody or antibody binding fragment thereof comprises $V_L$Eb and $V_H$Lb. In some embodiments, an antibody or antibody binding fragment thereof comprises $V_L$Fb and $V_H$Lb. In some embodiments, an antibody or antibody binding fragment thereof comprises $V_L$Gb and $V_H$Lb. In some embodiments, an antibody or antibody binding fragment thereof comprises $V_L$Hb and $V_H$Lb. In some embodiments, an antibody or antibody binding fragment thereof comprises $V_L$Ib and $V_H$Lb. In some embodiments, an antibody or antibody binding fragment thereof comprises $V_L$Jb and $V_H$Lb. In some embodiments, an antibody or antibody binding fragment thereof comprises $V_L$Kb and $V_H$Lb. In some embodiments, an antibody or antibody binding fragment thereof comprises $V_L$Lb and $V_H$Lb. In some embodiments, an antibody or antibody binding fragment thereof comprises $V_L$Mb and $V_H$Lb. In some embodiments, an antibody or antibody binding fragment thereof comprises $V_L$Nb and $V_H$Lb. In some embodiments, an antibody or antibody binding fragment thereof comprises $V_L$Ob and $V_H$b. In some embodiments, an antibody or antibody binding fragment thereof comprises $V_L$Pb and $V_H$Lb. In some embodiments, an antibody or antibody binding fragment thereof comprises $V_L$Qb and $V_H$Lb. In some embodiments, an antibody or antibody binding fragment thereof comprises $V_L$Rb and $V_H$Lb. In some embodiments, an antibody or antibody binding fragment thereof comprises $V_L$Sb and $V_H$Lb. In some embodiments, an antibody or antibody binding fragment thereof comprises $V_L$Tb and $V_H$Lb. In some embodiments, an antibody or antibody binding fragment thereof comprises $V_L$Ub and $V_H$Lb. In some embodiments, an antibody or antibody binding fragment thereof comprises $V_L$Vb and $V_H$Lb. In some embodiments, an antibody or antibody binding fragment thereof comprises $V_L$Wb and $V_H$Lb. In some embodiments, an antibody or antibody binding fragment thereof comprises $V_L$Xb and $V_H$Lb. In some embodiments, an antibody or antibody binding fragment thereof comprises $V_L$Yb and $V_H$Lb. In some embodiments, an antibody or antibody binding fragment thereof comprises $V_L$Zb and $V_H$Lb. In some embodiments, an antibody or antibody binding fragment thereof comprises $V_L$ABb and $V_H$Lb.

In some embodiments, an antibody or antibody binding fragment thereof comprises $V_L$Ab and $V_H$Mb. In some embodiments, an antibody or antibody binding fragment thereof comprises $V_L$Bb and $V_H$Mb. In some embodiments, an antibody or antibody binding fragment thereof comprises $V_L$Cb and $V_H$Mb. In some embodiments, an antibody or antibody binding fragment thereof comprises $V_L$Db and $V_H$Mb. In some embodiments, an antibody or antibody binding fragment thereof comprises $V_L$Eb and $V_H$Mb. In some embodiments, an antibody or antibody binding fragment thereof comprises $V_L$Fb and $V_H$Mb. In some embodiments, an antibody or antibody binding fragment thereof comprises $V_L$Gb and $V_H$Mb. In some embodiments, an antibody or antibody binding fragment thereof comprises $V_L$Hb and $V_H$Mb. In some embodiments, an antibody or antibody binding fragment thereof comprises $V_L$Ib and $V_H$Mb. In some embodiments, an antibody or antibody binding fragment thereof comprises $V_L$Jb and $V_H$Mb. In some embodiments, an antibody or antibody binding fragment thereof comprises $V_L$Kb and $V_H$Mb. In some embodiments, an antibody or antibody binding fragment thereof comprises $V_L$Lb and $V_H$Mb. In some embodiments, an antibody or antibody binding fragment thereof comprises $V_L$Mb and $V_H$Mb. In some embodiments, an antibody or antibody binding fragment thereof comprises $V_L$Nb and $V_H$Mb. In some embodiments, an antibody or antibody binding fragment thereof comprises $V_L$Ob and $V_H$Mb. In some embodiments, an antibody or antibody binding fragment thereof comprises $V_L$Pb and $V_H$Mb. In some embodiments, an antibody or antibody binding fragment thereof comprises $V_L$Qb and $V_H$Mb. In some embodiments, an antibody or antibody binding fragment thereof comprises $V_L$Rb and $V_H$Mb. In some embodiments, an antibody or antibody binding fragment thereof comprises $V_L$Sb and $V_H$Mb. In some embodiments, an antibody or antibody binding fragment thereof comprises $V_L$Tb and $V_H$Mb. In some embodiments, an antibody or antibody binding fragment thereof comprises $V_L$Ub and $V_H$Mb. In some embodiments, an antibody or antibody binding fragment thereof comprises $V_L$Vb and $V_H$Mb. In some embodiments, an antibody or antibody binding fragment thereof comprises $V_L$Wb and $V_H$Mb. In some embodiments, an antibody or antibody binding fragment thereof comprises $V_L$Xb and $V_H$Mb. In some embodiments, an antibody or antibody binding fragment thereof comprises $V_L$Yb and $V_H$Mb. In some embodiments, an antibody or antibody binding fragment thereof comprises $V_L$Zb and $V_H$Mb. In some embodiments, an antibody or antibody binding fragment thereof comprises $V_L$ABb and $V_H$Mb.

In some embodiments, an antibody or antibody binding fragment thereof comprises $V_L$Ab and $V_H$Nb. In some embodiments, an antibody or antibody binding fragment thereof comprises $V_L$Bb and $V_H$Nb. In some embodiments, an antibody or antibody binding fragment thereof comprises $V_L$Cb and $V_H$Nb. In some embodiments, an antibody or antibody binding fragment thereof comprises $V_L$Db and $V_H$Nb. In some embodiments, an antibody or antibody binding fragment thereof comprises $V_L$Eb and $V_H$Nb. In some embodiments, an antibody or antibody binding fragment thereof comprises $V_L$Fb and $V_H$Nb. In some embodiments, an antibody or antibody binding fragment thereof comprises $V_L$Gb and $V_H$Nb. In some embodiments, an antibody or antibody binding fragment thereof comprises $V_L$Hb and $V_H$Nb. In some embodiments, an antibody or antibody binding fragment thereof comprises $V_L$Ib and $V_H$Nb. In some embodiments, an antibody or antibody binding fragment thereof comprises $V_L$Jb and $V_H$Nb. In some embodiments, an antibody or antibody binding fragment thereof comprises $V_L$Kb and $V_H$Nb. In some embodiments, an antibody or antibody binding fragment thereof comprises $V_L$Lb and $V_H$Nb. In some embodiments, an antibody or antibody binding fragment thereof comprises $V_L$Mb and $V_H$Nb. In some embodiments, an antibody or antibody binding fragment thereof comprises $V_L$Nb and $V_H$Nb. In some embodiments, an antibody or antibody binding fragment thereof comprises $V_L$Ob and $V_H$Nb. In some embodiments, an antibody or antibody binding fragment thereof comprises $V_L$Pb and $V_H$Nb. In some embodiments, an antibody or antibody binding fragment thereof comprises $V_L$Qb and $V_H$Nb. In some embodiments, an antibody or antibody binding fragment thereof comprises $V_L$Rb and $V_H$Nb. In some embodiments, an antibody or antibody binding fragment thereof comprises $V_L$Sb and $V_H$Nb. In some embodiments, an antibody or antibody binding fragment thereof comprises $V_L$Tb and $V_H$Nb. In some embodiments, an antibody or antibody binding fragment thereof comprises $V_L$Ub and $V_H$Nb. In some embodiments, an antibody or antibody binding fragment thereof comprises $V_L$Vb and $V_H$Nb. In some embodiments, an antibody or antibody binding fragment thereof comprises $V_L$Wb and $V_H$Nb. In some embodiments, an antibody or antibody binding fragment thereof comprises $V_L$Xb and $V_H$Nb. In some embodiments, an antibody or antibody binding fragment thereof comprises $V_L$Yb and $V_H$Nb. In some embodiments, an antibody or antibody binding fragment thereof comprises $V_L$Zb and $V_H$Nb. In some embodiments, an antibody or antibody binding fragment thereof comprises $V_L$ABb and $V_H$Nb.

In some embodiments, an antibody or antibody binding fragment thereof comprises $V_L$Ab and $V_H$Ob. In some embodiments, an antibody or antibody binding fragment thereof comprises $V_L$Bb and $V_H$Ob. In some embodiments, an antibody or antibody binding fragment thereof comprises $V_L$Cb and $V_H$Ob. In some embodiments, an antibody or antibody binding fragment thereof comprises $V_L$Db and $V_H$Ob. In some embodiments, an antibody or antibody binding fragment thereof comprises $V_L$Eb and $V_H$Ob. In some embodiments, an antibody or antibody binding fragment thereof comprises $V_L$Fb and $V_H$Ob. In some embodiments, an antibody or antibody binding fragment thereof comprises $V_L$Gb and $V_H$Ob. In some embodiments, an antibody or antibody binding fragment thereof comprises $V_L$Hb and $V_H$Ob. In some embodiments, an antibody or antibody binding fragment thereof comprises $V_L$Ib and $V_H$Ob. In some embodiments, an antibody or antibody binding fragment thereof comprises $V_L$Jb and $V_H$Ob. In some embodiments, an antibody or antibody binding fragment thereof comprises $V_L$Kb and $V_H$Ob. In some embodiments, an antibody or antibody binding fragment thereof comprises $V_L$Lb and $V_H$Ob. In some embodiments, an antibody or antibody binding fragment thereof comprises $V_L$Mb and $V_H$Ob. In some embodiments, an antibody or antibody binding fragment thereof comprises $V_L$Nb and $V_H$Ob. In some embodiments, an antibody or antibody binding fragment thereof comprises $V_L$Ob and $V_H$Ob. In some embodiments, an antibody or antibody binding fragment thereof comprises $V_L$Pb and $V_H$Ob. In some embodiments, an antibody or antibody binding fragment thereof comprises $V_L$Qb and $V_H$Ob. In some embodiments, an antibody or antibody binding fragment thereof comprises $V_L$Rb and $V_H$Ob. In some embodiments, an antibody or antibody binding fragment thereof comprises $V_L$Sb and $V_H$Ob. In some embodiments, an antibody or antibody binding fragment thereof comprises $V_L$Tb and $V_H$Ob. In some embodiments, an antibody or antibody binding fragment thereof comprises $V_L$Ub and $V_H$Ob. In some embodiments, an antibody or antibody binding fragment thereof comprises $V_L$Vb and $V_H$Ob. In some embodiments, an antibody or antibody binding fragment thereof comprises $V_L$Wb and $V_H$Ob. In some embodiments, an antibody or antibody binding fragment thereof comprises $V_L$Xb and $V_H$Ob. In some embodiments, an antibody or antibody binding fragment thereof comprises $V_L$Yb and $V_H$Ob. In some embodiments, an antibody or antibody binding fragment thereof comprises $V_L$Zb and $V_H$Ob. In some embodiments, an antibody or antibody binding fragment thereof comprises $V_L$ABb and $V_H$Ob.

In some embodiments, an antibody or antibody binding fragment thereof comprises $V_L$Ab and $V_H$Pb. In some embodiments, an antibody or antibody binding fragment thereof comprises $V_L$Bb and $V_H$Pb. In some embodiments, an antibody or antibody binding fragment thereof comprises $V_L$Cb and $V_H$Pb. In some embodiments, an antibody or antibody binding fragment thereof comprises $V_L$Db and $V_H$Pb. In some embodiments, an antibody or antibody binding fragment thereof comprises $V_L$Eb and $V_H$Pb. In some embodiments, an antibody or antibody binding fragment thereof comprises $V_L$Fb and $V_H$Pb. In some embodiments, an antibody or antibody binding fragment thereof comprises $V_L$Gb and $V_H$Pb. In some embodiments, an antibody or antibody binding fragment thereof comprises $V_L$Hb and $V_H$Pb. In some embodiments, an antibody or antibody binding fragment thereof comprises $V_L$Ib and $V_H$Pb. In some embodiments, an antibody or antibody binding fragment thereof comprises $V_L$Jb and $V_H$Pb. In some embodiments, an antibody or antibody binding fragment thereof comprises $V_L$Kb and $V_H$Pb. In some embodiments, an antibody or antibody binding fragment thereof comprises $V_L$Lb and $V_H$Pb. In some embodiments, an antibody or antibody binding fragment thereof comprises $V_L$Mb and $V_H$Pb. In some embodiments, an antibody or antibody binding fragment thereof comprises $V_L$Nb and $V_H$Pb. In some embodiments, an antibody or antibody binding fragment thereof comprises $V_L$Ob and $V_H$Pb. In some embodiments, an antibody or antibody binding fragment thereof comprises $V_L$Pb and $V_H$Pb. In some embodiments, an antibody or antibody binding fragment thereof comprises $V_L$Qb and $V_H$Pb. In some embodiments, an antibody or antibody binding fragment thereof comprises $V_L$Rb and $V_H$Pb. In some embodiments, an antibody or antibody binding fragment thereof comprises $V_L$Sb and $V_H$Pb. In some embodiments, an antibody or antibody binding fragment thereof comprises $V_L$Tb and $V_H$Pb. In some embodiments, an antibody or antibody binding fragment thereof comprises $V_L$Ub and $V_H$Pb. In some embodiments, an antibody or antibody binding fragment thereof comprises $V_L$Vb and $V_H$Pb. In some embodiments, an antibody or antibody binding fragment thereof comprises $V_L$Wb and $V_H$Pb. In some embodiments, an antibody or antibody binding fragment thereof comprises $V_L$Xb and $V_H$Pb. In some embodiments, an antibody or antibody binding fragment thereof comprises $V_L$Yb and $V_H$Pb. In some embodiments, an antibody or antibody binding fragment thereof comprises $V_L$Zb and $V_H$Pb. In some embodiments, an antibody or antibody binding fragment thereof comprises $V_L$ABb and $V_H$Pb.

In some embodiments, an antibody or antibody binding fragment thereof comprises $V_L$Ab and $V_H$Qb. In some embodiments, an antibody or antibody binding fragment thereof comprises $V_L$Bb and $V_H$Qb. In some embodiments, an antibody or antibody binding fragment thereof comprises $V_L$Cb and $V_H$Qb. In some embodiments, an antibody or antibody binding fragment thereof comprises $V_L$Db and $V_H$Qb. In some embodiments, an antibody or antibody binding fragment thereof comprises $V_L$Eb and $V_H$Qb. In some embodiments, an antibody or antibody binding fragment thereof comprises $V_L$Fb and $V_H$Qb. In some embodiments, an antibody or antibody binding fragment thereof comprises $V_L$Gb and $V_H$Qb. In some embodiments, an antibody or antibody binding fragment thereof comprises $V_L$Hb and $V_H$Qb. In some embodiments, an antibody or antibody binding fragment thereof comprises $V_L$Ib and $V_H$Qb. In some embodiments, an antibody or antibody binding fragment thereof comprises $V_L$Jb and $V_H$Qb. In some embodiments, an antibody or antibody binding fragment thereof comprises $V_L$Kb and $V_H$Qb. In some embodiments, an antibody or antibody binding fragment thereof comprises $V_L$Lb and $V_H$Qb. In some embodiments, an antibody or antibody binding fragment thereof comprises $V_L$Mb and $V_H$Qb. In some embodiments, an antibody or antibody binding fragment thereof comprises $V_L$Nb and $V_H$Qb. In some embodiments, an antibody or antibody binding fragment thereof comprises $V_L$Ob and $V_H$Qb. In some embodiments, an antibody or antibody binding fragment thereof comprises $V_L$Pb and $V_H$Qb. In some embodiments, an antibody or antibody binding fragment thereof comprises $V_L$Qb and $V_H$Qb. In some embodiments, an antibody or antibody binding fragment thereof comprises $V_L$Rb and $V_H$Qb. In some embodiments, an antibody or antibody binding fragment thereof comprises $V_L$Sb and $V_H$Qb. In some embodiments, an antibody or antibody binding fragment thereof comprises $V_L$Tb and $V_H$Qb. In some embodiments, an antibody or antibody binding fragment thereof comprises $V_L$Ub and $V_H$Qb. In some embodiments, an antibody or antibody binding fragment thereof comprises $V_L$Vb and $V_H$Qb. In some embodiments, an antibody or antibody binding fragment thereof comprises $V_L$Wb and $V_H$Qb. In some embodiments, an antibody or antibody binding fragment thereof comprises $V_L$Xb and $V_H$Qb. In some embodiments, an antibody or antibody binding fragment thereof comprises $V_L$Yb and $V_H$Qb. In some embodiments, an antibody or antibody binding fragment thereof comprises $V_L$Zb and $V_H$Qb. In some embodiments, an antibody or antibody binding fragment thereof comprises $V_L$ABb and $V_H$Qb.

In some embodiments, an antibody or antibody binding fragment thereof comprises $V_L$Ab and $V_H$Rb. In some embodiments, an antibody or antibody binding fragment thereof comprises $V_L$Bb and $V_H$Rb. In some embodiments, an antibody or antibody binding fragment thereof comprises $V_L$Cb and $V_H$Rb. In some embodiments, an antibody or antibody binding fragment thereof comprises $V_L$Db and $V_H$Rb. In some embodiments, an antibody or antibody binding fragment thereof comprises $V_L$Eb and $V_H$Rb. In some embodiments, an antibody or antibody binding fragment thereof comprises $V_L$Fb and $V_H$Rb. In some embodiments, an antibody or antibody binding fragment thereof comprises $V_L$Gb and $V_H$Rb. In some embodiments, an antibody or antibody binding fragment thereof comprises $V_L$Hb and $V_H$Rb. In some embodiments, an antibody or antibody binding fragment thereof comprises $V_L$Ib and $V_H$Rb. In some embodiments, an antibody or antibody binding fragment thereof comprises $V_L$Jb and $V_H$Rb. In some embodiments, an antibody or antibody binding fragment thereof comprises $V_L$Kb and $V_H$Rb. In some embodiments, an antibody or antibody binding fragment thereof comprises $V_L$Lb and $V_H$Rb. In some embodiments, an antibody or antibody binding fragment thereof comprises $V_L$Mb and $V_H$Rb. In some embodiments, an antibody or antibody binding fragment thereof comprises $V_L$Nb and $V_H$Rb. In some embodiments, an antibody or antibody binding fragment thereof comprises $V_L$Ob and $V_H$Rb. In some embodiments, an antibody or antibody binding fragment thereof comprises $V_L$Pb and $V_H$Rb. In some embodiments, an antibody or antibody binding fragment thereof comprises $V_L$Qb and $V_H$Rb. In some embodiments, an antibody or antibody binding fragment thereof comprises $V_L$Rb and $V_H$Rb. In some embodiments, an antibody or antibody binding fragment thereof comprises $V_L$Sb and $V_H$Rb. In some embodiments, an antibody or antibody binding fragment thereof comprises $V_L$Tb and $V_H$Rb. In some embodiments, an antibody or antibody binding fragment thereof comprises $V_L$Ub and $V_H$Rb. In some embodiments, an antibody or antibody binding fragment thereof comprises $V_L$Vb and $V_H$Rb. In some embodiments, an antibody or antibody binding fragment thereof comprises $V_L$Wb and $V_H$Rb. In some embodiments, an antibody or antibody binding fragment thereof comprises $V_L$Xb and $V_H$Rb. In some embodiments, an antibody or antibody binding fragment thereof comprises $V_L$Yb and $V_H$Rb. In some embodiments, an antibody or antibody binding fragment thereof comprises $V_L$Zb and $V_H$Rb. In some embodiments, an antibody or antibody binding fragment thereof comprises $V_L$ABb and $V_H$Rb.

In some embodiments, an antibody or antibody binding fragment thereof comprises $V_L$Ab and $V_H$Sb. In some embodiments, an antibody or antibody binding fragment thereof comprises $V_L$Bb and $V_H$Sb. In some embodiments, an antibody or antibody binding fragment thereof comprises $V_L$Cb and $V_H$Sb. In some embodiments, an antibody or antibody binding fragment thereof comprises $V_L$Db and $V_H$Sb. In some embodiments, an antibody or antibody binding fragment thereof comprises $V_L$Eb and $V_H$Sb. In some embodiments, an antibody or antibody binding fragment thereof comprises $V_L$Fb and $V_H$Sb. In some embodiments, an antibody or antibody binding fragment thereof comprises $V_L$Gb and $V_H$Sb. In some embodiments, an antibody or antibody binding fragment thereof comprises $V_L$Hb and $V_H$Sb. In some embodiments, an antibody or antibody binding fragment thereof comprises $V_L$Ib and $V_H$Sb. In some embodiments, an antibody or antibody binding fragment thereof comprises $V_L$Jb and $V_H$Sb. In some embodiments, an antibody or antibody binding fragment thereof comprises $V_L$Kb and $V_H$Sb. In some embodiments, an antibody or antibody binding fragment thereof comprises $V_L$Lb and $V_H$Sb. In some embodiments, an antibody or antibody binding fragment thereof comprises $V_L$Mb and $V_H$Sb. In some embodiments, an antibody or antibody binding fragment thereof comprises $V_L$Nb and $V_H$Sb. In some embodiments, an antibody or antibody binding fragment thereof comprises $V_L$Ob and $V_H$Sb. In some embodiments, an antibody or antibody binding fragment thereof comprises $V_L$Pb and $V_H$Sb. In some embodiments, an antibody or antibody binding fragment thereof comprises $V_L$Qb and $V_H$Sb. In some embodiments, an antibody or antibody binding fragment thereof comprises $V_L$Rb and $V_H$Sb. In some embodiments, an antibody or antibody binding fragment thereof comprises $V_L$Sb and $V_H$Sb. In some embodiments, an antibody or antibody binding fragment thereof comprises $V_L$Tb and $V_H$Sb. In some embodiments, an antibody or antibody binding fragment thereof comprises $V_L$Ub and $V_H$Sb. In some embodiments, an antibody or antibody binding fragment thereof comprises $V_L$Vb and $V_H$Sb. In some embodiments, an antibody or antibody binding fragment thereof comprises $V_L$Wb and $V_H$Sb. In some embodiments, an antibody or antibody binding fragment thereof comprises $V_L$Xb and $V_H$Sb. In some embodiments, an antibody or antibody binding fragment thereof comprises $V_L$Yb and $V_H$Sb. In some embodiments, an antibody or antibody binding fragment thereof comprises $V_L$Zb and $V_H$Sb. In some embodiments, an antibody or antibody binding fragment thereof comprises $V_L$ABb and $V_H$Sb.

In some embodiments, an antibody or antibody binding fragment thereof comprises $V_L$Ab and $V_H$Tb. In some embodiments, an antibody or antibody binding fragment thereof comprises $V_L$Bb and $V_H$Tb. In some embodiments, an antibody or antibody binding fragment thereof comprises $V_L$Cb and $V_H$Tb. In some embodiments, an antibody or antibody binding fragment thereof comprises $V_L$Db and $V_H$Tb. In some embodiments, an antibody or antibody binding fragment thereof comprises $V_L$Eb and $V_H$Tb. In some embodiments, an antibody or antibody binding fragment thereof comprises $V_L$Fb and $V_H$Tb. In some embodiments, an antibody or antibody binding fragment thereof comprises $V_L$Gb and $V_H$Tb. In some embodiments, an antibody or antibody binding fragment thereof comprises $V_L$Hb and $V_H$Tb. In some embodiments, an antibody or antibody binding fragment thereof comprises $V_L$Ib and $V_H$Tb. In some embodiments, an antibody or antibody binding fragment thereof comprises $V_L$Jb and $V_H$Tb. In some embodiments, an antibody or antibody binding fragment thereof comprises $V_L$Kb and $V_H$Tb. In some embodiments, an antibody or antibody binding fragment thereof comprises $V_L$Lb and $V_H$Tb. In some embodiments, an antibody or antibody binding fragment thereof comprises $V_L$Mb and $V_H$Tb. In some embodiments, an antibody or antibody binding fragment thereof comprises $V_L$Nb and $V_H$Tb. In some embodiments, an antibody or antibody binding fragment thereof comprises $V_L$Ob and $V_H$Tb. In some embodiments, an antibody or antibody binding fragment thereof comprises $V_L$Pb and $V_H$Tb. In some embodiments, an antibody or antibody binding fragment thereof comprises $V_L$Qb and $V_H$Tb. In some embodiments, an antibody or antibody binding fragment thereof comprises $V_L$Rb and $V_H$Tb. In some embodiments, an antibody or antibody binding fragment thereof comprises $V_L$Sb and $V_H$Tb. In some embodiments, an antibody or antibody binding fragment thereof comprises $V_L$Tb and $V_H$Tb. In some embodiments, an antibody or antibody binding fragment thereof comprises $V_L$Ub and $V_H$Tb. In some embodiments, an antibody or antibody binding fragment thereof comprises $V_L$Vb and $V_H$Tb. In some embodiments, an antibody or antibody binding fragment thereof comprises $V_LWb$ and $V_HTb$. In some embodiments, an antibody or antibody binding fragment thereof comprises $V_LXb$ and $V_HTb$. In some embodiments, an antibody or antibody binding fragment thereof comprises $V_LYb$ and $V_HTb$. In some embodiments, an antibody or antibody binding fragment thereof comprises $V_LZb$ and $V_HTb$. In some embodiments, an antibody or antibody binding fragment thereof comprises $V_LABb$ and $V_HTb$.

In some embodiments, an antibody or antibody binding fragment thereof comprises $V_LAb$ and $V_HUb$. In some embodiments, an antibody or antibody binding fragment thereof comprises $V_LBb$ and $V_HUb$. In some embodiments, an antibody or antibody binding fragment thereof comprises $V_LCb$ and $V_HUb$. In some embodiments, an antibody or antibody binding fragment thereof comprises $V_LDb$ and $V_HUb$. In some embodiments, an antibody or antibody binding fragment thereof comprises $V_LEb$ and $V_HUb$. In some embodiments, an antibody or antibody binding fragment thereof comprises $V_LFb$ and $V_HUb$. In some embodiments, an antibody or antibody binding fragment thereof comprises $V_LGb$ and $V_HUb$. In some embodiments, an antibody or antibody binding fragment thereof comprises $V_LHb$ and $V_HUb$. In some embodiments, an antibody or antibody binding fragment thereof comprises $V_LIb$ and $V_HUb$. In some embodiments, an antibody or antibody binding fragment thereof comprises $V_LJb$ and $V_HUb$. In some embodiments, an antibody or antibody binding fragment thereof comprises $V_LKb$ and $V_HUb$. In some embodiments, an antibody or antibody binding fragment thereof comprises $V_LLb$ and $V_HUb$. In some embodiments, an antibody or antibody binding fragment thereof comprises $V_LMb$ and $V_HUb$. In some embodiments, an antibody or antibody binding fragment thereof comprises $V_LNb$ and $V_HUb$. In some embodiments, an antibody or antibody binding fragment thereof comprises $V_LOb$ and $V_HUb$. In some embodiments, an antibody or antibody binding fragment thereof comprises $V_LPb$ and $V_HUb$. In some embodiments, an antibody or antibody binding fragment thereof comprises $V_LQb$ and $V_HUb$. In some embodiments, an antibody or antibody binding fragment thereof comprises $V_LRb$ and $V_HUb$. In some embodiments, an antibody or antibody binding fragment thereof comprises $V_LSb$ and $V_HUb$. In some embodiments, an antibody or antibody binding fragment thereof comprises $V_LTb$ and $V_HUb$. In some embodiments, an antibody or antibody binding fragment thereof comprises $V_LUb$ and $V_HUb$. In some embodiments, an antibody or antibody binding fragment thereof comprises $V_LVb$ and $V_HUb$. In some embodiments, an antibody or antibody binding fragment thereof comprises $V_LWb$ and $V_HUb$. In some embodiments, an antibody or antibody binding fragment thereof comprises $V_LXb$ and $V_HUb$. In some embodiments, an antibody or antibody binding fragment thereof comprises $V_LYb$ and $V_HUb$. In some embodiments, an antibody or antibody binding fragment thereof comprises $V_LZb$ and $V_HUb$. In some embodiments, an antibody or antibody binding fragment thereof comprises $V_LABb$ and $V_HUb$.

In some embodiments, an antibody or antibody binding fragment thereof comprises $V_LAb$ and $V_HVb$. In some embodiments, an antibody or antibody binding fragment thereof comprises $V_LBb$ and $V_HVb$. In some embodiments, an antibody or antibody binding fragment thereof comprises $V_LCb$ and $V_HVb$. In some embodiments, an antibody or antibody binding fragment thereof comprises $V_LDb$ and $V_HVb$. In some embodiments, an antibody or antibody binding fragment thereof comprises $V_LEb$ and $V_HVb$. In some embodiments, an antibody or antibody binding fragment thereof comprises $V_LFb$ and $V_HVb$. In some embodiments, an antibody or antibody binding fragment thereof comprises $V_LGb$ and $V_HVb$. In some embodiments, an antibody or antibody binding fragment thereof comprises $V_LHb$ and $V_HVb$. In some embodiments, an antibody or antibody binding fragment thereof comprises $V_LIb$ and $V_HVb$. In some embodiments, an antibody or antibody binding fragment thereof comprises $V_LJb$ and $V_HVb$. In some embodiments, an antibody or antibody binding fragment thereof comprises $V_LKb$ and $V_HVb$. In some embodiments, an antibody or antibody binding fragment thereof comprises $V_LLb$ and $V_HVb$. In some embodiments, an antibody or antibody binding fragment thereof comprises $V_LMb$ and $V_HVb$. In some embodiments, an antibody or antibody binding fragment thereof comprises $V_LNb$ and $V_HVb$. In some embodiments, an antibody or antibody binding fragment thereof comprises $V_LOb$ and $V_HVb$. In some embodiments, an antibody or antibody binding fragment thereof comprises $V_LPb$ and $V_HVb$. In some embodiments, an antibody or antibody binding fragment thereof comprises $V_LQb$ and $V_HVb$. In some embodiments, an antibody or antibody binding fragment thereof comprises $V_LRb$ and $V_HVb$. In some embodiments, an antibody or antibody binding fragment thereof comprises $V_LSb$ and $V_HVb$. In some embodiments, an antibody or antibody binding fragment thereof comprises $V_LTb$ and $V_HVb$. In some embodiments, an antibody or antibody binding fragment thereof comprises $V_LUb$ and $V_HVb$. In some embodiments, an antibody or antibody binding fragment thereof comprises $V_LVb$ and $V_HVb$. In some embodiments, an antibody or antibody binding fragment thereof comprises $V_LWb$ and $V_HVb$. In some embodiments, an antibody or antibody binding fragment thereof comprises $V_LXb$ and $V_HVb$. In some embodiments, an antibody or antibody binding fragment thereof comprises $V_LYb$ and $V_HVb$. In some embodiments, an antibody or antibody binding fragment thereof comprises $V_LZb$ and $V_HVb$. In some embodiments, an antibody or antibody binding fragment thereof comprises $V_LABb$ and $V_HVb$.

In some embodiments, an antibody or antibody binding fragment thereof comprises $V_LAb$ and $V_HWb$. In some embodiments, an antibody or antibody binding fragment thereof comprises $V_LBb$ and $V_HWb$. In some embodiments, an antibody or antibody binding fragment thereof comprises $V_LCb$ and $V_HWb$. In some embodiments, an antibody or antibody binding fragment thereof comprises $V_LDb$ and $V_HWb$. In some embodiments, an antibody or antibody binding fragment thereof comprises $V_LEb$ and $V_HWb$. In some embodiments, an antibody or antibody binding fragment thereof comprises $V_LFb$ and $V_HWb$. In some embodiments, an antibody or antibody binding fragment thereof comprises $V_LGb$ and $V_HWb$. In some embodiments, an antibody or antibody binding fragment thereof comprises $V_LHb$ and $V_HWb$. In some embodiments, an antibody or antibody binding fragment thereof comprises $V_LIb$ and $V_HWb$. In some embodiments, an antibody or antibody binding fragment thereof comprises $V_LJb$ and $V_HWb$. In some embodiments, an antibody or antibody binding fragment thereof comprises $V_LKb$ and $V_HWb$. In some embodiments, an antibody or antibody binding fragment thereof comprises $V_LLb$ and $V_HWb$. In some embodiments, an antibody or antibody binding fragment thereof comprises $V_LMb$ and $V_HWb$. In some embodiments, an antibody or antibody binding fragment thereof comprises $V_LNb$ and $V_HWb$. In some embodiments, an antibody or antibody binding fragment thereof comprises $V_LOb$ and $V_HWb$. In some embodiments, an antibody or antibody binding fragment thereof comprises $V_L$Pb and $V_H$Wb. In some embodiments, an antibody or antibody binding fragment thereof comprises $V_L$Qb and $V_H$Wb. In some embodiments, an antibody or antibody binding fragment thereof comprises $V_L$Rb and $V_H$Wb. In some embodiments, an antibody or antibody binding fragment thereof comprises $V_L$Sb and $V_H$Wb. In some embodiments, an antibody or antibody binding fragment thereof comprises $V_L$Tb and $V_H$Wb. In some embodiments, an antibody or antibody binding fragment thereof comprises $V_L$Ub and $V_H$Wb. In some embodiments, an antibody or antibody binding fragment thereof comprises $V_L$Vb and $V_H$Wb. In some embodiments, an antibody or antibody binding fragment thereof comprises $V_L$Wb and $V_H$Wb. In some embodiments, an antibody or antibody binding fragment thereof comprises $V_L$Xb and $V_H$Wb. In some embodiments, an antibody or antibody binding fragment thereof comprises $V_L$Yb and $V_H$Wb. In some embodiments, an antibody or antibody binding fragment thereof comprises $V_L$Zb and $V_H$Wb. In some embodiments, an antibody or antibody binding fragment thereof comprises $V_L$ABb and $V_H$Wb.

In some embodiments, an antibody or antibody binding fragment thereof comprises $V_L$Ab and $V_H$Xb. In some embodiments, an antibody or antibody binding fragment thereof comprises $V_L$Bb and $V_H$Xb. In some embodiments, an antibody or antibody binding fragment thereof comprises $V_L$Cb and $V_H$Xb. In some embodiments, an antibody or antibody binding fragment thereof comprises $V_L$Db and $V_H$Xb. In some embodiments, an antibody or antibody binding fragment thereof comprises $V_L$Eb and $V_H$Xb. In some embodiments, an antibody or antibody binding fragment thereof comprises $V_L$Fb and $V_H$Xb. In some embodiments, an antibody or antibody binding fragment thereof comprises $V_L$Gb and $V_H$Xb. In some embodiments, an antibody or antibody binding fragment thereof comprises $V_L$Hb and $V_H$Xb. In some embodiments, an antibody or antibody binding fragment thereof comprises $V_L$Ib and $V_H$Xb. In some embodiments, an antibody or antibody binding fragment thereof comprises $V_L$Jb and $V_H$Xb. In some embodiments, an antibody or antibody binding fragment thereof comprises $V_L$Kb and $V_H$Xb. In some embodiments, an antibody or antibody binding fragment thereof comprises $V_L$Lb and $V_H$Xb. In some embodiments, an antibody or antibody binding fragment thereof comprises $V_L$Mb and $V_H$Xb. In some embodiments, an antibody or antibody binding fragment thereof comprises $V_L$Nb and $V_H$Xb. In some embodiments, an antibody or antibody binding fragment thereof comprises $V_L$Ob and $V_H$Xb. In some embodiments, an antibody or antibody binding fragment thereof comprises $V_L$Pb and $V_H$Xb. In some embodiments, an antibody or antibody binding fragment thereof comprises $V_L$Qb and $V_H$Xb. In some embodiments, an antibody or antibody binding fragment thereof comprises $V_L$Rb and $V_H$Xb. In some embodiments, an antibody or antibody binding fragment thereof comprises $V_L$Sb and $V_H$Xb. In some embodiments, an antibody or antibody binding fragment thereof comprises $V_L$Tb and $V_H$Xb. In some embodiments, an antibody or antibody binding fragment thereof comprises $V_L$Ub and $V_H$Xb. In some embodiments, an antibody or antibody binding fragment thereof comprises $V_L$Vb and $V_H$Xb. In some embodiments, an antibody or antibody binding fragment thereof comprises $V_L$Wb and $V_H$Xb. In some embodiments, an antibody or antibody binding fragment thereof comprises $V_L$Xb and $V_H$Xb. In some embodiments, an antibody or antibody binding fragment thereof comprises $V_L$Yb and $V_H$Xb. In some embodiments, an antibody or antibody binding fragment thereof comprises $V_L$Zb and $V_H$Xb. In some embodiments, an antibody or antibody binding fragment thereof comprises $V_L$ABb and $V_H$Xb.

In some embodiments, an antibody or antibody binding fragment thereof comprises $V_L$Ab and $V_H$Yb. In some embodiments, an antibody or antibody binding fragment thereof comprises $V_L$Bb and $V_H$Yb. In some embodiments, an antibody or antibody binding fragment thereof comprises $V_L$Cb and $V_H$Yb. In some embodiments, an antibody or antibody binding fragment thereof comprises $V_L$Db and $V_H$Yb. In some embodiments, an antibody or antibody binding fragment thereof comprises $V_L$Eb and $V_H$Yb. In some embodiments, an antibody or antibody binding fragment thereof comprises $V_L$Fb and $V_H$Yb. In some embodiments, an antibody or antibody binding fragment thereof comprises $V_L$Gb and $V_H$Yb. In some embodiments, an antibody or antibody binding fragment thereof comprises $V_L$Hb and $V_H$Yb. In some embodiments, an antibody or antibody binding fragment thereof comprises $V_L$Ib and $V_H$Yb. In some embodiments, an antibody or antibody binding fragment thereof comprises $V_L$Jb and $V_H$Yb. In some embodiments, an antibody or antibody binding fragment thereof comprises $V_L$Kb and $V_H$Yb. In some embodiments, an antibody or antibody binding fragment thereof comprises $V_L$Lb and $V_H$Yb. In some embodiments, an antibody or antibody binding fragment thereof comprises $V_L$Mb and $V_H$Yb. In some embodiments, an antibody or antibody binding fragment thereof comprises $V_L$Nb and $V_H$Yb. In some embodiments, an antibody or antibody binding fragment thereof comprises $V_L$Ob and $V_H$Yb. In some embodiments, an antibody or antibody binding fragment thereof comprises $V_L$Pb and $V_H$Yb. In some embodiments, an antibody or antibody binding fragment thereof comprises $V_L$Qb and $V_H$Yb. In some embodiments, an antibody or antibody binding fragment thereof comprises $V_L$Rb and $V_H$Yb. In some embodiments, an antibody or antibody binding fragment thereof comprises $V_L$Sb and $V_H$Yb. In some embodiments, an antibody or antibody binding fragment thereof comprises $V_L$Tb and $V_H$Yb. In some embodiments, an antibody or antibody binding fragment thereof comprises $V_L$Ub and $V_H$Yb. In some embodiments, an antibody or antibody binding fragment thereof comprises $V_L$Vb and $V_H$Yb. In some embodiments, an antibody or antibody binding fragment thereof comprises $V_L$Wb and $V_H$Yb. In some embodiments, an antibody or antibody binding fragment thereof comprises $V_L$Xb and $V_H$Yb. In some embodiments, an antibody or antibody binding fragment thereof comprises $V_L$Yb and $V_H$Yb. In some embodiments, an antibody or antibody binding fragment thereof comprises $V_L$Zb and $V_H$Yb. In some embodiments, an antibody or antibody binding fragment thereof comprises $V_L$ABb and $V_H$Yb.

In some embodiments, an antibody or antibody binding fragment thereof comprises $V_L$Ab and $V_H$Zb. In some embodiments, an antibody or antibody binding fragment thereof comprises $V_L$Bb and $V_H$Zb. In some embodiments, an antibody or antibody binding fragment thereof comprises $V_L$Cb and $V_H$Zb. In some embodiments, an antibody or antibody binding fragment thereof comprises $V_L$Db and $V_H$Zb. In some embodiments, an antibody or antibody binding fragment thereof comprises $V_L$Eb and $V_H$Zb. In some embodiments, an antibody or antibody binding fragment thereof comprises $V_L$Fb and $V_H$Zb. In some embodiments, an antibody or antibody binding fragment thereof comprises $V_L$Gb and $V_H$Zb. In some embodiments, an antibody or antibody binding fragment thereof comprises $V_L$Hb and $V_H$Zb. In some embodiments, an antibody or antibody binding fragment thereof comprises $V_L$Ib and $V_H$Zb. In some embodiments, an antibody or antibody binding fragment thereof comprises $V_L$Jb and $V_H$Zb. In some embodiments, an antibody or antibody binding fragment thereof comprises $V_L$Kb and $V_H$Zb. In some embodiments, an antibody or antibody binding fragment thereof comprises $V_L$Lb and $V_H$Zb. In some embodiments, an antibody or antibody binding fragment thereof comprises $V_L$Mb and $V_H$Zb. In some embodiments, an antibody or antibody binding fragment thereof comprises $V_L$Nb and $V_H$Zb. In some embodiments, an antibody or antibody binding fragment thereof comprises $V_L$Ob and $V_H$Zb. In some embodiments, an antibody or antibody binding fragment thereof comprises $V_L$Pb and $V_H$Zb. In some embodiments, an antibody or antibody binding fragment thereof comprises $V_L$Qb and $V_H$Zb. In some embodiments, an antibody or antibody binding fragment thereof comprises $V_L$Rb and $V_H$Zb. In some embodiments, an antibody or antibody binding fragment thereof comprises $V_L$Sb and $V_H$Zb. In some embodiments, an antibody or antibody binding fragment thereof comprises $V_L$Tb and $V_H$Zb. In some embodiments, an antibody or antibody binding fragment thereof comprises $V_L$Ub and $V_H$Zb. In some embodiments, an antibody or antibody binding fragment thereof comprises $V_L$Vb and $V_H$Zb. In some embodiments, an antibody or antibody binding fragment thereof comprises $V_L$Wb and $V_H$Zb. In some embodiments, an antibody or antibody binding fragment thereof comprises $V_L$Xb and $V_H$Zb. In some embodiments, an antibody or antibody binding fragment thereof comprises $V_L$Yb and $V_H$Zb. In some embodiments, an antibody or antibody binding fragment thereof comprises $V_L$Zb and $V_H$Zb. In some embodiments, an antibody or antibody binding fragment thereof comprises $V_L$ABb and $V_H$Zb.

In some embodiments, an antibody or antibody binding fragment thereof comprises $V_L$Ab and $V_H$ABb. In some embodiments, an antibody or antibody binding fragment thereof comprises $V_L$Bb and $V_H$ABb. In some embodiments, an antibody or antibody binding fragment thereof comprises $V_L$Cb and $V_H$ABb. In some embodiments, an antibody or antibody binding fragment thereof comprises $V_L$Db and $V_H$ABb. In some embodiments, an antibody or antibody binding fragment thereof comprises $V_L$Eb and $V_H$ABb. In some embodiments, an antibody or antibody binding fragment thereof comprises $V_L$Fb and $V_H$ABb. In some embodiments, an antibody or antibody binding fragment thereof comprises $V_L$Gb and $V_H$ABb. In some embodiments, an antibody or antibody binding fragment thereof comprises $V_L$Hb and $V_H$ABb. In some embodiments, an antibody or antibody binding fragment thereof comprises $V_L$Ib and $V_H$ABb. In some embodiments, an antibody or antibody binding fragment thereof comprises $V_L$Jb and $V_H$ABb. In some embodiments, an antibody or antibody binding fragment thereof comprises $V_L$Kb and $V_H$ABb. In some embodiments, an antibody or antibody binding fragment thereof comprises $V_L$Lb and $V_H$ABb. In some embodiments, an antibody or antibody binding fragment thereof comprises $V_L$Mb and $V_H$ABb. In some embodiments, an antibody or antibody binding fragment thereof comprises $V_L$Nb and $V_H$ABb. In some embodiments, an antibody or antibody binding fragment thereof comprises $V_L$Ob and $V_H$ABb. In some embodiments, an antibody or antibody binding fragment thereof comprises $V_L$Pb and $V_H$ABb. In some embodiments, an antibody or antibody binding fragment thereof comprises $V_L$Qb and $V_H$ABb. In some embodiments, an antibody or antibody binding fragment thereof comprises $V_L$Rb and $V_H$ABb. In some embodiments, an antibody or antibody binding fragment thereof comprises $V_L$Sb and $V_H$ABb. In some embodiments, an antibody or antibody binding fragment thereof comprises $V_L$Tb and $V_H$ABb. In some embodiments, an antibody or antibody binding fragment thereof comprises $V_L$Ub and $V_H$ABb. In some embodiments, an antibody or antibody binding fragment thereof comprises $V_L$Vb and $V_H$ABb. In some embodiments, an antibody or antibody binding fragment thereof comprises $V_L$Wb and $V_H$ABb. In some embodiments, an antibody or antibody binding fragment thereof comprises $V_L$Xb and $V_H$ABb. In some embodiments, an antibody or antibody binding fragment thereof comprises $V_L$Yb and $V_H$ABb. In some embodiments, an antibody or antibody binding fragment thereof comprises $V_L$Zb and $V_H$ABb. In some embodiments, an antibody or antibody binding fragment thereof comprises $V_L$ABb and $V_H$ABb.

In some embodiments, the light chain variable region LCDR1 is replaced with any of the other light chain LCDR1 sequences. In some embodiments, the light chain variable region LCDR2 is replaced with any of the other light chain LCDR2 sequences. In some embodiments, the light chain variable region LCDR3 is replaced with any of the other light chain LCDR3 sequences. In some embodiments, the heavy chain variable region HCDR1 is replaced with any of the other heavy chain HCDR1 sequences. In some embodiments, the heavy chain variable region HCDR2 is replaced with any of the other heavy chain HCDR2 sequences. In some embodiments, the heavy chain variable region HCDR3 is replaced with any of the other heavy chain HCDR3 sequences.

In some embodiments, any LCDR1, LCDR2, and LCDR3 pairing from any of the Kabat, IMGT, or CHOTHIA designations may be paired with any HCDR1, HCDR2, and HCDR3 pairing from any of the Kabat, IMGT, or CHOTHIA designations. For example, using the designations as recited in Tables 6-10, an antibody or antibody fragment may comprise $V_L$A and any one of $V_H$A, $V_H$B, $V_H$C, $V_L$D, $V_H$E, $V_H$F, $V_H$G, $V_H$H, $V_H$I, $V_H$J, $V_H$K, $V_H$L, $V_H$M, $V_H$N, $V_H$O, $V_H$P, $V_H$Q, $V_H$R, $V_H$S, $V_H$T, $V_H$U, $V_H$V, $V_H$W, $V_H$X, $V_H$Y, $V_H$Z, $V_H$AB, $V_H$Aa, $V_H$Ba, $V_H$Ca, $V_H$Da, $V_H$Ea, $V_H$Fa, $V_H$Ga, $V_H$Ha, $V_H$Ia, $V_H$Ja, $V_H$Ka, $V_H$La, $V_H$Ma, $V_H$Na, $V_H$Oa, $V_H$Pa, $V_H$Qa, $V_H$Ra, $V_H$Sa, $V_H$Ta, $V_H$Ua, $V_H$Va, $V_H$Wa, $V_H$Xa, $V_H$Ya, $V_H$Za, $V_H$ABa, $V_H$Ab, $V_H$Bb, $V_H$Cb, $V_H$Db, $V_H$Eb, $V_H$Fb, $V_H$Gb, $V_L$Hb, $V_H$Ib, $V_L$Jb, $V_L$Kb, $V_H$Lb, $V_H$Mb, $V_H$Nb, $V_H$OD, $V_H$Pb, $V_H$Qb, $V_H$Rb, $V_H$Sb, $V_H$Tb, $V_H$Ub, $V_H$VO, $V_H$Wb, $V_H$Xb, $V_H$Yb, $V_H$Zb, or $V_H$ABb. It is to be understood that the above example is for illustrative purposes only and is not meant to be limiting in any way. Thus, it is to be understood that the above embodiment recited for $V_L$A is also true for $V_L$B, $V_L$C, $V_L$D, $V_L$E, $V_L$F, $V_L$G, $V_L$H, $V_L$I, $V_L$J, $V_L$K, $V_L$L, $V_L$M, $V_L$N, $V_L$O, $V_L$P, $V_L$Q, $V_L$R, $V_L$S, $V_L$T, $V_L$U, $V_L$V, $V_L$W, $V_L$X, $V_L$Y, $V_L$Z, $V_L$AB, $V_L$Aa, $V_L$Ba, $V_L$Ca, $V_L$Da, $V_L$Ea, $V_L$Fa, $V_L$Ga, $V_L$Ha, $V_L$Ia, $V_L$Ja, $V_L$Ka, $V_L$La, $V_L$Ma, $V_L$Na, $V_L$Oa, $V_L$Pa, $V_L$Qa, $V_L$Ra, $V_L$Sa, $V_L$Ta, $V_L$Ua, $V_L$Va, $V_L$Wa, $V_L$Xa, $V_L$Ya, $V_L$Za, $V_L$ABa, $V_L$Ab, $V_L$Bb, $V_L$Cb, $V_L$Db, $V_L$Eb, $V_L$Fb, $V_L$Gb, $V_L$Hb, $V_L$Ib, $V_L$Jb, $V_L$Kb, $V_L$Lb, $V_L$Mb, $V_L$Nb, $V_L$Ob, $V_L$Pb, $V_L$Qb, $V_L$Rb, $V_L$Sb, $V_L$Tb, $V_L$Ub, $V_L$Vb, $V_L$Wb, $V_L$Xb, $V_L$Yb, $V_L$Zb, and $V_H$ABb, and all such combinations are within the scope of the present disclosure.

In some embodiments, an antibody or antigen-binding fragment thereof is provided, wherein the HCDR1, HCDR2, and HCDR3 are selected from SEQ ID NO: 9, SEQ ID NO: 10, and SEQ ID NO: 11, respectively, from SEQ ID NO: 27, SEQ ID NO: 28, and SEQ ID NO: 11, respectively, or from SEQ ID NO: 42, SEQ ID NO: 43, and SEQ ID NO: 44, respectively, and the LCDR1, LCDR2, and LCDR3 are selected from SEQ ID NO: 12, SEQ ID NO: 13, and SEQ ID NO: 14, respectively, from SEQ ID NO: 29, SEQ ID NO: 30, and SEQ ID NO: 31, respectively, or from SEQ ID NO: 45, SEQ ID NO: 30, and SEQ ID NO: 14 respectively.

In some embodiments, an antibody or antigen-binding fragment thereof is provided, wherein the HCDR1, HCDR2, and HCDR3 are selected from SEQ ID NO: 15, SEQ ID NO: 16, and SEQ ID NO: 17, respectively, from SEQ ID NO: 32, SEQ ID NO: 33, and SEQ ID NO: 17, respectively, or from SEQ ID NO: 46, SEQ ID NO: 47, and SEQ ID NO: 48, respectively, and the LCDR1, LCDR2, and LCDR3 are selected from SEQ ID NO: 18, SEQ ID NO: 19, and SEQ ID NO: 20, respectively, from SEQ ID NO: 34, SEQ ID NO: 35, and SEQ ID NO: 36, respectively, or from SEQ ID NO: 49, SEQ ID NO: 35, and SEQ ID NO: 20 respectively.

In some embodiments, an antibody or antigen-binding fragment thereof is provided, wherein the HCDR1, HCDR2, and HCDR3 are selected from SEQ ID NO: 21, SEQ ID NO: 22, and SEQ ID NO: 23, respectively, from SEQ ID NO: 37, SEQ ID NO: 38, and SEQ ID NO: 23, respectively, or from SEQ ID NO: 50, SEQ ID NO: 51, and SEQ ID NO: 52, respectively, and the LCDR1, LCDR2, and LCDR3 are selected from SEQ ID NO: 24, SEQ ID NO: 25, and SEQ ID NO: 26, respectively, from SEQ ID NO: 39, SEQ ID NO: 40, and SEQ ID NO: 41, respectively, or from SEQ ID NO: 53, SEQ ID NO: 40, and SEQ ID NO: 26 respectively.

In some embodiments, the antibody comprises a heavy chain variable region peptide having one of the following sequences, or a variant thereof:

TABLE 11

| SEQ ID NO: | AB ID NO. | Sequence |
| --- | --- | --- |
| 1 | MAB1 | QVQLVQSGAEVKKPGASVKVSCKVSGDTLTELSMHWVRQAPGKGLEWMGTFDPEEGETIYAQKFQGRVTMTEDTSTDTAYMELSSLRSEDTAVYYCVTEGLAGRPFDSWGQGTLVTVSS |
| 3 | MAB2 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDETDYALDYWGQGTLVTVSS |
| 5 | MAB3 | EVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGNYYYYYMDVWGKGTTVTVSS |

In some embodiments, the antibody comprises a light chain variable region peptide having one of the following sequences, or a variant thereof:

TABLE 12

| SEQ ID NO: | AB ID NO. | Sequence |
| --- | --- | --- |
| 2 | MAB1 | DIQMTQSPSTLSASVGDRVTITCRASQSISSWLAWYQQKPGKAPKLLIYKASSLESGVPSRFSGSGSGTEFTLTISSLQPDDFATYYCQQYNSYSWTFGQGTKVEIK |
| 4 | MAB2 | DIQMTQSPSSLSASVGDRVTITCQASQDISNYLNWYQQKPGKAPKLLIYDASNLETGVPSRFSGSGSGTDFTFTISSLQPEDIATYYCQQYEDLPLTFGGGTKVEIK |
| 6 | MAB3 | DIQMTQSPSSLSASVGDRVTITCRASQGIRNDLGWYQQKPGKAPKRLIYTASNLQSGVPSRFSGSGSGTEFTLTISSLQPEDFATYYCLQYNSYPLTFGGGTKVEIK |

In some embodiments, an antibody, or antigen binding fragment thereof, comprises a sequence selected from one or more of SEQ ID NO: 1, SEQ ID NO: 2, SEQ ID NO: 3, SEQ ID NO: 4, SEQ ID NO: 5, SEQ ID NO: 6, or any variants thereof.

In some embodiments, an antibody, or antigen binding fragment thereof, comprises a $V_H$ peptide of SEQ ID NO: 1, 3, or 5, or any variant thereof. In some embodiments, an antibody, or antigen binding fragment thereof, comprises a $V_H$ peptide having at least 85% identity to SEQ ID NO: 1, 3, or 5. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 1, 3, or 5. In some embodiments, an antibody, or antigen binding fragment thereof, comprises a $V_H$ peptide of SEQ ID NO: 1, 3, or 5. In some embodiments, an antibody, or antigen binding fragment thereof, comprises a $V_H$ peptide of SEQ ID NO: 1. In some embodiments, an antibody, or antigen binding fragment thereof, comprises a $V_H$ peptide having at least 85% identity to SEQ ID NO: 1. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 1. In some embodiments, an antibody, or antigen binding fragment thereof, comprises a $V_H$ peptide of SEQ ID NO: 3. In some embodiments, an antibody, or antigen binding fragment thereof, comprises a $V_H$ peptide having at least 85% identity to SEQ ID NO: 3. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 3. In some embodiments, an antibody, or antigen binding fragment thereof, comprises a $V_H$ peptide of SEQ ID NO: 5. In some embodiments, an antibody, or antigen binding fragment thereof, comprises a $V_H$ peptide having at least 85% identity to SEQ ID NO: 5. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 5. In some embodiments, an antibody, or antigen binding fragment thereof, comprises a $V_L$ peptide of SEQ ID NO: 2, 4, or 6, or any variant thereof. In some embodiments, an antibody, or antigen binding fragment thereof, comprises a $V_L$ peptide having at least 85% identity to SEQ ID NO: 2, 4, or 6. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 2, 4, or 6. In some embodiments, an antibody, or antigen binding fragment thereof, comprises a $V_L$ peptide of SEQ ID NO: 2, 4, or 6. In some embodiments, an antibody, or antigen binding fragment thereof, comprises a $V_L$ peptide of SEQ ID NO: 2. In some embodiments, an antibody, or antigen binding fragment thereof, comprises a $V_L$ peptide having at least 85% identity to SEQ ID NO: 2. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 2. In some embodiments, an antibody, or antigen binding fragment thereof, comprises a $V_L$ peptide of SEQ ID NO: 4. In some embodiments, an antibody, or antigen binding fragment thereof, comprises a $V_L$ peptide having at least 85% identity to SEQ ID NO: 4. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 4. In some embodiments, an antibody, or antigen binding fragment thereof, comprises a $V_L$ peptide of SEQ ID NO: 6. In some embodiments, an antibody, or antigen binding fragment thereof, comprises a $V_L$ peptide having at least 85% identity to SEQ ID NO: 6. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 6. In some embodiments, an antibody, or antigen binding fragment thereof, comprises a $V_H$ peptide and a $V_L$ peptide, wherein the wherein the $V_H$ peptide comprises a sequence of SEQ ID NO: 1, 3, or 5 or a variant thereof; and the $V_L$ peptide comprises a sequence of SEQ ID NO: 2, 4, or 6 or a variant thereof. In some embodiments, an antibody, or antigen binding fragment thereof, comprises a $V_H$ peptide and a $V_L$ peptide, wherein the wherein the $V_H$ peptide has at least 85%, 86%, 87%, 88%, 89%, 90%, 91%, 92%, 93%, 94%, 95%, 96%, 97%, 98%, or 99% identity to SEQ ID NO: 1, 3, or 5; and the $V_L$ peptide has at least 85%, 86%, 87%, 88%, 89%, 90%, 91%, 92%, 93%, 94%, 95%, 96%, 97%, 98%, or 99% identity to SEQ ID NO: 2, 4, or 6. In some of these embodiments, the $V_H$ peptide comprises a sequence of SEQ ID NO: 1, 3, or 5; and the $V_L$ peptide comprises a sequence of SEQ ID NO: 2, 4, or 6.

In some embodiments, the heavy chain of the antibody or antigen binding fragment thereof comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 1, wherein the antibody or antigen binding fragment thereof maintains a HCDR1 sequence of SEQ ID NO: 9, SEQ ID NO: 27, or SEQ ID NO: 42, maintains a HCDR2 sequence of SEQ ID NO: 10, SEQ ID NO: 28, or SEQ ID NO: 43, maintains a HCDR3 sequence of SEQ ID NO: 11 or SEQ ID NO: 44, maintains a LCDR1 sequence of SEQ ID NO: 12, SEQ ID NO: 29, or SEQ ID NO: 45, maintains a LCDR2 sequence of SEQ ID NO: 13, or SEQ ID NO: 30, and maintains a LCDR3 sequence SEQ ID NO: 14, or SEQ ID NO: 31.

In some embodiments, the heavy chain of the antibody or antigen binding fragment thereof comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 3, wherein the antibody or antigen binding fragment thereof maintains a HCDR1 sequence of SEQ ID NO: 15, SEQ ID NO: 32, or SEQ ID NO: 46, maintains a HCDR2 sequence of SEQ ID NO: 16, SEQ ID NO: 33, or SEQ ID NO: 47, maintains a HCDR3 sequence of SEQ ID NO: 17 or SEQ ID NO: 48, maintains a LCDR1 sequence of SEQ ID NO: 18, SEQ ID NO: 34, or SEQ ID NO: 49, maintains a LCDR2 sequence of SEQ ID NO: 19, or SEQ ID NO: 35, and maintains a LCDR3 sequence SEQ ID NO: 20, or SEQ ID NO: 36.

In some embodiments, the heavy chain of the antibody or antigen binding fragment thereof comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 5, wherein the antibody or antigen binding fragment thereof maintains a HCDR1 sequence of SEQ ID NO: 21, SEQ ID NO: 37, or SEQ ID NO: 50, maintains a HCDR2 sequence of SEQ ID NO: 22, SEQ ID NO: 38, or SEQ ID NO: 51, maintains a HCDR3 sequence of SEQ ID NO: 23 or SEQ ID NO: 52, maintains a LCDR1 sequence of SEQ ID NO: 24, SEQ ID NO: 39, or SEQ ID NO: 53, maintains a LCDR2 sequence of SEQ ID NO: 25, or SEQ ID NO: 40, and maintains a LCDR3 sequence SEQ ID NO: 26, or SEQ ID NO: 41.

In some embodiments, the light chain of the antibody or antigen binding fragment thereof comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 2, wherein the antibody or antigen binding fragment thereof maintains a HCDR1 sequence of SEQ ID NO: 9, SEQ ID NO: 27, or SEQ ID NO: 42, maintains a HCDR2 sequence of SEQ ID NO: 10, SEQ ID NO: 28, or SEQ ID NO: 43, maintains a HCDR3 sequence of SEQ ID NO: 11 or SEQ ID NO: 44, maintains a LCDR1 sequence of SEQ ID NO: 12, SEQ ID NO: 29, or SEQ ID NO: 45, maintains a LCDR2 sequence of SEQ ID NO: 13, or SEQ ID NO: 30, and maintains a LCDR3 sequence SEQ ID NO: 14, or SEQ ID NO: 31.

In some embodiments, the light chain of the antibody or antigen binding fragment thereof comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 4, wherein the antibody or antigen binding fragment thereof maintains a HCDR1 sequence of SEQ ID NO: 15, SEQ ID NO: 32, or SEQ ID NO: 46, maintains a HCDR2 sequence of SEQ ID NO: 16, SEQ ID NO: 33, or SEQ ID NO: 47, maintains a HCDR3 sequence of SEQ ID NO: 17 or SEQ ID NO: 48, maintains a LCDR1 sequence of SEQ ID NO: 18, SEQ ID NO: 34, or SEQ ID NO: 49, maintains a LCDR2 sequence of SEQ ID NO: 19, or SEQ ID NO: 35, and maintains a LCDR3 sequence SEQ ID NO: 20, or SEQ ID NO: 36.

In some embodiments, the light chain of the antibody or antigen binding fragment thereof comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 6, wherein the antibody or antigen binding fragment thereof maintains a HCDR1 sequence of SEQ ID NO: 21, SEQ ID NO: 37, or SEQ ID NO: 50, maintains a HCDR2 sequence of SEQ ID NO: 22, SEQ ID NO: 38, or SEQ ID NO: 51, maintains a HCDR3 sequence of SEQ ID NO: 23 or SEQ ID NO: 52, maintains a LCDR1 sequence of SEQ ID NO: 24, SEQ ID NO: 39, or SEQ ID NO: 53, maintains a LCDR2 sequence of SEQ ID NO: 25, or SEQ ID NO: 40, and maintains a LCDR3 sequence SEQ ID NO: 26, or SEQ ID NO: 41.

The $V_H$ and the $V_L$ sequences can be in any format, including, but not limited to an scFv format where the $V_H$ and $V_H$ regions are linked with a peptide linker. Examples of peptide linkers that can be used to link various peptides provided for herein include, but are not limited to: $(GGGGS)_n$ (SEQ ID NO: 54); $(GGGGA)_n$ (SEQ ID NO: 55), or any combination thereof, wherein each n is independently 1-5. In some embodiments, each n is, independently, 1. In some embodiments, each n is, independently, 2. In some embodiments, each n is, independently, 3. In some embodiments, each n is, independently, 4. In some embodiments, each n is, independently, 5. In some embodiments, the variable regions are not linked with a peptide linker. In some embodiments, the antibody comprises SEQ ID NO: 1 and SEQ ID NO: 2. In some embodiments, the antibody comprises SEQ ID NO: 3 and SEQ ID NO: 4. In some embodiments, the antibody comprises SEQ ID NO: 5 and SEQ ID NO: 6.

As provided for herein, the different peptides (Vu or $V_L$) described herein can be linked with a peptide linker or not linked with a peptide linker and instead form a contiguous sequence. In some embodiments, the heavy chain variable region and the light chain variable region are not linked by a linker. In some embodiments, the heavy chain variable region and the light chain variable region are linked via a peptide linker. In some embodiments, the peptide linker comprises a sequence of $(GGGGS)_n$ (SEQ ID NO: 54); $(GGGGA)_n$ (SEQ ID NO: 55), or any combination thereof, wherein each n is independently 1-5. In some embodiments, each n is, independently, 1. In some embodiments, each n is, independently, 2. In some embodiments, each n is, independently, 3. In some embodiments, each n is, independently, 4. In some embodiments, each n is, independently, 5. The linked peptide format can be represented by a formula of $V_H$-Z-$V_L$ or $V_L$-Z-$V_H$, wherein Z is the peptide linker. In some embodiments, Z is $(GGGGS)_n$ (SEQ ID NO: 54); $(GGGGA)_n$ (SEQ ID NO: 55), or any combination thereof, wherein each n is independently 1-5. In some embodiments, each n is, independently, 1. In some embodiments, each n is, independently, 2. In some embodiments, each n is, independently, 3. In some embodiments, each n is, independently, 4. In some embodiments, each n is, independently, 5.

In some embodiments, the $V_H$ and $V_H$ polypeptides are linked to a Fc region, such as "IgG4 S228P L235E LS" or "IgG4 S228P L235E YTE". In some embodiments, the Fc region is as provided for herein. In some embodiments, the Fc region is "IgG4 S228P L235E LS". In some embodiments, the Fc region is "IgG4 S228 L235E YTE".

In some embodiments, an antibody, or antigen binding fragment thereof, comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 1, 3, or 5, and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 2, 4, or 6. In some embodiments, the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 1. In some embodiments, the $V_H$ peptide comprises a sequence of SEQ ID NO: 1. In some embodiments, the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 3. In some embodiments, the $V_H$ peptide comprises a sequence of SEQ ID NO: 3. In some embodiments, the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 5. In some embodiments, the $V_H$ peptide comprises a sequence of SEQ ID NO: 5. In some embodiments, the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 2. In some embodiments, the $V_L$ peptide comprises a sequence of SEQ ID NO: 2. In some embodiments, the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 4. In some embodiments, the $V_L$ peptide comprises a sequence of SEQ ID NO: 4. In some embodiments, the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 6. In some embodiments, the $V_L$ peptide comprises a sequence of SEQ ID NO: 6.

In some embodiments, an antibody, or antigen binding fragment thereof, comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 1, 3, or 5, and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 2, 4, or 6 provided that the $V_H$ peptide and a $V_L$ peptide comprises a light chain LCDR having a sequence of SEQ ID NO: 12, 13, 14, 18, 19, 20, 24, 25, 26, 29, 30, 31, 34, 35, 36, 39, 40, 41, 45, 49, or 53; and/or a heavy chain HCDR having a sequence of SEQ ID NO: 9, 10, 11, 15, 16, 17, 21, 22, 23, 27, 28, 32, 33, 37, 38, 42, 43, 44, 46, 47, 48, 50, 51, or 52. In some embodiments, the CDRs in the $V_H$ or $V_L$ chain are as set forth in the combinations provided for herein.

In some embodiments, an antibody, or antigen binding fragment thereof, comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 1, 3, or 5, and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 2, 4, or 6 provided that the $V_L$ peptide comprises a LCDR1 having a sequence selected from SEQ ID NO: 12, 18, 24, 29, 34, 39, 45, 49, or 53; a LCDR2 having a sequence selected from SEQ ID NO: 13, 19, 25, 30, 35, or 40; and a LCDR3 having a sequence selected from SEQ ID NO: 14, 20, 26, 31, 36, or 41; and the $V_H$ peptide comprises a HCDR1 having a sequence selected from SEQ ID NO: 9, 15, 21, 27, 32, 37, 42, 46, or 50; a HCDR2 having a sequence selected from SEQ ID NO: 10, 16, 22, 28, 33, 38, 43, 47, or 51; and a HCDR3 having a sequence selected from SEQ ID NO: 11, 17, 23, 44, 48, or 52.

In some embodiments, an antibody, or antigen binding fragment thereof, comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 1, 3, or 5, and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 2, 4, or 6, provided that the $V_L$ peptide comprises a LCDR1 having a sequence selected from SEQ ID NO: 12, 18, 24, 29, 34, 39, 45, 49, or 53, wherein the LCDR1 comprises at most 1 conservative amino acid substitution, a LCDR2 having a sequence selected from SEQ ID NO: 13, 19, 25, 30, 35, or 40, wherein the LCDR2 comprises at most 1 conservative amino acid substitution, and a LCDR3 having a sequence selected from SEQ ID NO: 14, 20, 26, 31, 36, or 41, wherein the LCDR3 comprises at most 1 conservative amino acid substitution and the $V_H$ peptide comprises a HCDR1 having a sequence selected from SEQ ID NO: 9, 15, 21, 27, 32, 37, 42, 46, or 50, wherein the HCDR1 comprises at most 1 conservative amino acid substitution, a HCDR2 having a sequence selected from SEQ ID NO: 10, 16, 22, 28, 33, 38, 43, 47, or 51, wherein the HCDR2 comprises at most 1 conservative amino acid substitution, and a HCDR3 having a sequence selected from SEQ ID NO: 11, 17, 23, 44, 48, or 52, wherein the HCDR3 comprises at most 1 conservative amino acid substitution.

In some embodiments, the antibody or antigen-binding fragment fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 1, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 2, and wherein the antibody or antigen binding fragment thereof maintains a HCDR1 sequence of SEQ ID NO: 9, SEQ ID NO: 27, or SEQ ID NO: 42, maintains a HCDR2 sequence of SEQ ID NO: 10, SEQ ID NO: 28, or SEQ ID NO: 43, maintains a HCDR3 sequence of SEQ ID NO: 11 or SEQ ID NO: 44, maintains a LCDR1 sequence of SEQ ID NO: 12, SEQ ID NO: 29, or SEQ ID NO: 45, maintains a LCDR2 sequence of SEQ ID NO: 13, or SEQ ID NO: 30, and maintains a LCDR3 sequence SEQ ID NO: 14, or SEQ ID NO: 31.

In some embodiments, the antibody or antigen-binding fragment fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 3, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 4, and wherein the antibody or antigen binding fragment thereof maintains a HCDR1 sequence of SEQ ID NO: 15, SEQ ID NO: 32, or SEQ ID NO: 46, maintains a HCDR2 sequence of SEQ ID NO: 16, SEQ ID NO: 33, or SEQ ID NO: 47, maintains a HCDR3 sequence of SEQ ID NO: 17 or SEQ ID NO: 48, maintains a LCDR1 sequence of SEQ ID NO: 18, SEQ ID NO: 34, or SEQ ID NO: 49, maintains a LCDR2 sequence of SEQ ID NO: 19, or SEQ ID NO: 35, and maintains a LCDR3 sequence SEQ ID NO: 20, or SEQ ID NO: 36.

In some embodiments, the antibody or antigen-binding fragment fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 5, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 6, and wherein the antibody or antigen binding fragment thereof maintains a HCDR1 sequence of SEQ ID NO: 21, SEQ ID NO: 37, or SEQ ID NO: 50, maintains a HCDR2 sequence of SEQ ID NO: 22, SEQ ID NO: 38, or SEQ ID NO: 51, maintains a HCDR3 sequence of SEQ ID NO: 23 or SEQ ID NO: 52, maintains a LCDR1 sequence of SEQ ID NO: 24, SEQ ID NO: 39, or SEQ ID NO: 53, maintains a LCDR2 sequence of SEQ ID NO: 25, or SEQ ID NO: 40, and maintains a LCDR3 sequence SEQ ID NO: 26, or SEQ ID NO: 41.

In some embodiments, an antibody, or antigen binding fragment thereof, comprises a $V_H$ peptide and a $V_L$ peptide, wherein the $V_H$ peptide comprises a sequence of SEQ ID NO: 1 and the $V_L$ peptide comprises a sequence of SEQ ID NO: 2.

In some embodiments, an antibody, or antigen binding fragment thereof, comprises a $V_H$ peptide and a $V_L$ peptide, wherein the $V_H$ peptide comprises a sequence of SEQ ID NO: 1 and the $V_L$ peptide comprises a sequence of SEQ ID NO: 4.

In some embodiments, an antibody, or antigen binding fragment thereof, comprises a $V_H$ peptide and a $V_L$ peptide, wherein the $V_H$ peptide comprises a sequence of SEQ ID NO: 1 and the $V_L$ peptide comprises a sequence of SEQ ID NO: 6.

In some embodiments, an antibody, or antigen binding fragment thereof, comprises a $V_H$ peptide and a $V_L$ peptide, wherein the $V_H$ peptide comprises a sequence of SEQ ID NO: 3 and the $V_L$ peptide comprises a sequence of SEQ ID NO: 2.

In some embodiments, an antibody, or antigen binding fragment thereof, comprises a $V_H$ peptide and a $V_L$ peptide, wherein the $V_H$ peptide comprises a sequence of SEQ ID NO: 3 and the $V_L$ peptide comprises a sequence of SEQ ID NO: 4.

In some embodiments, an antibody, or antigen binding fragment thereof, comprises a $V_H$ peptide and a $V_L$ peptide, wherein the $V_H$ peptide comprises a sequence of SEQ ID NO: 3 and the $V_L$ peptide comprises a sequence of SEQ ID NO: 6.

In some embodiments, an antibody, or antigen binding fragment thereof, comprises a $V_H$ peptide and a $V_L$ peptide, wherein the $V_H$ peptide comprises a sequence of SEQ ID NO: 5 and the $V_L$ peptide comprises a sequence of SEQ ID NO: 2.

In some embodiments, an antibody, or antigen binding fragment thereof, comprises a $V_H$ peptide and a $V_L$ peptide, wherein the $V_H$ peptide comprises a sequence of SEQ ID NO: 5 and the $V_L$ peptide comprises a sequence of SEQ ID NO: 4.

In some embodiments, an antibody, or antigen binding fragment thereof, comprises a $V_H$ peptide and a $V_L$ peptide, wherein the $V_H$ peptide comprises a sequence of SEQ ID NO: 5 and the $V_L$ peptide comprises a sequence of SEQ ID NO: 6.

In some embodiments, the antibody comprises a heavy chain as set forth below, which includes the variable region and the constant domain:

TABLE 13

| SEQ ID NO: | AB ID NO. | Sequence |
|---|---|---|
| 66 | MAB1 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGRPFDSWGQGTLVTVSSA STKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFEGGPSVFLFPPKP KDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVLHEALHSHYTQKSLSLSLG |
| 67 | MAB1 with with constant domain PE and YTE mutations | QVQLVQSGAEVKKPGASVKVSCKVSGDTLTELSMHWVRQAPGKG LEWMGTFDPEEGETIYAQKFQGRVTMTEDTSTDTAYMELSSLRSED TAVYYCVTEGLAGRPFDSWGQGTLVTVSSASTKGPSVFPLAPCSRS TSESTAALGCLVKDYFPEPVTVSWNSGALTSGVHTFPAVLQSSGLY SLSSVVTVPSSSLGTKTYTCNVDHKPSNTKVDKRVESKYGPPCPPCP APEFEGGPSVFLFPPKPKDTLYITREPEVTCVVVDVSQEDPEVQFNW YVDGVEVHNAKTKPREEQFNSTYRVVSVLTVLHQDWLNGKEYKC KVSNKGLPSSIEKTISKAKGQPREPQVYTLPPSQEEMTKNQVSLTCL VKGFYPSDIAVEWESNGQPENNYKTTPPVLDSDGSFFLYSRLTVDK SRWQEGNVFSCSVMHEALHNHYTQKSLSLSLG |
| 68 | MAB2 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYALDYWGQGTLVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEFEGGPSVFLFPPKPKDTL MISRTPEVTCVVVDVSQEDPEVQFNWYVDGVEVHNAKTKP REEQFNSTYRVVSVLTVLHQDWLNGKEYKCKVSNKGLPSSI EKTISKAKGQPREPQVYTLPPSQEEMTKNQVSLTCLVKGFYP SDIAVEWESNGQPENNYKTTPPVLDSDGSFFLYSRLTVDKSR WQEGNVFSCSVLHEALHSHYTQKSLSLSLG |
| 69 | MAB2 with with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYALDYWGQGTLVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEFEGGPSVFLFPPKPKDTL YITREPEVTCVVVDVSQEDPEVQFNWYVDGVEVHNAKTKP REEQFNSTYRVVSVLTVLHQDWLNGKEYKCKVSNKGLPSSI EKTISKAKGQPREPQVYTLPPSQEEMTKNQVSLTCLVKGFYP SDIAVEWESNGQPENNYKTTPPVLDSDGSFFLYSRLTVDKSR WQEGNVFSCSVMHEALHNHYTQKSLSLSLG |
| 70 | MAB3 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGNYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK |

TABLE 13-continued

| SEQ ID NO: | AB ID NO. | Sequence |
|---|---|---|
| | | VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVLHEALHSHYTQKSLSLSLG |
| 71 | MAB3 with with constant domain PE and YTE mutations | EVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGNYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLYITREPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVMHEALHNHYTQKSLSLSLG |

In some embodiments, the antibody comprises a light chain as set forth below, which includes the variable region and a constant domain, such as the human kappa constant domain:

TABLE 14

| SEQ ID NO: | AB ID NO. | Sequence |
|---|---|---|
| 72 | MAB1 plus kappa constant domain | DIQMTQSPSTLSASVGDRVTITCRASQSISSWLAWYQQKPGKAPKL<br>LIYKASSLESGVPSRFSGSGSGTEFTLTISSLQPDDFATYYCQQYNSY<br>SWTFGQGTKVEIKRTVAAPSVFIFPPSDEQLKSGTASVVCLLNNFYP<br>REAKVQWKVDNALQSGNSQESVTEQDSKDSTYSLSSTLTLSKADY<br>EKHKVYACEVTHQGLSSPVTKSFNRGEC |
| 73 | MAB2 plus kappa constant domain | DIQMTQSPSSLSASVGDRVTITCQASQDISNYLNWYQQKPG<br>KAPKLLIYDASNLETGVPSRFSGSGSGTDFTFTISSLQPEDIAT<br>YYCQQYEDLPLTFGGGTKVEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC |
| 74 | MAB3 plus kappa constant domain | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYNSYPLTFGGGTKVEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC |

In some embodiments, the antibody or antigen binding fragment thereof of any of the embodiments as provided for herein may comprise any constant domain known, such as but not limited to an IgG constant domain. In some embodiments, the constant domain is as provided for herein. In some non-limiting embodiments, the constant domain is selected from the group including, but not limited to, SEQ ID NO: 7, 8, 57, 58, 65, or a variant thereof as provided for herein. In some embodiments, the constant domain has at least 90, 91, 92, 93, 94, 95, 96, 97, 98, or 99% sequence identity to a sequence selected from the group including, but not limited to, SEQ ID NO: 7, 8, 57, 58, 65, or a variant thereof as provided for herein.

In some embodiments, the antibody, or antigen-binding fragment thereof, comprises a heavy chain that has at least 90, 91, 92, 93, 94, 95, 96, 97, 98, or 99% sequence identity to SEQ ID NO: 66 or SEQ ID NO: 67, wherein the antibody or antigen binding fragment thereof maintains the sequences of the heavy chain and light chain CDRs of MAB1. In some embodiments, the antibody, or antigen-binding fragment thereof, comprises a heavy chain that has at least 85%, 86%, 87%, 88%, 89%, 90%, 91%, 92%, 93%, 94%, 95%, 96%, 97%, 98%, 99%, or 100% sequence identity to SEQ ID NO: 66 or SEQ ID NO: 67, wherein the antibody or antigen binding fragment thereof maintains a HCDR1 sequence of SEQ ID NO: 9, SEQ ID NO: 27, or SEQ ID NO: 42, maintains a HCDR2 sequence of SEQ ID NO: 10, SEQ ID NO: 28, or SEQ ID NO: 43, maintains a HCDR3 sequence of SEQ ID NO: 11 or SEQ ID NO: 44, maintains a LCDR1 sequence of SEQ ID NO: 12, SEQ ID NO: 29, or SEQ ID NO: 45, maintains a LCDR2 sequence of SEQ ID NO: 13, or SEQ ID NO: 30, and maintains a LCDR3 sequence SEQ ID NO: 14, or SEQ ID NO: 31.

In some embodiments, the antibody, or antigen-binding fragment thereof, comprises a heavy chain that has at least 90, 91, 92, 93, 94, 95, 96, 97, 98, or 99% sequence identity to SEQ ID NO: 68 or SEQ ID NO: 69, wherein the antibody or antigen binding fragment thereof maintains the sequences of the heavy chain and light chain CDRs of MAB2. In some embodiments, the antibody, or antigen-binding fragment thereof, comprises a heavy chain that has at least 85%, 86%, 87%, 88%, 89%, 90%, 91%, 92%, 93%, 94%, 95%, 96%, 97%, 98%, 99%, or 100% sequence identity to SEQ ID NO: 68 or SEQ ID NO: 69, wherein the antibody or antigen binding fragment thereof maintains a HCDR1 sequence of SEQ ID NO: 15, SEQ ID NO: 32, or SEQ ID NO: 46, maintains a HCDR2 sequence of SEQ ID NO: 16, SEQ ID NO: 33, or SEQ ID NO: 47, maintains a HCDR3 sequence of SEQ ID NO: 17 or SEQ ID NO: 48, maintains a LCDR1 sequence of SEQ ID NO: 18, SEQ ID NO: 34, or SEQ ID NO: 49, maintains a LCDR2 sequence of SEQ ID NO: 19, or SEQ ID NO: 35, and maintains a LCDR3 sequence SEQ ID NO: 20, or SEQ ID NO: 36.

In some embodiments, the antibody, or antigen-binding fragment thereof, comprises a heavy chain that has at least 90, 91, 92, 93, 94, 95, 96, 97, 98, or 99% sequence identity to SEQ ID NO: 70 or SEQ ID NO: 71, wherein the antibody or antigen binding fragment thereof maintains the sequences of the heavy chain and light chain CDRs of MAB3. In some embodiments, the antibody, or antigen-binding fragment thereof, comprises a heavy chain that has at least 85%, 86%, 87%, 88%, 89%, 90%, 91%, 92%, 93%, 94%, 95%, 96%, 97%, 98%, 99%, or 100% sequence identity to SEQ ID NO: 70 or SEQ ID NO: 71, wherein the antibody or antigen binding fragment thereof maintains a HCDR1 sequence of SEQ ID NO: 21, SEQ ID NO: 37, or SEQ ID NO: 50, maintains a HCDR2 sequence of SEQ ID NO: 22, SEQ ID NO: 38, or SEQ ID NO: 51, maintains a HCDR3 sequence of SEQ ID NO: 23 or SEQ ID NO: 52, maintains a LCDR1 sequence of SEQ ID NO: 24, SEQ ID NO: 39, or SEQ ID NO: 53, maintains a LCDR2 sequence of SEQ ID NO: 25, or SEQ ID NO: 40, and maintains a LCDR3 sequence SEQ ID NO: 26, or SEQ ID NO: 41.

In some embodiments, the antibody, or antigen-binding fragment thereof, comprises a light chain that has at least 90, 91, 92, 93, 94, 95, 96, 97, 98, or 99% sequence identity to SEQ ID NO: 72, wherein the antibody or antigen binding fragment thereof maintains the sequences of the heavy chain and light chain CDRs of MAB1. In some embodiments, the antibody, or antigen-binding fragment thereof, comprises a light chain that has at least 85%, 86%, 87%, 88%, 89%, 90%, 91%, 92%, 93%, 94%, 95%, 96%, 97%, 98%, 99%, or 100% sequence identity to SEQ ID NO: 72, wherein the antibody or antigen binding fragment thereof maintains a HCDR1 sequence of SEQ ID NO: 9, SEQ ID NO: 27, or SEQ ID NO: 42, maintains a HCDR2 sequence of SEQ ID NO: 10, SEQ ID NO: 28, or SEQ ID NO: 43, maintains a HCDR3 sequence of SEQ ID NO: 11 or SEQ ID NO: 44, maintains a LCDR1 sequence of SEQ ID NO: 12, SEQ ID NO: 29, or SEQ ID NO: 45, maintains a LCDR2 sequence of SEQ ID NO: 13, or SEQ ID NO: 30, and maintains a LCDR3 sequence SEQ ID NO: 14, or SEQ ID NO: 31.

In some embodiments, the antibody, or antigen-binding fragment thereof, comprises a light chain that has at least 90, 91, 92, 93, 94, 95, 96, 97, 98, or 99% sequence identity to SEQ ID NO: 73, wherein the antibody or antigen binding fragment thereof maintains the sequences of the heavy chain and light chain CDRs of MAB2. In some embodiments, the antibody, or antigen-binding fragment thereof, comprises a light chain that has at least 85%, 86%, 87%, 88%, 89%, 90%, 91%, 92%, 93%, 94%, 95%, 96%, 97%, 98%, 99%, or 100% sequence identity to SEQ ID NO: 73, wherein the antibody or antigen binding fragment thereof maintains a HCDR1 sequence of SEQ ID NO: 15, SEQ ID NO: 32, or SEQ ID NO: 46, maintains a HCDR2 sequence of SEQ ID NO: 16, SEQ ID NO: 33, or SEQ ID NO: 47, maintains a HCDR3 sequence of SEQ ID NO: 17 or SEQ ID NO: 48, maintains a LCDR1 sequence of SEQ ID NO: 18, SEQ ID NO: 34, or SEQ ID NO: 49, maintains a LCDR2 sequence of SEQ ID NO: 19, or SEQ ID NO: 35, and maintains a LCDR3 sequence SEQ ID NO: 20, or SEQ ID NO: 36.

In some embodiments, the antibody, or antigen-binding fragment thereof, comprises a light chain that has at least 90, 91, 92, 93, 94, 95, 96, 97, 98, or 99% sequence identity to SEQ ID NO: 74, wherein the antibody or antigen binding fragment thereof maintains the sequences of the heavy chain and light chain CDRs of MAB3. In some embodiments, the antibody, or antigen-binding fragment thereof, comprises a light chain that has at least 85%, 86%, 87%, 88%, 89%, 90%, 91%, 92%, 93%, 94%, 95%, 96%, 97%, 98%, 99%, or 100% sequence identity to SEQ ID NO: 74, wherein the antibody or antigen binding fragment thereof maintains a HCDR1 sequence of SEQ ID NO: 21, SEQ ID NO: 37, or SEQ ID NO: 50, maintains a HCDR2 sequence of SEQ ID NO: 22, SEQ ID NO: 38, or SEQ ID NO: 51, maintains a HCDR3 sequence of SEQ ID NO: 23 or SEQ ID NO: 52, maintains a LCDR1 sequence of SEQ ID NO: 24, SEQ ID NO: 39, or SEQ ID NO: 53, maintains a LCDR2 sequence of SEQ ID NO: 25, or SEQ ID NO: 40, and maintains a LCDR3 sequence SEQ ID NO: 26, or SEQ ID NO: 41.

In some embodiments, the antibody or antigen-binding fragment thereof, comprises a light chain that has at least 90, 91, 92, 93, 94, 95, 96, 97, 98, or 99% sequence identity to SEQ ID NO: 72, and a heavy chain that has at least 90, 91, 92, 93, 94, 95, 96, 97, 98, or 99% sequence identity to SEQ ID NO:66 or SEQ ID NO: 67 (HC of MAB1), wherein the antibody or antigen binding fragment thereof maintains the sequences of the heavy chain and light chain CDRs of MAB1. In some embodiments, the antibody or antigen-binding fragment thereof, comprises a light chain that has at least 90, 91, 92, 93, 94, 95, 96, 97, 98, or 99% sequence identity to SEQ ID NO: 72, and a heavy chain that has at least 90, 91, 92, 93, 94, 95, 96, 97, 98, or 99% sequence identity to SEQ ID NO:66 or SEQ ID NO: 67, wherein the antibody or antigen binding fragment thereof maintains a HCDR1 sequence of SEQ ID NO: 9, SEQ ID NO: 27, or SEQ ID NO: 42, maintains a HCDR2 sequence of SEQ ID NO: 10, SEQ ID NO: 28, or SEQ ID NO: 43, maintains a HCDR3 sequence of SEQ ID NO: 11 or SEQ ID NO: 44, maintains a LCDR1 sequence of SEQ ID NO: 12, SEQ ID NO: 29, or SEQ ID NO: 45, maintains a LCDR2 sequence of SEQ ID NO: 13, or SEQ ID NO: 30, and maintains a LCDR3 sequence SEQ ID NO: 14, or SEQ ID NO: 31.

In some embodiments, the antibody or antigen-binding fragment thereof, comprises a light chain that has at least 90, 91, 92, 93, 94, 95, 96, 97, 98, or 99% sequence identity to SEQ ID NO: 73, and a heavy chain that has at least 90, 91, 92, 93, 94, 95, 96, 97, 98, or 99% sequence identity to SEQ ID NO:68 or SEQ ID NO: 69, wherein the antibody or antigen binding fragment thereof maintains the sequences of the heavy chain and light chain CDRs of MAB2. In some embodiments, the antibody or antigen-binding fragment thereof, comprises a light chain that has at least 90, 91, 92, 93, 94, 95, 96, 97, 98, or 99% sequence identity to SEQ ID NO:73, and a heavy chain that has at least 90, 91, 92, 93, 94, 95, 96, 97, 98, or 99% sequence identity to SEQ ID NO:68 or SEQ ID NO: 69, wherein the antibody or antigen binding fragment thereof maintains a HCDR1 sequence of SEQ ID NO: 15, SEQ ID NO: 32, or SEQ ID NO: 46, maintains a HCDR2 sequence of SEQ ID NO: 16, SEQ ID NO: 33, or SEQ ID NO: 47, maintains a HCDR3 sequence of SEQ ID NO: 17 or SEQ ID NO: 48, maintains a LCDR1 sequence of SEQ ID NO: 18, SEQ ID NO: 34, or SEQ ID NO: 49, maintains a LCDR2 sequence of SEQ ID NO: 19, or SEQ ID NO: 35, and maintains a LCDR3 sequence SEQ ID NO: 20, or SEQ ID NO: 36.

In some embodiments, the antibody or antigen-binding fragment thereof, comprises a light chain that has at least 90, 91, 92, 93, 94, 95, 96, 97, 98, or 99% sequence identity to SEQ ID NO: 74 (LC of MAB3), and a heavy chain that has at least 90, 91, 92, 93, 94, 95, 96, 97, 98, or 99% sequence identity to SEQ ID NO:70 or SEQ ID NO: 71, wherein the antibody or antigen binding fragment thereof maintains the sequences of the heavy chain and light chain CDRs of MAB3. In some embodiments, the antibody or antigen-binding fragment thereof, comprises a light chain that has at least 90, 91, 92, 93, 94, 95, 96, 97, 98, or 99% sequence identity to SEQ ID NO: 74, and a heavy chain that has at least 90, 91, 92, 93, 94, 95, 96, 97, 98, or 99% sequence identity to SEQ ID NO:70 or SEQ ID NO: 71, wherein the antibody or antigen binding fragment thereof maintains a HCDR1 sequence of SEQ ID NO: 21, SEQ ID NO: 37, or SEQ ID NO: 50, maintains a HCDR2 sequence of SEQ ID NO: 22, SEQ ID NO: 38, or SEQ ID NO: 51, maintains a HCDR3 sequence of SEQ ID NO: 23 or SEQ ID NO: 52, maintains a LCDR1 sequence of SEQ ID NO: 24, SEQ ID NO: 39, or SEQ ID NO: 53, maintains a LCDR2 sequence of SEQ ID NO: 25, or SEQ ID NO: 40, and maintains a LCDR3 sequence SEQ ID NO: 26, or SEQ ID NO: 41.

In some embodiments, the antibody, or antigen-binding fragment thereof, comprises a light chain having a sequence of SEQ ID NO:72 and a heavy chain that comprises a sequence of SEQ ID NO: 66 or SEQ ID NO: 67.

In some embodiments, the antibody, or antigen-binding fragment thereof, comprises a light chain having a sequence of SEQ ID NO:73 and a heavy chain that comprises a sequence of SEQ ID NO: 68 or SEQ ID NO: 69.

In some embodiments, the antibody, or antigen-binding fragment thereof, comprises a light chain having a sequence of SEQ ID NO:74 and a heavy chain that comprises a sequence of SEQ ID NO: 70 or SEQ ID NO: 71.

As provided for herein, the antibodies, or antigen binding fragments thereof can be variants of the sequences. Accordingly, in some embodiments, a variant of an antibody or antigen binding fragment thereof provided for herein is provided. In some embodiments, the variant comprises mutations selected from substitutions, deletions, insertions, or a combination thereof. In some embodiments, the variant comprises between 1 and 20 mutations. In some embodiments, the variant comprises between 1 and 10 mutations. In some embodiments, the variant comprises between 1 and 5 mutations. In some embodiments, the variant comprises 1, 2, 3, 4, 5, 6, 7, 8, 9, 10, 11, 12, 13, 14, 15, 16, 17, 18, 19, or 20 mutations. In some embodiments, the variant comprises at least 1 mutation. Accordingly, in some embodiments, the variant comprises up to or more than 20 mutations. In some embodiments, the variant comprises 1-10 mutations, wherein the mutations are selected from substitutions, deletions, insertions, or a combination thereof. In some embodiments, the variant comprises 1-10 mutations, wherein the mutations are conservative substitutions. Examples of conservative substitutions are as provided for herein (Table 1). Further, one of skill in the art will recognize and understand the substitutions that are encompassed by the term "conservative substitutions". Such substitutions are within the scope of the present disclosure.

The antibody or antigen binding fragment may comprise an antibody fragment as defined and provided for herein. In some embodiments, the antibody binding fragment is as provided for herein. In some embodiments, the antibody fragment is a scFv antibody, a Fab fragment, a Fab' fragment, or a F(ab')₂ fragment. In some embodiments, the antibody fragment is a scFv antibody. In some embodiments, the antibody fragment is a Fab fragment. In some embodiments, the antibody fragment is a Fab' fragment. In some embodiments, the antibody fragment is a F(ab')₂ fragment.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind C1s. This can be in the form of an antibody drug conjugate ("ADC"), or a multi-specific molecule. The sequences can also be made into chimeric antibodies as described herein.

In some embodiments, the antibody comprises an amino acid sequence comprising a sequence provided for herein or a fragment thereof. In some embodiments, the antibody is a monoclonal antibody. In some embodiments, the antibody is a polyclonal antibody. In some embodiments, the antibody is a humanized antibody. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid molecule encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, an isolated nucleic acid molecule is provided. In some embodiments, the nucleic acid molecule encodes for an antibody, or antigen binding fragment thereof as provided for herein. In some embodiments, the nucleic acid molecule encodes for an antibody, or antigen binding fragment thereof comprising a heavy chain variable region, a light chain variable region, a heavy chain, a light chain or any combination thereof as provided for herein. In some embodiments, the nucleic acid molecule encoding the variable heavy chain is as set forth below:

TABLE 15

| SEQ ID NO: | AB ID NO. | Sequence |
|---|---|---|
| 59 | MAB1 | CAAGTTCAACTGGTTCAAAGCGGGGCCGAGGTAAAGAAG CCAGGCGCTTCTGTGAAAGTCAGTTGCAAGGTGAGTGGG GATACATTGACCGAGCTGAGTATGCACTGGGTCCGGCAA GCTCCTGGCAAGGGTTTGGAATGGATGGGTACTTTTGACC CGGAGGAGGGAGAGACCATCTACGCGCAAAAATTCCAAG GTAGGGTGACCATGACGGAGGATACCAGCACGGATACTG CTTACATGGAGCTCAGCTCCCTCAGAAGTGAAGATACTGC CGTCTACTACTGTGTGACCGAGGGTTTGGCCGGGCGCCCG TTTGATTCATGGGGGCAGGGGACGCTGGTAACGGTCTCG AGT |
| 61 | MAB2 | CAGGTGCAGCTTGTTGAAAGTGGTGGGGGTTTGGTTAAAC CTGGCGGTTCCCTTCGACTTAGCTGCGCGGCGTCAGGGTT CACATTCTCAGATTATTACATGTCTTGGATTCGGCAAGCC CCTGGTAAGGGACTGGAGTGGGTAAGCTACATATCTCGG TCAGGAAGTACAAAGTACTATGCAGATTCAGTGAAGGGC AGGTTTACGATTAGCCGAGACAACGCAAAGAACTCTCTTT ATCTGCAGATGAATTCACTGAGAGCAGAAGATACCGCTG TCTATTATTGTGCCAGAGACGAGACCGATTACGCTCTTGA CTACTGGGGCCAAGGTACGCTGGTTACGGTCTCGAGT |
| 63 | MAB3 | GAAGTCCAGCTTGTTGAGTCTGGCGGAGGGGTGGTTAGG CCAGGAGGTTCCCTTAGGCTTTCCTGTGCGGCATCAGGAT TTACCTTCGATGACTACGGAATGTCATGGGTACGACAAGC TCCCGGCAAAGGCCTCGAATGGGTTTCTGGCATCAACTGG GAGGGCGGTTCCACTGGCTACGCGGACTCAGTTAAGGGT |

TABLE 15-continued

| SEQ ID NO: | AB ID NO. | Sequence |
|---|---|---|
| | | AGGTTCACCATAAGCAGGGACAATGCGAAGAACTCACTG TATCTCCAAATGAACAGTCTCCGCGCCGAGGATACAGCCC TTTACTATTGTGCACGAGATGAGCAATTGGGGGGAATTA TTATTATTACTATTACATGGACGTGTGGGGTAAAGGAACG ACCGTCACAGTCTCGAGT |

In some embodiments, the nucleic acid molecule encoding the variable light chain is as set forth below:

TABLE 16

| SEQ ID NO: | AB ID NO. | Sequence |
|---|---|---|
| 60 | MAB1 | GACATACAAATGACTCAATCACCCTCTACACTTTCCGCCT CTGTCGGCGACAGGGTAACGATAACTTGCCGGGCAAGTC AATCAATCAGCTCCTGGCTTGCTTGGTATCAACAAAAACC AGGCAAGGCACCTAAGCTCCTCATTTACAAGGCGTCATCA CTTGAATCAGGGGTGCCTTCACGATTCAGCGGATCAGGAT CTGGTACTGAATTCACTCTGACCATTTCAAGTCTTCAGCC TGATGACTTTGCGACCTATTATTGCCAGCAGTACAATAGC TACTCATGGACGTTCGGGCAGGGTACTAAAGTCGAGATT AAA |
| 62 | MAB2 | GACATTCAGATGACGCAAAGCCCCTCTAGCTTGTCCGCTA GTGTGGGTGACAGGGTCACCATTACCTGCCAGGCTTCACA AGACATCAGTAATTACCTCAACTGGTATCAGCAGAAACCT GGGAAGGCCCCTAAGCTGTTGATTTACGATGCTAGTAACT TGGAGACCGGGGTACCCAGCAGATTTAGCGGGAGCGGAA GTGGTACGGATTTTACGTTTACCATTAGCAGCTTGCAGCC CGAGGACATCGCTACATATTACTGTCAGCAGTATGAGGA CCTCCCTCTTACCTTCGGCGGTGGAACGAAAGTTGAGATT AAG |
| 64 | MAB3 | GACATACAGATGACTCAGTCCCCAAGTAGTCTGAGCGCCT CTGTCGGCGACCGCGTTACCATTACTTGCCGGGCGAGTCA AGGGATACGCAACGATTTGGGTTGGTATCAGCAAAAGCC CGGAAAGGCCCCAAAGCGGCTGATATACACCGCCTCAAA CCTCCAGTCTGGAGTTCCATCAAGGTTTAGTGGATCTGGA TCTGGCACTGAGTTTACTCTCACTATAAGCTCCCTTCAGC CTGAAGACTTCGCAACTTATTATTGCTTGCAGTATAATAG TTATCCACTCACTTTTGGCGGTGGCACCAAAGTGGAGATT AAG |

In some embodiments, the nucleic acid molecule comprises a sequence of SEQ ID NO: 59, SEQ ID NO: 61, or SEQ ID NO: 63. In some embodiments, the nucleic acid molecule comprises a sequence of SEQ ID NO: 59. In some embodiments, the nucleic acid molecule comprises a sequence of SEQ ID NO: 61. In some embodiments, the nucleic acid molecule comprises a sequence of SEQ ID NO: 63. In some embodiments, a nucleic acid molecule is provided that comprises a sequence of SEQ ID NO: 60, SEQ ID NO: 62, or SEQ ID NO: 64. In some embodiments, the nucleic acid molecule comprises a sequence of SEQ ID NO: 60. In some embodiments, the nucleic acid molecule comprises a sequence of SEQ ID NO: 62. In some embodiments, the nucleic acid molecule comprises a sequence of SEQ ID NO: 64. It is to be understood that the sequences of SEQ ID NO. 59, 60, 61, 62, 63, and 64 (as well as other nucleotide sequences provided for herein) are exemplary sequences and are not meant to be limiting in any way. Due to the degenerate nature of codons, other nucleic acid molecules can be used. In some embodiments, the nucleic acid molecule is codon optimized for expression in a bacterial system. In some embodiments, the nucleic acid molecule is codon optimized for expression in a eukaryotic system or cell. In some embodiments, the nucleic acid molecule is a DNA or RNA molecule that encodes a polypeptide as provided for herein. In some embodiments, the RNA molecule is a mRNA molecule. Accordingly, in some embodiments, the nucleic acid molecule comprises a sequence that is substantially similar to SEQ ID NO: 59, SEQ ID NO: 61, or SEQ ID NO: 63. In some embodiments, the nucleic acid molecule comprises a sequence that has at least 60% % identity to SEQ ID NO: 59, SEQ ID NO: 61, or SEQ ID NO: 63. In some embodiments, the nucleic acid molecule comprises a sequence that has at least 60%, 65%, 70%, 75%, 80%, 85%, 90%, 95%, or 100% identity to SEQ ID NO: 59, SEQ ID NO: 61, or SEQ ID NO: 63, or any percent identity falling within any of the recited percent identities. In some embodiments, the nucleic acid molecule comprises a sequence that is substantially similar to SEQ ID NO: 60, SEQ ID NO: 62, or SEQ ID NO: 64. In some embodiments, the nucleic acid molecule comprises a sequence that has at least 60% % identity to SEQ ID NO: 60, SEQ ID NO: 62, or SEQ ID NO: 64. In some embodiments, the nucleic acid molecule comprises a sequence that has at least 60%, 65%, 70%, 75%, 80%, 85%, 90%, 95%, or 100% identity to SEQ ID NO: 60, SEQ ID NO: 62, or SEQ ID NO: 64, or any percent identity falling within any of the recited percent identities.

In some embodiments, an expression vector is provided. In some embodiments, the expression vector comprises a nucleic acid molecule encoding an antibody or antigen-binding fragment thereof as provided for herein. In some embodiments, the expression vector comprises a nucleic acid molecule as provided for herein. The vector may be any vector known in the art. In some embodiments the vector is as provided for herein. In some embodiments, the vector is a plasmid. In some embodiments the vector is a virus.

In some embodiments, "derivatives" of the antibodies, fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

The identification of these antibodies, or antigen binding fragments thereof, provide the information necessary to generate additional monoclonal antibodies with similar binding characteristics and therapeutic or diagnostic utility that parallel the embodiments of this application.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vásquez M, Kumar S. (2004), which is incorporated by reference in its entirety.

In some embodiments, a host cell is provided. In some embodiments, the host cell comprises an antibody or antigen-binding fragment thereof as provided for herein. In some embodiments, the host cell comprises a nucleic acid molecule encoding for antibody or antigen-binding fragment thereof as provided for herein. In some embodiments, the host cell comprises nucleic acid molecules selected from the group including, but not limited to, SEQ ID NO. 59, 60, 61, 62, 63, 64, any variants thereof as provided for herein, or any combination thereof. In some embodiments, the host cell comprises a vector, said vector comprising comprises a nucleic acid molecule encoding for antibody or antigen-binding fragment thereof as provided for herein. In some embodiments, the vector comprises nucleic acid molecules selected from the group including, but not limited to, SEQ ID NO. 59, 60, 61, 62, 63, 64, any variants thereof as provided for herein, or any combination thereof.

In some embodiments, the host cell produces an antibody or antigen-binding fragment thereof as provided for herein. In some embodiments, an antibody or antigen-binding fragment thereof as provided for herein is provided, wherein the antibody or antigen-binding fragment thereof as provided for herein is produced by the host cell.

In some embodiments, a method of producing a polypeptide is provided. In some embodiments, the polypeptide comprises a heavy chain variable region as provided for herein, a light chain variable region as provided for herein, or a combination thereof. In some embodiments, the method comprises growing a host cell under conditions so that the host cell expresses the polypeptide comprising the heavy chain variable region, light chain variable region, or combination thereof, and purifying the polypeptide comprising the heavy chain variable region, the light chain variable region, or a combination thereof, thereby producing the polypeptide. In some embodiments, the host cell is a host cell as provided for herein.

In some embodiments, a method of producing an antibody or antigen binding fragment thereof is provided. In some embodiments, the antibody binds human C1s. In some embodiments, the antigen binding fragment binds human C1s. In some embodiments, the method comprises growing a host cell under conditions so that the host cell expresses a polypeptide or polypeptides comprising the immunoglobulin heavy chain variable region and/or the immunoglobulin light chain variable region, thereby producing the antibody or the antigen binding fragment of the antibody, and purifying the antibody or the antigen binding fragment of the antibody. In some embodiments, the polypeptide or polypeptides comprise the immunoglobulin heavy chain variable region. In some embodiments, the polypeptide or polypeptides comprise the immunoglobulin light chain variable region. In some embodiments, the polypeptide or polypeptides comprise the immunoglobulin heavy chain variable region and the immunoglobulin light chain variable region. In some embodiments, the host cell is a host cell as provided for herein. In some embodiments, the antibody or antigen binding fragment thereof is as provided for herein.

The polypeptide or antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g., Ausubel infra, Harlow infra, and Colligan infra, the contents of which references are incorporated entirely herein by reference. The cell fusions are accomplished by standard procedures well known to those skilled in the field of immunology, such as producing cells can also be a hybridoma which is generated by fusing a B-cell with an immortal myeloma cell. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize C1s can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C region genes can be derived from any human cell including those which express and produce human immunoglobulins. The human $C_H$ region can be derived from any of the known classes or isotypes of human H chains, including gamma, µ, α, δ or ε, and subtypes thereof, such as G1, G2, G3 and G4. Since the H chain isotype is responsible for the various effector functions of an antibody, as well as antibody recycling by interaction with FcRn, the choice of $C_H$ region will be guided by the desired effector functions, such as complement fixation, or activity in antibody-dependent cellular cytotoxicity (ADCC). Preferably, the Cu region is derived from gamma 1 (IgG1), gamma 3 (IgG3), gamma 4 (IgG4), or µ (IgM). The human $C_L$ region can be derived from either human L chain isotype, kappa or lambda.

Methods of purifying polypeptides or proteins (including antibodies or antigen binding fragments thereof) are known in the art, and any such method is within the scope of the present application. Further, the host cell is not limited by the examples recited above. Any suitable cell may be used to generate the polypeptides or proteins of the present disclosure.

Pharmaceutical Compositions

In some embodiments, a pharmaceutical composition is provided. In some embodiments, the pharmaceutical composition comprises an antibody or antigen-binding fragment thereof as provided for herein.

In some embodiments, to prepare pharmaceutical or sterile compositions of the anti-C1s antibodies or other proteins provided herein, the antibody or antigen binding fragment thereof or other proteins provided herein are admixed with a pharmaceutically acceptable carrier or excipient. See, e.g., *Remington's Pharmaceutical Sciences* and *U.S. Pharmacopeia: National Formulary*, Mack Publishing Company, Easton, PA (1984).

Formulations of therapeutic or the antibodies provided herein may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY). In some embodiments, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In some embodiments, a composition is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In some embodiments, the composition is an injectable pharmaceutical composition. In some embodiments, the composition is formulated for intravenous or subcutaneous injection. In some embodiments, the composition is formulated for intravenous injection. In some embodiments, the composition id formulated for subcutaneous injection.

In some embodiments, the antibody or antigen binding fragment thereof can be administered by an invasive route such as by injection. In some embodiments, the antibodies or antigen binding fragment thereof, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present embodiments.

In some embodiments, the anti-C1s antibody, or antigen binding fragment thereof, is administered in combination with at least one additional therapeutic agent, such as, but not limited to any therapeutic used to treat the disorders provided for herein. In some embodiments, the antibody is administered in combination with another treatment for the disorders provided for herein.

Compositions can be administered with medical devices known in the art. For example, a pharmaceutical composition of the invention can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096, 002; 5,399,163; 5,383,851; 5,312,335; 5,064,413; 4,941, 880; 4,790,824 or 4,596,556.

The pharmaceutical compositions may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose can be made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable.

Antibodies or antigen binding fragments thereof can be provided by continuous infusion, or by doses administered, e.g., daily, 1-7 times per week, weekly, bi-weekly, monthly, bimonthly, or quarterly. In some embodiments, a total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of the antibody in the subject's serum, such as 0.1, 0.3, 1, 3, 10, 30, 100, 300 µg/ml or more. In other embodiments, a fully human antibody is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat or ameliorate tumors or gastric tumors.

The term "subject" as used throughout includes any organism, such as an animal, including a mammal (e.g., rat, mouse, dog, cat, rabbit) and, for example, a human. In one embodiment, the subject is a human. A subject can also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

In some embodiments, the methods comprise administering a therapeutically or prophylactically effective amount of one or more antibodies or antigen binding fragments of the antibodies described herein to a susceptible subject or to one exhibiting a condition in which C1s is known to have caused the pathology observed. Any active form of the antibody can be administered, including, but not limited to scFv, Fab and F(ab')₂ fragments and other forms of antibodies provided for herein.

The present disclosure provides a method to treat an individual having a complement-mediated disease or disorder, the method comprising administering to the individual an anti-C1s antibody of any of the embodiments disclosed herein or a pharmaceutical composition thereof. In some embodiments, the individual is a mammal. In some embodiments, the individual is a human. In some embodiments, the administering is intravenous. In some embodiments, the administering is intrathecal. In some embodiments, the administering results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction in autoantibody mediated blister formation; (ad) a reduction in autoantibody induced pruritis; (ae) a reduction in autoantibody induced erythematosus; (af) a reduction in autoantibody mediated skin erosion; (ag) a reduction in red blood cell destruction due to transfusion reactions; (ah) a reduction in red blood cell lysis due to alloantibodies; (ai) a reduction in hemolysis due to transfusion reactions; (aj) a reduction in allo-antibody mediated platelet lysis; and (ak) a reduction in platelet lysis due to transfusion reactions. In some embodiments, the reduction in glial cell activation comprises reduction in astrocyte activation or reduction in microglia activation.

In some embodiments, a method of treating a subject with a C1s mediated disorder is provided. In some embodiments, the method comprises administering to the subject an antibody or antigen-binding fragment thereof as provided for herein or a pharmaceutical composition comprising an antibody or antigen-binding fragment thereof as provided for herein, thereby treating the C1s mediated disorder. The an antibody or antigen-binding fragment thereof of any of the embodiments provided for herein or the pharmaceutical compositions of any of the embodiments provided for herein inhibit complement C1s activity in an individual having a complement-mediated disease or disorder. In some embodiments, the individual is a mammal. In some embodiments, the individual is a human. In some embodiments, the administering is intravenous. In some embodiments, the administering is intrathecal. In some embodiments, the administering results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction in autoantibody mediated blister formation; (ad) a reduction in autoantibody induced pruritis; (ae) a reduction in autoantibody induced erythematosus; (af) a reduction in autoantibody mediated skin erosion; (ag) a reduction in red blood cell destruction due to transfusion reactions; (ah) a reduction in red blood cell lysis due to alloantibodies; (ai) a reduction in hemolysis due to transfusion reactions; (aj) a reduction in allo-antibody mediated platelet lysis; and (ak) a reduction in platelet lysis due to transfusion reactions. In some embodiments, the reduction in glial cell activation comprises reduction in astrocyte activation or reduction in microglia activation. In some embodiments, the C1s mediated disorder is selected from the group including, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopaties. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection.

In some embodiments, the antibody or antigen-binding fragment thereof of any of the embodiments as provided for herein, or a pharmaceutical composition comprising the antibody or antigen-binding fragment thereof of any of the embodiments as provided for herein is for the use in the treatment of a complement-mediated disease or disorder. In some embodiments, the complement-mediated disorder is selected from the group including, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopaties. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is selected from the group including, but not limited to, hemolysis and Cold Agglutinin Disease. In some embodiments, the C1s mediated disorder is hemolysis. In some embodiments, the C1s mediated disorder is Cold Agglutinin Disease.

The present disclosure provides use of an anti-C1s antibody of any of the embodiments in the manufacture of a medicament for the treatment of an individual having a complement-mediated disease or disorder. Accordingly, in some embodiments, an antibody or binding fragment thereof or a pharmaceutical composition is provided for use as a medicament. In some embodiments, an antibody or binding fragment thereof is provided for use as a medicament. In some embodiments, a pharmaceutical composition is provided for use as a medicament. In some embodiments, the antibody or binding fragment thereof is an antibody or antigen binding fragment as provided for herein. In some embodiments, the pharmaceutical composition comprises an antibody or antigen binding fragment as provided for herein. In some embodiments, the pharmaceutical composition is as provided for herein. In some embodiments, the medicament is for use in treatment of a C1s mediated disease or disorder. In some embodiments, the complement-mediated disorder is, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopaties. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection.

In some embodiments, a use of an antibody or antigen binding fragment as provided for herein or a pharmaceutical composition as provided for herein is provided. In some embodiments, the use is for the treatment of a C1a mediated disorder. In some embodiments, a use of an antibody or antigen binding fragment as provided for herein is provided, the use for the treatment of a C1a mediated disorder. In some embodiments, a use of a pharmaceutical composition comprising an antibody or antigen binging fragment as provided for herein is provided, the use for the treatment of a C1a mediated disorder. In some embodiments, the pharmaceutical composition is as provided for herein. The antibody of any of the embodiments or pharmaceutical compositions thereof inhibit complement C1s activity in an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopaties. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection.

The present disclosure provides use of an anti-C1s antibody of any of the embodiments or a pharmaceutical composition thereof in the manufacture of a medicament for inhibiting complement C1s activity. In some embodiments, the present disclosure provides use of an anti-C1s antibody of any of the embodiments or a pharmaceutical composition thereof in the manufacture of a medicament for inhibiting complement C1s activity in an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection.

The present disclosure provides an anti-C1s antibody of any of the embodiments or a pharmaceutical composition thereof for use in medical therapy.

The present disclosure provides an anti-C1s antibody of any of the embodiments or a pharmaceutical composition thereof for treating an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopaties. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection.

The present disclosure provides an anti-C1s antibody of any of the embodiments or a pharmaceutical composition thereof for inhibiting complement C1s protein activity. The present disclosure provides an anti-C1s antibody of any of the embodiments or a pharmaceutical composition thereof for inhibiting complement C1s protein activity in an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopaties. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection.

The present disclosure provides a method to diagnose a complement-mediated disease or disorder in an individual, the method comprising: (a) determining the amount of a complement C1s protein in a biological sample obtained from the individual, wherein the step of determining comprises: (i) contacting the biological sample with an anti-C1s antibody of any of the embodiments; and (ii) quantitating binding of the antibody to complement C1s protein present in the sample; and (b) comparing the amount of the complement C1s protein to a normal control value that indicates the amount of complement C1s protein in a normal control individual, wherein a significant difference between the amount of C1s protein in the biological sample and the normal control value indicates that the individual has a complement-mediated disease or disorder. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

The present disclosure provides a method to monitor progression of a complement-mediated disease or disorder in an individual, the method comprising: (a) determining a first amount of complement a C1s protein in a biological sample obtained from the individual at a first time point; (b) determining a second amount of complement a C1s protein in a biological sample obtained from the individual at a second time point; and (c) comparing the second amount of complement C1s protein with the first amount of complement C1s protein. The steps of determining comprise: (i) contacting the biological sample with an anti-C1s antibody of any of the embodiments; and (ii) quantitating binding of the antibody to complement C1s protein present in the sample. In some embodiments, the first time point is a time point before initiation of a treatment regimen, and the second time point is a time point after initiation of a treatment regimen. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

The present disclosure provides an in vitro method to detect complement C1s protein in a biological sample obtained from an individual, the method comprising: (a) contacting the biological sample with an anti-C1s antibody of any of the embodiments; and (b) detecting binding of the antibody to complement C1s protein present in the sample. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample. In some embodiments, the method is quantitative.

The present disclosure provides a method to detect complement C1s protein in a living individual in vivo, the method comprising: (a) administering to the individual an anti-C1s antibody of any of the embodiments; and (b) detecting binding of the antibody to complement C1s protein in the individual using an imaging method. In some embodiments, the binding is detected in the individual at a site altered by a complement-mediated disease or disorder. In some embodiments, the binding is detected in the brain of the individual. In some of the embodiments, the antibody comprises a contrast agent suitable for use in the imaging method. In some embodiments, the imaging method is selected from the group consisting of magnetic resonance imaging, positron emission tomography, and IVIS instrumentation. In some embodiments, the method is quantitative.

In some embodiments, the biological sample is selected from the group consisting of blood, serum, plasma, urine, saliva, cerebrospinal fluid, interstitial fluid, ocular fluid, synovial fluid, solid tissue sample, tissue culture sample, and a cellular sample.

In some embodiments, the methods of the present disclosure provide that the individual is suspected of having a complement-mediated disease or disorder, has been diagnosed as having a complement-mediated disease or disorder, or has a genetic predisposition to developing a complement-mediated disease or disorder.

The present disclosure provides a composition comprising: (a) an anti-C1s antibody of any of the embodiments; and (b) a solution comprising one or more agents that maintain an organ or a tissue intended for transplantation into a recipient individual. In some embodiments, the solution is an organ preservation solution or a tissue preservation solution. In some embodiments, the solution is an organ perfusion solution or a tissue perfusion solution. In some embodiments, the solution comprises: i) a salt; ii) an agent that reduces edema; iii) an oxygen free radical scavenger; and iii) an energy supply system component. In some embodiments, the composition comprises potassium lactobionate, $KH_2PO_4$, $MgSO_4$, raffinose, adenosine, glutathione, allopurinol, and/or hydroxyethyl starch.

The present disclosure provides an organ or tissue preservation solution comprising an anti-C1s antibody of any of the embodiments or a pharmaceutical composition thereof.

The present disclosure provides an organ or tissue perfusion solution comprising an anti-C1s antibody of any of the embodiments or a pharmaceutical composition thereof.

The present disclosure provides a method for maintaining an organ or tissue for transplant, the method comprising contacting the organ or the tissue with a composition comprising: (a) an anti-C1s antibody of any of the embodiments; and (b) an organ or tissue preservation solution of any of the embodiments or an organ or tissue perfusion solution of any of the embodiments.

The present disclosure provides an isolated organ or tissue maintained in a composition comprising: (a) an anti-C1s antibody of any of the embodiments; and (b) an organ or tissue preservation solution of any of the embodiments or an organ or tissue perfusion solution of any of the embodiments. In some embodiments, the organ is selected from the group consisting of an eye, a heart, an intestine, a kidney, a liver, a lung, a pancreas, a stomach, and a thymus. In some embodiments, the tissue is selected from the group consisting of bone, bone marrow, cornea, heart valve, islet of Langerhans, tendon, skin, and vein.

The present disclosure provides an in vitro method for inhibiting complement C1s activity in an organ or a tissue, the method comprising contacting the organ or the tissue with an anti-C1s antibody of any of the embodiments or a pharmaceutical composition thereof.

Treatment of individuals may comprise the administration of a therapeutically effective amount of the antibodies described herein. The antibodies can be provided in a kit, such as those provided herein. The antibodies can be used or administered alone or in admixture with another therapeutic, analgesic, or diagnostic agent, such as provided for herein. In providing a patient with an antibody, or fragment thereof, capable of binding to C1s, or an antibody capable of protecting against C1s in a recipient patient, the dosage of administered agent will vary depending upon such factors as the patient's age, weight, height, sex, general medical condition, previous medical history, etc.

An antibody, capable treating a condition associated with C1s activity or use to treat a C1s related pathology, is intended to be provided to subjects in an amount sufficient to affect a reduction, resolution, or amelioration in the C1s related symptom or pathology. Examples of such pathologies are provided for herein.

Accordingly, in some embodiments, methods of treating a subject with a C1s mediated disorder are provided. In some embodiments, the method comprises administering a pharmaceutical composition comprising an antibody, or antigen binding fragment thereof, as provided herein. In some embodiments, the disorder is as provided for herein.

As provided for herein, the antibodies, or antigen binding fragments thereof, can be administered with other therapeutics. These can be administered simultaneously or sequentially.

Kits are also provided which are useful for carrying out embodiments described herein. The present kits can comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

In some embodiments, antibodies that bind to a C1s protein are provided. In some embodiments, the antibodies are antibodies or antigen binding fragments as provided for herein. In some embodiments, the antibodies or antigen binding fragments comprise an amino acid sequence as provided for herein, or a variant thereof as provided for herein. In some embodiments, the antibody is isolated. In some embodiments, the antibody binds specifically to the active form of C1s.

In some embodiments, the antibody inhibits or neutralizes the function of an active form of C1s protein. As used herein, the term "neutralize" means that the activity or function of the protein is inhibited. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody. In some embodiments, the antibody inhibits the function facilitated by C1s.

Enumerated Embodiments

In some embodiments, the following embodiments are provided.

1. An antibody, or an antigen binding fragment thereof, wherein the antibody or antibody fragment comprises:
   (a) a heavy chain variable region comprising heavy chain HCDR1, HCDR2, and HCDR3 sequences, wherein the heavy chain HCDR1 sequence has the amino acid sequence of SEQ ID NO: 9; the heavy chain HCDR2 has the amino acid sequence of SEQ ID NO: 10 and the heavy chain HCDR3 sequence has the amino acid sequence of SEQ ID NO: 11 or variants of any of the foregoing; and (ii) a light chain variable region comprising light chain LCDR1, LCDR2, and LCDR3 sequences, wherein the light chain LCDR1 sequence has the amino acid sequence SEQ ID NO: 12; the light chain LCDR2 sequence has the amino acid sequence of SEQ ID NO: 13; and the light chain LCDR3 sequence has the amino acid sequence of SEQ ID NO: 14; or variants of any of the foregoing;
   (b) a heavy chain variable region comprising heavy chain HCDR1, HCDR2, and HCDR3 sequences, wherein the heavy chain HCDR1 sequence has the amino acid sequence of SEQ ID NO: 15; the heavy chain HCDR2 has the amino acid sequence of SEQ ID NO: 16 and the heavy chain HCDR3 sequence has the amino acid sequence of SEQ ID NO: 17 or variants of any of the foregoing; and (ii) a light chain variable region comprising light chain LCDR1, LCDR2, and LCDR3 sequences, wherein the light chain LCDR1 sequence has the amino acid sequence SEQ ID NO: 18; the light chain LCDR2 sequence has the amino acid sequence of SEQ ID NO: 19; and the light chain LCDR3 sequence has the amino acid sequence of SEQ ID NO: 20; or variants of any of the foregoing; or
   (c) a heavy chain variable region comprising heavy chain HCDR1, HCDR2, and HCDR3 sequences, wherein the heavy chain HCDR1 sequence has the amino acid sequence of SEQ ID NO: 21; the heavy chain HCDR2 has the amino acid sequence of SEQ ID NO: 22 and the heavy chain HCDR3 sequence has the amino acid sequence of SEQ ID NO: 23 or variants of any of the foregoing; and (ii) a light chain variable region comprising light chain LCDR1, LCDR2, and LCDR3 sequences, wherein the light chain LCDR1 sequence has the amino acid sequence SEQ ID NO: 24; the light chain LCDR2 sequence has the amino acid sequence of SEQ ID NO: 25; and the light chain LCDR3 sequence has the amino acid sequence of SEQ ID NO: 26; or variants of any of the foregoing.

2. An antibody, or an antigen binding fragment thereof, wherein the antibody or antibody fragment comprises:
   (a) a heavy chain variable region comprising heavy chain HCDR1, HCDR2, and HCDR3 sequences, wherein the heavy chain HCDR1 sequence has the amino acid sequence of SEQ ID NO: 27; the heavy chain HCDR2 has the amino acid sequence of SEQ ID NO: 28 and the heavy chain HCDR3 sequence has the amino acid sequence of SEQ ID NO: 11 or variants of any of the foregoing; and (ii) a light chain variable region comprising light chain LCDR1, LCDR2, and LCDR3 sequences, wherein the light chain LCDR1 sequence has the amino acid sequence SEQ ID NO: 29; the light chain LCDR2 sequence has the amino acid sequence of SEQ ID NO: 30; and the light chain LCDR3 sequence has the amino acid sequence of SEQ ID NO: 31; or variants of any of the foregoing;
   (b) a heavy chain variable region comprising heavy chain HCDR1, HCDR2, and HCDR3 sequences, wherein the heavy chain HCDR1 sequence has the amino acid sequence of SEQ ID NO: 32; the heavy chain HCDR2 has the amino acid sequence of SEQ ID NO: 33 and the heavy chain HCDR3 sequence has the amino acid sequence of SEQ ID NO: 17 or variants of any of the foregoing; and (ii) a light chain variable region comprising light chain LCDR1, LCDR2, and LCDR3 sequences, wherein the light chain LCDR1 sequence has the amino acid sequence SEQ ID NO: 34; the light chain LCDR2 sequence has the amino acid sequence of SEQ ID NO: 35; and the light chain LCDR3 sequence has the amino acid sequence of SEQ ID NO: 36; or variants of any of the foregoing; or
   (c) a heavy chain variable region comprising heavy chain HCDR1, HCDR2, and HCDR3 sequences, wherein the heavy chain HCDR1 sequence has the amino acid sequence of SEQ ID NO: 37; the heavy chain HCDR2 has the amino acid sequence of SEQ ID NO: 38 and the heavy chain HCDR3 sequence has the amino acid sequence of SEQ ID NO: 23 or variants of any of the foregoing; and (ii) a light chain variable region comprising light chain LCDR1, LCDR2, and LCDR3 sequences, wherein the light chain LCDR1 sequence has the amino acid sequence SEQ ID NO: 39; the light chain LCDR2 sequence has the amino acid sequence of SEQ ID NO: 40; and the light chain LCDR3 sequence has the amino acid sequence of SEQ ID NO: 41; or variants of any of the foregoing.

3. An antibody, or an antigen binding fragment thereof, wherein the antibody or antibody fragment comprises:
- (a) a heavy chain variable region comprising heavy chain HCDR1, HCDR2, and HCDR3 sequences, wherein the heavy chain HCDR1 sequence has the amino acid sequence of SEQ ID NO: 42; the heavy chain HCDR2 has the amino acid sequence of SEQ ID NO: 43 and the heavy chain HCDR3 sequence has the amino acid sequence of SEQ ID NO: 44 or variants of any of the foregoing; and (ii) a light chain variable region comprising light chain LCDR1, LCDR2, and LCDR3 sequences, wherein the light chain LCDR1 sequence has the amino acid sequence SEQ ID NO: 45; the light chain LCDR2 sequence has the amino acid sequence of SEQ ID NO: 30; and the light chain LCDR3 sequence has the amino acid sequence of SEQ ID NO: 14; or variants of any of the foregoing;
- (b) a heavy chain variable region comprising heavy chain HCDR1, HCDR2, and HCDR3 sequences, wherein the heavy chain HCDR1 sequence has the amino acid sequence of SEQ ID NO: 46; the heavy chain HCDR2 has the amino acid sequence of SEQ ID NO: 47 and the heavy chain HCDR3 sequence has the amino acid sequence of SEQ ID NO: 48 or variants of any of the foregoing; and (ii) a light chain variable region comprising light chain LCDR1, LCDR2, and LCDR3 sequences, wherein the light chain LCDR1 sequence has the amino acid sequence SEQ ID NO: 49; the light chain LCDR2 sequence has the amino acid sequence of SEQ ID NO: 35; and the light chain LCDR3 sequence has the amino acid sequence of SEQ ID NO: 20; or variants of any of the foregoing; or
- (c) a heavy chain variable region comprising heavy chain HCDR1, HCDR2, and HCDR3 sequences, wherein the heavy chain HCDR1 sequence has the amino acid sequence of SEQ ID NO: 50; the heavy chain HCDR2 has the amino acid sequence of SEQ ID NO: 51 and the heavy chain HCDR3 sequence has the amino acid sequence of SEQ ID NO: 52 or variants of any of the foregoing; and (ii) a light chain variable region comprising light chain LCDR1, LCDR2, and LCDR3 sequences, wherein the light chain LCDR1 sequence has the amino acid sequence SEQ ID NO: 53; the light chain LCDR2 sequence has the amino acid sequence of SEQ ID NO: 40; and the light chain LCDR3 sequence has the amino acid sequence of SEQ ID NO: 26; or variants of any of the foregoing.

4. An antibody, or antigen-binding fragment thereof, wherein:
- a. the HCDR1, HCDR2 and HCDR3 are selected from SEQ ID NO: 9, SEQ ID NO: 10, SEQ ID NO: 11, respectively, from SEQ ID NO: 27, SEQ ID NO: 28, SEQ ID NO: 11, respectively, and from SEQ ID NO: 42, SEQ ID NO: 43, SEQ ID NO: 44, respectively, and the LCDR1, LCDR2 and LCDR3 are selected from from SEQ ID NO: 12, SEQ ID NO: 13, SEQ ID NO: 14, respectively, from SEQ ID NO: 29, SEQ ID NO: 30, SEQ ID NO: 31, respectively, and from SEQ ID NO: 45, SEQ ID NO: 30, SEQ ID NO: 14, respectively; or
- b. the HCDR1, HCDR2 and HCDR3 are selected from SEQ ID NO: 15, SEQ ID NO: 16, SEQ ID NO: 17, respectively, from SEQ ID NO: 32, SEQ ID NO: 33, SEQ ID NO: 17, respectively, and from SEQ ID NO: 46, SEQ ID NO: 47, SEQ ID NO: 48, respectively, and the LCDR1, LCDR2 and LCDR3 are selected from from SEQ ID NO: 18, SEQ ID NO: 19, SEQ ID NO: 20, respectively, from SEQ ID NO: 34, SEQ ID NO: 35, SEQ ID NO: 36, respectively, and from SEQ ID NO: 49, SEQ ID NO: 35, SEQ ID NO: 20, respectively; or
- c. the HCDR1, HCDR2 and HCDR3 are selected from SEQ ID NO: 21, SEQ ID NO: 22, SEQ ID NO: 23, respectively, SEQ ID NO: 37, SEQ ID NO: 38, SEQ ID NO: 23, respectively, and SEQ ID NO: 50, SEQ ID NO: 51, SEQ ID NO: 52, respectively, and the LCDR1, LCDR2 and LCDR3 are selected from SEQ ID NO: 24, SEQ ID NO: 25, SEQ ID NO: 26, respectively, SEQ ID NO: 39, SEQ ID NO: 40, SEQ ID NO: 41, respectively, and SEQ ID NO: 53, SEQ ID NO: 40, SEQ ID NO: 26, respectively.

5. The antibody or antigen-binding fragment thereof of any one of embodiments 1-4, wherein the heavy chain comprises:
- a. a heavy chain variable region having at least 90% sequence identity to SEQ ID NO: 1, wherein the antibody or antigen binding fragment thereof maintains the sequences of HCDR1, HCDR2, HCDR3, LCDR1, LCDR2, and LCDR3 set forth in subpart a of any one of embodiments 1-4; or
- b. a heavy chain variable region having at least 90% sequence identity to SEQ ID NO: 3, wherein the antibody or antigen binding fragment thereof maintains the sequences of HCDR1, HCDR2, HCDR3, LCDR1, LCDR2, and LCDR3 set forth in subpart b of any one of embodiments 1-4; or
- c. a heavy chain variable region having at least 90% sequence identity to SEQ ID NO: 5, wherein the antibody or antigen binding fragment thereof maintains the sequences of HCDR1, HCDR2, HCDR3, LCDR1, LCDR2, and LCDR3 set forth in subpart c of any one of embodiments 1-4.

6. The antibody or antigen-binding fragment thereof of any one of embodiments 1-4, wherein the light chain comprises:
- a. a light chain variable region having at least 90% sequence identity to SEQ ID NO: 2, wherein the antibody or antigen binding fragment thereof maintains the sequences of HCDR1, HCDR2, HCDR3, LCDR1, LCDR2, and LCDR3 set forth in subpart a of any one of embodiments 1-4; or
- b. a light chain variable region having at least 90% sequence identity to SEQ ID NO: 4, wherein the antibody or antigen binding fragment thereof maintains the sequences of HCDR1, HCDR2, HCDR3, LCDR1, LCDR2, and LCDR3 set forth in subpart b of any one of embodiments 1-4; or
- c. a light chain variable region having at least 90% sequence identity to SEQ ID NO: 6, wherein the antibody or antigen binding fragment thereof maintains the sequences of HCDR1, HCDR2, HCDR3, LCDR1, LCDR2, and LCDR3 set forth in subpart c of any one of embodiments 1-4.

7. The antibody or antigen-binding fragment thereof of any one of embodiments 1-4, wherein the antibody or antigen binding fragment thereof comprises:
   a. a light chain variable region of the light chain having at least 90% sequence identity to SEQ ID NO:2, and a heavy chain variable region of the heavy chain having at least 90% sequence identity to SEQ ID NO:1, wherein the antibody or antigen binding fragment thereof maintains the sequences of HCDR1, HCDR2, HCDR3, LCDR1, LCDR2, and LCDR3 set forth in subpart a of any one of embodiments 1-4; or
   b. a light chain variable region of the light chain having at least 90% sequence identity to SEQ ID NO:4, and a heavy chain variable region of the heavy chain having at least 90% sequence identity to SEQ ID NO:3, wherein the antibody or antigen binding fragment thereof maintains the sequences of HCDR1, HCDR2, HCDR3, LCDR1, LCDR2, and LCDR3 set forth in subpart b of any one of embodiments 1-4; or
   c. a light chain variable region of the light chain having at least 90% sequence identity to SEQ ID NO:6, and a heavy chain variable region of the heavy chain having at least 90% sequence identity to SEQ ID NO:5, wherein the antibody or antigen binding fragment thereof maintains the sequences of HCDR1, HCDR2, HCDR3, LCDR1, LCDR2, and LCDR3 set forth in subpart c of any one of embodiments 1-4.

8. The antibody or antigen-binding fragment thereof of embodiment 7, wherein the light chain variable region comprises SEQ ID NO:2, and the heavy chain variable region comprises SEQ ID NO:1.

9. The antibody or antigen-binding fragment thereof of any one of embodiments 1-4, wherein:
   a. the heavy chain has at least 90% sequence identity to SEQ ID NO:66 or SEQ ID NO: 67, wherein the antibody or antigen binding fragment thereof maintains the sequences of HCDR1, HCDR2, HCDR3, LCDR1, LCDR2, and LCDR3 set forth in subpart a of any one of embodiments 1-4; or
   b. the heavy chain has at least 90% sequence identity to SEQ ID NO:68 or SEQ ID NO: 69, wherein the antibody or antigen binding fragment thereof maintains the sequences of HCDR1, HCDR2, HCDR3, LCDR1, LCDR2, and LCDR3 set forth in subpart b of any one of embodiments 1-4; or
   c. the heavy chain has at least 90% sequence identity to SEQ ID NO:70 or SEQ ID NO: 71, wherein the antibody or antigen binding fragment thereof maintains the sequences of HCDR1, HCDR2, HCDR3, LCDR1, LCDR2, and LCDR3 set forth in subpart c of any one of embodiments 1-4.

10. The antibody or antigen-binding fragment thereof of any one of embodiments 1-4, wherein the light chain comprises:
   a. the light chain has at least 90% sequence identity to SEQ ID NO:72, wherein the antibody or antigen binding fragment thereof maintains the sequences of HCDR1, HCDR2, HCDR3, LCDR1, LCDR2, and LCDR3 set forth in subpart a of any one of embodiments 1-4; or
   b. the light chain has least 90% sequence identity to SEQ ID NO:73, wherein the antibody or antigen binding fragment thereof maintains the sequences of HCDR1, HCDR2, HCDR3, LCDR1, LCDR2, and LCDR3 set forth in subpart b of any one of embodiments 1-4; or
   c. the light chain has at least 90% sequence identity to SEQ ID NO:74, wherein the antibody or antigen binding fragment thereof maintains the sequences of HCDR1, HCDR2, HCDR3, LCDR1, LCDR2, and LCDR3 set forth in subpart c of any one of embodiments 1-4.

11. The antibody or antigen-binding fragment thereof of any one of embodiments 1-4, wherein:
   a. the light chain has at least 90% sequence identity to SEQ ID NO:72, and the heavy chain has at least 90% sequence identity to SEQ ID NO:66 or SEQ ID NO: 67, wherein the antibody or antigen binding fragment thereof maintains the sequences of HCDR1, HCDR2, HCDR3, LCDR1, LCDR2, and LCDR3 set forth in subpart a of any one of embodiments 1-4; or
   b. the light chain has at least 90% sequence identity to SEQ ID NO:73, and the heavy chain has at least 90% sequence identity to SEQ ID NO:68 or SEQ ID NO: 69, wherein the antibody or antigen binding fragment thereof maintains the sequences of HCDR1, HCDR2, HCDR3, LCDR1, LCDR2, and LCDR3 set forth in subpart b of any one of embodiments 1-4; or
   c. the light chain has at least 90% sequence identity to SEQ ID NO:74, and the heavy chain has at least 90% sequence identity to SEQ ID NO:70 or SEQ ID NO: 71, wherein the antibody or antigen binding fragment thereof maintains the sequences of HCDR1, HCDR2, HCDR3, LCDR1, LCDR2, and LCDR3 set forth in subpart c of any one of embodiments 1-4.

12. The antibody or antigen-binding fragment thereof of embodiment 11, wherein:
   the light chain comprises SEQ ID NO:72, and the heavy chain comprises SEQ ID NO: 66 or SEQ ID NO: 67;
   the light chain comprises SEQ ID NO:73, and the heavy chain comprises SEQ ID NO: 68 or SEQ ID NO: 69; or
   the light chain comprises SEQ ID NO:74, and the heavy chain comprises SEQ ID NO: 70 or SEQ ID NO: 71;

13. The antibody or antigen-binding fragment thereof of any one of the preceding embodiments, wherein the antibody binding fragment is a scFv antibody, a Fab fragment, a Fab' fragment, or an F(ab')$_2$ fragment.

14. The antibody or antigen binding fragment thereof of any one of the preceding embodiments, wherein the antibody is a monoclonal antibody.

15. The antibody or antigen binding fragment thereof of any one of the preceding embodiments, wherein the antibody is a humanized antibody.

16. The antibody or antigen binding fragment thereof of any one of the preceding embodiments, wherein the antibody or antigen binding fragment thereof comprises the sequence selected from one or more of the following sequences: SEQ ID NO: 1; SEQ ID NO: 2; SEQ ID NO: 3; SEQ ID NO: 4; SEQ ID NO: 5, SEQ ID NO: 6, or a variant thereof.

17. The antibody or antigen binding fragment thereof of any one of the preceding embodiments, wherein the antibody, or antigen binding fragment thereof, comprises a $V_L$ peptide of SEQ ID NOs: 2, 4, or 6, or any variant thereof.

18. The antibody or antigen binding fragment thereof of any one of the preceding embodiments, wherein the antibody, or antigen binding fragment thereof, comprises a $V_H$ peptide of SEQ ID NOs: 1, 3, or 5, or any variant thereof.

19. The antibody or antigen binding fragment thereof of any one of the preceding embodiments, wherein the antibody, or antigen binding fragment thereof, comprises a constant region as provided for herein.

20. The antibody or antigen binding fragment thereof of any one of the preceding embodiments, wherein the heavy chain variable region and the light chain variable region are not linked by a linker.

21. The antibody or antigen binding fragment thereof of any one of the preceding embodiments, wherein the heavy chain variable region and the light chain variable region are linked with a peptide linker.

22. The antibody or antigen binding fragment thereof of embodiment 21, wherein the peptide linker comprises a sequence of (GGGGS)$_n$ (SEQ ID NO:54); (GGGGA)$_n$ (SEQ ID NO: 55), or any combination thereof, wherein each n is independently 1-5.

23. A variant of the antibody or antigen binding fragment thereof of any one of the preceding embodiments, wherein the variant has 1-10 substitutions, deletions, or insertions.

24. A variant of the antibody or antigen binding fragment thereof of any one of the preceding embodiments, wherein the variant has 1-10 conservative substitutions.

25. A recombinant antibody or an antigen binding fragment thereof that binds to a C1s, wherein the antibody or antigen binding fragment thereof comprises an amino acid sequence, or a variant thereof, as provided for herein.

26. An isolated nucleic acid molecule encoding an antibody, or an antigen binding fragment thereof, a heavy chain variable region, a light chain variable region, heavy chain, or light chain, of any of the preceding embodiments.

27. The isolated nucleic acid sequence of embodiment 26 comprising SEQ ID NO:59, SEQ ID NO: 61, or SEQ ID NO:63.

28. The isolated nucleic acid sequence of embodiment 27 comprising SEQ ID NO:59.

29. The isolated nucleic acid sequence of embodiment 26 comprising SEQ ID NO:60, SEQ ID NO: 62, or SEQ ID NO:64.

30. The isolated nucleic acid sequence of embodiment 29 comprising SEQ ID NO:60.

31. An expression vector comprising the nucleic acid molecule of any one of embodiments 26-30.

32. A host cell comprising the nucleic acid molecule of any one of embodiments 26-30 or the vector of embodiment 31.

33. An antibody or antigen-binding fragment produced by the host cell of embodiment 32.

34. A pharmaceutical composition comprising an antibody, or antigen binding fragment thereof, of any one of embodiments 1-25.

35. The pharmaceutical composition of embodiment 34, wherein the composition is formulated for intravenous or subcutaneous injection.

36. The pharmaceutical composition of embodiment 34, wherein the composition is an injectable pharmaceutical composition.

37. A method of producing a polypeptide comprising a heavy chain variable region or light chain variable region, the method comprising:
(a) growing the host cell of embodiment 32 under conditions so that the host cell expresses the polypeptide comprising the heavy chain variable region or the light chain variable region; and
(b) purifying the polypeptide comprising the heavy chain variable region or the light chain variable region.

38. A method of producing an antibody that binds human C1s, or an antigen binding fragment of the antibody, the method comprising:
(a) growing the host cell of embodiment 32 under conditions so that the host cell expresses a polypeptide or polypeptides comprising the immunoglobulin heavy chain variable region and/or the immunoglobulin light chain variable region, thereby producing the antibody or the antigen-binding fragment of the antibody; and
(b) purifying the antibody or the antigen-binding fragment of the antibody.

39. A method of treating a subject with C1s mediated disorder, the method comprising administering to the subject an antibody, or antigen binding fragment thereof, of any one of embodiments 1-25 or 33 or a pharmaceutical composition of any one of embodiments 34-36.

40. The method of embodiment 39, wherein the disorder is hemolysis, Cold Agglutinin Disease, Immune Thrombocytopenia (ITP), Myasthenia Gravis, Glomerulopaties, Atypical Hemolytic uremic syndrome, antiphospholipid antibody syndrome, or transplant rejection.

41. An antibody or antigen binding fragment thereof of any one of embodiments 1-25 or 33, or a pharmaceutical composition comprising the antibody or antigen binding fragment thereof, for the use in the treatment of a C1s mediated disorder, such as those provided for herein, such as hemolysis, Cold Agglutinin Disease.

42. An antibody or binding fragment thereof of any one of embodiments 1-25 or 33 or a pharmaceutical composition comprising the antibody or antigen binding fragment thereof for use as a medicament.

43. The antibody or binding fragment thereof, or pharmaceutical composition of embodiment 42 for use in the treatment of a C1s mediated disorder, such as those provided for herein.

44. Use of the antibody or binding fragment thereof of any one of embodiments 1-25 or 33, or a pharmaceutical composition comprising the antibody or antigen binding fragment thereof, for the treatment of a C1s mediated disorder, such as those provided for herein.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: Production of Monoclonal Antibodies

Human immunoglobulin variable domain transgenic mice (Alloy Therapeutics) were immunized at LakePharma with human C1s (active form, Complement Technologies Cat. #A104, 10 ug per dose) via hock route using proprietary adjuvants once weekly for 4 weeks. Serum titers were monitored over time using an ELISA assay with 1 ug/ml C1s coated Maxisorb plates. Mice received a final boost with recombinant CCP2-SP, a fragment of C1s consisting of the second CCP domain and the serine protease domain, amino acids 358-688 of Uniprot P09871). Highest titer mice were sacrificed and lymphocytes from draining lymph nodes were harvested. One hundred million lymphocytes were transferred to Single Cell Technologies (SCT) for plasma cell enrichment and single cell screening. Thirty million lymphocytes were fused to generate hybridomas at LakePharma.

Hybridomas produced by electrofusion were plated in eight 384-well plates at an average density of 2.0 hybridomas per well. Supernatants were screened by ELISA for binding to C1s and proC1s (Complement Technologies Cat. #A103). Based on strong binding to C1s and lower signal to proC1s 192 lines were selected for propagation and secondary screening.

Example 2: Characterization of Hybridoma Hits

Supernatants with confirmed binding profile were tested at 50% dilution for inhibition of C1s enzymatic activity using N-Carbobenzyloxy-Lys-ThioBenzyl ester (ZKSBzl) (Bachem, Catalog #M1300) as substrate, as well as in the Classical Pathway (CP) Wieslab Kit (Eagle Biosciences COMPL CP310) at 1:2 dilution. Hybridomas with inhibitory signal in either assay were subcloned, expanded, IgG purified from spent supernatants, and heavy and light chain variable domains determined. Purified IgG from hybridomas were tested at varying concentrations to determine potency in CP Wieslab assay. Recombinantly expressed anti-C1s antibodies TNT009 or TNT020, anti-C5 antibody eculizumab, as well as human plasma C1INH were used as reference standards.

Example 3: Single Plasma Cell Screening

Lymphocytes harvested from immunized mice and transferred to SCT were enriched for plasma cells, which were distributed into the microfluidics device and cultured for 3 hrs. Secreted antibody was captured onto a slide and interrogated with fluorescently labeled C1s and proC1s. Barcoded primers were added to the wells and the cells were processed for Next-Gen sequencing of IgG variable domains. Forty-eight unique sequences representing various patterns of C1s and proC1s staining signals were expressed as IgG and purified antibodies were tested at 300 nM for inhibitory activity in the CP Wieslab kit resulting in 16 lineages that showed >80% inhibition. These were further tested in the CP Wieslab assay at varying concentrations to determine potency of CP inhibition (FIG. 1).

Example 4: C3b Deposition and RBC Lysis Assays

Figure 2:
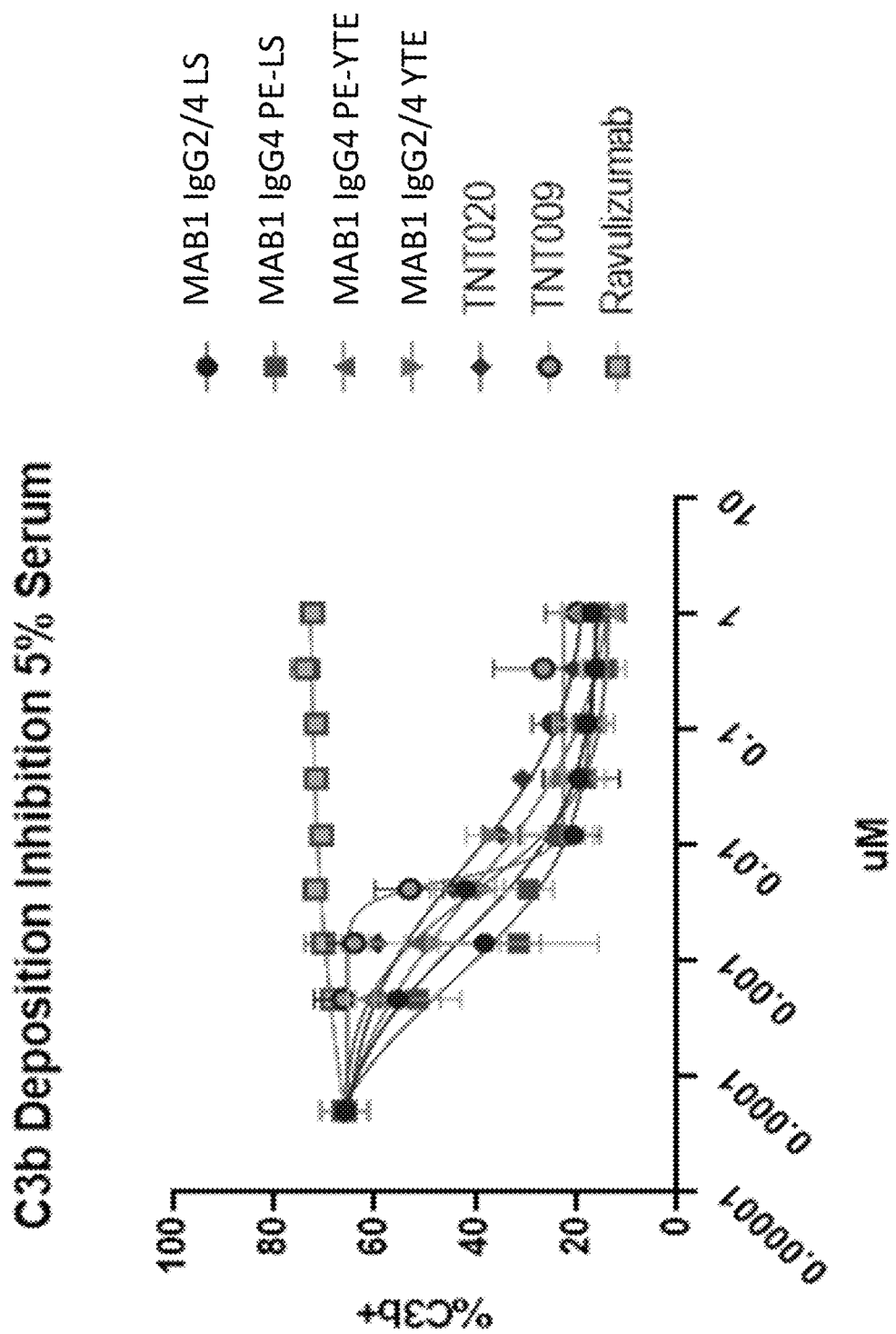
FIG. 2 shows the dose response of four 4O11g variants along with TNT009, TNT020 and ravulizumab in C3b deposition in a FACS based assay using rabbit antibody sensitized human RBCs and 5% human serum

C3b deposition: To evaluate ability of antibodies to inhibit C3b deposition which leads to extravascular hemolysis select antibodies were tested by Flow Contract Site (Bothel, WA) for inhibition of C3b deposition on human red blood cells (RBCs) sensitized with rabbit anti-human RBC serum in the presence of 5% human serum. Four Fc variants of MAB1 were tested along side C1s inhibitory antibodies TNT009 and TNT020, as well as the C5 inhibitory antibody Ravulizumab. Lead antibodies of the invention inhibited C3b deposition in a dose dependent manner (FIG. 2), with IC50 values ranging between 0.63 and 3.92 nM. As expected, Ravulizumab showed no inhibition, being downstream of C1s in the cascade. TNT009 and TNT020 also showed inhibitory activity with IC50 values of 5.0 and 6.5 nM, respectively.

Figure 3:
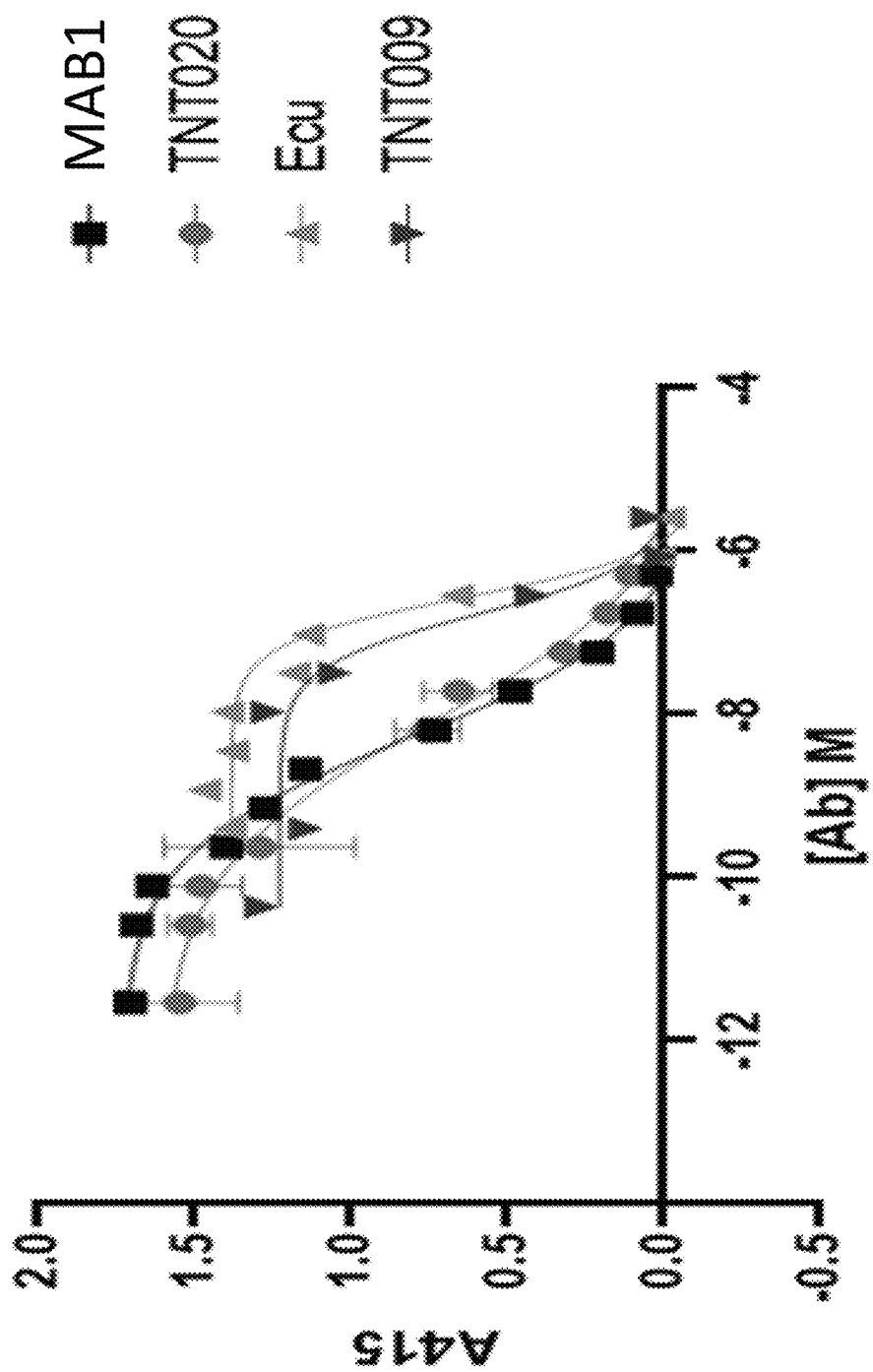
FIG. 3 shows the dose response of 4O11g antibody with TNT009, TNT020 and eculizumab in a human RBC lysis assay using 10% human serum

RBC lysis: as a measure of ability of antibodies to inhibit intravascular lysis O-negative human red blood cells (RBCs) were washed 3 times in Gelatin Veronal Buffer (GVB) and sensitized with 1:60 dilution of rabbit anti-human RBC antibody (LSBio LS-C63000-2) for 30 min, centrifuged, and resuspended in GVB++ (GVB+0.15 mM $CaCl_2$), 0.5 mM $MgCl_2$). Normal human serum (Quidel A113) preincubated with anti-complement antibodies at varying concentrations was added to 10% final serum concentration, and incubated for 1 hr at 37° C. The hemolytic reaction was stopped by adding EDTA to a final concentration of 20 mM and absorbance of supernatants at 540 nm were read on a plate reader. Test sample lysis was calculated as a percentage of samples lysed with water (100% lysis). As shown in FIG. 3 MAB1 variants inhibited RBC lysis more potently than TNT009, TNT020 and eculizumab.

Example 5: Assessment of Selectivity Against proC1s

Figure 4:
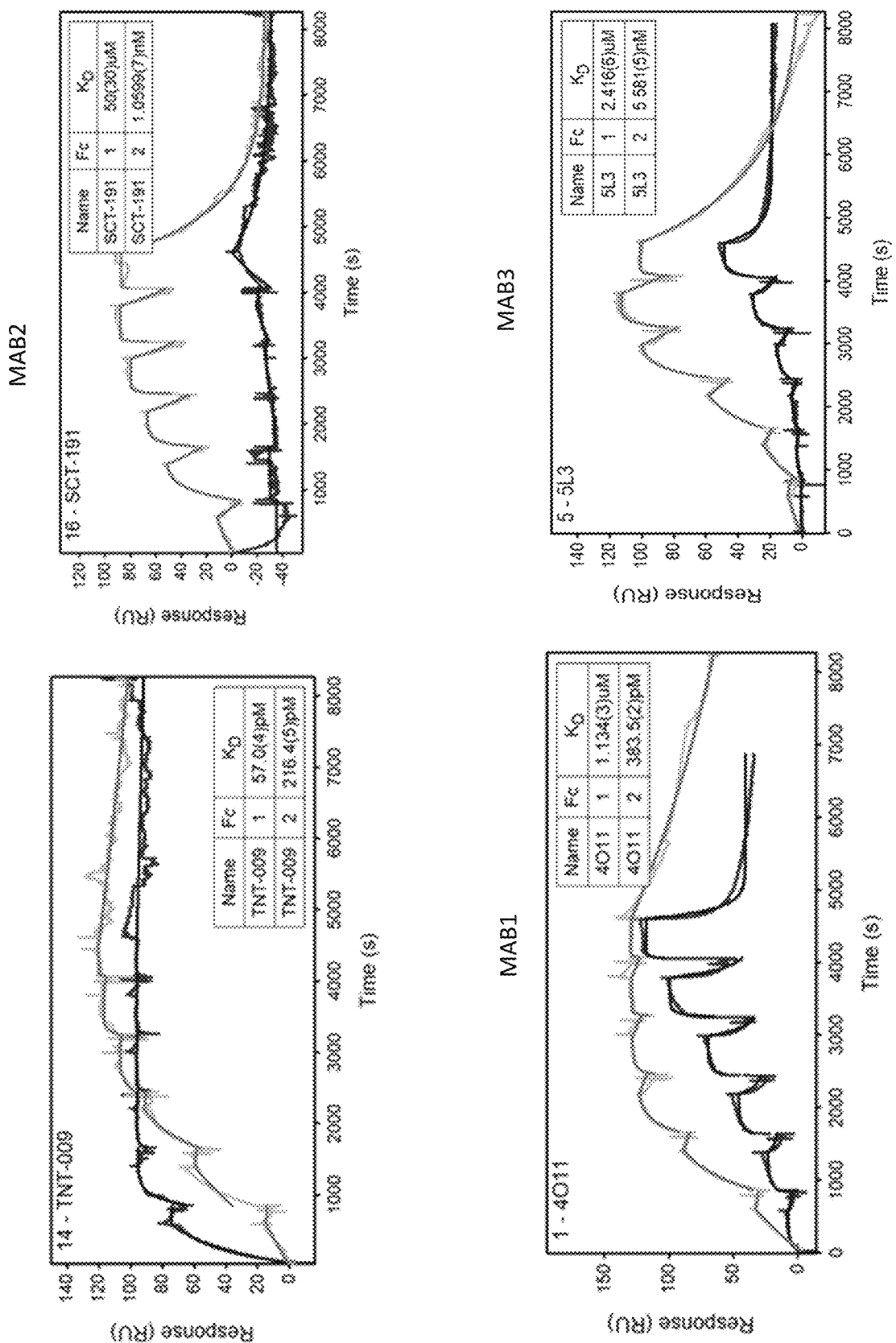
FIG. 4 depicts SPR sensograms where anti-Fc coated surfaces were used to capture test antibodies, and human C1s or proC1s_RQ was used as analyte.

Hybridoma and single-cell hits that demonstrated good inhibition of the Classical Pathway were evaluated for selectivity by SPR at Biosensor Tools (Salt Lake City, UT). For this purpose, a non-cleavable version of proC1s (proC1s_RQ) was used to avoid artifacts due to partial activation of proC1s during experimental manipulation. Test IgGs were captured on an anti-Fc surface, and C1s or proC1s_RQ binding was evaluated at various concentrations. Kinetic parameters and equilibrium dissociation constants were derived by global fitting of the data (FIG. 4). Two hybridoma derived clones (MAB1 and MAB3) and one single cell derived clone (MAB2) showed favorable selectivity as well as potency of inhibition of the classical pathway.

Example 6: Sequence Modifications

Variable domain sequences of lead antibodies were examined for structural liabilities such as NG (deamidation risk) and DG (isomerization risk), and variants were expressed, purified and tested for activity in the CP Wieslab assay. In each case variants that removed the liability and maintained functional potency were identified.

To further modify the variable domain sequences by reducing risk of immunogenicity nearest human germline genes were identified and variants that had non-germline framework region residues converted to germline were expressed and tested. The most germlined, liability fixed constructs that maintained functional potency were designated as MAB1, MAB2, and MAB3.

The Fc region of lead antibodies was engineered in several ways. IgG4 and IgG2/4 chimeric scaffolds were tested to avoid effector function, and half-life extension mutations (Xencor LS or MedImmune YTE) were introduced to improve pharmacokinetic properties.

Example 7: Pharmacokinetics in Cynomolgus Monkeys

Lead antibodies and TNT009 were administered to cynomolgus monkeys at relatively low doses (0.05-0.1 mg/kg) where impact of target mediated clearance would be seen clearly. Consistent with published data, TNT009 at 0.1 mg/kg had fast clearance and a short half-life (~0.2 days), while the more selective leads 4011, 5L3 and sct-191 had half-lives of ~14 days. LS and YTE modified variants extended half-life even further to 18-23 days.

Example 8: Serine Protease Specificity

Lead antibodies were tested for inhibitory activity of a panel of related serine protease at Reaction Biology (Malvern, PA). The panel consisted of C1r, Protein C, Cathepsin G, Chymase, Factor VIIa, Factor Xa, Factor XIa, Granzyme B, Kallikrein 1, plasma kallikrein, Matripase 2, Plasmin, Thrombin, TPA and Urokinase. Enzyme and substrate concentrations were optimized in preliminary assays, followed by screening of lead antibodies. Inhibition by lead antibodies at 1 uM concentration was less than 50% in all cases. In addition, lead antibodies were tested in Complement Lectin Pathway and Alternative Pathway Wieslab kits as a surrogate for inhibition of MASP1, MASP2, MASP3 and Factor D.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications in addition to those described herein will become apparent to those skilled in the art from the foregoing description and the accompanying figures. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

What is claimed is:

1. An antibody, or antigen-binding fragment thereof, comprising a heavy chain variable region and a light chain variable region, wherein the heavy chain variable region comprises a HCDR1, a HCDR2, and a HCDR3; and the light chain variable region comprises a LCDR1, a LCDR2, and a LCRD3, and wherein:
the HCDR1 comprises the amino acid sequence of SEQ ID NO: 32;
the HCDR2 comprises the amino acid sequence of SEQ ID NO: 33;
the HCDR3 comprises the amino acid sequence of SEQ ID NO: 17;
the LCDR1 comprises the amino acid sequence of SEQ ID NO: 34;
the LCDR2 comprises the amino acid sequence of SEQ ID NO: 35; and
the LCDR3 comprises the amino acid sequence of SEQ ID NO: 36.

2. The antibody, or antigen-binding fragment thereof, of claim 1, wherein the antibody, or antigen binding fragment thereof, comprises the heavy chain variable region comprising an amino acid sequence that is at least 95% identical to the amino acid sequence of SEQ ID NO: 3 and the light chain variable region comprising an amino acid sequence that is at least 95% identical to the amino acid sequence of SEQ ID NO: 4.

3. The antibody, or antigen-binding fragment thereof, of claim 2, wherein the heavy chain variable region comprises the amino acid sequence of SEQ ID NO: 3 and the light chain variable region comprises the amino acid sequence of SEQ ID NO: 4.

4. The antibody, or antigen binding fragment thereof, of claim 2, wherein the heavy chain variable region is linked to a constant region comprising the amino acid sequence selected from the group consisting of SEQ ID NO: 7, 8, 57, and 58.

5. The antibody, or antigen-binding fragment thereof, of claim 4, wherein the constant region comprises the amino acid sequence of SEQ ID NO: 8.

6. The antibody, or antigen-binding fragment thereof, of claim 4, wherein the constant region comprises the amino acid sequence of SEQ ID NO: 58.

7. The antibody, or antigen binding fragment thereof, of claim 2, wherein the light chain variable region is linked to a constant domain comprising the amino acid sequence of SEQ ID NO: 65.

8. The antibody, or antigen binding fragment thereof, of claim 2, wherein the antibody, or antigen binding fragment thereof, comprises:
a heavy chain comprising an amino acid sequence that is at least 95% identical to the amino acid sequence of SEQ ID NO: 68 or the amino acid sequence of SEQ ID NO: 69; and
a light chain comprising an amino acid sequence that is at least 95% identical to the amino acid sequence of SEQ ID NO: 73.

9. The antibody, or antigen binding fragment thereof, of claim 2, wherein the antibody, or antigen binding fragment thereof, comprises a heavy chain comprising the amino acid sequence of SEQ ID NO: 69 and a light chain comprising the amino acid sequence of SEQ ID NO: 73.

10. The antibody, or antigen binding fragment thereof, of claim 2, wherein the antibody, or antigen binding fragment thereof, comprises a heavy chain comprising the amino acid sequence of SEQ ID NO: 68 and a light chain comprising the amino acid sequence of SEQ ID NO: 73.

11. A pharmaceutical composition comprising an antibody, or antigen binding fragment thereof, of claim 4.

12. A pharmaceutical composition comprising an antibody, or antigen binding fragment thereof, of claim 7.

13. A pharmaceutical composition comprising an antibody, or antigen binding fragment thereof, of claim 1.

14. A pharmaceutical composition comprising an antibody, or antigen binding fragment thereof, of claim 2.

15. A pharmaceutical composition comprising an antibody, or antigen binding fragment thereof, of claim 3.

16. A method of treating a subject with Myasthenia Gravis, hemolysis, Cold Agglutinin Disease, Immune Thrombocytopenia (ITP), Glomerulopaties, Atypical Hemolytic uremic syndrome, antiphospholipid antibody syndrome, or transplant rejection, the method comprising administering to the subject an antibody, or antigen binding fragment thereof, of claim 2.

17. A method of treating a subject with Myasthenia Gravis, hemolysis, Cold Agglutinin Disease, Immune Thrombocytopenia (ITP), Glomerulopaties, Atypical Hemolytic uremic syndrome, antiphospholipid antibody syndrome, or transplant rejection, the method comprising administering to the subject an antibody, or antigen binding fragment thereof, of claim 1.

18. A method of treating a subject with Myasthenia Gravis, hemolysis, Cold Agglutinin Disease, Immune Thrombocytopenia (ITP), Glomerulopaties, Atypical Hemolytic uremic syndrome, antiphospholipid antibody syndrome, or transplant rejection, the method comprising administering to the subject an antibody, or antigen binding fragment thereof, of claim 3.

19. A method of treating a subject with Myasthenia Gravis, hemolysis, Cold Agglutinin Disease, Immune Thrombocytopenia (ITP), Glomerulopaties, Atypical Hemolytic uremic syndrome, antiphospholipid antibody syndrome, or transplant rejection, the method comprising administering to the subject an antibody, or antigen binding fragment thereof, of claim 8.

20. A method of treating a subject with Myasthenia Gravis, hemolysis, Cold Agglutinin Disease, Immune Thrombocytopenia (ITP), Glomerulopaties, Atypical Hemolytic uremic syndrome, antiphospholipid antibody syndrome, or transplant rejection, the method comprising administering to the subject an antibody, or antigen binding fragment thereof, of claim 9.

21. A method of treating a subject with Myasthenia Gravis, hemolysis, Cold Agglutinin Disease, Immune Thrombocytopenia (ITP), Glomerulopaties, Atypical Hemolytic uremic syndrome, antiphospholipid antibody syndrome, or transplant rejection, the method comprising administering to the subject an antibody, or antigen binding fragment thereof, of claim 10.

* * * * *

SEQUENCE LISTING

```
<160> NUMBER OF SEQ ID NOS: 76

<210> SEQ ID NO 1
<211> LENGTH: 119
<212> TYPE: PRT
<213> ORGANISM: Artificial Sequence
<220> FEATURE:
<223> OTHER INFORMATION: Synthetic peptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Leu Thr Glu Leu
            20                  25                  30

Ser Met His Trp Val Arg Gln Ala Pro Gly Lys Gly Leu Glu Trp Met
        35                  40                  45

Gly Thr Phe Asp Pro Glu Glu Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Thr Glu Gly Leu Ala Gly Arg Pro Phe Asp Ser Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic peptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Trp
                 85                  90                  95

Thr Phe Gly Gln Gly Thr Lys Val Glu Ile Lys
            100                 105
```

<210> SEQ ID NO 3
<211> LENGTH: 118
<212> TYPE: PRT
<213> ORGANISM: Artificial Sequence
<220> FEATURE:
<223> OTHER INFORMATION: Synthetic sequence

<400> SEQUENCE: 3

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
             35                  40                  45

Ser Tyr Ile Ser Arg Ser Gly Ser Thr Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Glu Thr Asp Tyr Ala Leu Asp Tyr Trp Gly Gln Gly Thr
            100                 105                 110

Leu Val Thr Val Ser Ser
        115
```

<210> SEQ ID NO 4
<211> LENGTH: 107
<212> TYPE: PRT
<213> ORGANISM: Artificial Sequence
<220> FEATURE:
<223> OTHER INFORMATION: Synthetic sequence

<400> SEQUENCE: 4

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Glu Asp Leu Pro Leu
                 85                  90                  95

Thr Phe Gly Gly Gly Thr Lys Val Glu Ile Lys
            100                 105
```

<210> SEQ ID NO 5

```
<211> LENGTH: 125
<212> TYPE: PRT
<213> ORGANISM: Artificial Sequence
<220> FEATURE:
<223> OTHER INFORMATION: Synthetic sequence

<400> SEQUENCE: 5

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Glu Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Gln Leu Gly Gly Asn Tyr Tyr Tyr Tyr Tyr Tyr Met
            100                 105                 110

Asp Val Trp Gly Lys Gly Thr Thr Val Thr Val Ser Ser
        115                 120                 125

<210> SEQ ID NO 6
<211> LENGTH: 107
<212> TYPE: PRT
<213> ORGANISM: Artificial Sequence
<220> FEATURE:
<223> OTHER INFORMATION: Synthetic sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Thr Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Leu
                85                  90                  95

Thr Phe Gly Gly Gly Thr Lys Val Glu Ile Lys
            100                 105

<210> SEQ ID NO 7
<211> LENGTH: 327
<212> TYPE: PRT
<213> ORGANISM: Artificial Sequence
<220> FEATURE:
<223> OTHER INFORMATION: Synthetic sequence

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
            290                 295                 300

Cys Ser Val Leu His Glu Ala Leu His Ser His Tyr Thr Gln Lys Ser
305                 310                 315                 320

Leu Ser Leu Ser Leu Gly Lys
                325

<210> SEQ ID NO 8
<211> LENGTH: 327
<212> TYPE: PRT
<213> ORGANISM: Artificial Sequence
<220> FEATURE:
<223> OTHER INFORMATION: Synthetic sequence

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence

<400> SEQUENCE: 9

Glu Leu Ser Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic sequence

<400> SEQUENCE: 10

Thr Phe Asp Pro Glu Glu Gly Glu Thr Ile Tyr Ala Gln Lys Phe Gln
1               5                   10                  15

Gly
```

```
<210> SEQ ID NO 11
<211> LENGTH: 10
<212> TYPE: PRT
<213> ORGANISM: Artificial Sequence
<220> FEATURE:
<223> OTHER INFORMATION: Synthetic sequence

<400> SEQUENCE: 11

Glu Gly Leu Ala Gly Arg Pro Phe Asp Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic sequence

<400> SEQUENCE: 12

Arg Ala Ser Gln Ser Ile Ser Ser Trp Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic sequence

<400> SEQUENCE: 13

Lys Ala Ser Ser Leu Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic sequence

<400> SEQUENCE: 14

Gln Gln Tyr Asn Ser Tyr Ser Trp Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic sequence

<400> SEQUENCE: 15

Asp Tyr Tyr Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic sequence

<400> SEQUENCE: 16

Tyr Ile Ser Arg Ser Gly Ser Thr Lys Tyr Tyr Ala Asp Ser Val Lys
1               5                   10                  15

Gly
```

```
<210> SEQ ID NO 17
<211> LENGTH: 9
<212> TYPE: PRT
<213> ORGANISM: Artificial Sequence
<220> FEATURE:
<223> OTHER INFORMATION: Synthetic sequence

<400> SEQUENCE: 17

Asp Glu Thr Asp Tyr Ala Leu Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic sequence

<400> SEQUENCE: 18

Gln Ala Ser Gln Asp Ile Ser Asn Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic sequence

<400> SEQUENCE: 19

Asp Ala Ser Asn Leu Glu Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic sequence

<400> SEQUENCE: 20

Gln Gln Tyr Glu Asp Leu Pro Leu Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic sequence

<400> SEQUENCE: 21

Asp Tyr Gly Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic sequence

<400> SEQUENCE: 22

Gly Ile Asn Trp Glu Gly Gly Ser Thr Gly Tyr Ala Asp Ser Val Lys
1               5                   10                  15
```

Gly

<210> SEQ ID NO 23
<211> LENGTH: 16
<212> TYPE: PRT
<213> ORGANISM: Artificial Sequence
<220> FEATURE:
<223> OTHER INFORMATION: Synthetic sequence

<400> SEQUENCE: 23

Asp Glu Gln Leu Gly Gly Asn Tyr Tyr Tyr Tyr Tyr Met Asp Val
1               5                   10                  15

<210> SEQ ID NO 24
<211> LENGTH: 11
<212> TYPE: PRT
<213> ORGANISM: Artificial Sequence
<220> FEATURE:
<223> OTHER INFORMATION: Synthetic sequence

<400> SEQUENCE: 24

Arg Ala Ser Gln Gly Ile Arg Asn Asp Leu Gly
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic sequence

<400> SEQUENCE: 25

Thr Ala Ser Asn Leu Gln Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic sequence

<400> SEQUENCE: 26

Leu Gln Tyr Asn Ser Tyr Pro Leu Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic sequence

<400> SEQUENCE: 27

Gly Asp Thr Leu Thr Glu Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic sequence

<400> SEQUENCE: 28

Asp Pro Glu Glu Gly Glu
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic sequence

<400> SEQUENCE: 29

Ser Gln Ser Ile Ser Ser Trp
1               5

<210> SEQ ID NO 30

<400> SEQUENCE: 30

000

<210> SEQ ID NO 31
<211> LENGTH: 6
<212> TYPE: PRT
<213> ORGANISM: Artificial Sequence
<220> FEATURE:
<223> OTHER INFORMATION: Synthetic sequence

<400> SEQUENCE: 31

Tyr Asn Ser Tyr Ser Trp
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic sequence

<400> SEQUENCE: 32

Gly Phe Thr Phe Ser Asp Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic sequence

<400> SEQUENCE: 33

Ser Arg Ser Gly Ser Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic sequence

<400> SEQUENCE: 34

Ser Gln Asp Ile Ser Asn Tyr
1               5

<210> SEQ ID NO 35

<400> SEQUENCE: 35

000

```
<210> SEQ ID NO 36
<211> LENGTH: 6
<212> TYPE: PRT
<213> ORGANISM: Artificial Sequence
<220> FEATURE:
<223> OTHER INFORMATION: Synthetic sequence

<400> SEQUENCE: 36

Tyr Glu Asp Leu Pro Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic sequence

<400> SEQUENCE: 37

Gly Phe Thr Phe Asp Asp Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic sequence

<400> SEQUENCE: 38

Asn Trp Glu Gly Gly Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic sequence

<400> SEQUENCE: 39

Ser Gln Gly Ile Arg Asn Asp
1               5

<210> SEQ ID NO 40

<400> SEQUENCE: 40

000

<210> SEQ ID NO 41
<211> LENGTH: 6
<212> TYPE: PRT
<213> ORGANISM: Artificial Sequence
<220> FEATURE:
<223> OTHER INFORMATION: Synthetic sequence

<400> SEQUENCE: 41

Tyr Asn Ser Tyr Pro Leu
1               5

<210> SEQ ID NO 42
<211> LENGTH: 8
<212> TYPE: PRT
<213> ORGANISM: Artificial Sequence
<220> FEATURE:
```

```
<223> OTHER INFORMATION: Synthetic sequence

<400> SEQUENCE: 42

Gly Asp Thr Leu Thr Glu Leu Ser
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic sequence

<400> SEQUENCE: 43

Phe Asp Pro Glu Glu Gly Glu Thr
1               5

<210> SEQ ID NO 44
<211> LENGTH: 12
<212> TYPE: PRT
<213> ORGANISM: Artificial Sequence
<220> FEATURE:
<223> OTHER INFORMATION: Synthetic sequence

<400> SEQUENCE: 44

Val Thr Glu Gly Leu Ala Gly Arg Pro Phe Asp Ser
1               5                   10

<210> SEQ ID NO 45
<211> LENGTH: 6
<212> TYPE: PRT
<213> ORGANISM: Artificial Sequence
<220> FEATURE:
<223> OTHER INFORMATION: Synthetic sequence

<400> SEQUENCE: 45

Gln Ser Ile Ser Ser Trp
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic sequence

<400> SEQUENCE: 46

Gly Phe Thr Phe Ser Asp Tyr Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic sequence

<400> SEQUENCE: 47

Ile Ser Arg Ser Gly Ser Thr Lys
1               5

<210> SEQ ID NO 48
<211> LENGTH: 11
<212> TYPE: PRT
<213> ORGANISM: Artificial Sequence
<220> FEATURE:
<223> OTHER INFORMATION: Synthetic sequence
```

```
<400> SEQUENCE: 48

Ala Arg Asp Glu Thr Asp Tyr Ala Leu Asp Tyr
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Synthetic sequence

<400> SEQUENCE: 49

Gln Asp Ile Ser Asn Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic sequence

<400> SEQUENCE: 50

Gly Phe Thr Phe Asp Asp Tyr Gly
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic sequence

<400> SEQUENCE: 51

Ile Asn Trp Glu Gly Gly Ser Thr
1               5

<210> SEQ ID NO 52
<211> LENGTH: 18
<212> TYPE: PRT
<213> ORGANISM: Artificial Sequence
<220> FEATURE:
<223> OTHER INFORMATION: Synthetic sequence

<400> SEQUENCE: 52

Ala Arg Asp Glu Gln Leu Gly Gly Asn Tyr Tyr Tyr Tyr Tyr Met
1               5                   10                  15

Asp Val

<210> SEQ ID NO 53
<211> LENGTH: 6
<212> TYPE: PRT
<213> ORGANISM: Artificial Sequence
<220> FEATURE:
<223> OTHER INFORMATION: Synthetic sequence

<400> SEQUENCE: 53

Gln Gly Ile Arg Asn Asp
1               5

<210> SEQ ID NO 54
<211> LENGTH: 25
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: SITE
<222> LOCATION: (1)..(25)
<223> OTHER INFORMATION: This sequence may encompass 1-5 "Gly Gly Gly
      Gly Ser" repeating units

<400> SEQUENCE: 54

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 55
<211> LENGTH: 25
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (1)..(25)
<223> OTHER INFORMATION: This sequence may encompass 1-5 "Gly Gly Gly
      Gly Ala" repeating units

<400> SEQUENCE: 55

Gly Gly Gly Gly Ala Gly Gly Gly Ala Gly Gly Gly Gly Ala Gly
1               5                   10                  15

Gly Gly Gly Ala Gly Gly Gly Gly Ala
            20                  25

<210> SEQ ID NO 56
<211> LENGTH: 688
<212> TYPE: PRT
<213> ORGANISM: Artificial Sequence
<220> FEATURE:
<223> OTHER INFORMATION: Synthetic sequence

<400> SEQUENCE: 56

Met Trp Cys Ile Val Leu Phe Ser Leu Leu Ala Trp Val Tyr Ala Glu
1               5                   10                  15

Pro Thr Met Tyr Gly Glu Ile Leu Ser Pro Asn Tyr Pro Gln Ala Tyr
            20                  25                  30

Pro Ser Glu Val Glu Lys Ser Trp Asp Ile Glu Val Pro Glu Gly Tyr
        35                  40                  45

Gly Ile His Leu Tyr Phe Thr His Leu Asp Ile Glu Leu Ser Glu Asn
    50                  55                  60

Cys Ala Tyr Asp Ser Val Gln Ile Ile Ser Gly Asp Thr Glu Glu Gly
65                  70                  75                  80

Arg Leu Cys Gly Gln Arg Ser Ser Asn Asn Pro His Ser Pro Ile Val
                85                  90                  95

Glu Glu Phe Gln Val Pro Tyr Asn Lys Leu Gln Val Ile Phe Lys Ser
            100                 105                 110

Asp Phe Ser Asn Glu Glu Arg Phe Thr Gly Phe Ala Ala Tyr Tyr Val
        115                 120                 125

Ala Thr Asp Ile Asn Glu Cys Thr Asp Phe Val Asp Val Pro Cys Ser
    130                 135                 140

His Phe Cys Asn Asn Phe Ile Gly Gly Tyr Phe Cys Ser Cys Pro Pro
145                 150                 155                 160

Glu Tyr Phe Leu His Asp Asp Met Lys Asn Cys Gly Val Asn Cys Ser
                165                 170                 175
```

```
Gly Asp Val Phe Thr Ala Leu Ile Gly Ile Ala Ser Pro Asn Tyr
            180                 185                 190

Pro Lys Pro Tyr Pro Glu Asn Ser Arg Cys Glu Tyr Gln Ile Arg Leu
        195                 200                 205

Glu Lys Gly Phe Gln Val Val Thr Leu Arg Arg Glu Asp Phe Asp
    210                 215                 220

Val Glu Ala Ala Asp Ser Ala Gly Asn Cys Leu Asp Ser Leu Val Phe
225                 230                 235                 240

Val Ala Gly Asp Arg Gln Phe Gly Pro Tyr Cys Gly His Gly Phe Pro
                245                 250                 255

Gly Pro Leu Asn Ile Glu Thr Lys Ser Asn Ala Leu Asp Ile Ile Phe
            260                 265                 270

Gln Thr Asp Leu Thr Gly Gln Lys Lys Gly Trp Lys Leu Arg Tyr His
        275                 280                 285

Gly Asp Pro Met Pro Cys Pro Lys Glu Asp Thr Pro Asn Ser Val Trp
    290                 295                 300

Glu Pro Ala Lys Ala Lys Tyr Val Phe Arg Asp Val Val Gln Ile Thr
305                 310                 315                 320

Cys Leu Asp Gly Phe Glu Val Val Glu Gly Arg Val Gly Ala Thr Ser
                325                 330                 335

Phe Tyr Ser Thr Cys Gln Ser Asn Gly Lys Trp Ser Asn Ser Lys Leu
            340                 345                 350

Lys Cys Gln Pro Val Asp Cys Gly Ile Pro Glu Ser Ile Glu Asn Gly
        355                 360                 365

Lys Val Glu Asp Pro Glu Ser Thr Leu Phe Gly Ser Val Ile Arg Tyr
    370                 375                 380

Thr Cys Glu Glu Pro Tyr Tyr Tyr Met Glu Asn Gly Gly Gly Glu
385                 390                 395                 400

Tyr His Cys Ala Gly Asn Gly Ser Trp Val Asn Glu Val Leu Gly Pro
                405                 410                 415

Glu Leu Pro Lys Cys Val Pro Val Cys Gly Val Pro Arg Glu Pro Phe
            420                 425                 430

Glu Glu Lys Gln Arg Ile Ile Gly Gly Ser Asp Ala Asp Ile Lys Asn
        435                 440                 445

Phe Pro Trp Gln Val Phe Phe Asp Asn Pro Trp Ala Gly Gly Ala Leu
    450                 455                 460

Ile Asn Glu Tyr Trp Val Leu Thr Ala Ala His Val Val Glu Gly Asn
465                 470                 475                 480

Arg Glu Pro Thr Met Tyr Val Gly Ser Thr Ser Val Gln Thr Ser Arg
                485                 490                 495

Leu Ala Lys Ser Lys Met Leu Thr Pro Glu His Val Phe Ile His Pro
            500                 505                 510

Gly Trp Lys Leu Leu Glu Val Pro Glu Gly Arg Thr Asn Phe Asp Asn
        515                 520                 525

Asp Ile Ala Leu Val Arg Leu Lys Asp Pro Val Lys Met Gly Pro Thr
    530                 535                 540

Val Ser Pro Ile Cys Leu Pro Gly Thr Ser Ser Asp Tyr Asn Leu Met
545                 550                 555                 560

Asp Gly Asp Leu Gly Leu Ile Ser Gly Trp Gly Arg Thr Glu Lys Arg
                565                 570                 575

Asp Arg Ala Val Arg Leu Lys Ala Ala Arg Leu Pro Val Ala Pro Leu
            580                 585                 590

Arg Lys Cys Lys Glu Val Lys Val Glu Lys Pro Thr Ala Asp Ala Glu
```

```
                    595                 600                 605
Ala Tyr Val Phe Thr Pro Asn Met Ile Cys Ala Gly Gly Glu Lys Gly
            610                 615                 620

Met Asp Ser Cys Lys Gly Asp Ser Gly Gly Ala Phe Ala Val Gln Asp
625                 630                 635                 640

Pro Asn Asp Lys Thr Lys Phe Tyr Ala Ala Gly Leu Val Ser Trp Gly
            645                 650                 655

Pro Gln Cys Gly Thr Tyr Gly Leu Tyr Thr Arg Val Lys Asn Tyr Val
            660                 665                 670

Asp Trp Ile Met Lys Thr Met Gln Glu Asn Ser Thr Pro Arg Glu Asp
            675                 680                 685

<210> SEQ ID NO 57
<211> LENGTH: 326
<212> TYPE: PRT
<213> ORGANISM: Artificial Sequence
<220> FEATURE:
<223> OTHER INFORMATION: Synthetic sequence

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
            275                 280                 285
Arg Leu Thr Val Asp Lys Ser Arg Trp Gln Glu Gly Asn Val Phe Ser
    290                 295                 300

Cys Ser Val Leu His Glu Ala Leu His Ser His Tyr Thr Gln Lys Ser
305                 310                 315                 320

Leu Ser Leu Ser Leu Gly
                325

<210> SEQ ID NO 58
<211> LENGTH: 326
<212> TYPE: PRT
<213> ORGANISM: Artificial Sequence
<220> FEATURE:
<223> OTHER INFORMATION: Synthetic sequence

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
```

Leu Ser Leu Ser Leu Gly
            325

<210> SEQ ID NO 59
<211> LENGTH: 357
<212> TYPE: DNA
<213> ORGANISM: Artificial Sequence
<220> FEATURE:
<223> OTHER INFORMATION: Synthetic sequence

<400> SEQUENCE: 59
caagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
ttggccgggc gcccgtttga ttcatggggg caggggacgc tggtaacggt ctcgagt      357

<210> SEQ ID NO 60
<211> LENGTH: 321
<212> TYPE: DNA
<213> ORGANISM: Artificial Sequence
<220> FEATURE:
<223> OTHER INFORMATION: Synthetic sequence

<400> SEQUENCE: 60
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagcg gatcaggatc tggtactgaa ttcactctga ccatttcaag tcttcagcct   240
gatgactttg cgacctatta ttgccagcag tacaatagct actcatggac gttcgggcag   300
ggtactaaag tcgagattaa a                                              321

<210> SEQ ID NO 61
<211> LENGTH: 354
<212> TYPE: DNA
<213> ORGANISM: Artificial Sequence
<220> FEATURE:
<223> OTHER INFORMATION: Synthetic sequence

<400> SEQUENCE: 61
caggtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca cgcaaagaa ctctctttat    240 ctgcagatga attcactgag agcagaagat accgctgtct attattgtgc cagagacgag   300
accgattacg ctcttgacta ctggggccaa ggtacgctgg ttacggtctc gagt          354

<210> SEQ ID NO 62
<211> LENGTH: 321
<212> TYPE: DNA
<213> ORGANISM: Artificial Sequence
<220> FEATURE:
<223> OTHER INFORMATION: Synthetic sequence -continued

<400> SEQUENCE: 62

```
gacattcaga tgacgcaaag cccctctagc ttgtccgcta gtgtgggtga cagggtcacc      60
attacctgcc aggcttcaca agacatcagt aattacctca actggtatca gcagaaacct     120
gggaaggccc ctaagctgtt gatttacgat gctagtaact tggagaccgg ggtacccagc     180
agatttagcg ggagcggaag tggtacggat tttacgttta ccattagcag cttgcagccc     240
gaggacatcg ctacatatta ctgtcagcag tatgaggacc tccctcttac cttcggcggt     300
ggaacgaaag ttgagattaa g                                               321
```

<210> SEQ ID NO 63
<211> LENGTH: 375
<212> TYPE: DNA
<213> ORGANISM: Artificial Sequence
<220> FEATURE:
<223> OTHER INFORMATION: Synthetic sequence

<400> SEQUENCE: 63

```
gaagtccagc ttgttgagtc tggcggaggg gtggttaggc caggaggttc ccttaggctt      60
tcctgtgcgg catcaggatt taccttcgat gactacggaa tgtcatgggt acgacaagct     120
cccggcaaag gcctcgaatg ggtttctggc atcaactggg agggcggttc cactggctac     180
gcggactcag ttaagggtag gttcaccata agcagggaca atgcgaagaa ctcactgtat     240
ctccaaatga acagtctccg cgccgaggat acagcccttt actattgtgc acgagatgag     300
caattggggg ggaattatta ttattactat tacatggacg tgtggggtaa aggaacgacc     360
gtcacagtct cgagt                                                      375
```

<210> SEQ ID NO 64
<211> LENGTH: 321
<212> TYPE: DNA
<213> ORGANISM: Artificial Sequence
<220> FEATURE:
<223> OTHER INFORMATION: Synthetic sequence

<400> SEQUENCE: 64

```
gacatacaga tgactcagtc cccaagtagt ctgagcgcct ctgtcggcga ccgcgttacc      60
attacttgcc gggcgagtca agggatacgc aacgatttgg gttggtatca gcaaaagccc     120
ggaaaggccc caaagcggct gatatacacc gcctcaaacc tccagtctgg agttccatca     180
aggtttagtg gatctggatc tggcactgag tttactctca ctataagctc ccttcagcct     240
gaagacttcg caacttatta ttgcttgcag tataatagtt atccactcac ttttggcggt     300
ggcaccaaag tggagattaa g                                               321
```

<210> SEQ ID NO 65
<211> LENGTH: 107
<212> TYPE: PRT
<213> ORGANISM: Artificial Sequence
<220> FEATURE:
<223> OTHER INFORMATION: Synthetic sequence

<400> SEQUENCE: 65

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45
```

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 66
<211> LENGTH: 445
<212> TYPE: PRT
<213> ORGANISM: Artificial Sequence
<220> FEATURE:
<223> OTHER INFORMATION: Synthetic sequence

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Leu Thr Glu Leu
                20                  25                  30

Ser Met His Trp Val Arg Gln Ala Pro Gly Lys Gly Leu Glu Trp Met
            35                  40                  45

Gly Thr Phe Asp Pro Glu Glu Gly Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Thr Glu Gly Leu Ala Gly Arg Pro Phe Asp Ser Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Leu His Glu Ala Leu His
            420                 425                 430

Ser His Tyr Thr Gln Lys Ser Leu Ser Leu Ser Leu Gly
            435                 440                 445

<210> SEQ ID NO 67
<211> LENGTH: 445
<212> TYPE: PRT
<213> ORGANISM: Artificial Sequence
<220> FEATURE:
<223> OTHER INFORMATION: Synthetic sequence

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Val Ser Gly Asp Thr Leu Thr Glu Leu
            20                  25                  30

Ser Met His Trp Val Arg Gln Ala Pro Gly Lys Gly Leu Glu Trp Met
        35                  40                  45

Gly Thr Phe Asp Pro Glu Glu Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Thr Glu Gly Leu Ala Gly Arg Pro Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220
```

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Tyr Ile Thr Arg Glu Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Gly
    435                 440                 445

<210> SEQ ID NO 68
<211> LENGTH: 444
<212> TYPE: PRT
<213> ORGANISM: Artificial Sequence
<220> FEATURE:
<223> OTHER INFORMATION: Synthetic sequence

<400> SEQUENCE: 68

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Ser Gly Ser Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Glu Thr Asp Tyr Ala Leu Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Leu His Glu Ala Leu His Ser
            420                 425                 430

His Tyr Thr Gln Lys Ser Leu Ser Leu Ser Leu Gly
        435                 440

<210> SEQ ID NO 69
<211> LENGTH: 444
<212> TYPE: PRT
<213> ORGANISM: Artificial Sequence
<220> FEATURE:
<223> OTHER INFORMATION: Synthetic sequence

<400> SEQUENCE: 69

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Ser Gly Ser Thr Lys Tyr Tyr Ala Asp Ser Val
    50                  55                  60

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Glu Thr Asp Tyr Ala Leu Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Tyr Ile Thr Arg Glu Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 70
<211> LENGTH: 451
<212> TYPE: PRT
<213> ORGANISM: Artificial Sequence
<220> FEATURE:
<223> OTHER INFORMATION: Synthetic sequence

<400> SEQUENCE: 70

| | | | | | | | | | | | | | | |
|---|---|---|---|---|---|---|---|---|---|---|---|---|---|---|
| Glu | Val | Gln | Leu | Val | Glu | Ser | Gly | Gly | Val | Val | Arg | Pro | Gly | Gly |
| 1 | | | | 5 | | | | | 10 | | | | | 15 |
| Ser | Leu | Arg | Leu | Ser | Cys | Ala | Ala | Ser | Gly | Phe | Thr | Phe | Asp | Asp | Tyr |
| | | | 20 | | | | | 25 | | | | | 30 | | |
| Gly | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Gly | Ile | Asn | Trp | Glu | Gly | Ser | Thr | Gly | Tyr | Ala | Asp | Ser | Val |
| 50 | | | | | 55 | | | | | 60 | | | | |
| Lys | Gly | Arg | Phe | Thr | Ile | Ser | Arg | Asp | Asn | Ala | Lys | Asn | Ser | Leu | Tyr |
| 65 | | | | 70 | | | | | 75 | | | | | 80 | |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 | |
| Ala | Arg | Asp | Glu | Gln | Leu | Gly | Gly | Asn | Tyr | Tyr | Tyr | Tyr | Tyr | Met |
| | | | 100 | | | | | 105 | | | | | 110 | |
| Asp | Val | Trp | Gly | Lys | Gly | Thr | Thr | Val | Thr | Val | Ser | Ser | Ala | Ser | Thr |
| | | | 115 | | | | | 120 | | | | | 125 | | |
| Lys | Gly | Pro | Ser | Val | Phe | Pro | Leu | Ala | Pro | Cys | Ser | Arg | Ser | Thr | Ser |
| 130 | | | | | 135 | | | | | 140 | | | | | |
| Glu | Ser | Thr | Ala | Ala | Leu | Gly | Cys | Leu | Val | Lys | Asp | Tyr | Phe | Pro | Glu |
| 145 | | | | 150 | | | | | 155 | | | | | 160 | |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Ser | Leu | Gly | Thr | Lys | Thr | Tyr | Thr | Cys |
| | | | 195 | | | | | 200 | | | | | 205 | | |
| Asn | Val | Asp | His | Lys | Pro | Ser | Asn | Thr | Lys | Val | Asp | Lys | Arg | Val | Glu |
| | 210 | | | | | 215 | | | | | 220 | | | | |
| Ser | Lys | Tyr | Gly | Pro | Pro | Cys | Pro | Pro | Cys | Pro | Ala | Pro | Glu | Phe | Glu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| Gln | Glu | Asp | Pro | Glu | Val | Gln | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Phe | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Gly | Leu | Pro | Ser | Ser |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Gln | Glu | Glu | Met | Thr | Lys | Asn | Gln | Val |
| | | | 355 | | | | | 360 | | | | | 365 | | |
| Ser | Leu | Thr | Cys | Leu | Val | Lys | Gly | Phe | Tyr | Pro | Ser | Asp | Ile | Ala | Val |
| | | 370 | | | | | 375 | | | | | 380 | | | |
| Glu | Trp | Glu | Ser | Asn | Gly | Gln | Pro | Glu | Asn | Asn | Tyr | Lys | Thr | Thr | Pro |
| 385 | | | | | 390 | | | | | 395 | | | | | 400 |
| Pro | Val | Leu | Asp | Ser | Asp | Gly | Ser | Phe | Phe | Leu | Tyr | Ser | Arg | Leu | Thr |

```
                    405                 410                 415
Val Asp Lys Ser Arg Trp Gln Glu Gly Asn Val Phe Ser Cys Ser Val
        420                 425                 430

Leu His Glu Ala Leu His Ser His Tyr Thr Gln Lys Ser Leu Ser Leu
        435                 440                 445

Ser Leu Gly
    450

<210> SEQ ID NO 71
<211> LENGTH: 451
<212> TYPE: PRT
<213> ORGANISM: Artificial Sequence
<220> FEATURE:
<223> OTHER INFORMATION: Synthetic sequence

<400> SEQUENCE: 71

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Glu Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Gln Leu Gly Gly Asn Tyr Tyr Tyr Tyr Tyr Tyr Met
            100                 105                 110

Asp Val Trp Gly Lys Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
```

```
              305                 310                 315                 320
        Gly Lys Glu Tyr Lys Cys Lys Val Ser Asn Lys Gly Leu Pro Ser Ser
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Gln Glu Met Thr Lys Asn Gln Val
                        355                 360                 365

Ser Leu Thr Cys Leu Val Lys Gly Phe Tyr Pro Ser Asp Ile Ala Val
                        370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Arg Leu Thr
                        405                 410                 415

Val Asp Lys Ser Arg Trp Gln Glu Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Leu Gly
                450

<210> SEQ ID NO 72
<211> LENGTH: 214
<212> TYPE: PRT
<213> ORGANISM: Artificial Sequence
<220> FEATURE:
<223> OTHER INFORMATION: Synthetic sequence

<400> SEQUENCE: 72

Asp Ile Gln Met Thr Gln Ser Pro Ser Thr Leu Ser Ala Ser Val Gly
        1               5                   10                  15

Asp Arg Val Thr Ile Thr Cys Arg Ala Ser Gln Ser Ile Ser Ser Trp
                        20                  25                  30

Leu Ala Trp Tyr Gln Gln Lys Pro Gly Lys Ala Pro Lys Leu Leu Ile
                        35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
        65                  70                  75                  80

Asp Asp Phe Ala Thr Tyr Tyr Cys Gln Gln Tyr Asn Ser Tyr Ser Trp
                        85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
```

-continued

```
<210> SEQ ID NO 73
<211> LENGTH: 214
<212> TYPE: PRT
<213> ORGANISM: Artificial Sequence
<220> FEATURE:
<223> OTHER INFORMATION: Synthetic sequence

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Asp Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 214
<212> TYPE: PRT
<213> ORGANISM: Artificial Sequence
<220> FEATURE:
<223> OTHER INFORMATION: Synthetic sequence

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Thr Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys Leu Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 75
<211> LENGTH: 15
<212> TYPE: PRT
<213> ORGANISM: Artificial Sequence
<220> FEATURE:
<223> OTHER INFORMATION: Synthetic sequence

<400> SEQUENCE: 75

Met Trp Cys Ile Val Leu Phe Ser Leu Leu Ala Trp Val Tyr Ala
1               5                   10                  15

<210> SEQ ID NO 76
<211> LENGTH: 673
<212> TYPE: PRT
<213> ORGANISM: Artificial Sequence
<220> FEATURE:
<223> OTHER INFORMATION: Synthetic sequence

<400> SEQUENCE: 76

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
            130                 135                 140

Pro Glu Tyr Phe Leu His Asp Asp Met Lys Asn Cys Gly Val Asn Cys
145                 150                 155                 160

-continued

```
Ser Gly Asp Val Phe Thr Ala Leu Ile Gly Glu Ile Ala Ser Pro Asn
            165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
            210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
            245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
            290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
            325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Tyr Met Glu Asn Gly Gly Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
            405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
            485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
            530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
            565                 570                 575
```

-continued

```
Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
        610             615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
            645                 650                 655

Val Asp Trp Ile Met Lys Thr Met Gln Glu Asn Ser Thr Pro Arg Glu
            660                 665                 670

Asp
```